(12) United States Patent
Arnold et al.

(10) Patent No.: US 12,121,591 B2
(45) Date of Patent: Oct. 22, 2024

(54) SULFUR-CONTAINING IONIZABLE LIPIDS FOR THE DELIVERY OF NUCLEIC ACIDS AND OTHER THERAPEUTIC AGENTS

(71) Applicant: NanoVation Therapeutics Inc., Vancouver (CA)

(72) Inventors: Deaglan Arnold, London (CA); Nagavenkata Durga Prasad Atmuri, Vancouver (CA); Fariba Saadati, Vancouver (CA); Huy Tran, Vancouver (CA); Marco A. Ciufolini, Vancouver (CA)

(73) Assignee: NanoVation Therapeutics Inc., Vancouver (CA)

( * ) Notice: Subject to any disclaimer, the term of this patent is extended or adjusted under 35 U.S.C. 154(b) by 0 days.

(21) Appl. No.: 18/392,458

(22) Filed: Dec. 21, 2023

(65) Prior Publication Data

US 2024/0261430 A1    Aug. 8, 2024

Related U.S. Application Data

(60) Provisional application No. 63/434,506, filed on Dec. 22, 2022.

(51) Int. Cl.
| | | |
|---|---|---|
| *A61K 47/69* | (2017.01) | |
| *A61K 9/51* | (2006.01) | |
| *A61K 47/20* | (2006.01) | |
| *C07C 323/12* | (2006.01) | |
| *C07C 323/25* | (2006.01) | |
| *C07D 205/04* | (2006.01) | |
| *C07D 317/28* | (2006.01) | |

(52) U.S. Cl.
CPC ........ *A61K 47/6929* (2017.08); *A61K 9/5123* (2013.01); *A61K 47/20* (2013.01); *C07C 323/12* (2013.01); *C07C 323/25* (2013.01); *C07D 205/04* (2013.01); *C07D 317/28* (2013.01); *C07B 2200/05* (2013.01)

(58) Field of Classification Search
CPC ... C07C 323/25; C07C 323/12; C07C 323/11; A61K 47/20

See application file for complete search history.

(56) References Cited

U.S. PATENT DOCUMENTS

| | | | |
|---|---|---|---|
| 9,012,498 | B2 | 4/2015 | Manoharan et al. |
| 9,061,063 | B2 | 6/2015 | Maier et al. |
| 9,511,024 | B2 | 12/2016 | Davidson et al. |
| 9,896,413 | B2 | 2/2018 | Payne et al. |
| 10,369,226 | B2 | 8/2019 | Maier et al. |
| 10,676,492 | B2 | 6/2020 | Jaffrès et al. |
| 11,229,609 | B2 | 1/2022 | Cheng et al. |
| 11,246,933 | B1 | 2/2022 | Maier et al. |
| 11,247,968 | B2 | 2/2022 | Siegwart et al. |
| 11,357,856 | B2 | 6/2022 | Ansell et al. |
| 11,400,158 | B2 | 8/2022 | Maier et al. |
| 11,666,539 | B2 | 6/2023 | Xu |
| 11,679,158 | B2 | 6/2023 | Maier et al. |
| 11,858,884 | B2 | 1/2024 | Siegwart et al. |
| 2020/0172472 | A1 | 6/2020 | Du |
| 2022/0323369 | A1 | 10/2022 | Xu |
| 2022/0347302 | A1 | 11/2022 | Maier et al. |
| 2024/0010614 | A1 | 1/2024 | Siegwart et al. |
| 2024/0025848 | A1 | 1/2024 | Siegwart et al. |
| 2024/0043378 | A1 | 2/2024 | Siegwart et al. |
| 2024/0083842 | A1 | 3/2024 | Siegwart et al. |
| 2024/0116859 | A1 | 4/2024 | Siegwart et al. |
| 2024/0116860 | A1 | 4/2024 | Siegwart et al. |

FOREIGN PATENT DOCUMENTS

| | | |
|---|---|---|
| CN | 114773217 | 10/2022 |
| CN | 114907243 | 10/2023 |
| EP | 4276090 | 11/2023 |

(Continued)

OTHER PUBLICATIONS

Halter et al. "Engineered Lipids That Cross-Link the Inner and Outer Leaflets of Lipid Bilayers", Langmuir 2004, 20, 2416-2423 (Year: 2004).*
Bouraoui et al., "Bis-Thioether-Containing Lipid Chains in Cationic Amphiphiles: Physicochemical Properties and Applications in Gene Delivery", ChemPhysChem, 2019, 20:2187-2194.
Bouraoui et al., "Substitution of unsaturated lipid chains by thioether containing lipid chains in cationic amphiphiles: physico-chemical consequences and application for gene therapy", Organic and Biomolecular Chemistry, 2019, 17:3609-3616.

(Continued)

*Primary Examiner* — James W Rogers
(74) *Attorney, Agent, or Firm* — Knobbe, Martens, Olson & Bear, LLP

(57) ABSTRACT

Provided herein is an ionizable, cationic amino lipid or a pharmaceutically acceptable salt thereof. The ionizable, cationic amino lipid has:
- a protonatable amino head group;
- two lipophilic chains, wherein the protonatable amino head group has a central carbon atom to which each of the two lipophilic chains are directly bonded;
- at least one of the two lipophilic chains has a structure of Formula C:

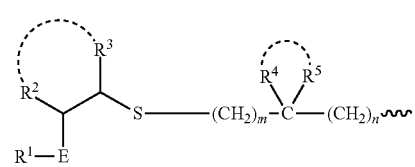

wherein E is an ester in either orientation. The compounds may be formulated in a lipid nanoparticle for use in the delivery of charged cargo such as nucleic acid.

10 Claims, 2 Drawing Sheets

(56) References Cited

FOREIGN PATENT DOCUMENTS

| | | |
|---|---|---|
| WO | WO 1999058152 | 11/1999 |
| WO | WO 2012045797 | 4/2012 |
| WO | WO 2016005318 | 1/2016 |
| WO | WO 2020219427 | 10/2020 |
| WO | WO 2022155728 | 7/2022 |
| WO | WO 2022246555 | 12/2022 |
| WO | WO 2022246568 | 12/2022 |
| WO | WO 2023144798 | 8/2023 |
| WO | WO 2023215989 | 11/2023 |
| WO | WO 2024065041 | 4/2024 |
| WO | WO 2024065042 | 4/2024 |

OTHER PUBLICATIONS

International Search Report and Written Opinion for PCT/CA2023/051272, Dec. 8, 2023.
International Search Report and Written Opinion for PCT/CA2023/051273, Dec. 1, 2023.
International Search Report and Written Opinion for PCT/CA2023/051727, Apr. 18, 2024.
Sun et al., 2023, "Structure and Function of Cationic and Ionizable Lipids for Nucleic Acid Delivery", Pharmaceutical Research, 40:27-46.
Suzuki et al., 2021, "Difference in the lipid nanoparticle technology employed in three approved siRNA (Patisiran) and mRNA (COVID-19 vaccine) drugs", Drug Metabolism and Pharmacokinetics, 41:100424.
Lee et al., "A Systematic Study of Unsaturation in Lipid Nanoparticles Leads to Improved mRNA Transfection In Vivo", Angewandte Chemie International Edition, 2020, 60(11): 5848-5853.
Lee et al., "A Systematic Study of Unsaturation in Lipid Nanoparticles Leads to Improved mRNA Transfection In Vivo", Angewandte Chemie International Edition, 2020, 60(11): 5848-5853 Supporting Information.
MedChemExpress, Certificate of Analysis for 5A2-SC8, Catalog. No. HY-145799, Cas No. 1857341-90-2.
Xiong et al., "Theranostic dendrimer-based lipid nanoparticles containing PEGylated BODIPY dyes for tumor imaging and systemic mRNA delivery in vivo", J Control Release, 2020, 325:198-205.
Zhou et al., "Modular degradable dendrimers enable small RNAs to extend survival in an aggressive liver cancer model", PNAS, 2016, 113(3):520-525.

* cited by examiner

SULFUR-CONTAINING IONIZABLE LIPIDS FOR THE DELIVERY OF NUCLEIC ACIDS AND OTHER THERAPEUTIC AGENTS

This application claims priority to U.S. Provisional Patent Application Ser. No. 63/434,506, filed on Dec. 22, 2022, which is hereby expressly incorporated herein by reference in its entirety.

TECHNICAL FIELD

Provided herein are sulfur-containing lipids that may be formulated in a delivery vehicle so as to facilitate the encapsulation of a wide range of therapeutic agents or prodrugs therein, such as, without limitation, nucleic acids (e.g., RNA or DNA), proteins, peptides, pharmaceutical drugs and salts thereof.

BACKGROUND

Nucleic acid-based therapeutics have enormous potential in medicine. To realize this potential, however, the nucleic acid must be delivered to a target site in a patient. This presents challenges since nucleic acid is rapidly degraded by enzymes in the plasma upon administration. Even if the nucleic acid is delivered to a disease site, there still remains the challenge of intracellular delivery. To address these problems, lipid nanoparticles have been developed that protect nucleic acid from such degradation and facilitate delivery across cellular membranes to gain access to the intracellular compartment, where the relevant translation machinery resides.

A key component of a lipid nanoparticle (LNP) is an ionizable lipid. The ionizable lipid is positively charged at low pH, which facilitates association with the negatively charged nucleic acid. However, the ionizable lipid is neutral at physiological pH, making it more biocompatible in biological systems. Further, it has been suggested that after the LNPs are taken up by a cell by endocytosis, the ionizability of these lipids at low pH enables endosomal escape. This in turn enables the nucleic acid to be released into the intracellular compartment.

An earlier example of an LNP product approved for clinical use and reliant on ionizable lipid is Onpattro®. Onpattro® is a lipid nanoparticle-based short interfering RNA (siRNA) drug for the treatment of polyneuropathies induced by hereditary transthyretin amyloidosis. Onpattro® is reliant on an ionizable lipid referred to as "DLin-MC3-DMA" or more commonly "MC3", 1 (Scheme 1), by investigators. Furthermore, MC3 represents an evolution of a structurally related ionizable lipid, referred to by investigators as "KC2", 2 (Scheme 1). MC3 is considered a state-of-the art ionizable lipid for the delivery of siRNA, requiring about 3 times less siRNA than KC2. As a consequence, MC3 is currently regarded as the benchmark against which the potency of new lipids is evaluated. Still, KC2 remains a valuable research tool.

Ionizable lipids are also crucial components of certain COVID-19 vaccines. To illustrate, the Pfizer/BioNTech and Moderna vaccines rely on LNPs to deliver mRNA to the cytoplasm of liver cells. This mRNA encodes for the highly immunogenic Sars-Cov-2 spike protein. Once inside the host cell, the mRNA is transcribed to produce antigenic proteins. The Pfizer/BioNTech vaccine comprises an ionizable lipid referred to as "ALC-0315", 3 (Scheme 1), while the Moderna vaccine comprises an ionizable lipid referred to as "SM-102", 4.

Scheme 1

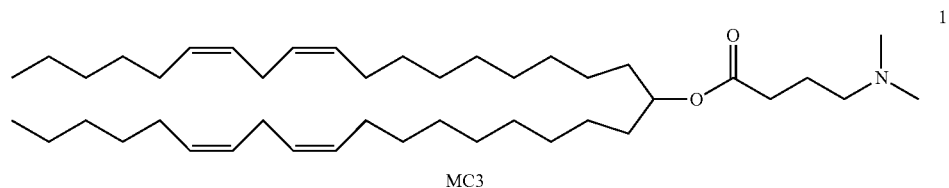

MC3

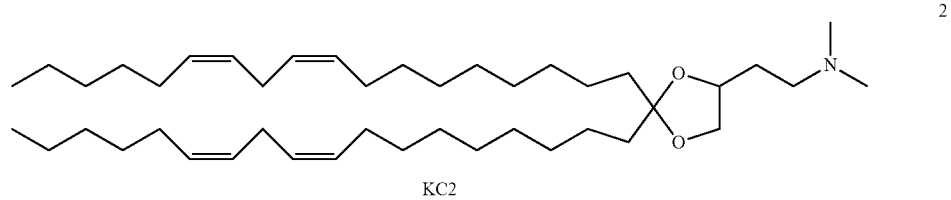

KC2

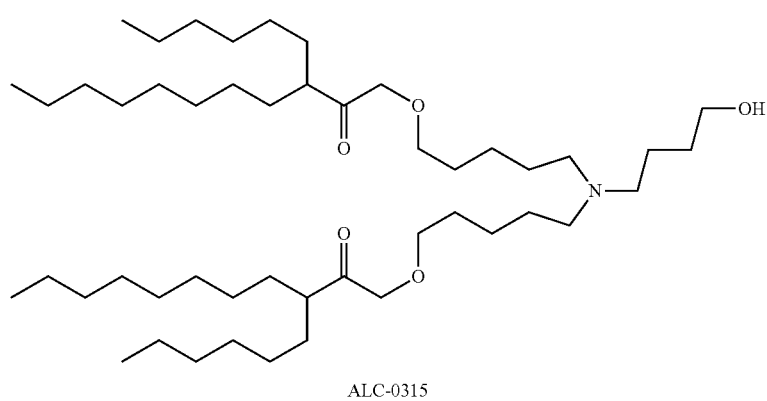

ALC-0315

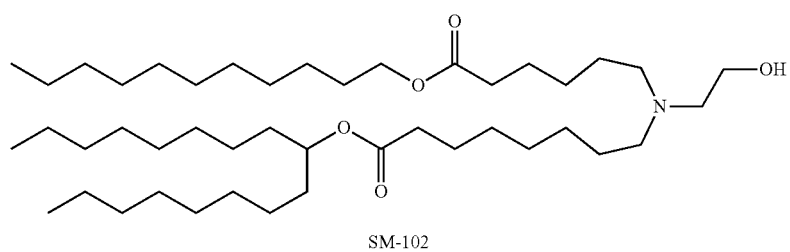

SM-102

All of the above ionizable lipids were optimized for delivery of therapeutic nucleic acids to the liver. However, there remains a need to develop new ionizable lipids for the delivery of charged cargo, such as nucleic acids, to other organs, such as the spleen, lungs, bone marrow, skin, etc. The delivery of therapeutics beyond the liver would expand the clinical utility of LNPs to target a wider range of disease conditions. There is also an ongoing need to develop LNPs with improved delivery of nucleic acid or other charged cargo to the liver.

The present disclosure seeks to address one or more of the above identified problems and/or provides useful alternatives to known products and/or compositions for the delivery of nucleic acid or other charged cargo.

Definitions

As used herein, "type 1 ionizable head" or "MC-type ionizable head" refers to a moiety that has a head group of the lipid of Formula I below, or equivalents thereof, with n ranging from 1 to 5:

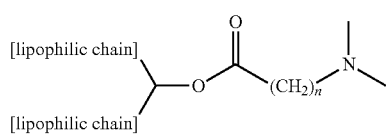

Formula I

As used herein, "type 2 ionizable head" or "KC-type ionizable head" refers to a moiety that has a head group of the lipid of Formula II below, or equivalents thereof, with n ranging from 1 to 5:

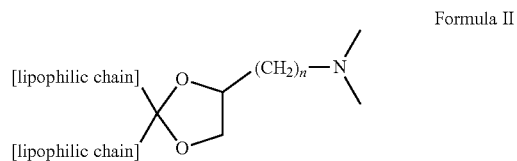

Formula II

As used herein, "type 3 ionizable head" refers to a moiety that is the head group of the structure as defined by Formula III below, or equivalents thereof, with m and n independently ranging from 1 to 5:

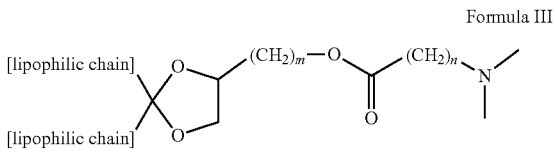

Formula III

As used herein, "type 4 ionizable head" refers to a moiety that is the head group of the structure as defined by Formula IV below, or equivalents thereof, with R=$C_1$-$C_6$ alkyl or cycloalkyl, and with m and n independently ranging from 2 to 5:

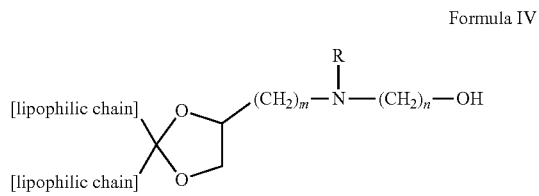

Formula IV

As used herein, "type 5 ionizable head" refers to a moiety that is the head group of the structure as defined by Formula V below, or equivalents thereof, with m and n independently ranging from 1 to 5:

Formula V

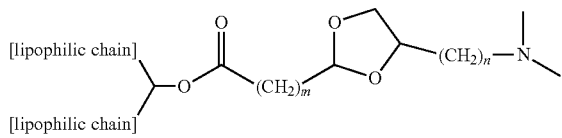

As used herein, "type 6 ionizable head" refers to a moiety that is the head group of the structure as defined by Formula VI below, or equivalents thereof, with R=$C_1$-$C_6$ alkyl, cycloalkyl, deuterated alkyl or deuterated cycloalkyl and with m ranging from 1 to 5, and n, independently, ranging from 2 to 5:

Formula VI

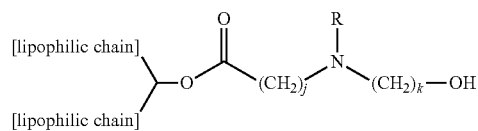

As used herein, "type 7 ionizable head" refers to a moiety that is the head group of the structure as defined by Formula VII below, or equivalents thereof, with R=$C_1$-$C_6$ alkyl, cycloalkyl, deuterated alkyl or deuterated cycloalkyl, and with n ranging from 1 to 5 wherein a methylene of $(CH_2)_n$ is optionally substituted with a sulfur or oxygen atom:

Formula VII

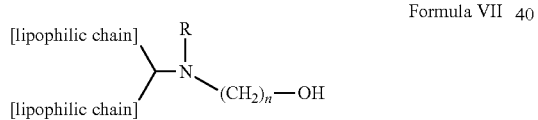

As used herein, "type 8 ionizable head" refers to a moiety that is the head group of the structure as defined by Formula VIII below, or equivalents thereof, with R=$C_1$-$C_6$ alkyl, cycloalkyl, deuterated alkyl or deuterated cycloalkyl, and with n ranging from 1 to 5:

Formula VIII

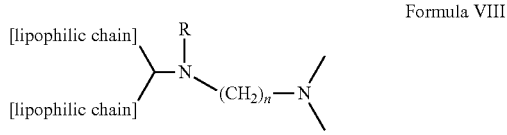

As used herein, "type 9 ionizable head" refers to a moiety that is the head group of the structure as defined by Formula IX below, or equivalents thereof, with m and n independently ranging from 1 to 5:

Formula IX

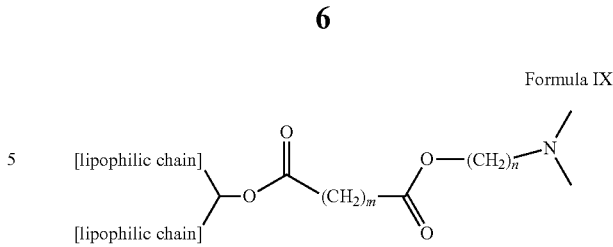

As used herein, "type 10 ionizable head" refers to a moiety that is the head group of the structure as defined by Formula X below, or equivalents thereof, wherein the curved lines represent atoms of a ring structure comprising the N atom, wherein the ring structure has from 2 to 8 C atoms, and wherein j ranges from 0 to 5:

Formula X

As used herein, "type 11 ionizable head" refers to a moiety that is the head group of the structure as defined by Formula XI below, or equivalents thereof, with R=$C_1$-$C_6$ alkyl, cycloalkyl, deuterated alkyl or deuterated cycloalkyl, wherein the circle represents a homocyclic or heterocyclic ring comprising from 3 to 8 atoms, and wherein j ranges from 0 to 5:

Formula XI

As used herein, "type 12 ionizable head" refers to a moiety that is the head group of the structure as defined by Formula XII below, or equivalents thereof, wherein R=$C_1$-$C_6$ alkyl, cycloalkyl, deuterated alkyl or deuterated cycloalkyl and wherein j ranges from 1 to 5:

Formula XII

As used herein, the term "ionizable lipid" refers to a lipid that, at a given pH, is in an electrostatically neutral form and that may either accept or donate protons, thereby becoming electrostatically charged, and for which the electrostatically neutral form has a calculated logarithm of the partition coefficient between water and 1-octanol (i.e., a cLogP) that is greater than 8.

As used herein, the term "ionizable, cationic amino lipid" refers to a lipid that, at physiological pH, is in an electrostatically neutral form and comprises a nitrogen atom in its head group that accepts a proton, thereby becoming electrostatically positively charged at a pH below its pKa.

The terms, "protonatable amino head group", "ionizable head group" or "head group" are used interchangeably herein and refer to a moiety of the ionizable, cationic amino lipid that comprises the nitrogen atom in its head group that accepts a proton, thereby becoming electrostatically positively charged at a pH below its pKa. The protonatable amino head group has a central carbon atom to which each of the two lipophilic chains are directly bonded.

For example, the type 2 ionizable head group has a central carbon atom to which each lipophilic chain is directly bonded as indicated by the * symbol:

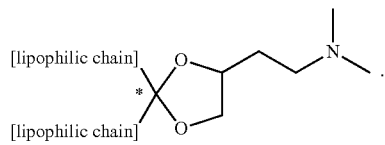

In another example, the central carbon atom of the type 12 ionizable head group is a carbon atom as indicated by the * symbol in the structure below:

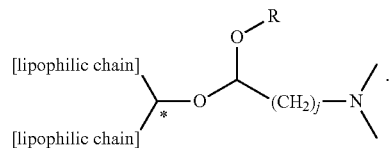

As used herein, the term "lipophilic chain" refers to an optionally substituted alkyl group bonded to the central carbon atom of the head group of the lipid, the alkyl group comprising at least 6 carbon atoms and optionally comprising C=C double bonds, wherein the parent compound of said alkyl group has a CLogP of at least 6.

For example, to illustrate, the known lipids MC3, 1, and KC2, 2, have a pair of lipophilic chains derived from (6Z,9Z)-octadeca-6,9-diene, which has a CLogP of 9.25:

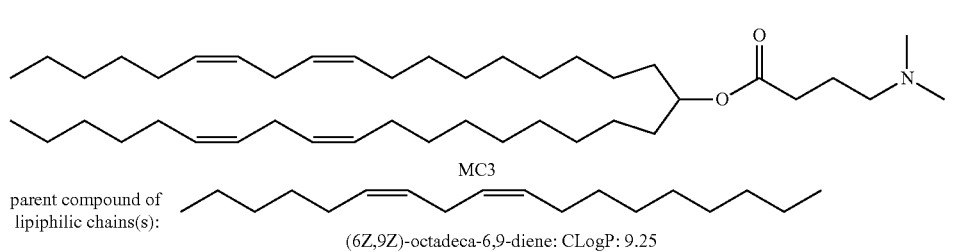

Lipid ALC-0315, 3, has a pair of lipophilic chains derived from hexyl 2-hexyldecanoate, which has a CLogP of 10.01:

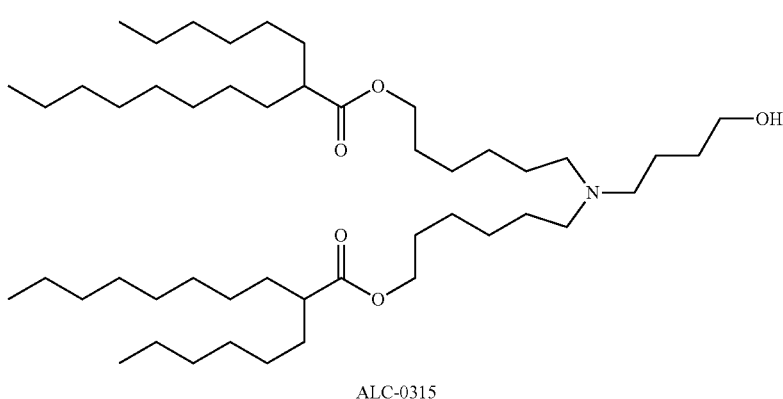

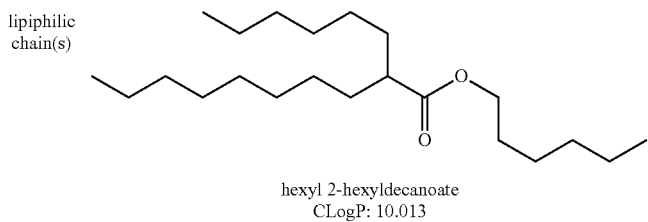

Lipid SM-102, 4, has one lipophilic chain derived from undecyl hexanoate, which has a CLogP of 7.59, and one lipophilic chain derived from heptadecane-9-yl octanoate, which has a CLogP of 11.6:

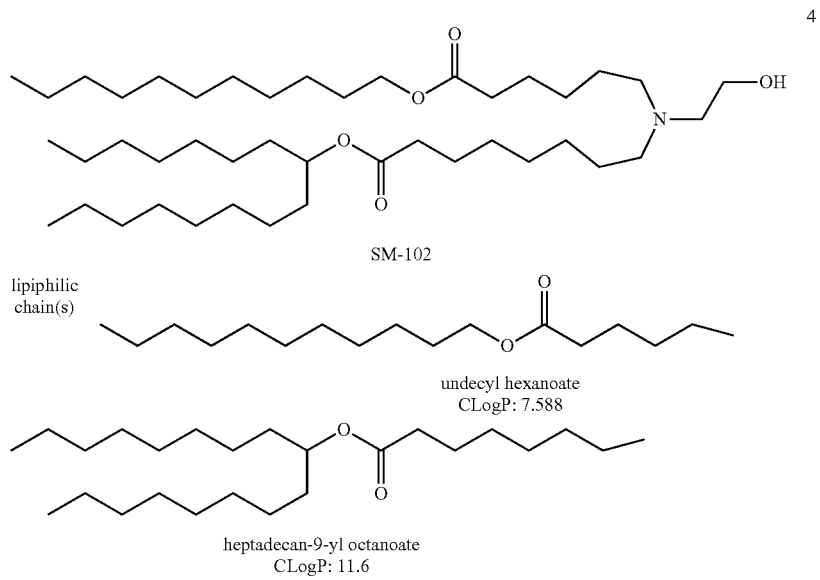

As used herein, the term "alkyl" or "alkyl group" is a $C_1$ to $C_{40}$ carbon-containing chain that is linear, cyclic (monocyclic or polycyclic) and/or branched and that optionally comprises C=C double bonds and/or one or more substituent ring structures, and that is optionally substituted.

As used herein, the term "$C_m$ to $C_n$ alkyl" or "$C_m$ to $C_n$ alkyl group" refers to a linear, cyclic and/or branched carbon chain having a total minimum of m carbon atoms and up to n carbon atoms, and that is optionally unsaturated and optionally substituted. For example, a "$C_1$ to $C_3$ alkyl" or "$C_1$ to $C_3$ alkyl group" is an alkyl having between 1 and 3 carbon atoms.

The term "ring structure" is a 3- to 22-membered monocyclic or polycyclic alkyl ring that is optionally substituted and optionally unsaturated. In some non-limiting examples, the ring structure is a 3- to 16-membered monocyclic or polycyclic alkyl ring that is optionally substituted. In further examples, the ring structure is a 3- to 8-membered monocyclic or polycyclic alkyl ring that is optionally substituted.

The term "monocyclic" is an optionally substituted alkyl group that is a single ring or that comprises a single ring substituent.

The term "polycyclic" is optionally substituted alkyl group that is, or comprises as a substituent(s), two or more ring structures that are chemically bonded to each other or two or more discrete ring structures.

The term "optionally substituted" with reference to an alkyl or alkyl group means that at least one hydrogen atom of the alkyl group can be replaced by a non-hydrogen atom or group of atoms (i.e., a "substituent"), and/or the alkyl is interrupted (i.e., a —(CH$_2$)— group replaced) by a non-carbon atom or one or more substituents, including but not limited to those comprising heteroatoms selected from O, S and NR', wherein R' is as defined below.

Non-limiting examples of atoms or substituents that may replace a hydrogen atom include halogen; deuterium; an alkyl group; a cycloalkyl group (mono or polycyclic); an oxo group (=O); a hydroxyl group (—OH); —(C=O)OR'; —O(C=O)R'; —C(=O)R'; O(C=O)OR'—; —OR'; —S(O)$_x$R'; —SR', —S—SR'; —C(=O)SR'; —SC(=O)R'; —NR'R'; —NR'C(=O)R'; —C(=O)NR'R'; —NR'C(=O) NR'R'; —OC(=O)NR'R'; —NR'C(=O)OR'; —NR'S(O)$_x$ NR'R'; —NR'S(O)$_x$R'; and —S(O)$_x$NR'R', wherein R' at each occurrence is independently selected from H, $C_1$-$C_{15}$ alkyl or cycloalkyl, and x is 0, 1 or 2. Non-limiting examples of atoms or substituents that may replace a carbon atom (interrupt the alkyl) include cycloalkyl groups (mono or polycyclic); —O—; —(C=O)O—; —O(C=O)—; —C(=O); —O(C=O)—; —S(O)$_x$—; —S—; —S—S—; —C(=O)S—; —SC(=O)—; —NR'—; —NR'C(=O)—; —C(=O)NR'—; —NR'C(=O)NR'—; —OC(=O)NR'—; —NR'C(=O)OR'—; —NR'S(O)$_x$NR'—; —NR'S(O)$_x$R'—; and —S(O)$_x$NR'—, wherein R' at each occurrence is independently selected from H, $C_1$-$C_{15}$ alkyl or cycloalkyl, and x is 0, 1 or 2.

As used herein, the term "helper lipid" means a compound selected from: a sterol such as cholesterol or a derivative thereof; a diacylglycerol or a derivative thereof, such as a glycerophospholipid, including phosphatidic acid (phosphatidate) (PA), phosphatidylethanolamine (cephalin) (PE), phosphatidylcholine (PC), phosphatidylserine (PS), and the like; and a sphingolipid, such as a ceramide, a sphingomyelin, a cerebroside, a ganglioside, or reduced analogues thereof, that lack a double bond in the sphingosine unit. An example of a diacylglycerol derivative is a glycerophospholipid-cholesterol conjugate in which one of the acyl chains is substituted with a moiety comprising cholesterol. The term encompasses lipids that are either naturally-occurring or synthetic.

As used herein, the term "delivery vehicle" includes any preparation in which the lipid described herein is capable of being formulated and includes but is not limited to delivery vehicles comprising one or a combination of the foregoing helper lipids.

As used herein, the term "nanoparticle" is any suitable particle in which the ionizable lipid can be formulated and that may comprise one or more of the helper lipids. The ionizable lipid is co-formulated with additional lipid components, such as the one or more helper lipids. The term includes, but is not limited to, particles with one or more bilayers, monolayers that are continuous or discontinuous, including multilamellar vesicles, unilamellar vesicles and particles with a core having an electron-dense region. The term also includes polymer-lipid hybrids, including particles in which the lipid is attached to a polymer.

As used herein, the term "encapsulated," with reference to incorporating a cargo molecule (e.g., nucleic acid such as mRNA) within a delivery vehicle refers to any association of the cargo with any component or compartment of the delivery vehicle such as a nanoparticle.

The term "pharmaceutically acceptable salt" with reference to a form of the lipid of the disclosure in a protonated form (i.e., charged) and/or as part of a pharmaceutical formulation in which an LNP is formulated refers to a salt prepared from pharmaceutically acceptable, non-toxic acids, including inorganic and organic acids.

SUMMARY

The present disclosure is based, at least in part, on the surprising discovery that LNP formulations of nucleic acids comprising ionizable, cationic amino lipids that incorporate at least one lipophilic chain substituted with a sulfur atom and an ester moiety are more potent than a benchmark nor-MC3 for the delivery of nucleic acid. As further described herein, such lipids may exhibit improved delivery to certain organs relative to known lipids. Non-limiting examples described herein demonstrate that such lipids promote the delivery of nucleic acid to the spleen and/or liver more efficiently than other known lipids. In addition, the chemical synthesis of the lipids of certain embodiments herein is more straightforward and/or economical than that of known lipids.

According to an aspect of the disclosure, there is provided an ionizable, cationic amino lipid or a pharmaceutically acceptable salt thereof comprising:
a protonatable amino head group;
two lipophilic chains, wherein the protonatable amino head group has a central carbon atom to which each of the two lipophilic chains are directly bonded;
at least one of the two lipophilic chains has a structure of Formula A.1:

Formula C

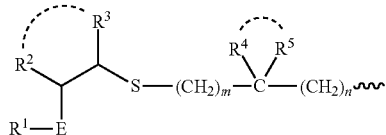

wherein the wavy line represents a bond to the central carbon atom;
wherein m and n are independently 2 to 8;
E is an ester group that is —(C=O)O— or —O(C=O)—;
$R^1$ is a linear, branched, monocyclic or polycyclic, optionally substituted, $C_3$ to $C_{20}$ alkyl group, comprising 0-2 carbon-carbon double bonds;

$R^2$ is a linear or branched, optionally substituted, $C_1$ to $C_{10}$ alkyl group, comprising 0-2 carbon-carbon double bonds, or $R^2$ is bound to $R^3$ to form a ring structure as indicated by the dashed curved line;
$R^3$ is H, or a linear or branched, optionally substituted, $C_1$ to $C_{10}$ alkyl group, comprising 0-2 carbon-carbon double bonds, or $R^3$ is bound to $R^2$ to form a ring structure as indicated by the dashed curved line;
$R^4$ and $R^5$ are, independently, H, or a linear or branched, optionally substituted, $C_1$ to $C_{10}$ alkyl group, comprising 0-2 carbon-carbon double bonds, or $R^4$ and $R^5$ are bound to each other to form a ring structure;
each lipophilic chain has between 15 and 40 carbon atoms in total; and wherein the lipid has (i) a $pK_a$ of between 6 and 7.5; and (ii) a log P of at least 11.

According to an embodiment of the foregoing second aspect of the disclosure a second one of the two lipophilic chains that is bonded to the central carbon atom of the head group has a structure as defined by Formula D:

Formula D

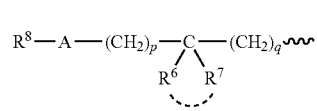

wherein the wavy line represents a bond to the central carbon atom of the head group;
$R^6$ and $R^7$ are, independently, H, or a linear or branched, optionally substituted, $C_1$ to $C_{10}$ alkyl group, comprising 0-2 carbon-carbon double bonds, or $R^6$ and $R^7$ are bonded to each other to form a ring structure,
A is O, S or a carbonyl (C=O), and
if A is O, then $R^8$ is an acyl group

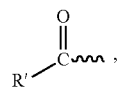

wherein the wavy line represents the bond to the A, and wherein the R' is as defined above for $R^1$;
if A is the carbonyl (C=O), then $R^8$ is an

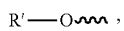

wherein the wavy line represents the bond to the A, and wherein the R' is as defined above for $R^1$;
if A is S, then $R^8$ is a group of Formula E:

Formula E

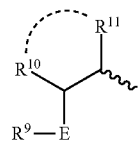

wherein the E' is the ester group that is —(C=O)O— or —O(C=O)—; and
wherein the wavy line represents the bond to A, and wherein $R^9$ is as defined above for $R^1$, $R^{10}$ is as defined above for $R^2$, and $R^{11}$ is as defined above for $R^3$.

In some non-limiting examples, the ring structures formed by the dotted curved lines between $R^2$ and $R^3$, $R^4$ and $R^5$, $R^6$ and $R^7$ and $R^{10}$ and $R^{11}$, are independently a 3- to 8-membered monocyclic or polycyclic alkyl ring that is optionally substituted.

According to one embodiment of the foregoing aspect, the head group has a structure of any one of the above Type 1 to 12 head groups as defined herein.

According to an alternative aspect of the disclosure, there is provided an ionizable, cationic amino lipid having a structure of Formula A:

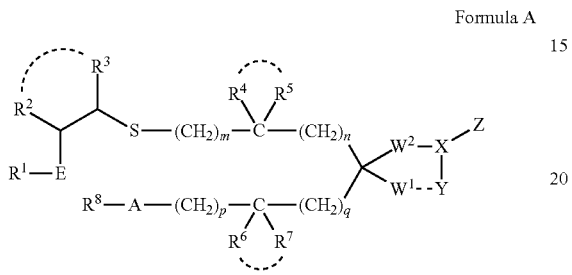

Formula A or a pharmaceutically acceptable salt thereof;
wherein
m, n, p, and q of Formula A are, independently 2 to 8;
$R^1$ is a linear, branched, monocyclic or polycyclic, optionally substituted $C_3$ to $C_{20}$ alkyl group, comprising 0-2 carbon-carbon double bonds;
E is an ester group that is —(C=O)O— or —O(C=O)—;
$R^2$ is a linear or branched, optionally substituted, $C_1$ to $C_{10}$ alkyl group, comprising 0-2 carbon-carbon double bonds, or $R^2$ is bound to $R^3$ to form a ring structure as indicated by the dashed curved line;
$R^3$ is H, or a linear or branched, optionally substituted, $C_1$ to $C_{10}$ alkyl group, comprising 0-2 carbon-carbon double bonds, or $R^3$ is bound to $R^2$ to form a ring structure as indicated by the dashed curved line;
$R^4$ and $R^5$ are, independently, H, or a linear or branched, optionally substituted, $C_1$ to $C_{10}$ alkyl group, comprising 0-2 carbon-carbon double bonds, or $R^4$ and $R^5$ are bound to each other to form a ring structure;
$R^6$ and $R^7$ are, independently, H, or a linear or branched, optionally substituted, $C_1$ to $C_{10}$ alkyl group, comprising 0-2 carbon-carbon double bonds, or $R^6$ and $R^7$ are bound to each other to form a ring structure,
A is O, S or a carbonyl (C=O), and
if A is O, then $R^8$ is an acyl group

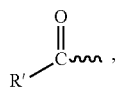

wherein the wavy line represents the bond to the A, and wherein the R' is as defined above for $R^1$;
if A is the carbonyl (C=O), then $R^8$ is an

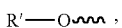

wherein the wavy line represents the bond to the A, and wherein the R' is as defined above for $R^1$;

if A is S, then $R^8$ is a group of structure:

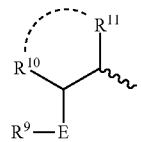

wherein E is an ester group that is —(C=O)O— or —O(C=O)—, wherein the wavy line represents the bond to A, and wherein $R^9$ is as defined for $R^1$, $R^{10}$ is as defined for $R^2$, and $R^{11}$ is as defined for $R^3$;
$W^1$ and Y are either bonded to each other or not bonded to each other, and
if $W^1$ and Y are bonded to each other, then
$W^1$ is O or S;
$W^2$ is O or S;
X is CH;
Y is $(CH_2)_t$, wherein t is 1 or 2;
Z is selected from one of structures a-c below, wherein the wavy line represents the bond to X:

a.

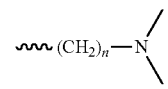

type 2 ionizable head group, wherein n of the type 2 ionizable head group is 1 to 5;

b.

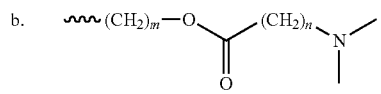

type 3 ionizable head group, wherein m and n of the type 3 ionizable head group are independently 1 to 5; and c.

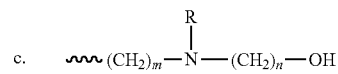

type 4 ionizable head group, wherein m and n of the type 4 ionizable head group are independent 2 to 5;
if $W^1$ and Y are not bonded to each other, then
$W^1$ is H;
$W^2$ is O, S, NH or $NR^{12}$, wherein $R^{12}$ is a $C_1$ to $C_4$ alkyl optionally substituted with an OH group; and
the moiety

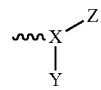

of Formula A is a group selected from any one of structures d to 1 below, wherein the wavy line represents the bond to $W^2$:

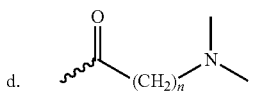

type 1 ionizable head group, wherein n of the type 1 ionizable head group is 1 to 5;

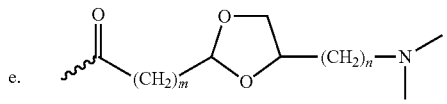

type 5 ionizable head group, wherein m and n of the type 5 ionizable head group are independently 1 to 5;

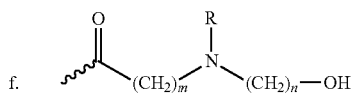

type 6 ionizable head group, wherein m is 1 to 5 and n is independently 2 to 5 and wherein R is $C_1$-$C_6$ alkyl, cycloalkyl, deuterated alkyl or deuterated cycloalkyl;

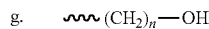

type 7 ionizable head group, wherein n of the type 7 ionizable head group is 1 to 5, wherein a methylene ($CH_2$) of the $(CH_2)_n$ of the type 7 ionizable head group is optionally substituted with a sulfur or an oxygen atom;

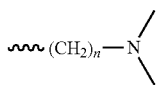

h. type 8 ionizable head group, wherein n of the type 8 ionizable head group is 1 to 5;

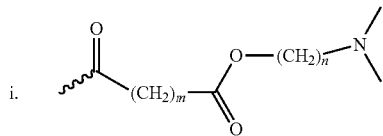

type 9 ionizable head group, wherein m and n of the type 9 ionizable head group are independently 1 to 5;

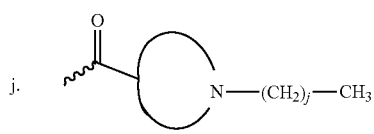

type 10 ionizable head group, wherein the curved lines represent atoms of a ring structure comprising the N atom, wherein the ring structure has 2 to 8 carbon atoms and wherein j of the type 10 ionizable head group is 0 to 5;

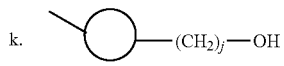

type 11 ionizable head group, wherein the circle represents a homocyclic or heterocyclic ring comprising from 3 to 8 atoms, and wherein j of the type 11 ionizable head group is 0 to 5; and

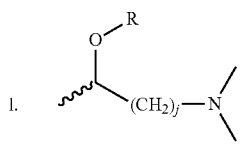

type 12 ionizable head group, wherein R=$C_1$-$C_6$ alkyl, cycloalkyl, deuterated alkyl or deuterated cycloalkyl, and wherein j ranges from 1 to 5.

According to the foregoing aspect or any embodiment thereof, the ionizable, cationic amino lipid of Formula A has (i) a p$K_a$ of between 6 and 7.5; and/or (ii) a log P of at least 11.

According to the foregoing aspect, the ionizable, cationic amino lipid may have a structure of any one of compounds 5-35 as defined below in Table 1, or a pharmaceutically acceptable salt thereof. In another embodiment, the ionizable, cationic amino lipid or the pharmaceutically acceptable salt has the structure of compound 5-13, 16-19, 22-31 or 33-35.

According to a further example of any one of the foregoing aspects or embodiments thereof, the ionizable, cationic amino lipid or pharmaceutically acceptable salt, when formulated in a lipid nanoparticle comprising an mRNA, results in an increase in biodistribution of the lipid nanoparticle of at least about 10-fold in the spleen relative to an otherwise identical lipid nanoparticle containing norDLin-MC3-DMA (nor-MC3) as measured by luminescence of the mRNA in vivo in the spleen.

According to further example of any one of the foregoing aspects or embodiments thereof, the ionizable, cationic amino lipid or pharmaceutically acceptable salt, when formulated in a lipid nanoparticle comprising an mRNA, results in an increase in biodistribution of the lipid nanoparticle of at least about 2-fold in the liver relative to a lipid nanoparticle containing norDLin-MC3-DMA (nor-MC3) as measured by luminescence of the mRNA in vivo in the liver.

According to a further aspect of the disclosure, there is provided a lipid nanoparticle comprising the ionizable, cationic amino lipid as described in any of the foregoing aspects or embodiments thereof and a nucleic acid.

In one embodiment, the lipid nanoparticle comprises a helper lipid. In one example, the helper lipid is selected from cholesterol, a diacylglycerol, a glycerophospholipid-cholesterol conjugate, a sphingolipid and mixtures thereof.

According to another aspect of the disclosure, there is provided a method for treating a subject in need of a nucleic acid therapy, the method comprising preparing or providing the lipid nanoparticle in any one of the foregoing aspects or embodiments thereof comprising the nucleic acid and administering the lipid nanoparticle to the subject.

According to another aspect of the disclosure, there is provided a method for delivering a nucleic acid molecule to a cell, the method comprising contacting the lipid nanoparticle described with the cell in vivo or in vitro.

According to another aspect of the disclosure, there is provided a use of the ionizable, cationic amino lipid or the pharmaceutically acceptable salt thereof or the lipid nanoparticle of any of the foregoing aspects or embodiments in the manufacture of a medicament to treat or prevent a disease, disorder or condition that is treatable and/or preventable by a nucleic acid.

According to another aspect of the disclosure, there is provided a use of the ionizable, cationic amino lipid or the pharmaceutically acceptable salt thereof, or the lipid nanoparticle of any one of any one of the foregoing aspects or embodiments to deliver a nucleic acid to a subject to treat or prevent a disease, disorder or condition that is treatable or preventable by the nucleic acid.

In one embodiment, the nucleic acid is an mRNA.

Other objects, features, and advantages of the present disclosure will be apparent to those of skill in the art from the following detailed description and figures.

DETAILED DESCRIPTION

Figure 1:
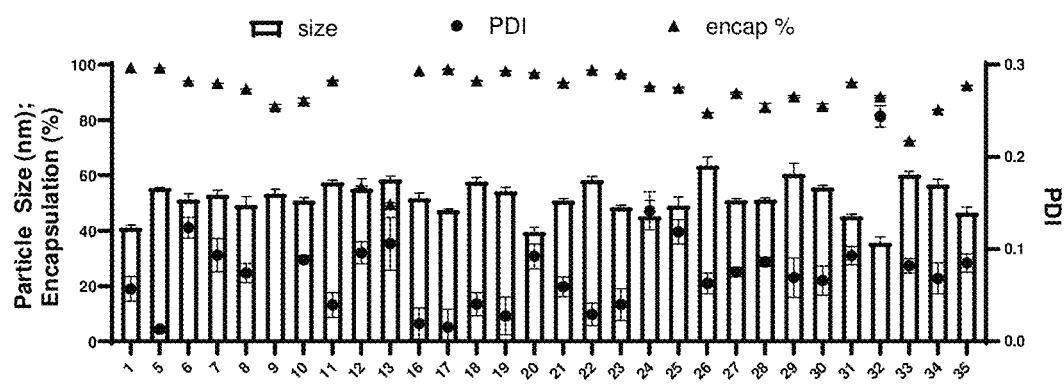
FIG. 1 is a bar graph showing encapsulation (%), particle size (nm) and polydispersity index (PDI) of mRNA-containing lipid nanoparticles (LNPs) comprising the ionizable lipids 1, 5-13 and 16-35 as set forth in Table 1 and Example 2. The LNPs are composed of 50/10/38.5/1.5 mol % of ionizable lipid/DSPC/chol/PEG$_{2000}$-DMG and the amine-to-phosphate charge ratio (N/P) was 6.

Various aspects and embodiments of the disclosure are directed to ionizable, cationic amino lipids having structures of Formula A and pharmaceutically acceptable salts thereof. Formulations comprising such lipids find use in the delivery of nucleic acid to any target site of interest. In some embodiments, such lipids have been found to be particularly efficacious for the delivery of mRNA when formulated in a suitable delivery vehicle. In further embodiments, such lipids can be easily synthesized and prepared by processes having improved economics relative to known methods for making ionizable lipids.

Embodiments disclosed herein relate to an ionizable, cationic amino lipid having a structure of Formula A:

Formula A

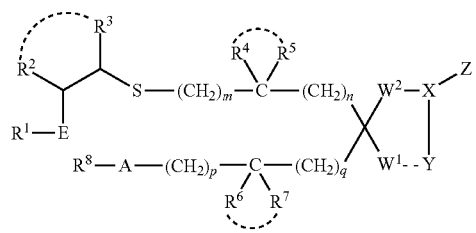

or a pharmaceutically acceptable salt thereof;
wherein
m, n, p, and q of Formula A are, independently 2 to 8;
$R^1$ is a linear, branched, monocyclic or polycyclic, optionally substituted $C_3$ to $C_{20}$ alkyl group, comprising 0-2 carbon-carbon double bonds;
E is an ester group that is —(C=O)O— or —O(C=O)—;
$R^2$ is a linear or branched, optionally substituted, $C_1$ to $C_{10}$ alkyl group, comprising 0-2 carbon-carbon double bonds, or $R^2$ is bound to $R^3$ to form a ring structure as indicated by the dashed curved line;
$R^3$ is H, or a linear or branched, optionally substituted, $C_1$ to $C_{10}$ alkyl group, comprising 0-2 carbon-carbon double bonds, or $R^3$ is bound to $R^2$ to form a ring structure as indicated by the dashed curved line;
$R^4$ and $R^5$ are, independently, H, or a linear or branched, optionally substituted, $C_1$ to $C_{10}$ alkyl group, comprising 0-2 carbon-carbon double bonds, or $R^4$ and $R^5$ are bound to each other to form a ring structure;
$R^6$ and $R^7$ are, independently, H, or a linear or branched, optionally substituted, $C_1$ to $C_{10}$ alkyl group, comprising 0-2 carbon-carbon double bonds, or $R^6$ and $R^7$ are bound to each other to form a ring structure,
A is O, S or a carbonyl (C=O), and
if A is O, then $R^8$ is an acyl group

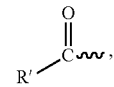

wherein the wavy line represents the bond to the A, and wherein the R' is as defined above for $R^1$;
if A is the carbonyl (C=O), then $R^8$ is an

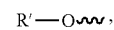

wherein the wavy line represents the bond to the A, and wherein the R' is as defined above for $R^1$;
if A is S, then $R^8$ is a group of structure:

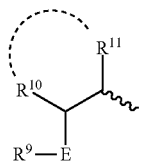

wherein E is an ester group that is —(C=O)O— or —O(C=O)—, wherein the wavy line represents the bond to A, and wherein $R^9$ is as defined for $R^1$, $R^{10}$ is as defined for $R^2$, and $R^{11}$ is as defined for $R^3$;
$W^1$ and Y are either bonded to each other or not bonded to each other, and
if $W^1$ and Y are bonded to each other, then
$W^1$ is O or S;
$W^2$ is O or S;
X is CH;
Y is (CH$_2$)$_t$, wherein t is 1 or 2;
Z is selected from one of structures a-c below, wherein the wavy line represents the bond to X:

a. 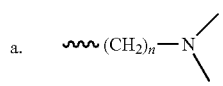

type 2 ionizable head group, wherein n of the type 2 ionizable head group is 1 to 5;

b. 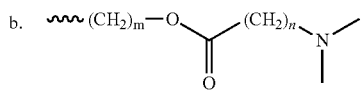

type 3 ionizable head group, wherein m and n of the type 3 ionizable head group are independently 1 to 5; and c. 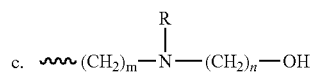

type 4 ionizable head group, wherein m and n of the type 4 ionizable head group are independent 2 to 5;

if $W^1$ and Y are not bonded to each other, then
$W^1$ is H;
$W^2$ is O, S, NH or $NR^{12}$, wherein $R^{12}$ is a $C_1$ to $C_4$ alkyl optionally substituted with an OH group; and
the moiety

of Formula A is a group selected from any one of structures d to below, wherein the wavy line represents the bond to $W^2$:

d. 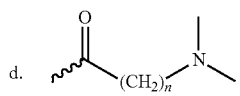

type 1 ionizable head group, wherein n of the type 1 ionizable head group is 1 to 5;

e. 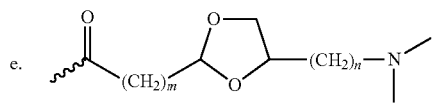

type 5 ionizable head group, wherein m and n of the type 5 ionizable head group are independently 1 to 5;

f. 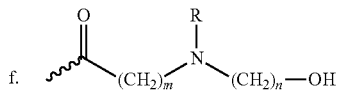

type 6 ionizable head group, wherein m is 1 to 5 and n is independently 2 to 5 and wherein R is $C_1$-$C_6$ alkyl, cycloalkyl, deuterated alkyl or deuterated cycloalkyl;

g. 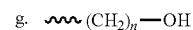

type 7 ionizable head group, wherein n of the type 7 ionizable head group is 1 to 5, wherein a methylene ($CH_2$) of the $(CH_2)_n$ of the type 7 ionizable head group is optionally substituted with a sulfur or an oxygen atom;

h. 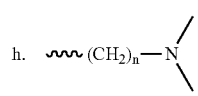

type 8 ionizable head group, wherein n of the type 8 ionizable head group is 1 to 5;

i. 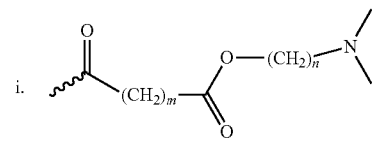

type 9 ionizable head group, wherein m and n of the type 9 ionizable head group are independently 1 to 5;

j. 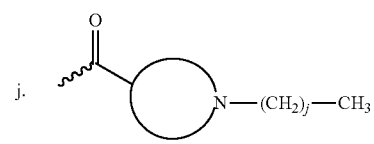

type 10 ionizable head group, wherein the curved lines represent atoms of a ring structure comprising the N atom, wherein the ring structure has 2 to 8 carbon atoms and wherein j of the type 10 ionizable head group is 0 to 5;

k. 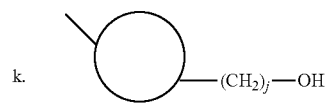

type 11 ionizable head group, wherein the circle represents a homocyclic or heterocyclic ring comprising from 3 to 8 atoms, and wherein j of the type 11 ionizable head group is 0 to 5; and l. 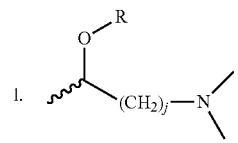

type 12 ionizable head group, wherein R=$C_1$-$C_6$ alkyl, cycloalkyl, deuterated alkyl or deuterated cycloalkyl, and wherein j ranges from 1 to 5.

Methods to Produce Lipids of Formula a

Lipids of Formula A or pharmaceutically acceptable salts thereof can be prepared using any suitable method known to those of skill in the art. Particularly suitable methods are described below. Those skilled in the art will appreciate that alternative starting materials could be employed in the same sequences, leading to congeners of the compound contemplated herein. Therefore, the synthetic schemes set forth below are merely illustrative of select embodiments.

Lipids of Formula A or pharmaceutically acceptable salts thereof, wherein ester group E is oriented so that $R^1$ is bound to the carbon atom of the ester carbonyl, can be represented with the general structure of Formula B:

Formula B

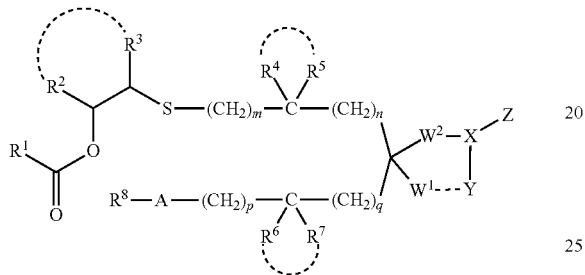

Without intending to be limiting, the synthesis of lipids of Formula B is exemplified with the synthesis of compound 5-35 of Table 1. Those skilled in the art will appreciate that alternative starting materials could be employed in the same sequences, leading to congeners of compound 5-35 as defined by Formula B. Therefore, the synthetic schemes set forth below are merely illustrative of select embodiments.

TABLE 1

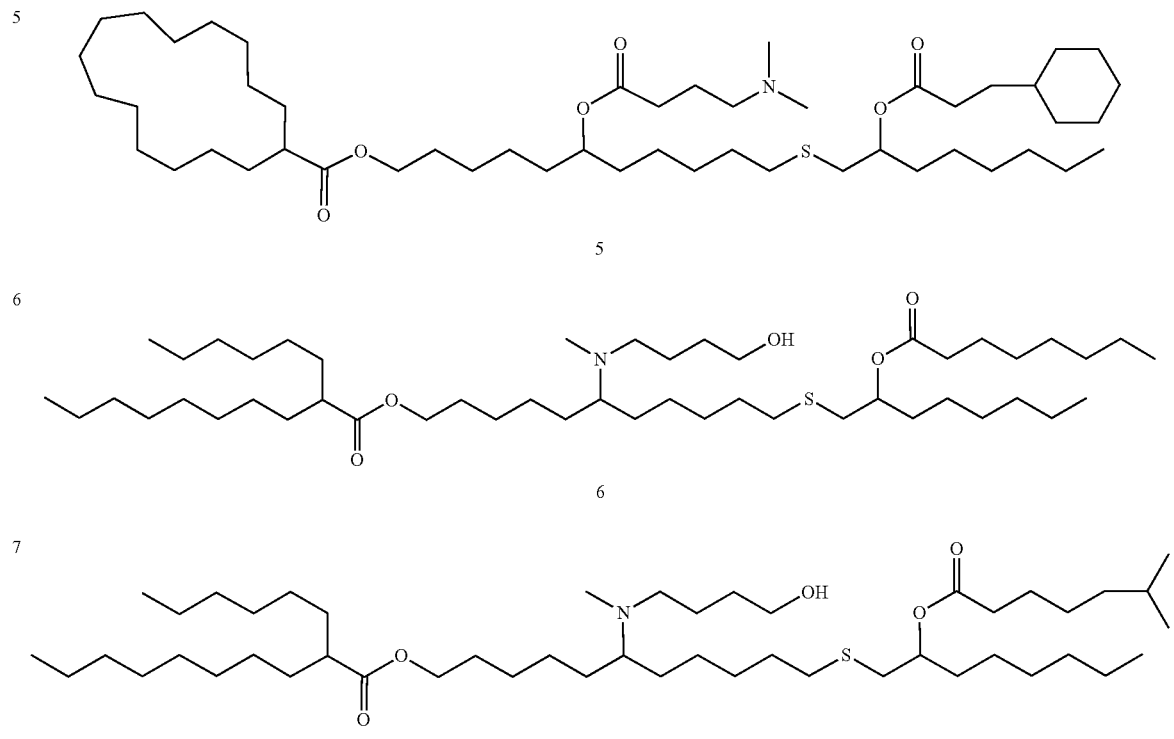

TABLE 1-continued
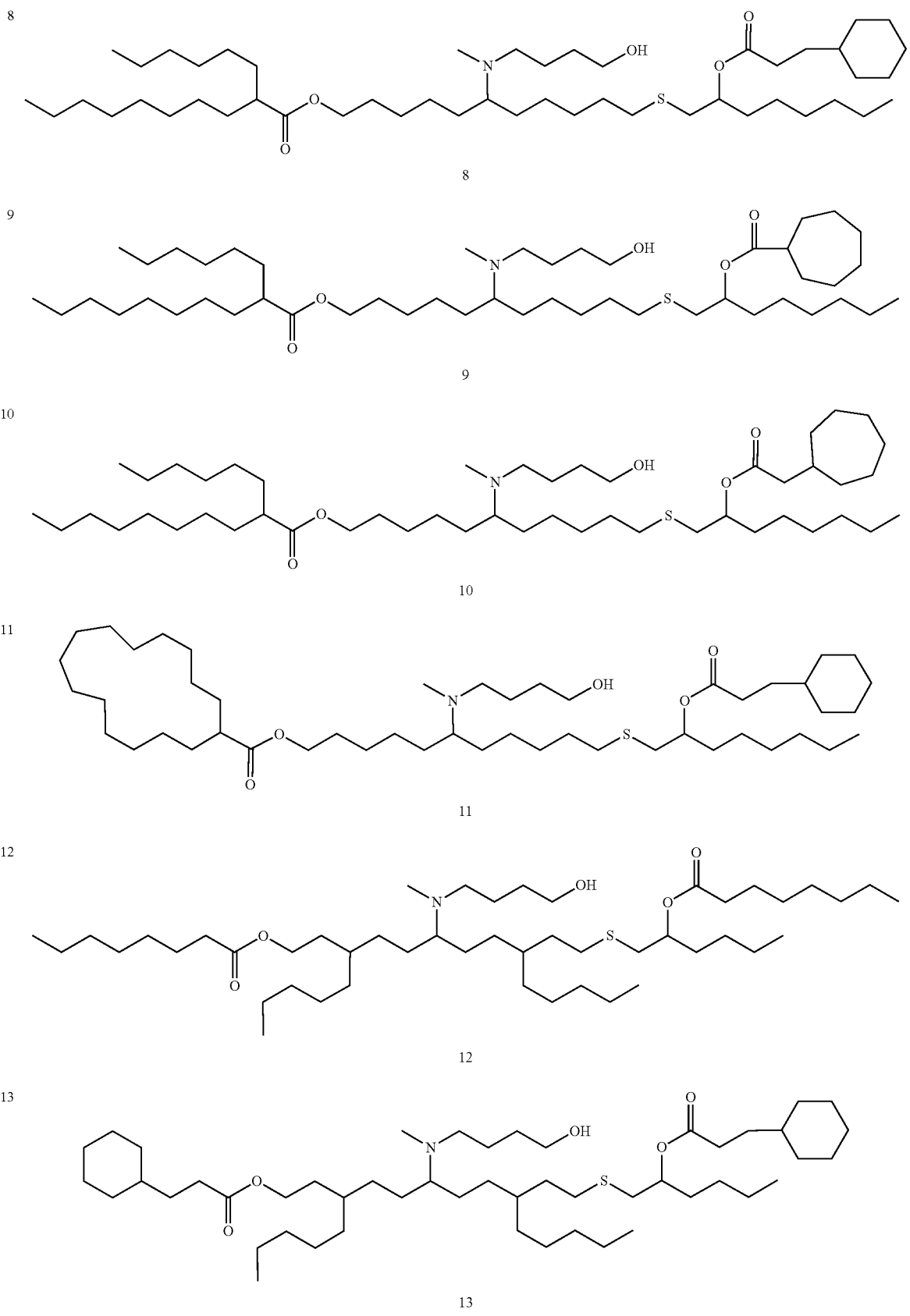

TABLE 1-continued
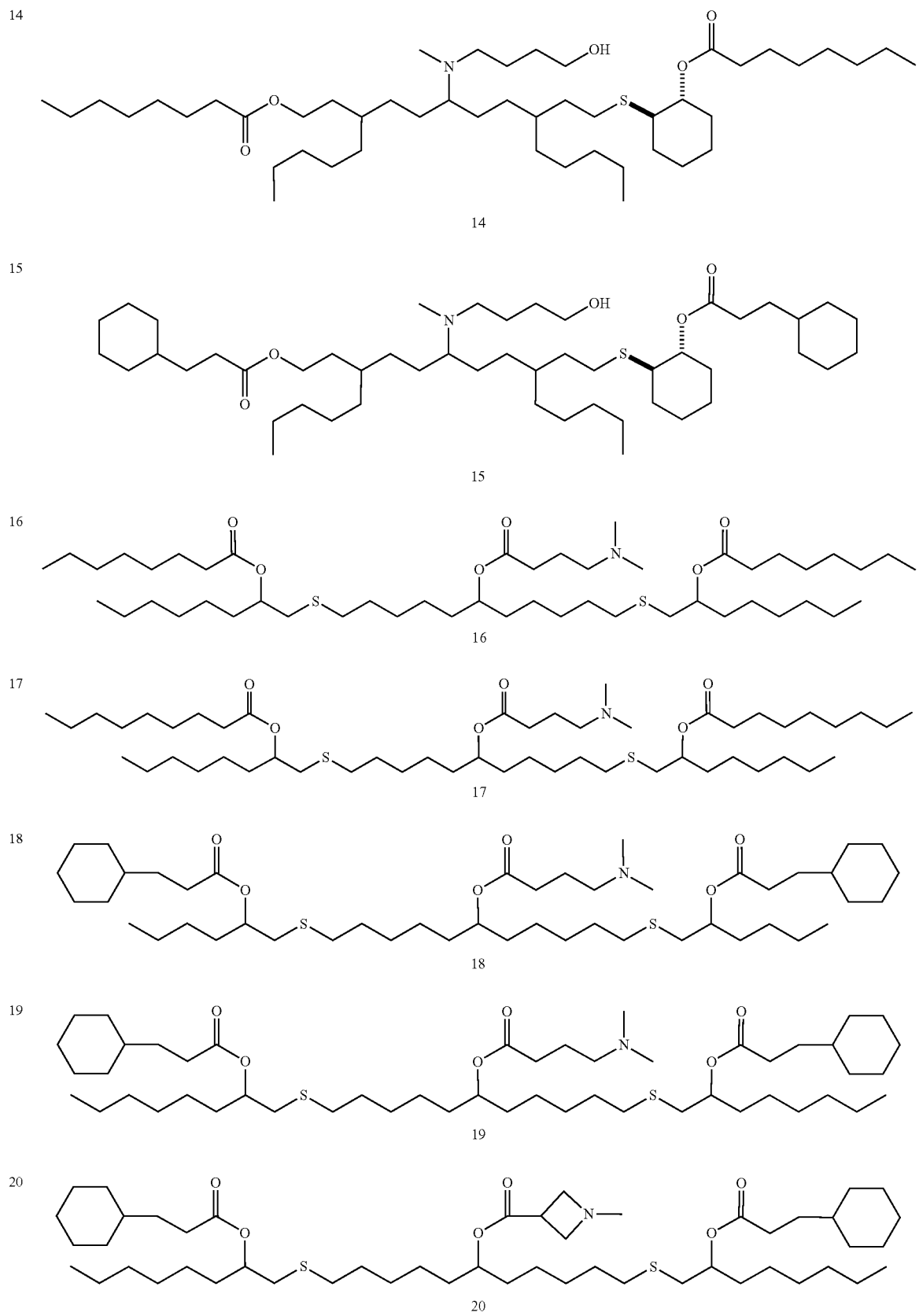

TABLE 1-continued
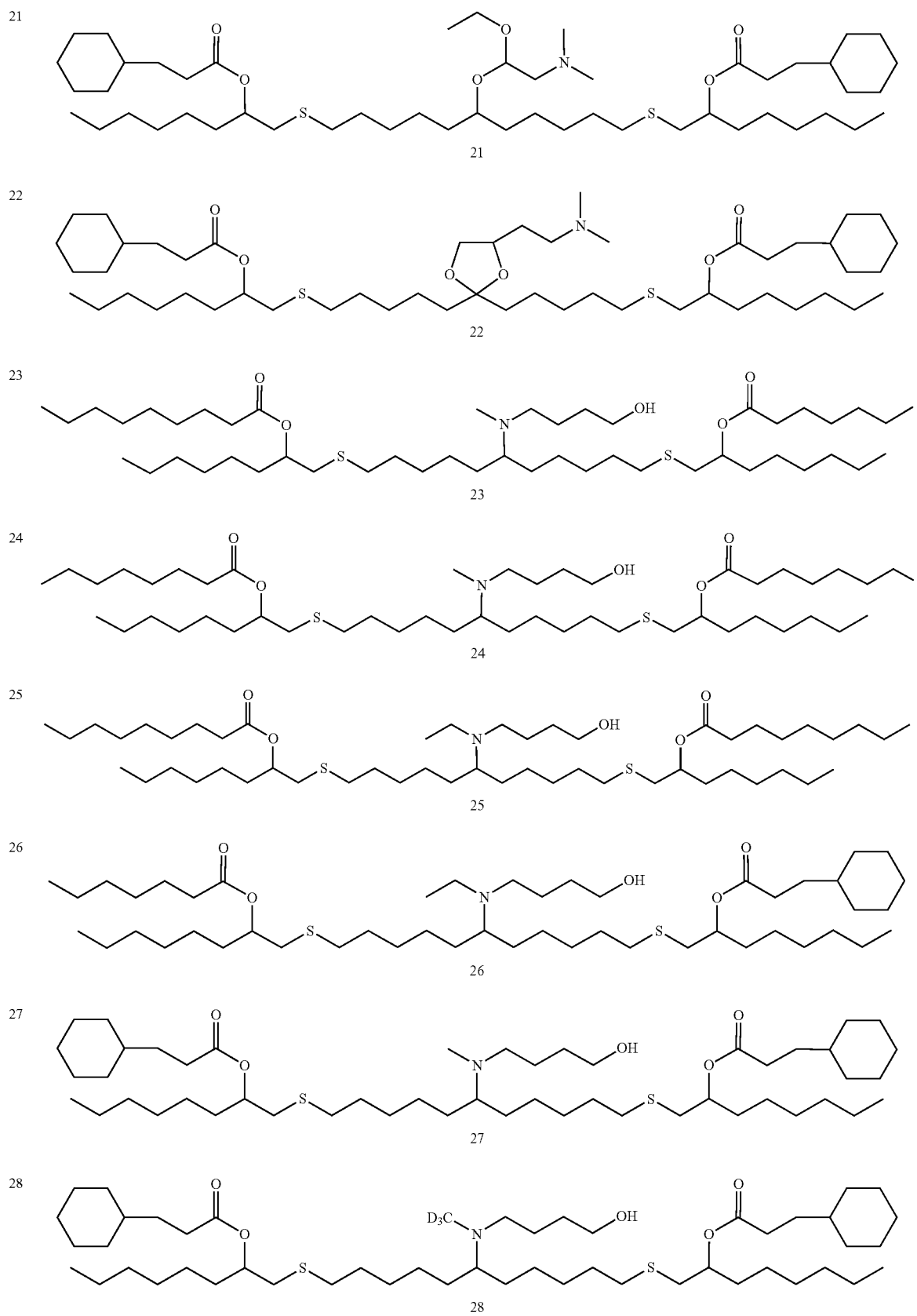

TABLE 1-continued

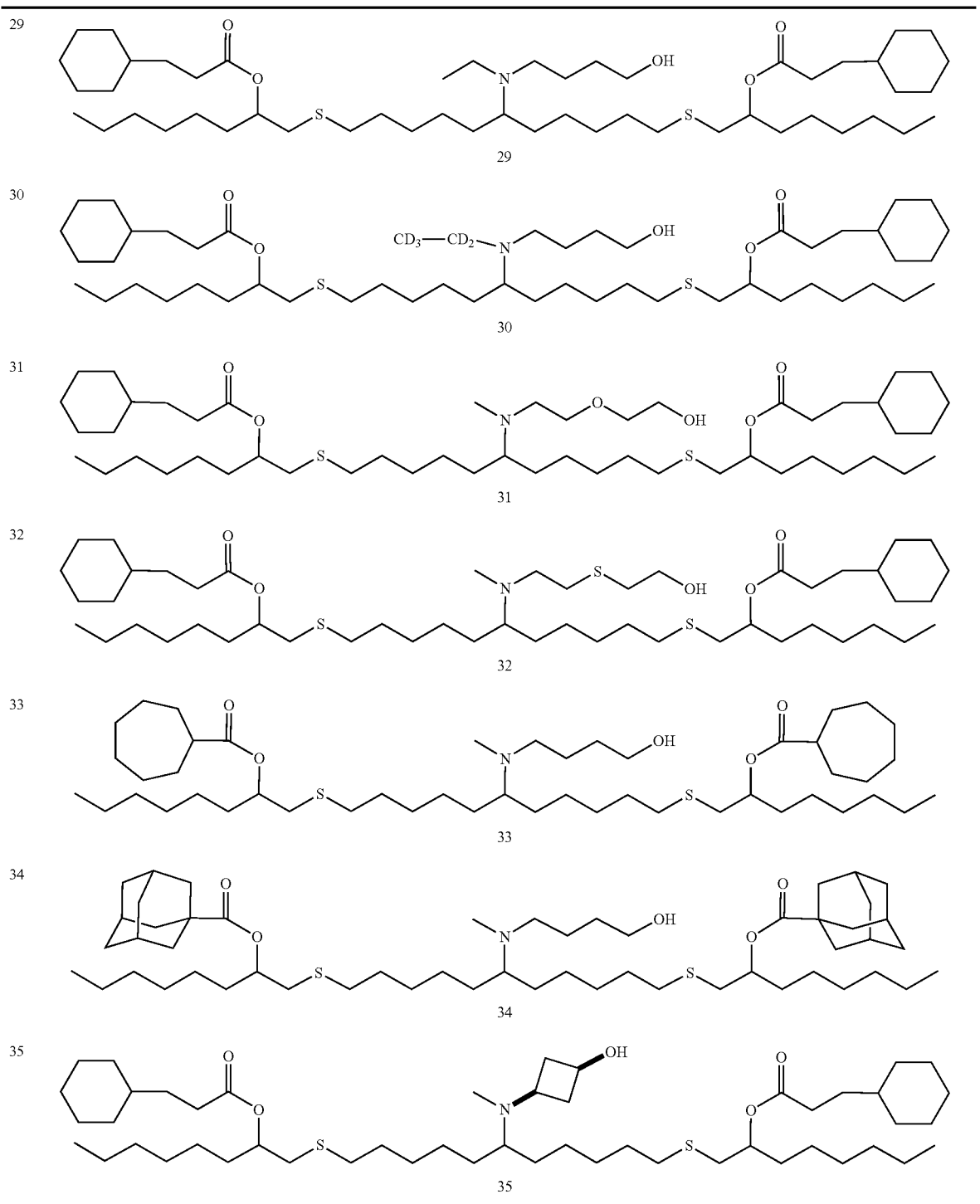

A lipid of Formula B can be prepared from an appropriate ketone of general structure 36 (Scheme 2), wherein, as indicated above, A can be either O or S or a carbonyl (C=O), by converting the keto group into an ionizable head group of type 1-12. If A is O, then compound 36 can be depicted more accurately as 37. If A is S, then compound 36 can be depicted more accurately as 38. If A is carbonyl, (C=), then compound 36 can be depicted more accurately as 39. Therefore, the synthesis of a lipid of Formula B wherein A=O starts with the preparation of a ketone of general structure 37, followed by conversion of the keto group into an ionizable head group; the synthesis of a lipid of Formula B wherein A=S starts with the preparation of a ketone of general structure 38, followed by conversion of the keto group into an ionizable head group, and the synthesis of a lipid of Formula B wherein A=carbonyl starts with the preparation of a ketone of general structure 39, followed by conversion of the keto group into an ionizable head group.

Scheme 2

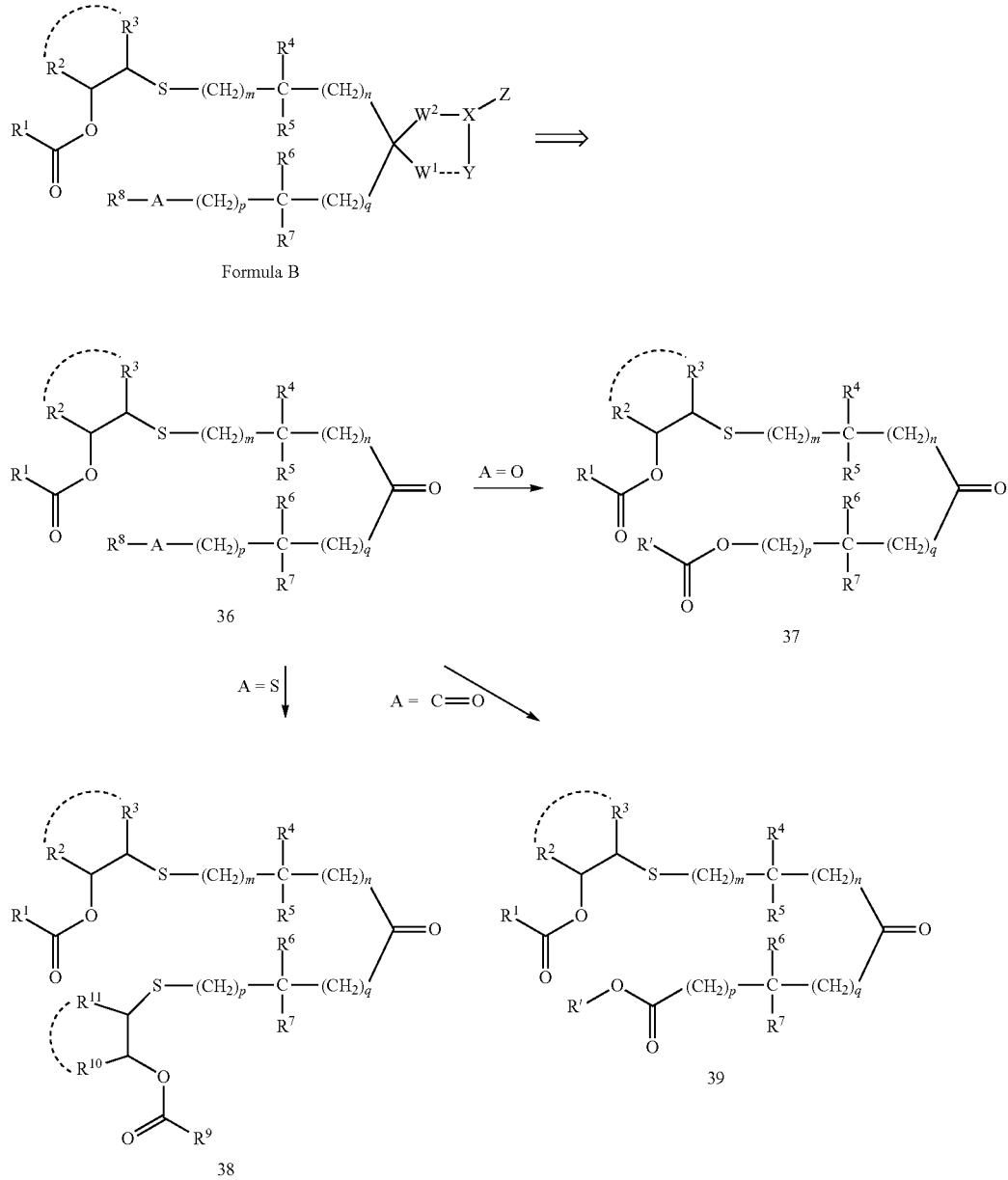

Certain steps of the synthesis of a ketone of general structure 37 wherein m=p, n=q, $R^4$=$R^6$, and $R^5$=$R^7$, that is, a ketone of general structure 46 of Scheme 3, are described in detail in co-pending and co-owned WO 2023/147657, which is incorporated herein by reference. As described in the aforementioned disclosure, one such step entails subjecting an appropriate lactone, 40, to Claisen condensation under Mukaiyama conditions, resulting in the formation of compound 41. The OH group in 41 can then be converted into a leaving group, for example, a sulfonate ester such as a tosylate, to give 42. The tosylate in 42 is displaced with a sulfur nucleophile that can function as a precursor of an SH group, for example, thioacetic acid. The resulting 43 is subsequently treated with a suitable base, for example, NaOH, in the presence of an appropriate epoxide, whereupon the acetyl group is released from 43, the lactone moiety undergoes opening, and the resulting beta-ketoacid undergoes decarboxylation. Furthermore, the anion of the mercaptan formed upon release of the acetyl group reacts with the epoxide to produce compound 44. The primary OH group in 44 can be selectively esterified with a carboxylic acid R'—COOH in the presence of a condensing agent, or with a chloroformate R'—OCOCl or equivalent reagent, to produce compound 45. Further esterification of the secondary OH group in 45 with a carboxylic acid $R^1$—COOH in the presence of a condensing agent, or with a chloroformate R'—OCOCl or equivalent reagent, transforms 45 into ketone 46.

Scheme 3
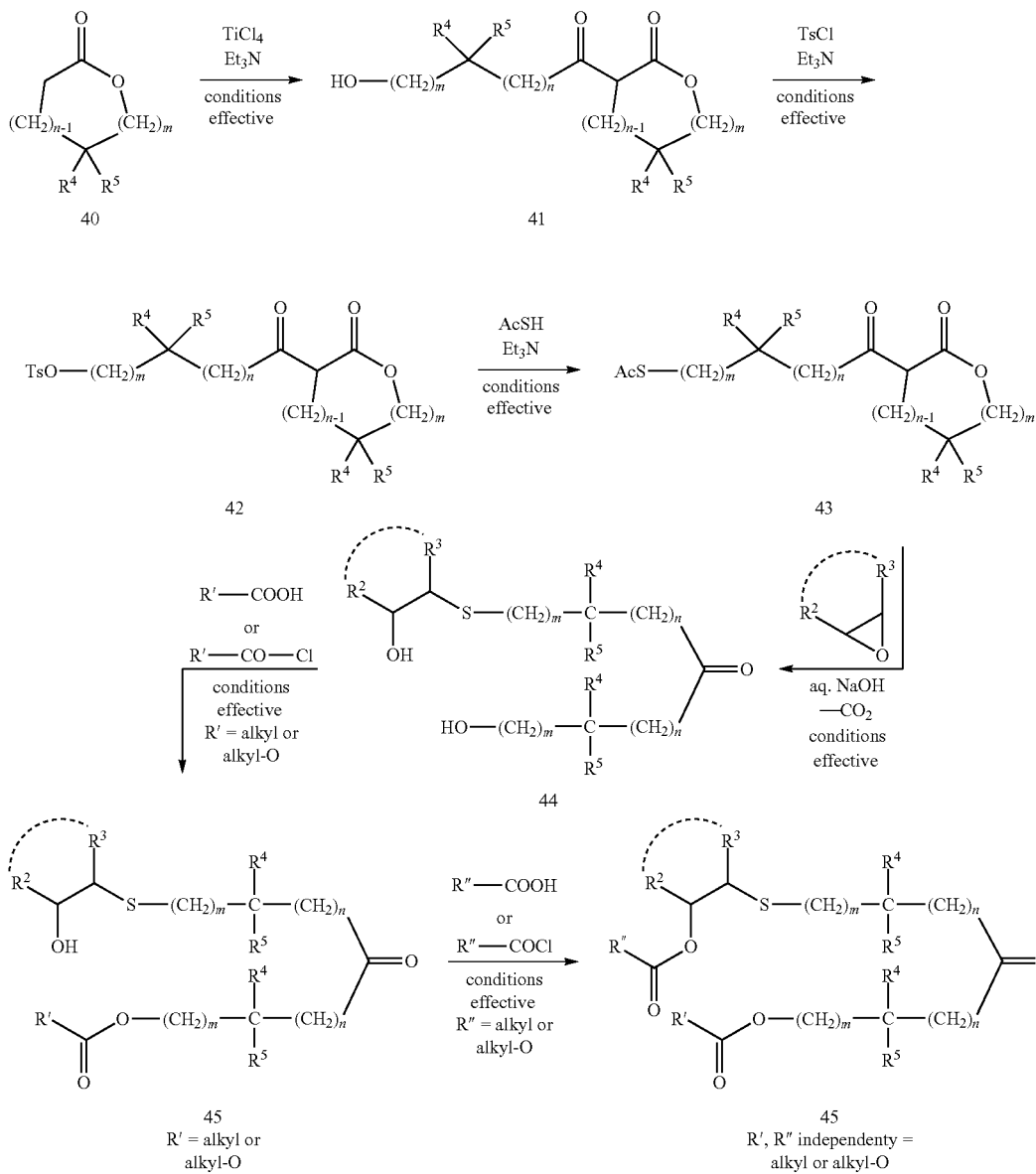
As described in the aforementioned application, a lactone such as 40 can be optionally converted directly into a ketodiol of general formula 48 (Scheme 4) under conditions that avoid the isolation of Claisen product 41.
Scheme 4
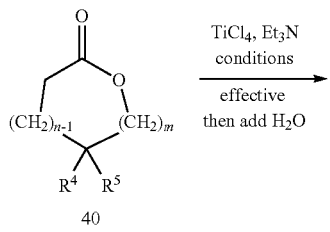

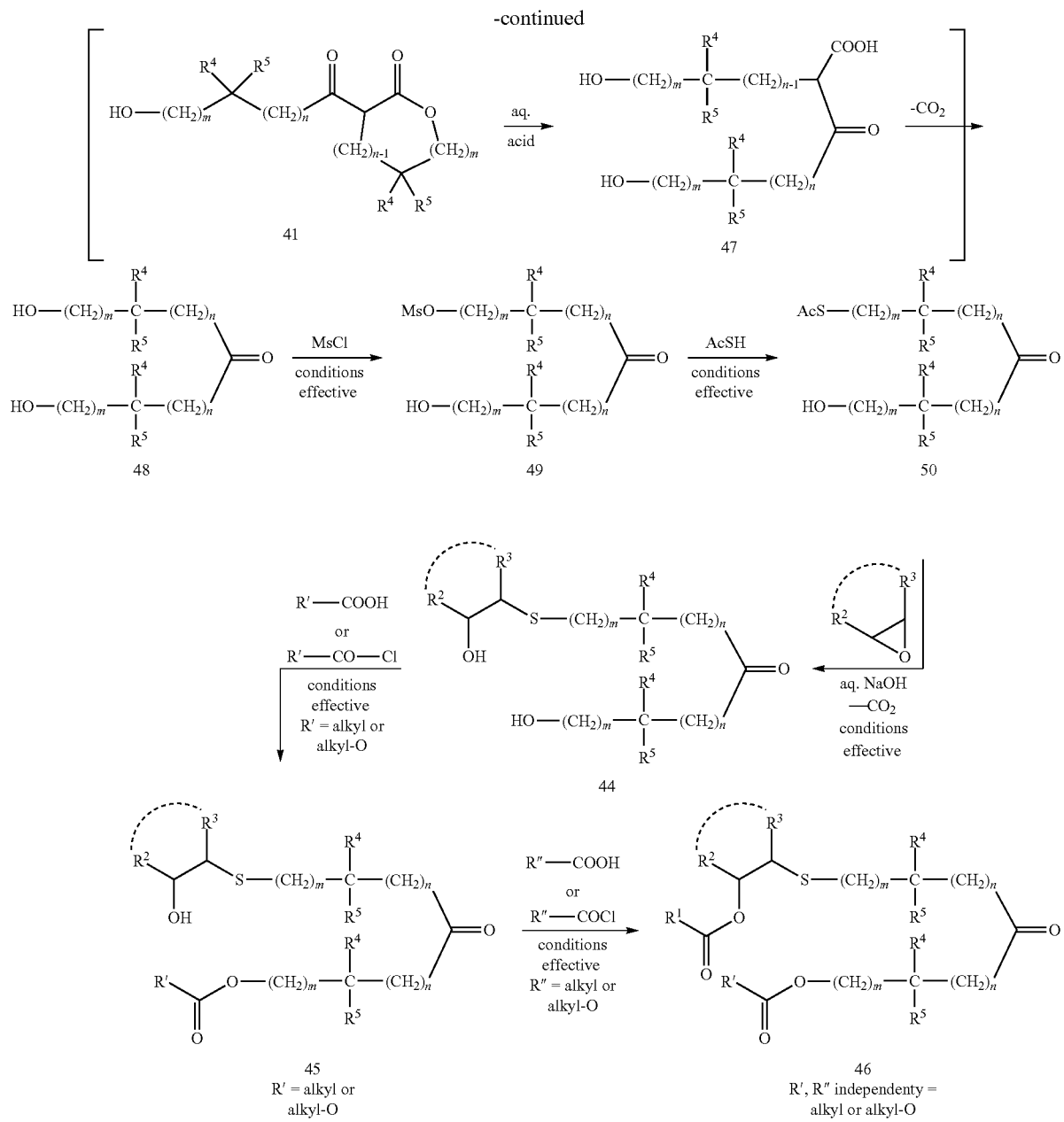

Thus, adding water to the reaction mixture in which 41 has formed results in liberation of acidity due to hydrolysis of $TiCl_4$. If the resulting mixture is stirred for a sufficiently long time, the strongly acidic aqueous medium promotes opening of the lactone to ketoacid 47, which undergoes decarboxylation to 48. The foregoing application teaches that a ketodiol such as 48 can be converted into a mono-sulfonate ester, for example, mono-mesylate 49, which upon reaction with a sulfur nucleophile that can function as a precursor of an SH group, for example, thioacetic acid, in the presence of an appropriate base, is converted into thioester 50. In accord with Scheme 3, when 50 is treated with a suitable base, for example, NaOH, in the presence of an appropriate epoxide, the acetyl group is released and the anion of the mercaptan thus formed reacts with the epoxide to produce compound 44. The latter can then be transformed into ketone 46 by the method shown earlier in Scheme 3.

There may be cases in which the lactone required for the preparation of a ketodiol of the type 48 is expensive and/or is not readily available. In such cases, it is advantageous to carry out the synthesis of the desired 48 starting with certain steps described in co-pending and co-owned WO 2023/147657, which is incorporated herein by reference. Thus, subjecting an appropriately O-protected derivative of a hydroxyester of general structure 51 to Claisen condensation under Mukaiyama conditions, followed by hydrolysis of the resulting beta-ketoester, release of the O-protecting groups, and decarboxylation, results in formation of ketodiol 48 (Scheme 5). In certain embodiments, these steps of hydrolysis of the beta-ketoester, release of the O-protecting groups, and decarboxylation, are most advantageously carried out in a "one-pot operation", meaning that synthetic intermediates 52 and 53, while isolable, need not be isolated.

Scheme 5
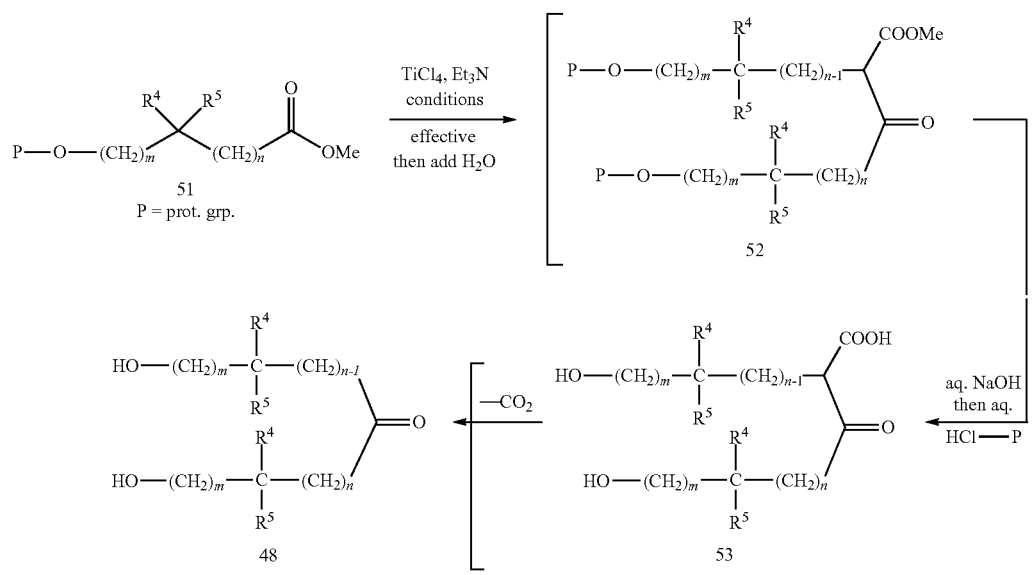
Without intending to be limiting, the process of Scheme 3 above is exemplified below with the synthesis of certain ketones that are the precursors of lipids 5-35. Lipids 5-11 can be made from ketones 54-59 of Scheme 6.
Scheme 6
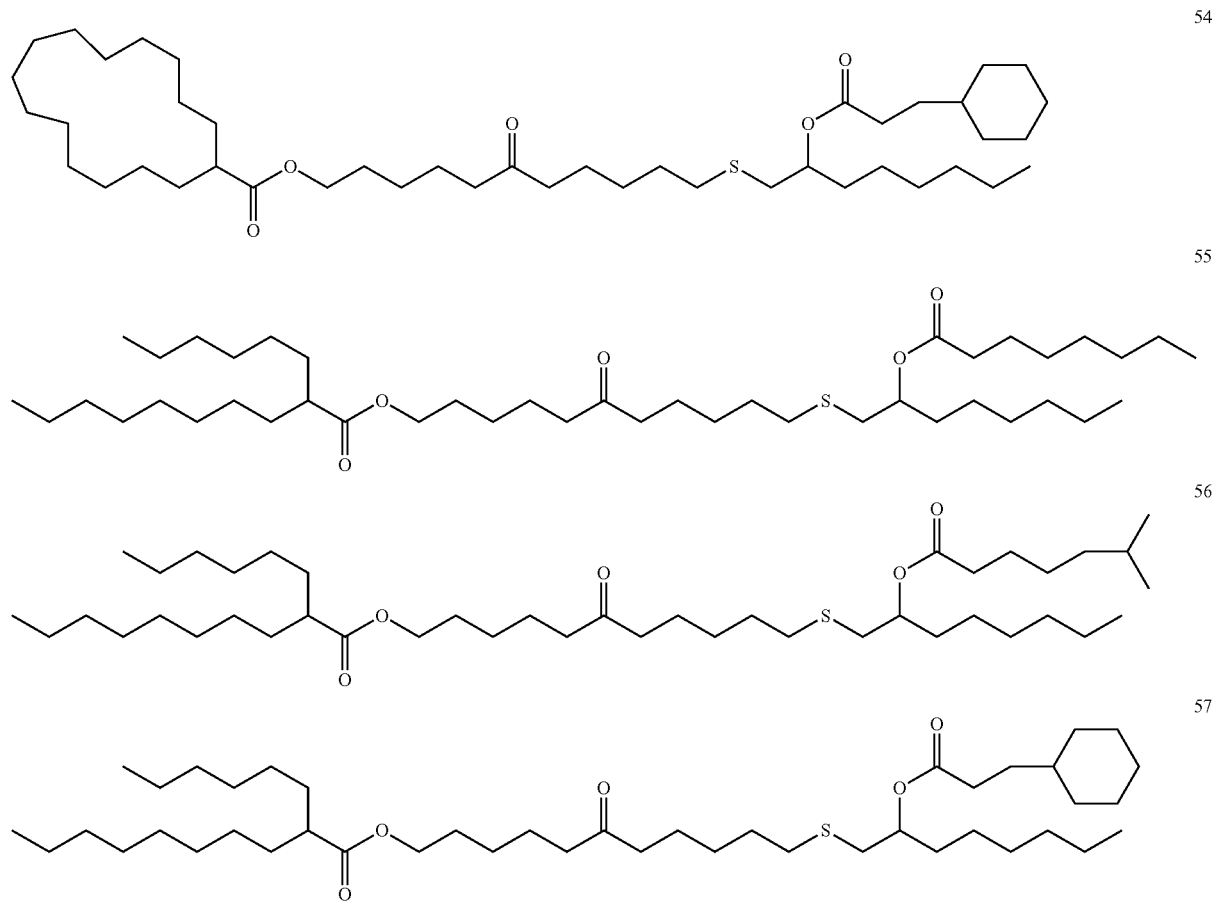

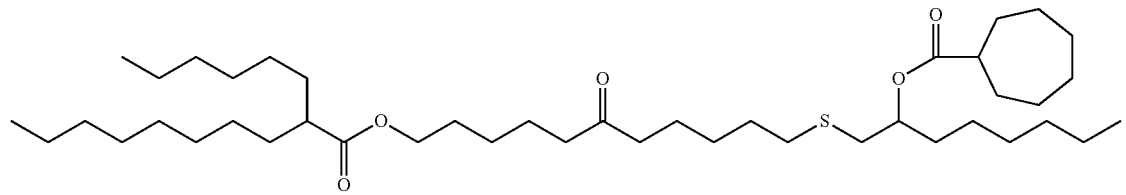

58

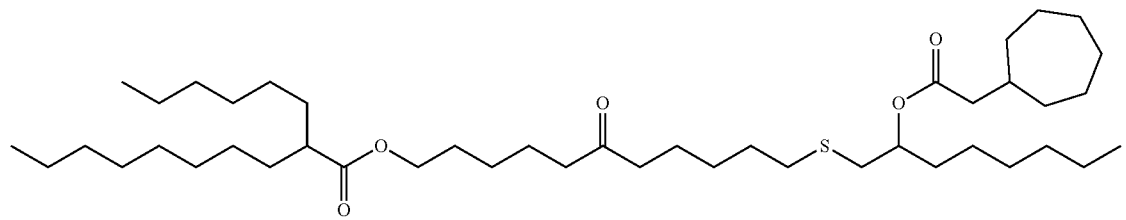

59

The lactone required for the synthesis of ketones 54-59 is caprolactone, 60 (Scheme 7), which upon Claisen condensation under Mukaiyama conditions in the presence of, for example, titanium tetrachloride and triethylamine in an inert solvent, for example, dichloromethane, initially at an appropriately low temperature comprised between −80 and 0° C., for example, −20° C., and subsequently increased gradually to ambient temperature, is transformed into 61. The OH group in 61 is transformed into a sulfonate ester, for example, tosylate 62, and the tosylate is displaced with a sulfur nucleophile that can function as a precursor of an SH group, for example, thioacetic acid, in the presence of an appropriate base, for example, a tertiary amine such as triethylamine, in a solvent that promotes the occurrence of nucleophilic substitution reactions; for example, in N,N-dimethylformamide (DMF). This results in formation of thioacetate ester 63, which upon treatment with a base capable of releasing the acetyl group from 63, and thus liberate the anion of the corresponding mercaptan, for example, NaOH, in the presence of an epoxide such as 1-epoxyoctane, and in an appropriate solvent, for example, an alcohol such as ethanol, produces compound 64.

Scheme 7

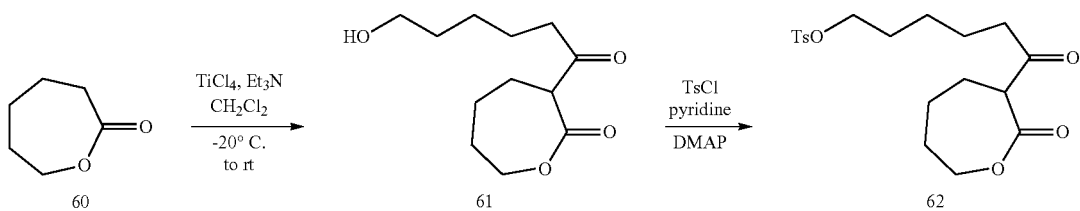

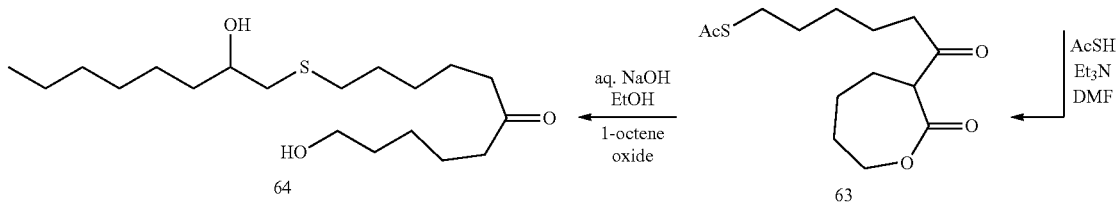

Selective acylation of the primary alcohol in 64 can be achieved by treatment with a carboxylic acid in the presence of a coupling agent; for example, a carbodiimide such as EDCI, optionally in the presence of a nucleophilic catalyst such as 4-(dimethylamino)-pyridine (DMAP), or by treatment with an alkyl chloroformate or an equivalent reagent, such as an alkoxycarbonylimidazolide or an alkyl 4-nitrocarbonate, in the presence of a base such as triethylamine and optionally in the presence of DMAP. Without intending to be limiting, Scheme 8 exemplifies the process with the selective esterification of 64 with cyclopentadecane carboxylic acid to produce 65, further esterification of which with 3-cyclohexylpropanoic acid in the presence of a coupling agent; for example, a carbodiimide such as EDCI, optionally in the presence of a nucleophilic catalyst such as DMAP gives 54. The interest of ionizable lipids possessing macrocyclic moieties such as a cyclopentadecyl group is describe in detail in co-owned and co-pending U.S. provisional patent application No. 63/517,628 filed on Aug. 4, 2023, incorporated herein by reference.

Scheme 8

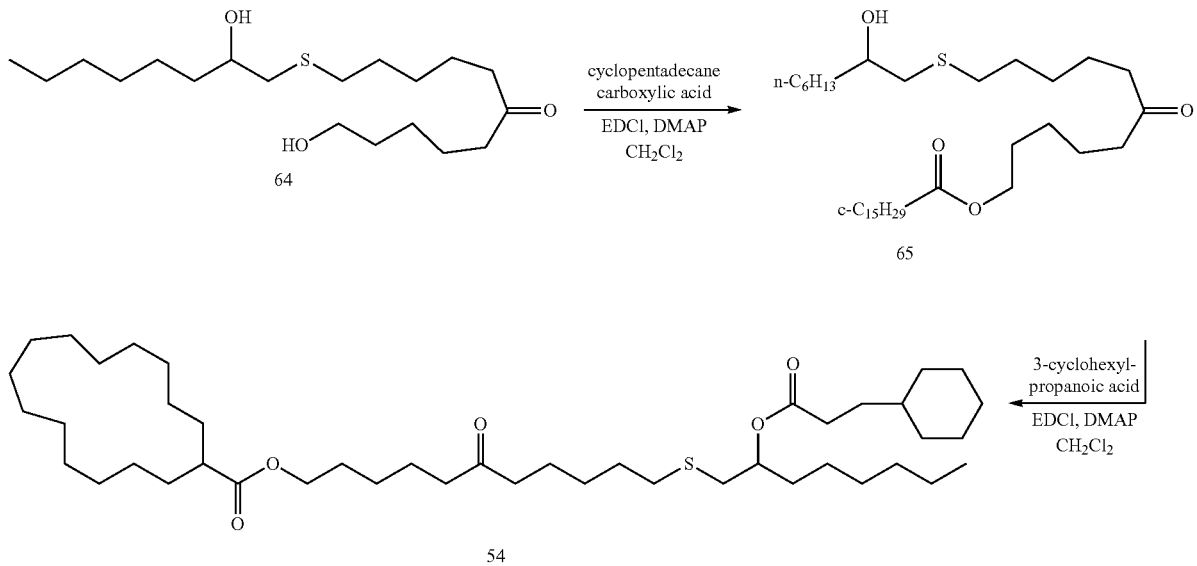

In a like manner, compound 64 can be transformed into ketones 55-59 starting with esterification of primary alcohol with 2-hexyldecanoic acid, followed by esterification of the secondary OH group in the resulting 66 with an appropriate carboxylic acid (Scheme 9).

Scheme 9

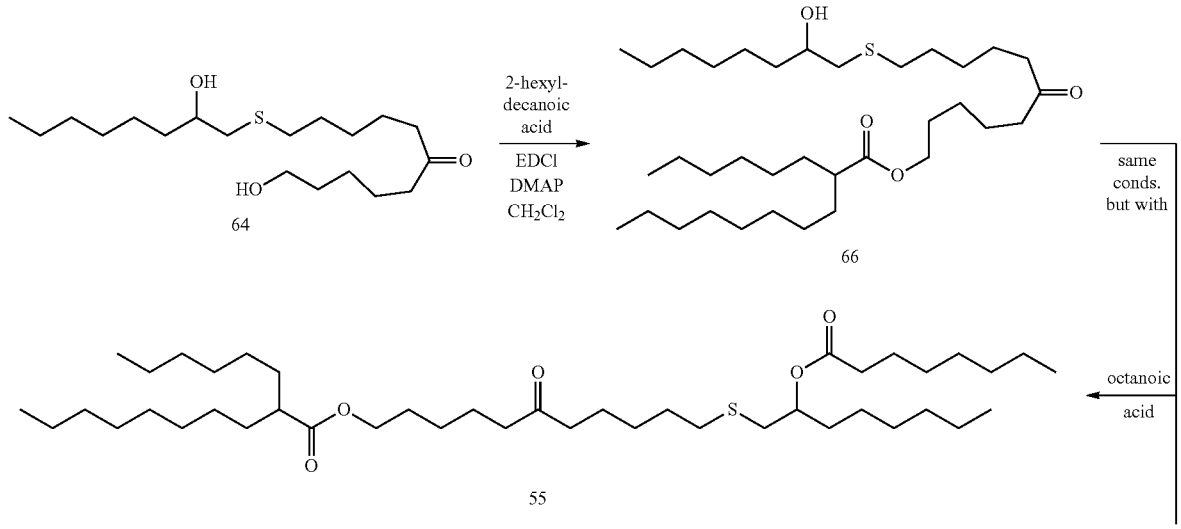

-continued

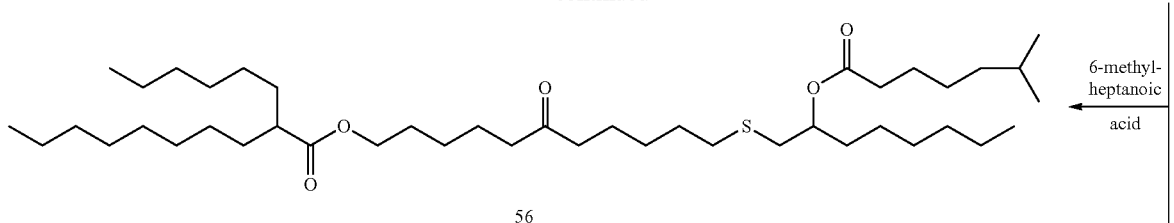

56

6-methyl-heptanoic acid

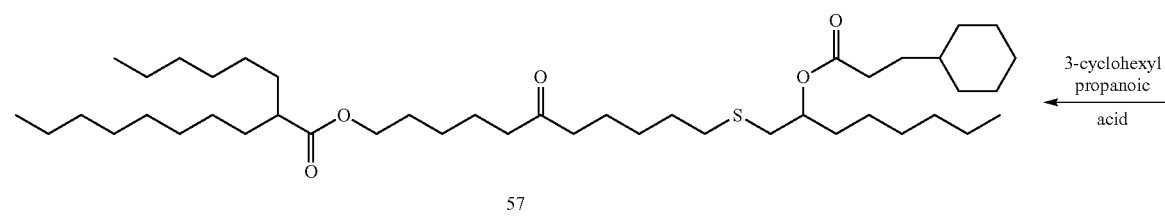

57

3-cyclohexyl propanoic acid

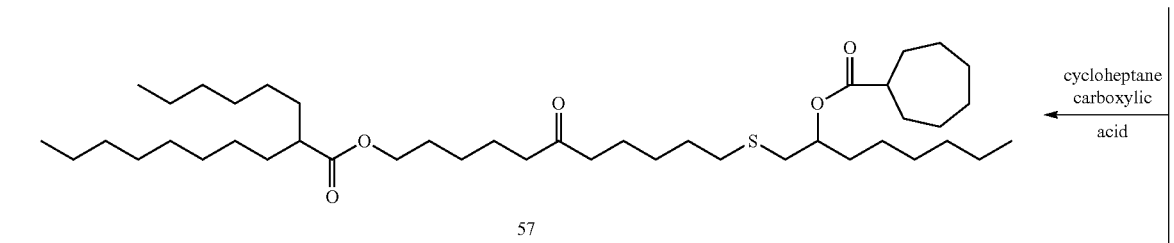

57 cycloheptane carboxylic acid

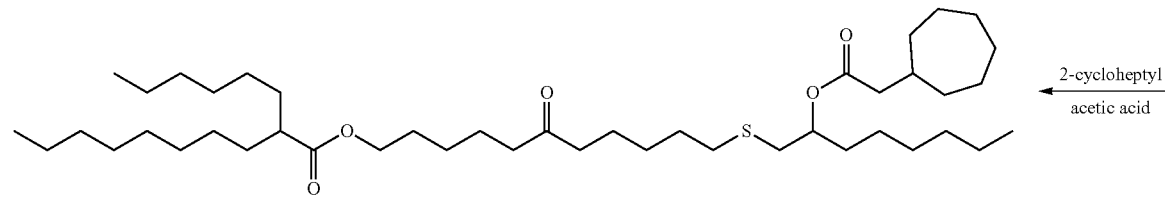

59

2-cycloheptyl acetic acid

Lipids 12-15 can be made from ketones 67-70 of Scheme 10. The lactone required for the synthesis of ketones 67-70 is 71 (Scheme 11), which can be prepared by Baeyer-Villiger oxidation of commercial 4-pentylcyclohexanone with a per-acid such as MCPBA. Claisen condensation of 71 under Mukaiyama conditions in the presence of, for example, titanium tetrachloride and triethylamine in an inert solvent, for example, dichloromethane, initially at an appropriately low temperature comprised between −80 and 0° C., for example, −20° C., and subsequently increased gradually to ambient temperature, produces 72. The OH group in 72 is transformed into a sulfonate ester, for example, tosylate 73, and the tosylate is displaced with a sulfur nucleophile that can function as a precursor of an SH group, for example, thioacetic acid, in the presence of an appropriate base, for example, a tertiary amine such as triethylamine, in a solvent that promotes the occurrence of nucleophilic substitution reactions; for example, in N,N-dimethylformamide (DMF). This results in the formation of thioacetate ester 74. Treatment with a base capable of releasing the acetyl group from 74, and thus liberate the anion of the corresponding mercaptan, for example, NaOH, in the presence of an epoxide such as 1-hexene oxide, and in an appropriate solvent, for example, an alcohol such as ethanol, produces compound 75. The same treatment, but in the presence of cyclohexene oxide, transforms 74 into 76. Compounds 75 and 76 can then be O-acylated as described above.

Scheme 10
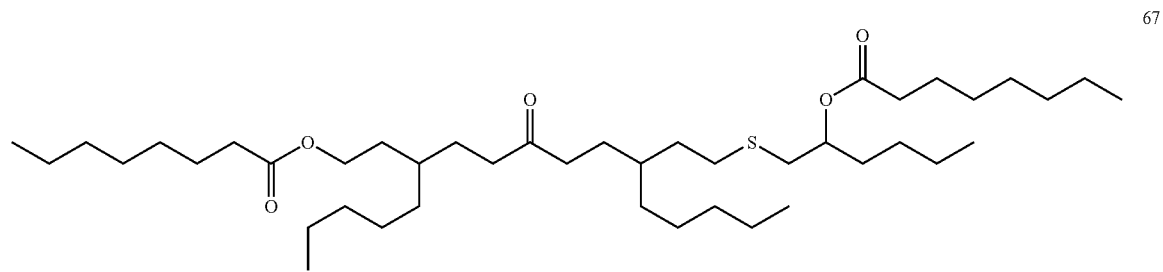
67
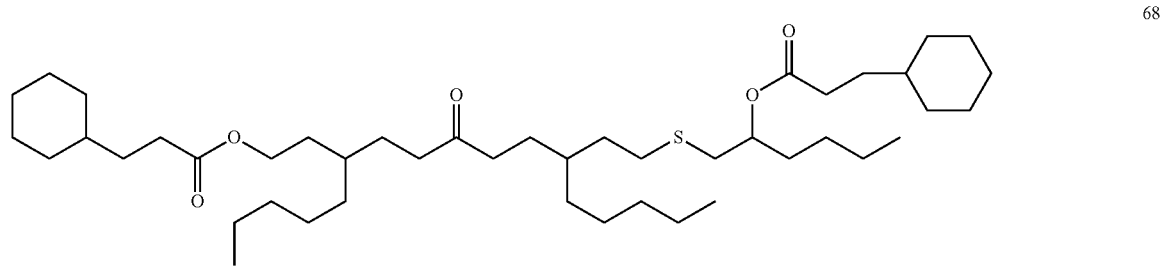
68
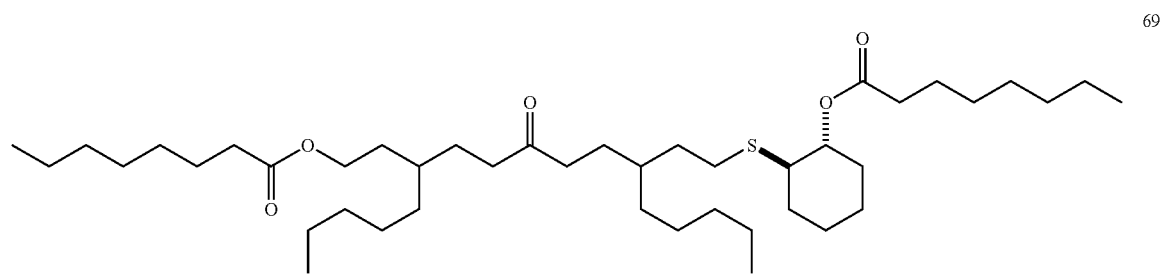
69
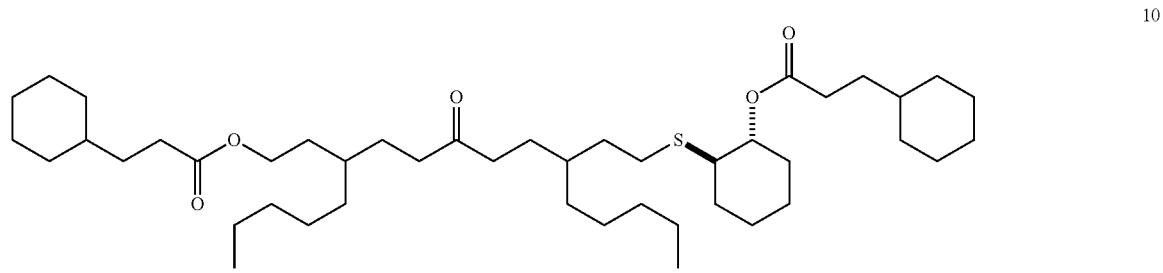
10
Scheme 11
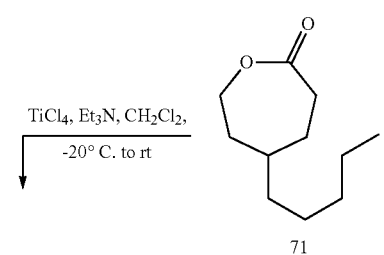
71

-continued

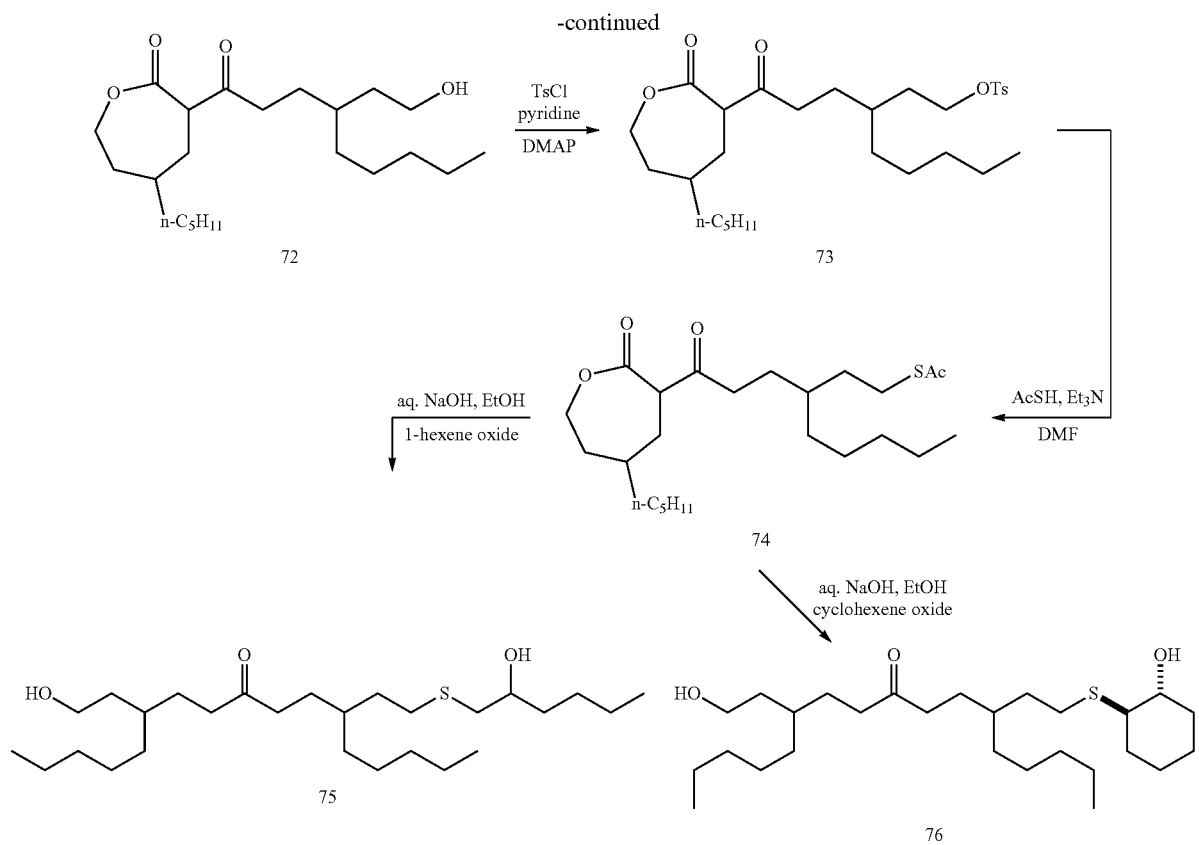

For the synthesis of ketones 67-70, the primary and secondary OH groups in 75-76 must be acylated with the same group. Therefore, 74 can be esterified with at least two equivalents of octanoic acid or 3-cyclohexylpropanoic acid in the presence of a coupling agent, for example, a carbodiimide such as EDCI, optionally in the presence of a nucleophilic catalyst such as DMAP, resulting in formation of ketones 67 and 68, respectively. Esterification of 75 in a like manner produces ketones 69 and 70.

Scheme 12

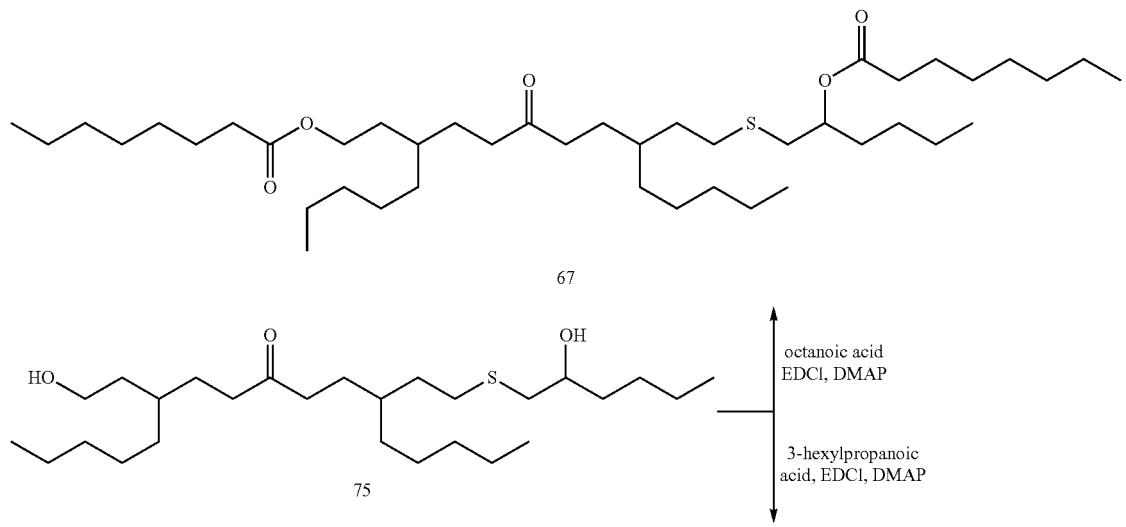

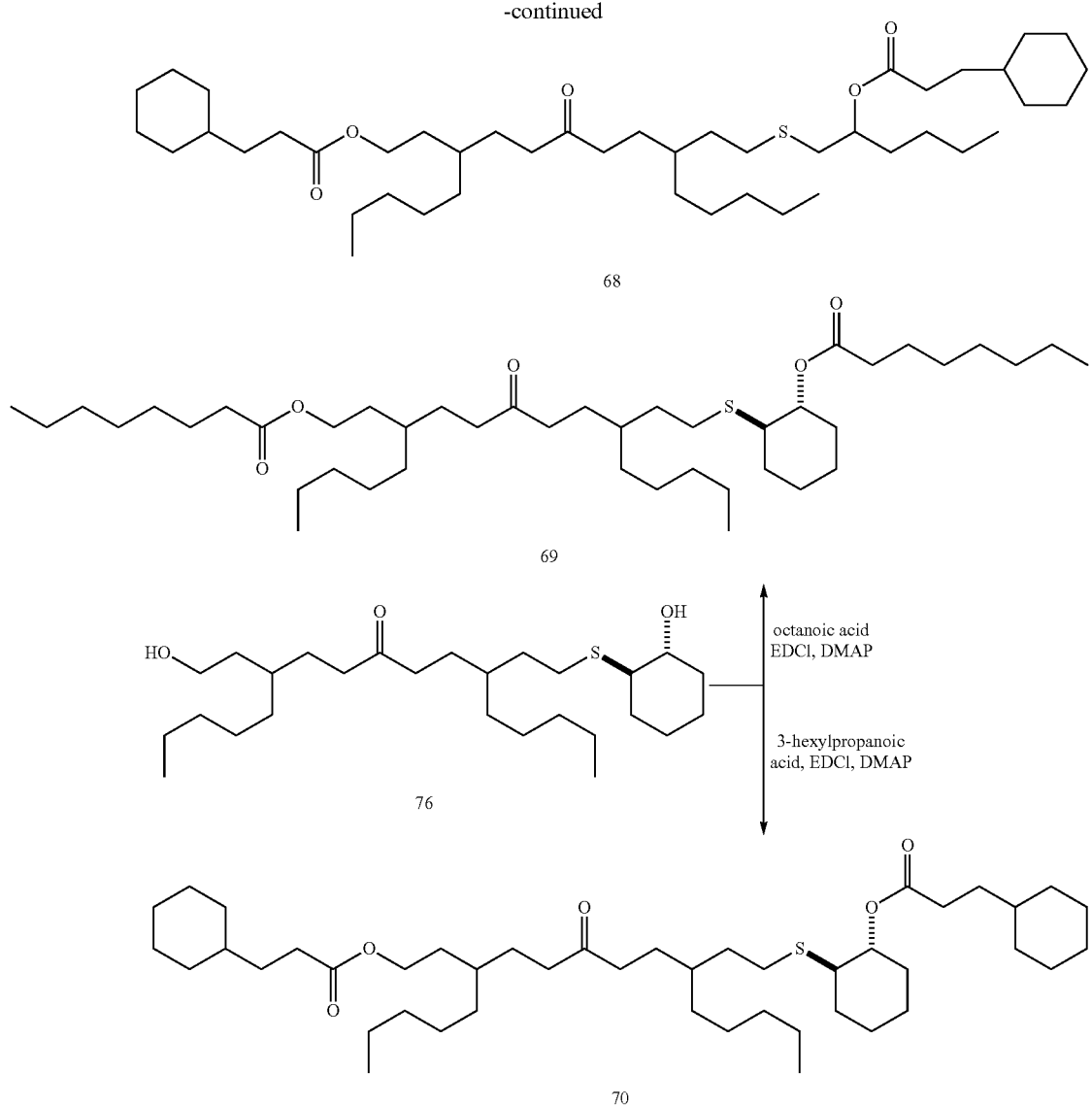

Lipids 16-35 can be made from ketones 77-83 of Scheme 13. Certain steps of the synthesis of ketones 77-83 are described in detail in co-pending and co-owned WO 2022/246555. As described in the aforementioned disclosure, one such step entails subjecting an appropriate ester of general structure 84 to Claisen condensation under Mukaiyama conditions, leading to the formation of a beta-ketoester product of general structure 85 (Scheme 14). Compound 85 is then converted into beta-ketoacid 86, which is not isolated (as indicated by the square brackets), but it is decarboxylated to produce ketone 87 directly.

Scheme 13

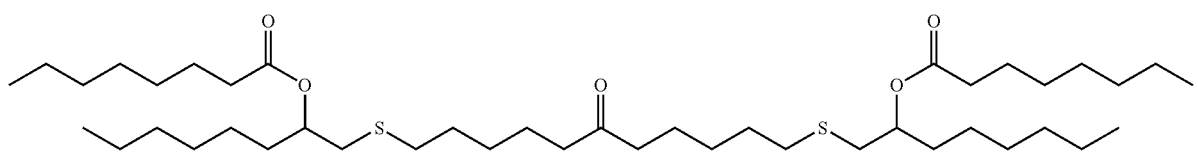

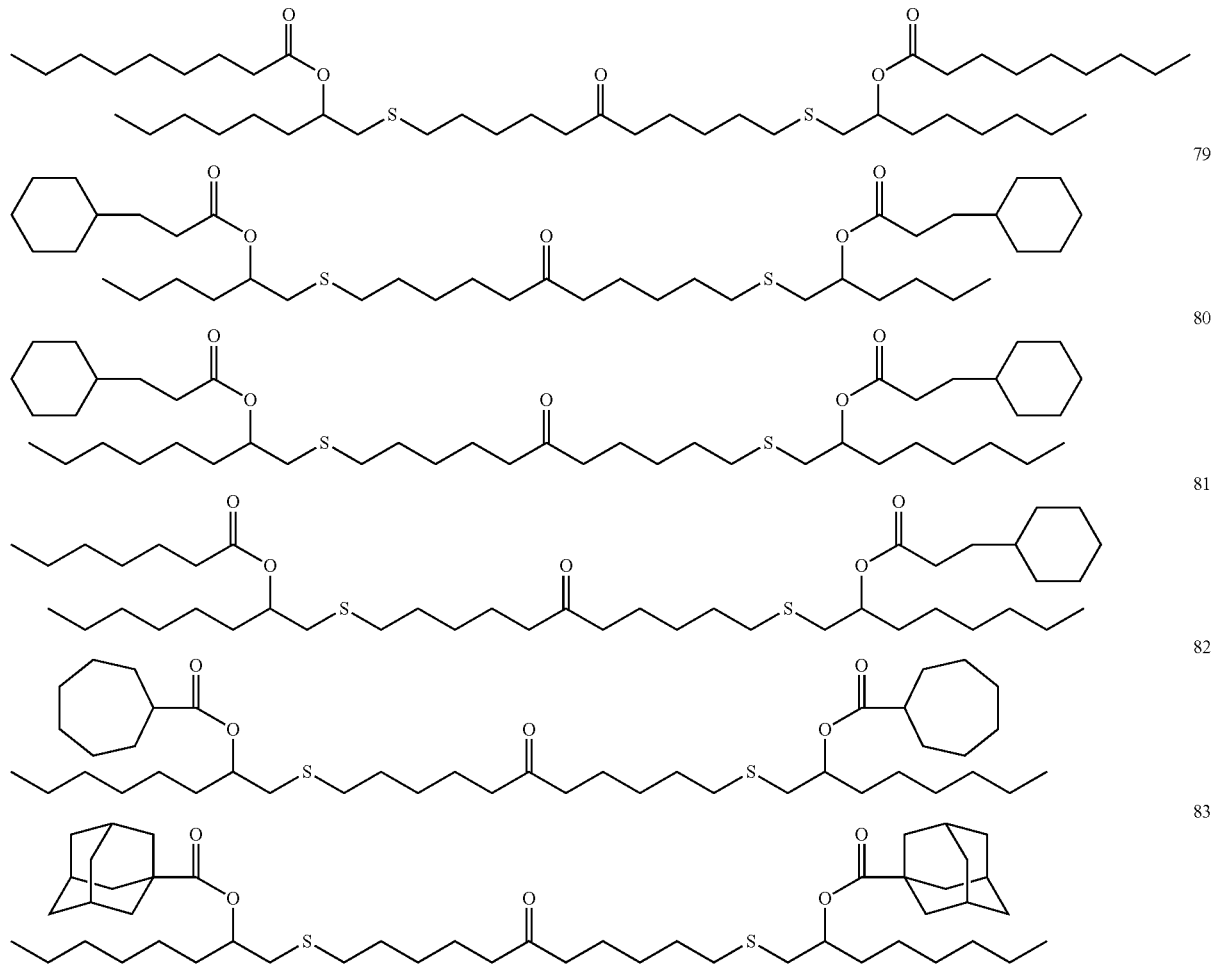

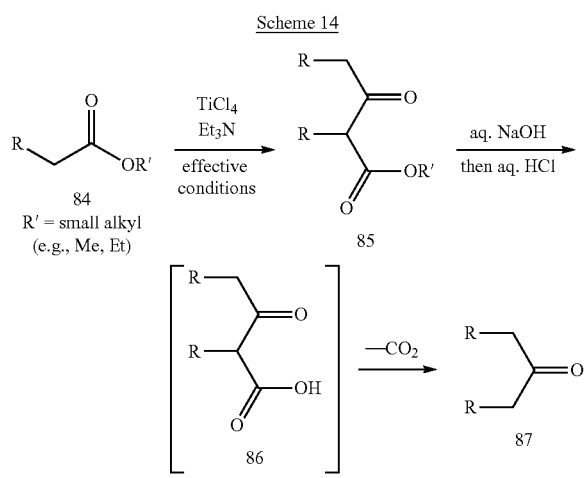

Without intending to be limiting, Scheme 15 below exemplifies the process with a route to ketones 77-83. The esters of type 84 required for the preparation of said ketones are compounds 90 and 91. The synthesis of these materials starts with the displacement of a leaving group, such a halide or a sulfonate, from a suitable haloester or sulfonyloxy ester, for example, bromoester 88, with an appropriate sulfur nucleophile that can function as a precursor to an SH group, for example, thioacetic acid, in the presence of a base, for example an amine such as triethylamine, in an appropriate solvent, for example, dimethylformamide (DMF). Treatment of the resulting 69 with a nucleophilic metal alkoxide, for example, sodium methoxide, in an appropriate solvent, for example, an alcohol such as methanol, in the presence of an epoxide, for example, 1-hexene oxide, leads to the formation of ester 90. The same reaction of 89 with 1-octene oxide produces instead compound 91. The conversion of 90-91 into ketones of the type 87 continues with the protection of the OH group as a trialkylsilyl ether, such as a trimethylsilyl, triethylsilyl, or tert-butyldimethylsilyl group. For example, treatment of 90-91 with tert-butyldimethylsilyl chloride (TBS-Cl) and imidazole produces silyl ethers 92 and 93, respectively. The latter are treated with, for example, TiCl$_4$, and a tertiary amine base such as triethylamine, tributylamine, and the like, in a solvent such as toluene, dichloromethane, and the like, at a suitable temperature, for example, −20° C. to room temperature, resulting in the formation of beta-ketoesters 94 and 95. Ester hydrolysis and acidification results in decarboxylation of transient ketoacids of the type 86 and in release of the silyl groups, leading directly to ketodiols 96 and 97. The use of a more labile silyl protecting group, such as a trimethylsilyl (TMS) group, may be advantageous in that said protecting group is more easily released during hydrolysis and decarboxylation. In cases wherein a more robust silyl protecting group is advantageous, a separate desilylation step may be applied to obtain the desired ketodiol.

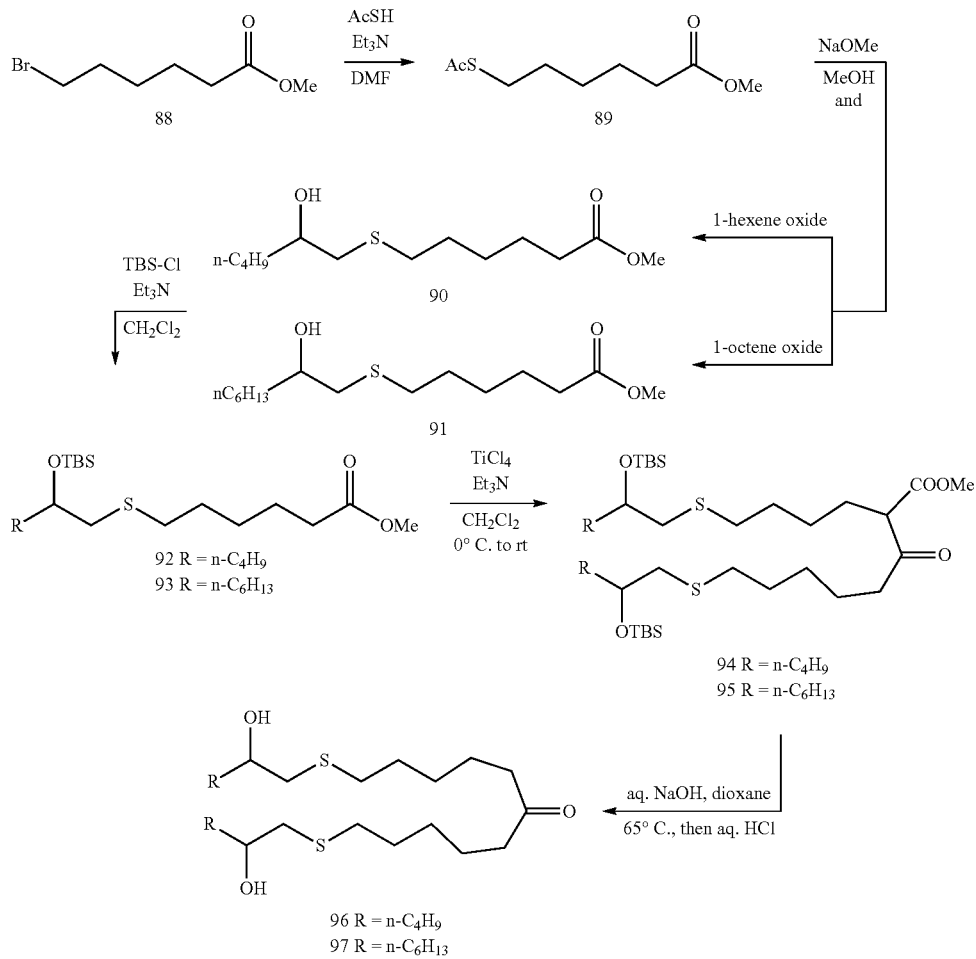

An alternative route to ketones such as 96 and 97 starts with the preparation of esters of the type 90-91 by halide or sulfonate displacement from a haloester of a sulfonyloxy ester, for example, 88, with a mercaptoalcohol, for example, 98, in the presence of a base, for example, an amine such as triethylamine, in an appropriate solvent, for example, DMF (Scheme 16). The resulting 91 in the exemplary, but not limiting, example of Scheme 16, can then be processed as shown above in Scheme 15 to produce ketone 97.

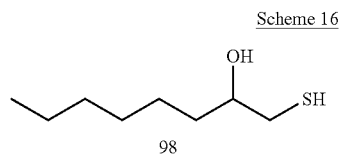

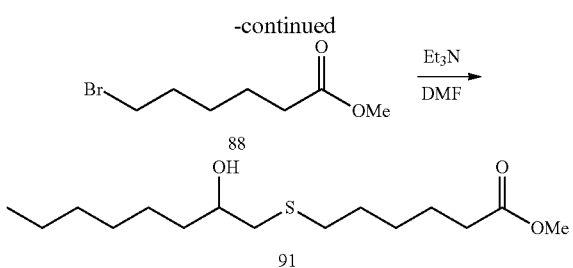

Alternatively, ketones such as 96-97 can be prepared by synthesis steps that are described in detail in the aforementioned co-pending and co-owned WO 2023/147657. One such step entails subjecting a lactone to Claisen condensation under Mukaiyama conditions, followed by hydrolysis of the resulting product and decarboxylation, and leading to the formation of a ketodiol. In certain embodiments, these steps are most advantageously carried out in a "one-pot operation", meaning that the various synthetic intermediates, while isolable, need not be isolated. Without intending to be limiting, the process is exemplified in Scheme 17 with the preparation of ketodiol 100 and its conversion into ketones 96-97, in which case the required lactone is caprolactone, 60, the synthetic intermediates that optionally need not be isolated are compounds 61 and 99, and the product of the reaction is ketodiol 100. The direct formation of 100 is achieved by adding water to the reaction mixture of the Claisen step as shown earlier in Scheme 4, whereupon the acidity generated by reaction of $TiCl_4$ with $H_2O$ causes lactone opening of 61 to 99, which undergoes decarboxylation during the operations leading to the isolation of 100.

Scheme 17

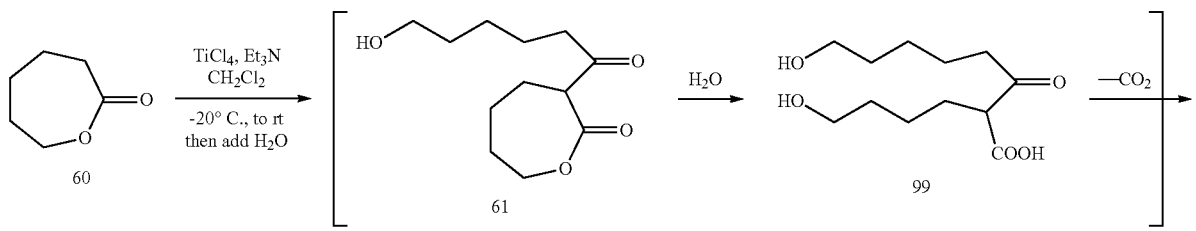

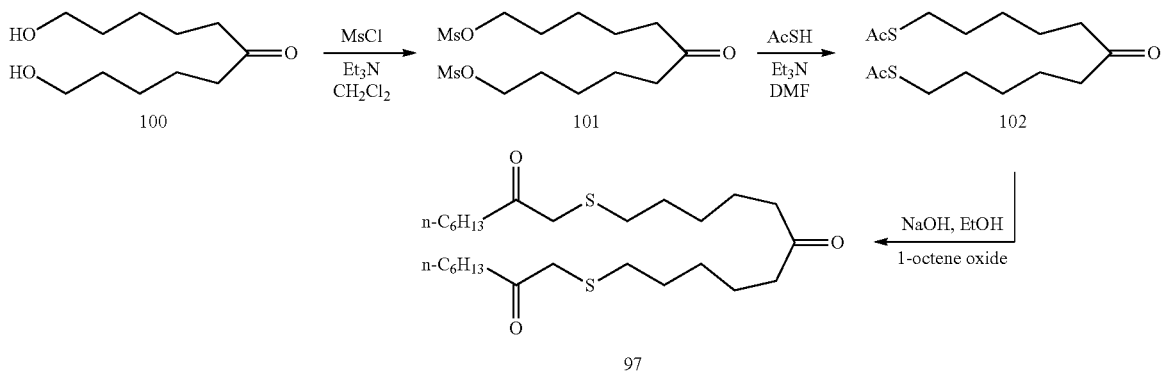

Finally, ketodiols of the type 100 can also be made by an alternative method also described in the aforementioned co-pending and co-owned WO 2023/147657. This synthetic method is especially advantageous in cases where a lactone suitable for the preparation of a ketodiol is not readily available. Thus, subjecting an appropriately O-protected derivative of a hydroxyester to Claisen condensation under Mukaiyama conditions, followed by hydrolysis of the resulting beta-ketoester, release of the O-protecting groups, and decarboxylation, results in formation of the ketodiol. In certain embodiments, these steps of hydrolysis of the beta-ketoester, release of the O-protecting groups, and decarboxylation, are most advantageously carried out in a "one-pot operation", meaning that the various synthetic intermediates, while isolable, need not be isolated. Without intending to be limiting, the method is exemplified in Scheme 18 with the synthesis of ketodiol 106, in which case the O-protected derivative of the hydroxyester is 103 and the synthetic intermediates that optionally need not be isolated are compounds 104 and 105.

Scheme 18

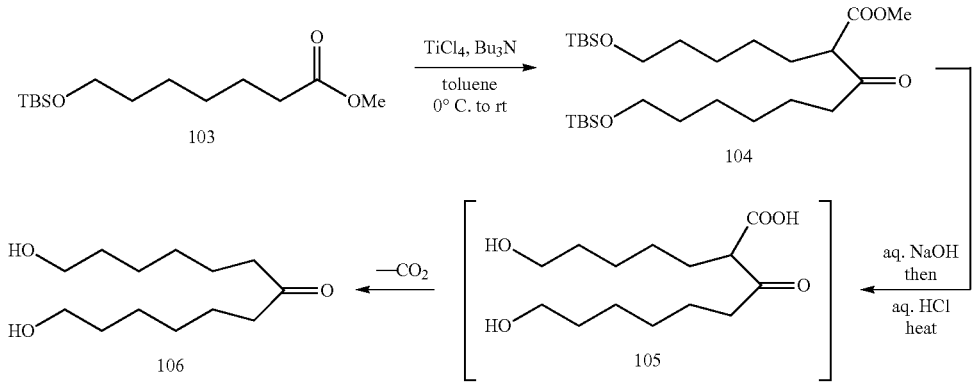

The synthetic methods described above produce ketones of general structure 37 and 38 (see Scheme 2) wherein m=p, n=q, $R^4$=$R^6$, and $R^5$=$R^7$. Ketones 37-38 wherein one or more of m and p, n and q, $R^4$ and $R^6$, and $R^5$ and $R^7$ differ can be prepared by the general schemes provided below. These schemes are merely illustrative of representative embodiments and must not be construed as being in any way limiting.

Ketones 37-38 wherein one or more of m and p, n and q, $R^4$ and $R^6$, and $R^5$ and $R^7$ differ can be advantageously made as shown in Scheme 19, starting from a compound of general structure 107, wherein $P^1$ and $P^2$ are orthogonal O-protecting groups, meaning that one of $P^1$ and $P^2$ can be released while leaving the other in place. Accordingly, release of, for example, $P^1$ gives 108, which can be transformed into 109 by obvious modifications of the method shown earlier in Scheme 3, 4, and 7. Compound 109 is then converted into 110 by release of $P^2$. Substance 110 can then be transformed into ketone 37 by obvious modifications of the method shown earlier in Scheme 8 and 9, or into ketone 38 by obvious modifications of the method shown earlier in Scheme 3, 4, and 7. Therefore, the synthesis of ketones 37-38 wherein one or more of m and p, n and q, $R^4$ and $R^6$, and $R^5$ and $R^7$ differ can be achieved by starting with a compound of general structure 107, wherein one or more of m and p, n and q, $R^4$ and $R^6$, and $R^5$ and $R^7$ differ.

A compound of general structure 107, wherein one or more of m and p, n and q, $R^4$ and $R^6$, and $R^5$ and $R^7$ differ, can be advantageously prepared by certain synthetic steps that are described in detail in co-owned and co-pending U.S. provisional patent application No. 63/445,854 filed on Feb. 15, 2023, incorporated herein by reference. Accordingly, tosyl methyl isonitrile (TosMIC) can be mono-alkylated with an alkyl halide (X=Cl, Br, I) or sulfonate (X=OTs, OTs, and the like) of structure 111, in the presence of a base, resulting in formation of product 112. Subsequent alkylation of 112 with an alkyl halide (X=$C_1$, Br, I) or sulfonate (X=OTs, OTs, and the like) of structure 113 gives 114, which can be hydrolyzed to ketone 107 by treatment with aqueous acid. It is expedient to utilize as one of $P^1$ or $P^2$ a protecting group that can be released under the acidic conditions required for the conversion of 114 into 107. For example, if $P^1$ is a protecting group that can be released under the acidic conditions required for the hydrolysis of 114, then 114 is advantageously transformed directly into 108. Otherwise, an appropriate deprotection step can be utilized to release one of $P^1$ or $P^2$.

Scheme 19

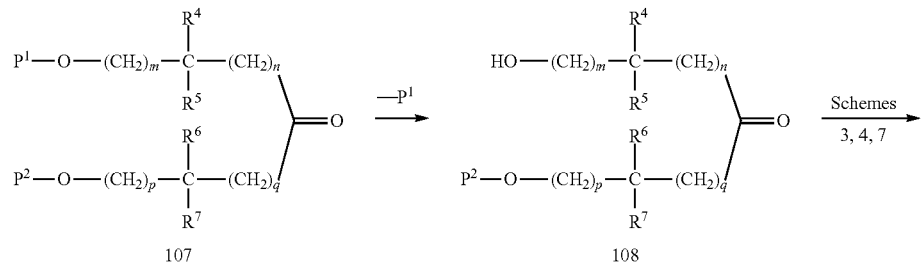

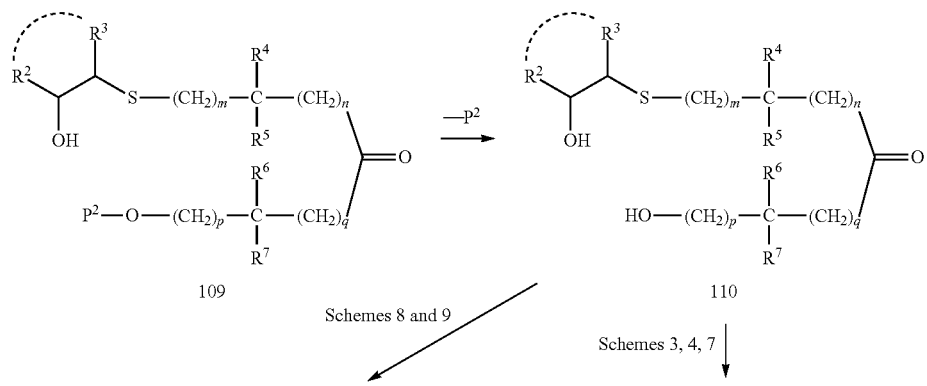
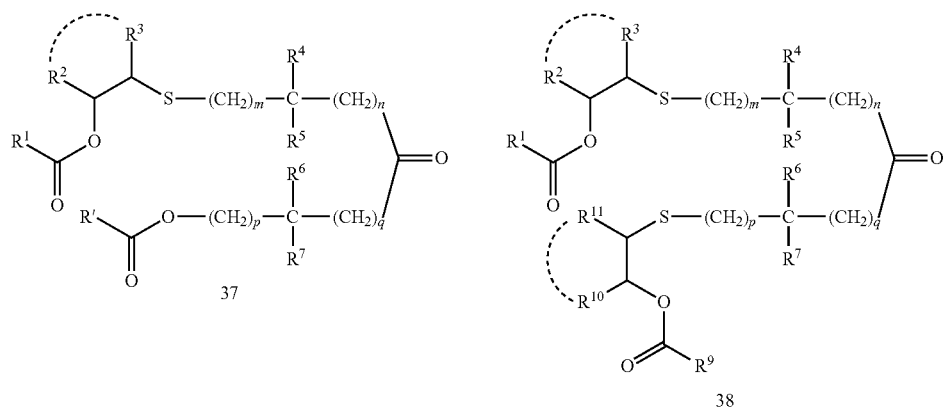
P¹, P² = orthogonal protecting groups
Scheme 20
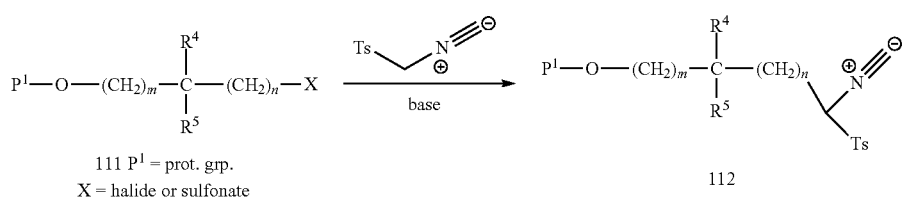
111 P¹ = prot. grp.
X = halide or sulfonate

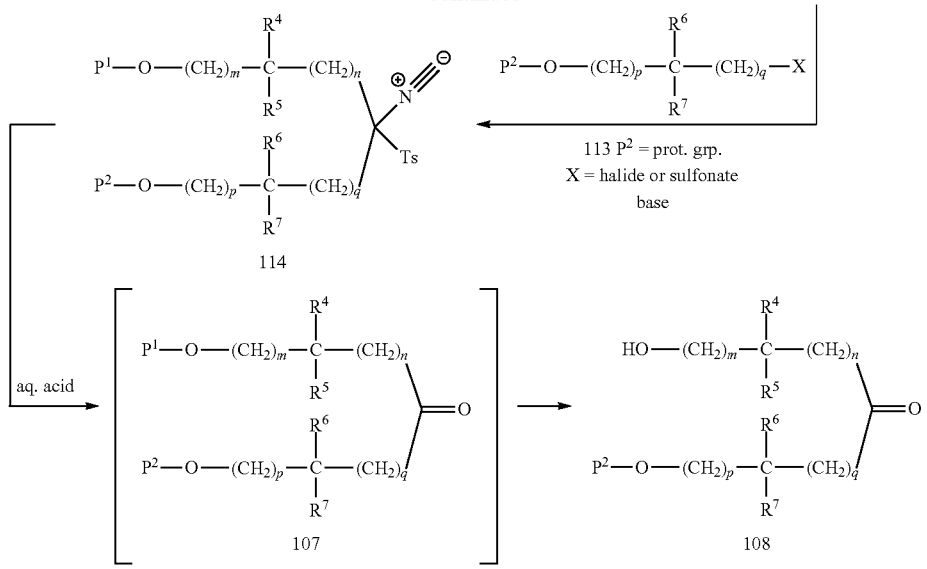

An alternative method for the synthesis of compound of general structure 106, wherein one or more of m and p, n and q, $R^4$ and $R^6$, and $R^5$ and $R^7$ differ, involves the conversion of an O-protected hydroxyacid of general structure 115 into beta-ketoester 117, for example by the method of Oikawa (Oikawa, T., et al., *Org. Syn.* 1985, 63, 198, incorporated herein by reference). Subsequent alkylation of 117 with an alkyl halide (X=Cl, Br, I) or sulfonate (X=OTs, OMs, and the like) of structure 118 gives 119, which upon ester saponification and decarboxylation produced ketone 107 (Scheme 21).

Scheme 21

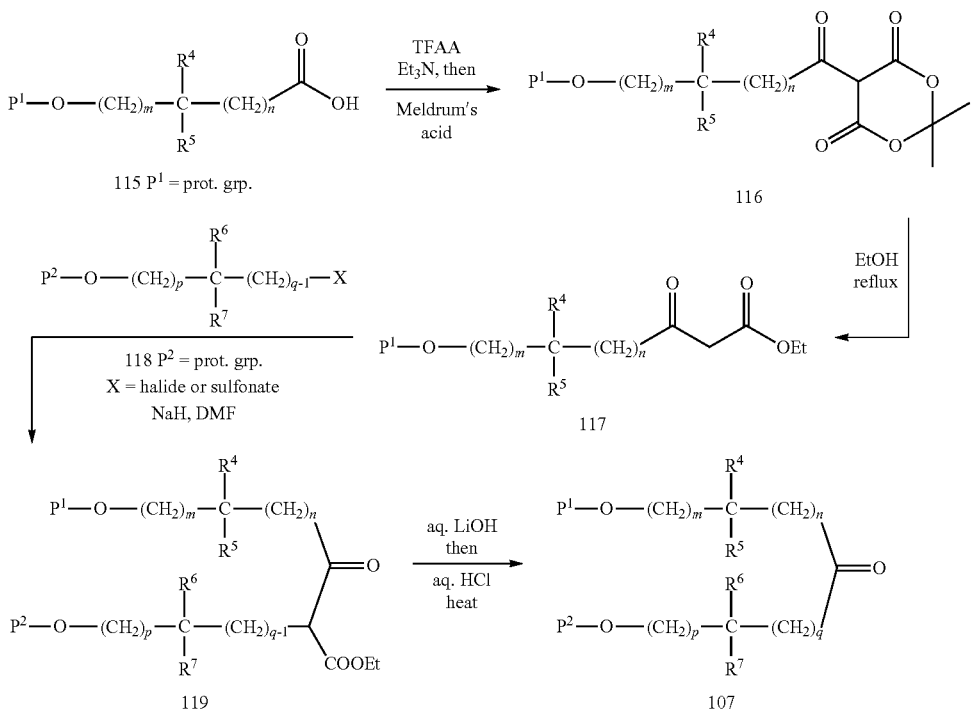

The representative ketones 77-83 of Scheme 13 can be prepared from ketodiols 96-97 of Scheme 15 by acylation of the OH groups with appropriate carboxylic acids or chloroformates (or equivalent reagents). Furthermore, the acylation step can be carried out so that either a diacyl or a monoacyl derivative of the starting ketodiol is obtained. Thus, the reaction of a ketodiol with slightly more than 2 equivalents of a carboxylic acid in the presence of a condensing agent, for example a carbodiimide such as EDCI, and optionally in the presence of DMAP, or a chloroformate or an equivalent reagent such as an alkoxycarbonylimidazolide or an alkyl 4-nitrophenylcarbonate in the presence of triethylamine and optionally and in the presence of DMAP, leads to a diester or a decarbonate product comprising two identical acyl groups. Without intending to be limiting, this is exemplified in Scheme 22 with the conversion of compound 96 into 79, and in Schemes 23 with the conversion of compound 97 into 77, 78, 80, 82, and 83.

Scheme 22

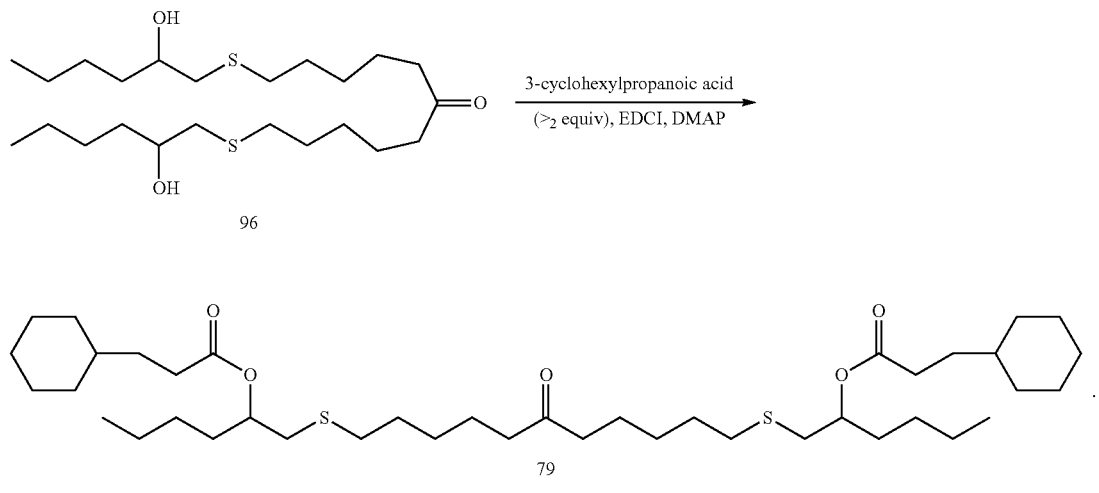

Conversely, the reaction of a ketodiol with about 1 equivalent of a carboxylic acid in the presence of a condensing agent, for example a carbodiimide such as EDCI, and optionally in the presence of DMAP, or a chloroformate or an equivalent reagent such as an alkoxycarbonylimidazolide or an alkyl 4-nitrophenylcarbonate in the presence of triethylamine and optionally and in the presence of DMAP, leads to a monoacyl derivative, which can be converted into a ketone comprising two different acyl groups by further acylation with a different carboxylic acid or chloroformate (or equivalent reagents) as described above. Without intending to be limiting, this is exemplified in Scheme 24 with the preparation of ketone 81 by way of monoester 120.

Scheme 23

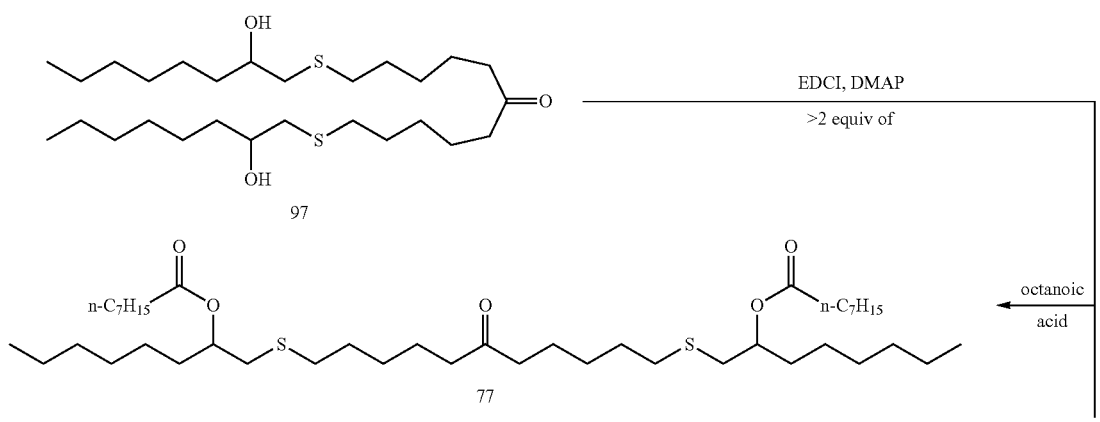

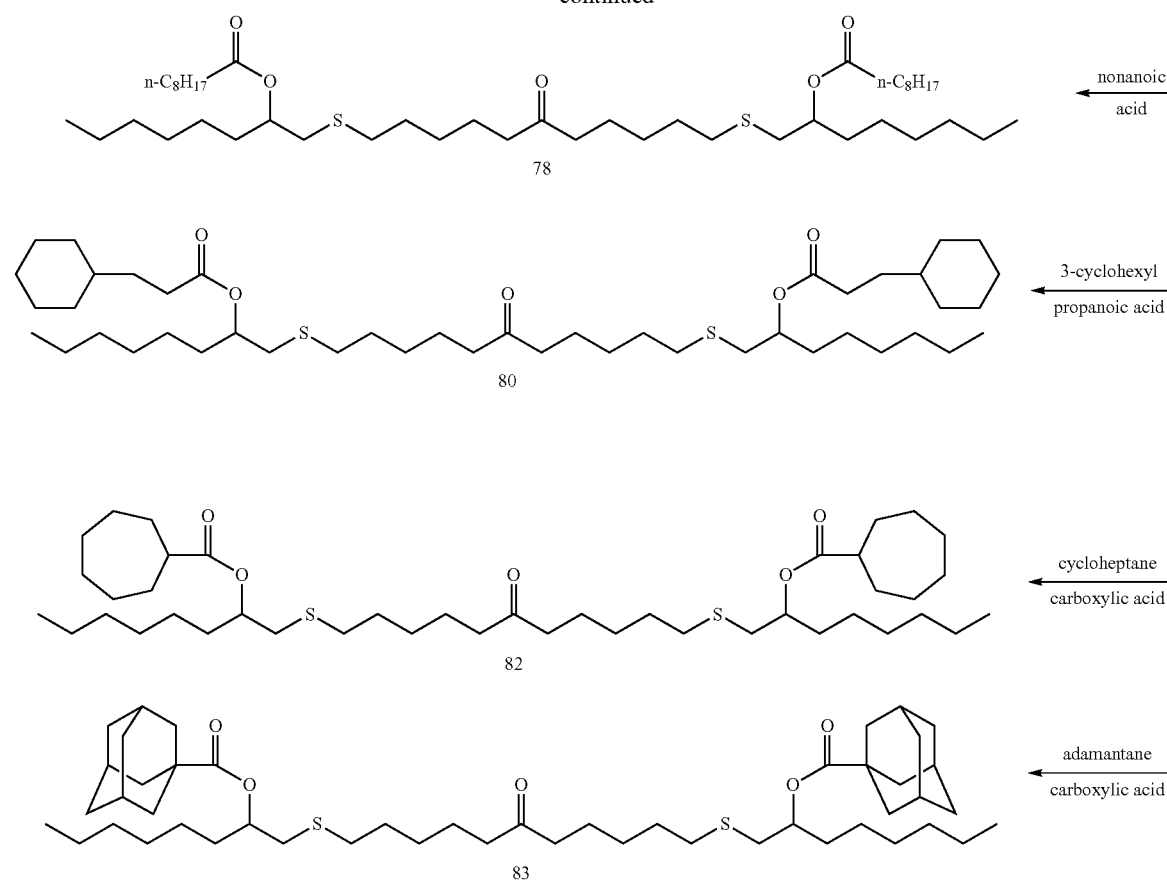
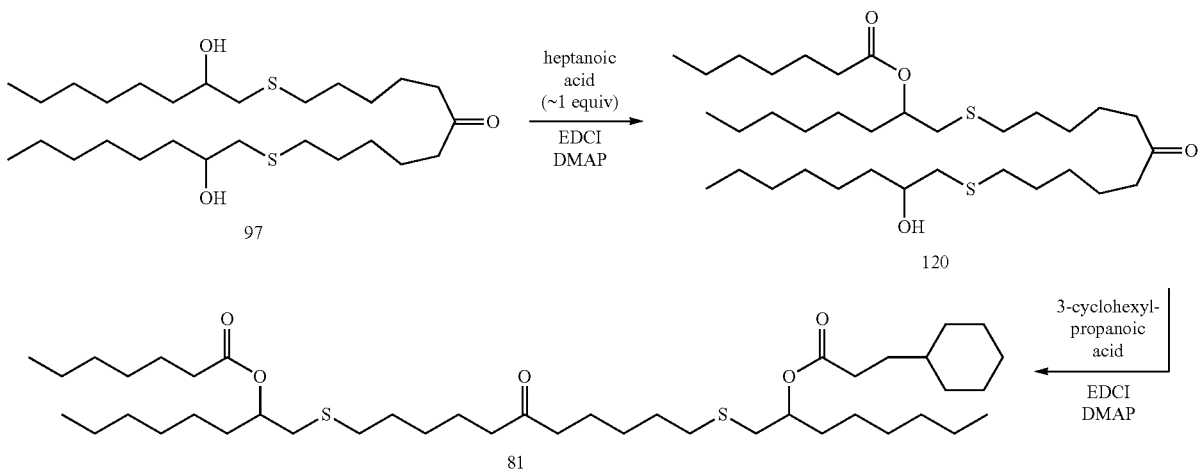
Schemed 24

Procedures for the preparation of representative lipids 5-35 from the ketones of Scheme 6, 10, and 13 are provided below. These procedures are merely illustrative of representative embodiments and must not be construed as being in any way limiting.

Lipid 5 can be made from ketone 54 through synthesis steps that convert the keto functionality into a type 1 ionizable head group. Accordingly, the ketone is selectively reduced with a hydride reagent, for example, sodium borohydride, and the resulting alcohol 121 is esterified with 4-(dimethylamino) butanoic acid hydrochloride in the presence of a condensing agent; for example, a carbodiimide such as EDCI, to produce lipid 5 (Scheme 25). The same synthesis steps can be employed to convert any of the ketones of Schemes 6, 10, and 13 into a corresponding lipid comprising a type 1 ionizable head group.

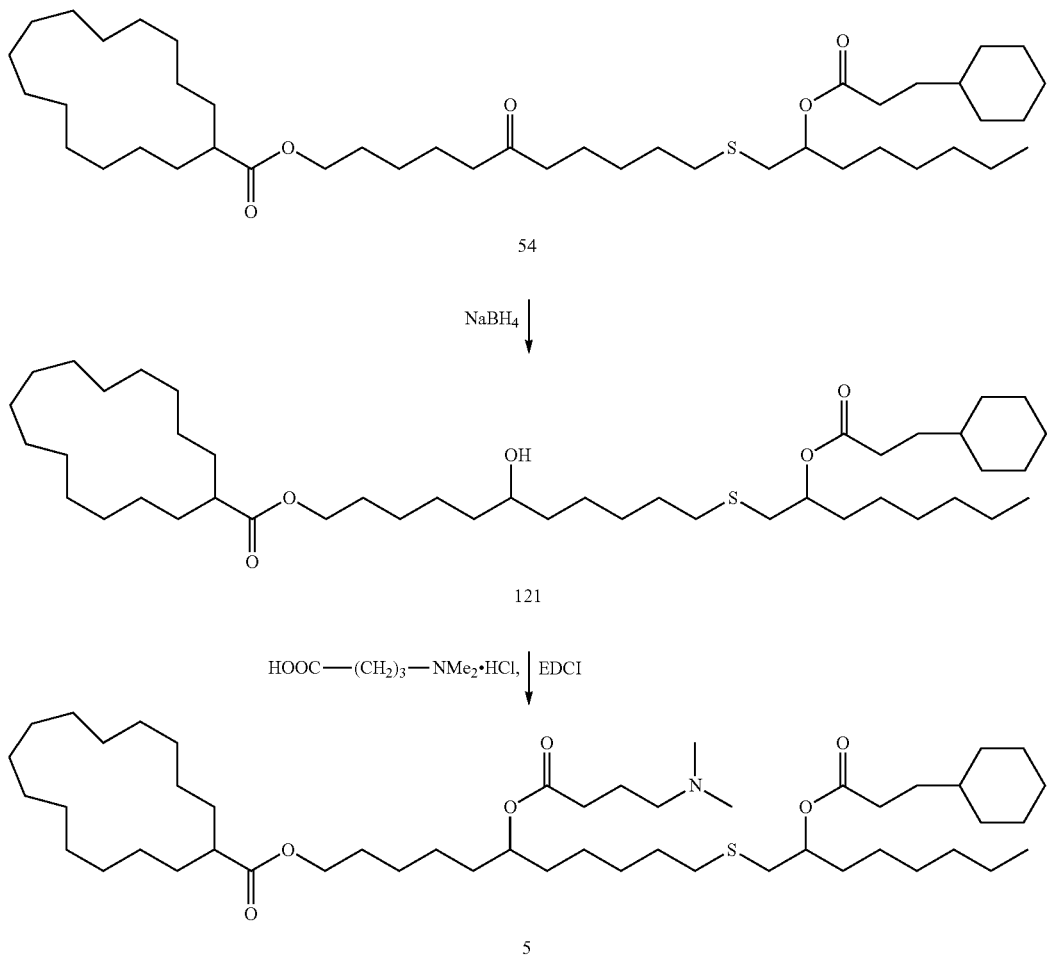

Lipid 6 can be made from ketone 55 through synthesis steps that convert the keto functionality into a type 7 ionizable head group. Accordingly, the ketone is reductively aminated with an O-protected derivative of 4-aminobutanol, for example, the O-tert-butyldiphenylsilyl derivative 122, in the presence of a hydride reagent, for example, sodium triacetoxyborohydride, and an acid catalyst, for example, acetic acid, to give 123. A second reductive alkylation with formaldehyde in the presence of, for example, sodium triacetoxyborohydride, converts 123 into 124, which can be transformed into lipid 6 by release of the silyl protecting group with a source of fluoride ion; for example, with HF-pyridine complex (Scheme 26). The same synthesis steps can be employed to convert any of the representative ketones of Schemes 6, 10, and 13 into a corresponding lipid comprising a type 7 ionizable head group. Accordingly, lipids 7, 8, 9, 10, 11, 12, 13, 14, and 15, all of which comprise a type 7 ionizable head group, can be prepared from ketones 56, 57, 58, 59, 54, 67, 68, 69, and 70, respectively, by the method of Scheme 26.

Scheme 26

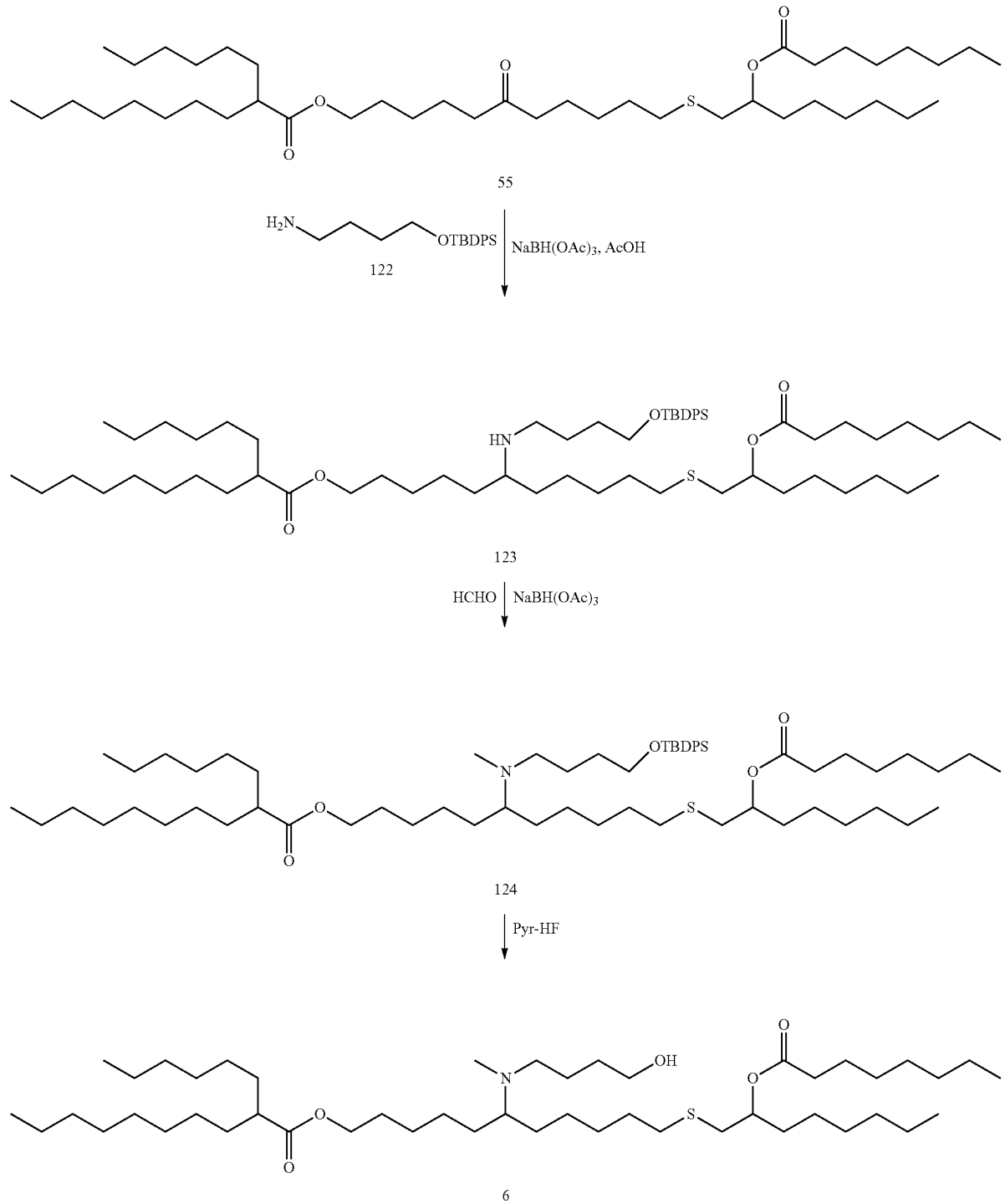

Lipids 16, 17, 18 and 19 comprise a type 1 ionizable head group. Therefore, they can be prepared from ketones 77, 78, 79, and 80, respectively, by the method of Scheme 25 above.

Lipid 20 can be made from ketone 80 through synthesis steps that convert the keto functionality into a type 10 ionizable head group. Accordingly, the ketone is selectively reduced with a hydride reagent, for example, sodium borohydride, and the resulting alcohol 125 is esterified with N-methylazetidine-3-carboxylic acid hydrochloride in the presence of a condensing agent; for example, a carbodiimide such as EDCI, to produce 20 (Scheme 27).

Lipid 21 can be made from alcohol 125 of Scheme 27 through synthesis steps that introduce a type 12 ionizable head group.

Scheme 27
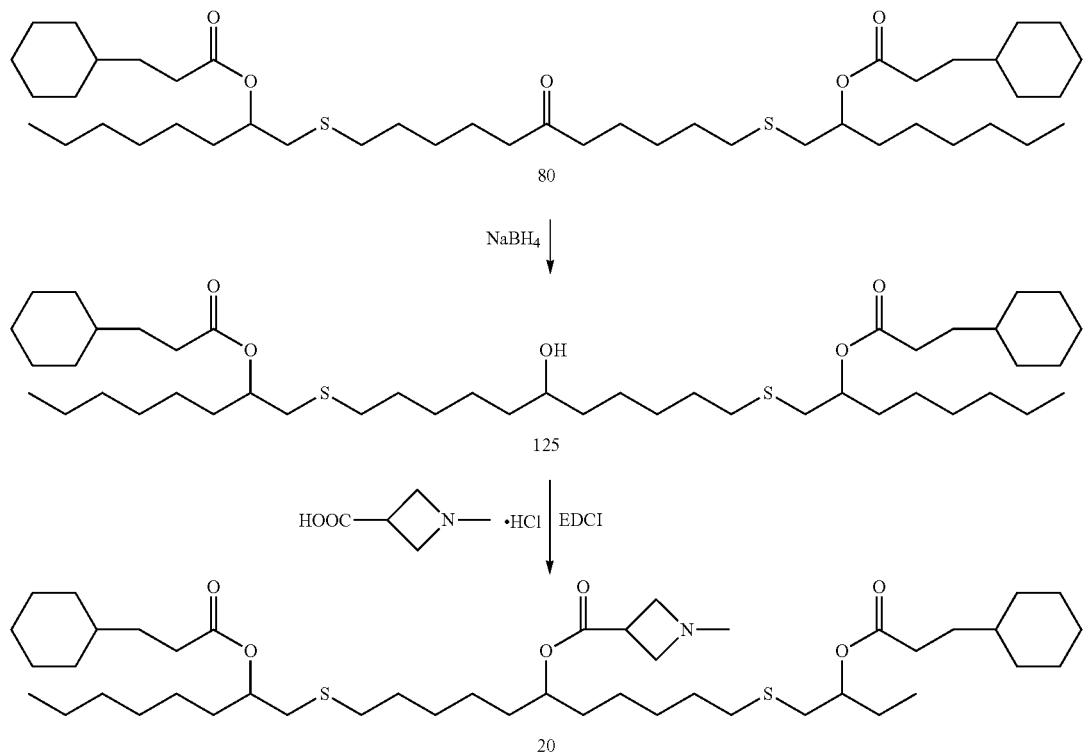
Thus, reaction of 125 with 1-bromo-2-ethoxyethene of E or Z configuration in the presence of a suitable catalyst; for example, a Bronsted acid such as pyridinium para-toluene-sulfonate (PPTS), produces bromoketal 126, which can be transformed into lipid 21 by reaction with methylamine, optionally under conditions of microwave irradiation (Scheme 28).
Scheme 28
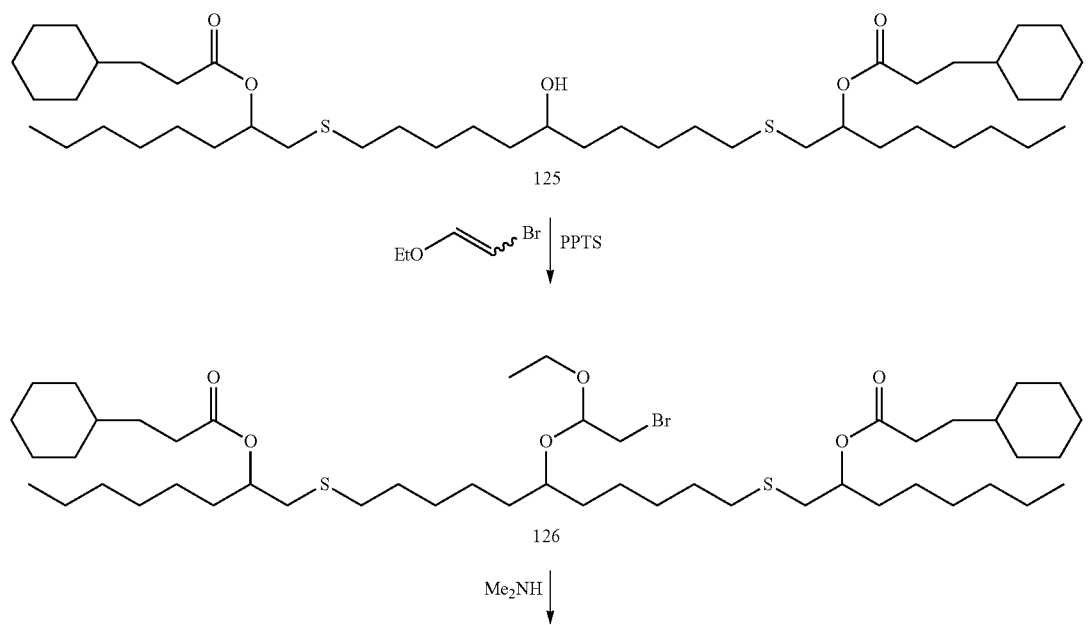

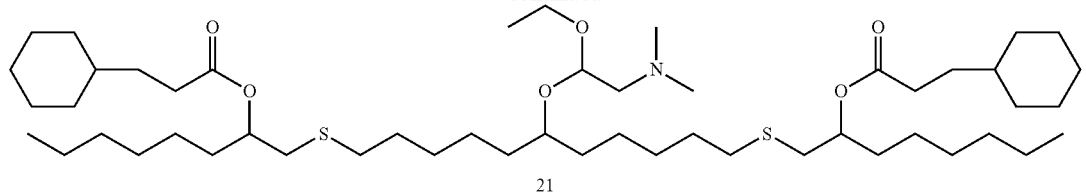 [SMILES: CCCCCCC(CSCCCCCC(CCCCCSCC(CCCCCC)OC(=O)CCC1CCCCC1)OC(CN(C)C)OCC)OC(=O)CCC1CCCCC1]

Lipid 22 can be made from ketone 80 through synthesis steps that convert the keto functionality into a type 2 ionizable head group. Accordingly, ketone 80 is transformed into ketal 127 by reaction with 1,2,4-butanetriol in the presence of a suitable catalyst; for example, a Bronsted acid such as PPTS. The OH group in 127 is converted into a good leaving group; for example, a sulfonate ester such as tosylate 128. Reaction of 128 with dimethylamine, optionally under conditions of microwave irradiation, produces lipid 22 (Scheme 29).

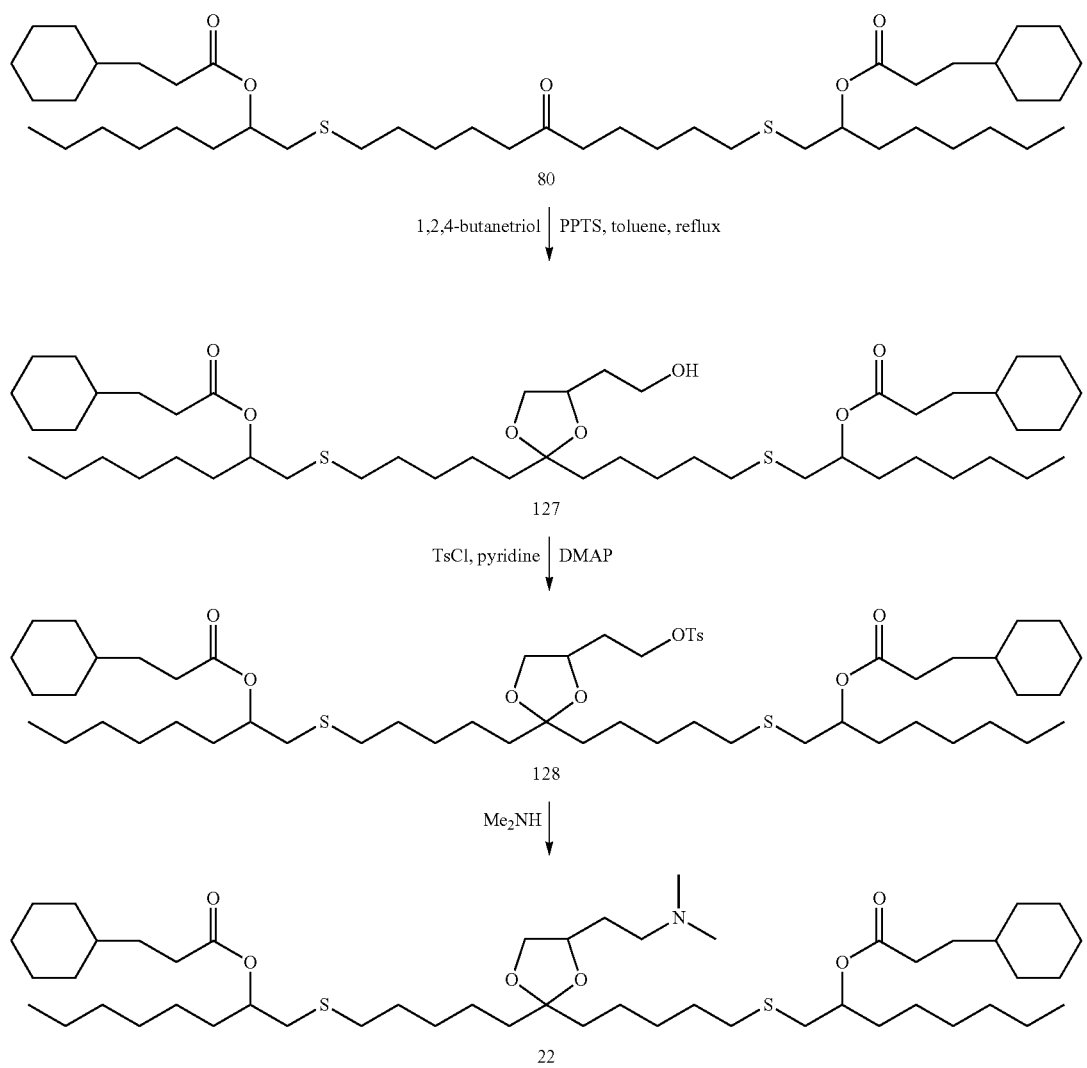

Lipids 23-35 comprise a type 7 ionizable head group. Therefore, they can be prepared from appropriate ketones of Scheme 13 by suitable modifications of the method of Scheme 26.

Lipids 23 and 24 can be obtained from ketones 78 and 77, respectively, as shown in Scheme 26 above.

Lipids 25 and 26 can be obtained from ketones 78 and 81, respectively, by a variant of the method of Scheme 26 above, wherein acetaldehyde, instead of formaldehyde, is utilized in the second reductive alkylation step.

Lipid 27 can be obtained from ketone 80 by the method of Scheme 26 above.

Lipid 28 can be prepared starting with the reductive amination of ketone 80 with compound 122 (Scheme 30). Product 129 thus obtained can be converted into 130 by reaction with $CD_3$-I. Release of the silyl group gives 28. The deuterated methyl group serves to alter the pKa of the lipid in a favorable manner.

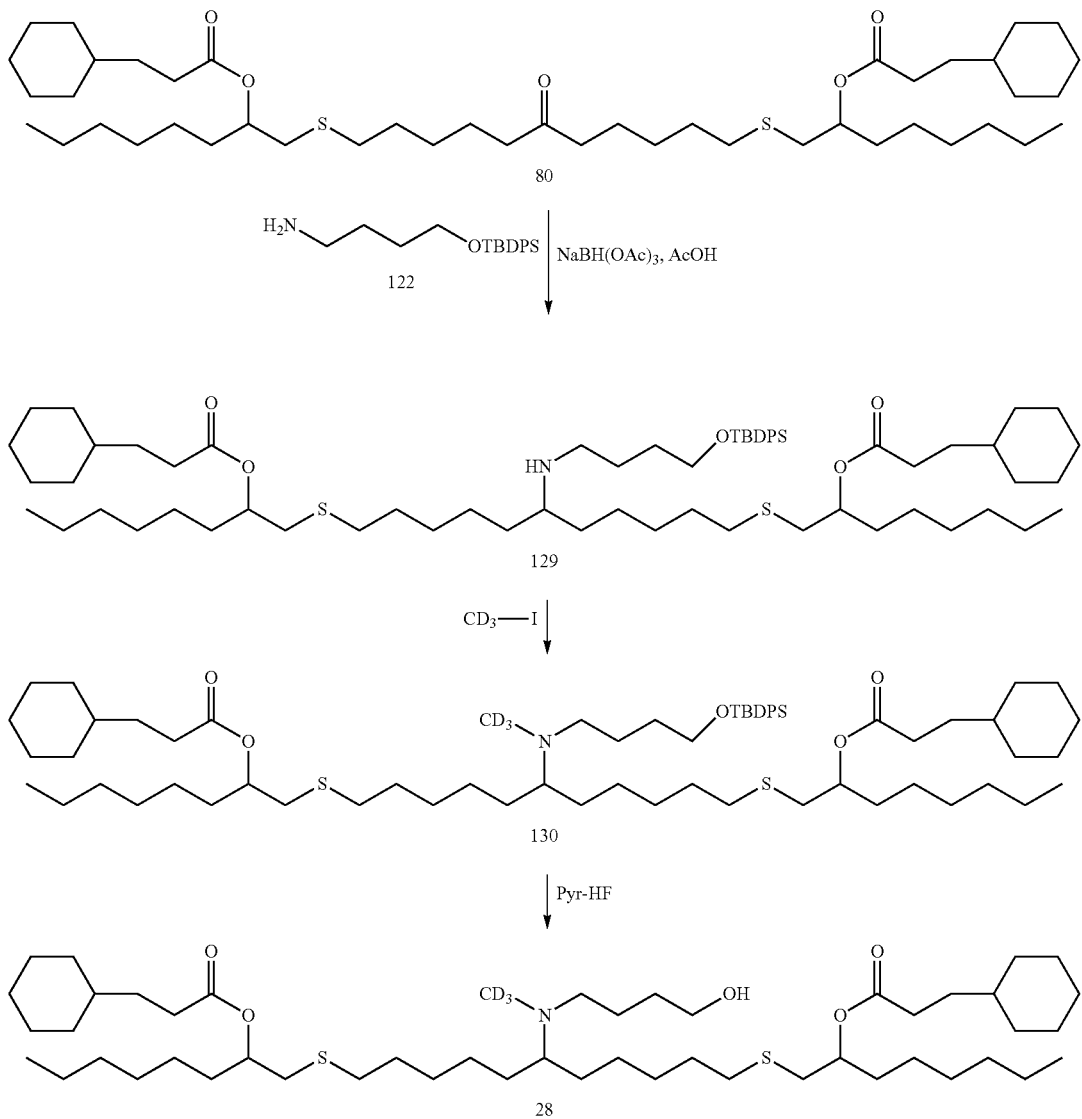

Scheme 30

Lipid 29 can be obtained from ketone 80 by the same method utilized for the synthesis of lipids 25 and 26; that is, by a variant of the method of Scheme 26 above, wherein acetaldehyde, instead of formaldehyde, is utilized in the second reductive amination step.

Lipid 30 can be obtained from ketone 80 by a variant of the method of Scheme 30 above, wherein compound 129 is N-alkylated with $CD_3$-$CD_2$-I instead of $CD_3$-I prior to release of the silyl group.

Lipids 31 and 32 can be obtained from ketone 80 by a variant of the method of Scheme 26 above, wherein the first reductive amination step is carried out with compounds 131 and 132, respectively, instead of 122 (Scheme 31).

Scheme 31

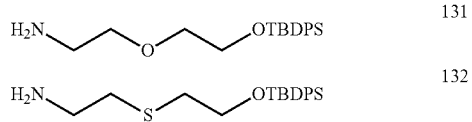

Lipids 33 and 34 can be obtained from ketones 82 and 83, respectively, by the method of Scheme 26 above.

Lipid 35 can be obtained from ketone 80 by a variant of the method of Scheme 26 above, wherein the first reductive amination step is carried out with compound 133 instead of 122 (Scheme 32).

Scheme 32

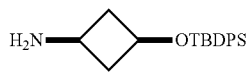

The person skilled in the art will appreciate that a diversity of lipids of the type 5-35 can be prepared by the use of alternative starting materials in the synthetic schemes above.

A ketone of general structure 39 of Scheme 2 can be prepared by appropriate modifications of the methods outlined in Schemes 20 and 21 above. For example, a route patterned after Scheme 20 start with the alkylation of TosMIC with a halide or tosylate of general formula 134 (THP=tetrahydropyranyl). This leads to 135, which can be alkylated again with a halide or tosylate of general formula 136 to produce a compound of general structure 137. Acidic hydrolysis of the latter occurs with concomitant loss of the THP group, transforming it into compound 138. The OH group in the latter can be converted into a good leaving group, for example a tosylate such as 139. Displacement of the tosylate with thioacetic acid in the presence of triethylamine converts 139 into 140, which upon reaction with methanolic NaOH and an epoxide produces 141 via release of the acetyl group and liberation of a thiolate, which nucleophilically opens the epoxide, and concomitant saponification of the methyl ester. The free acid is esterified with alcohol R'—OH and the secondary alcohol is acylated, for example with carboxylic acid $R^1$—COOH in the presence of EDCI, to give 39 (Scheme 33).

Scheme 34 shows an alternative synthetic route patterned after Scheme 21 and leading to compound 148, which is the ethyl ester analogue of 138 and can be converted into 39 by the same method shown in Scheme 33. Thus, dicarboxylic acid monoester 143 is converted into beta-ketoester 145 by the method of Oikawa, and 145 is alkylated with a halide or sulfonate of general formula 146. Compound 147 thus produced is subject to Krapcho decarbethoxylation and THP group release to give 148, which is transformed into 39 by the method described in Scheme 33.

Scheme 33

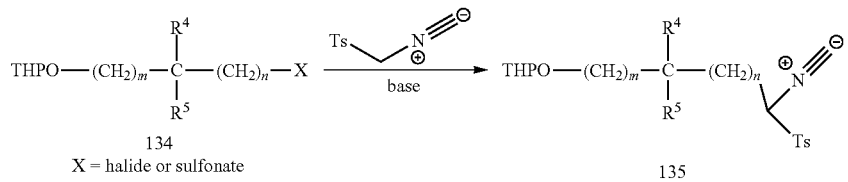

-continued
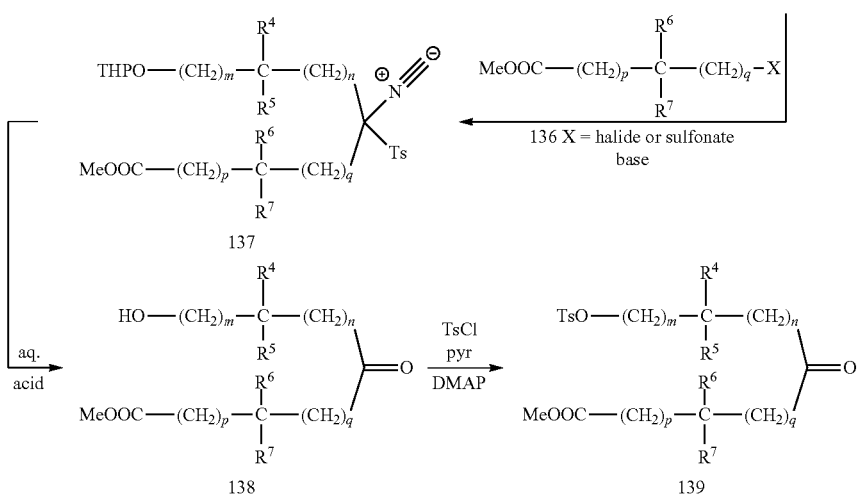
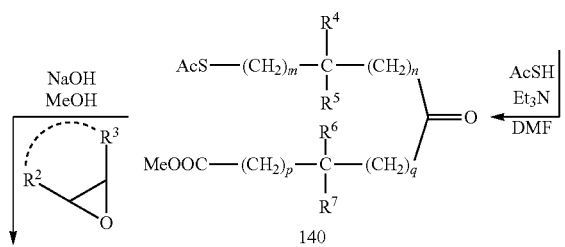
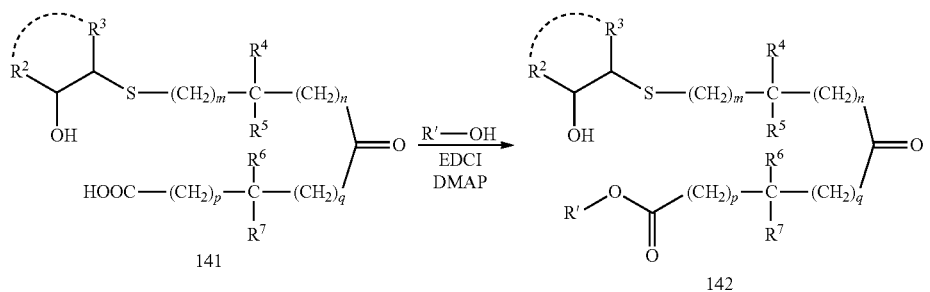
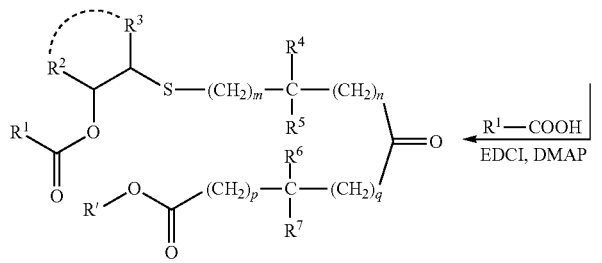

The keto group in 39 can subsequently be converted into any ionizable head group of type 1-12 by the methods described in the schemes above, thus producing lipids of Formula B wherein A is a carbonyl group.

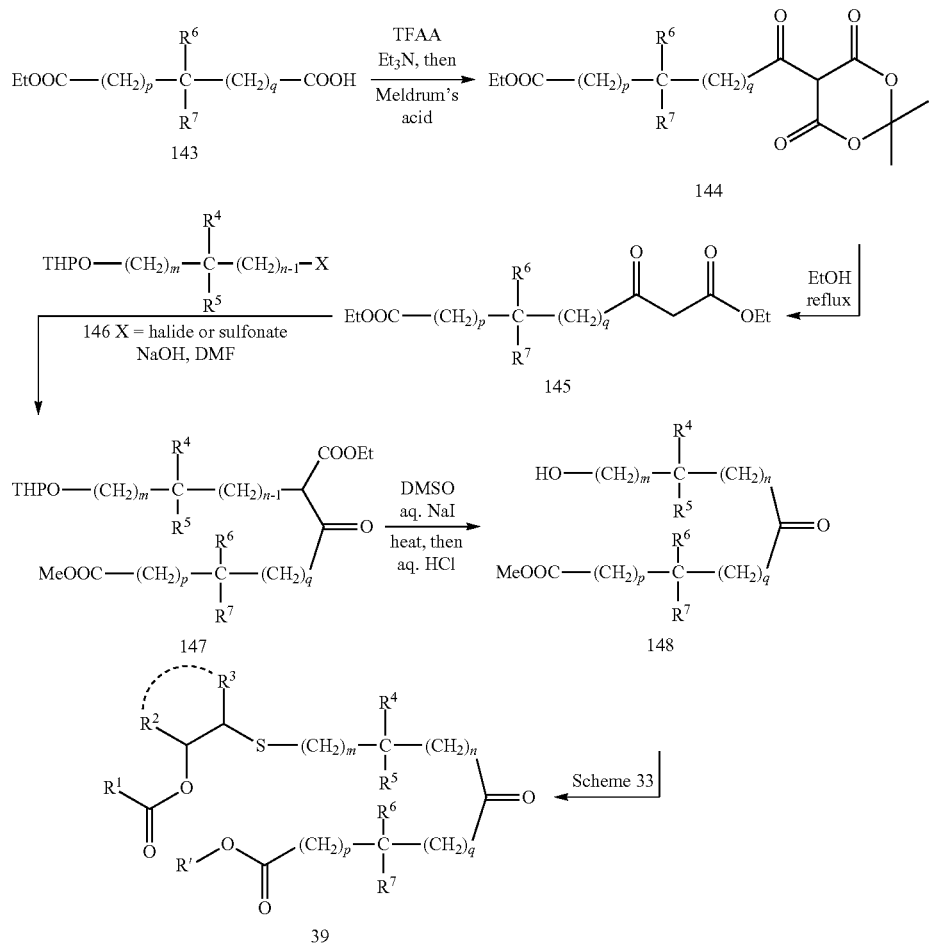

Scheme 34

Lipids of Formula A or pharmaceutically acceptable salts thereof, wherein ester group E is oriented so that $R^1$ is bound to the oxygen atom of the ester carbonyl, can be represented with the general structure of Formula C:

Formula C

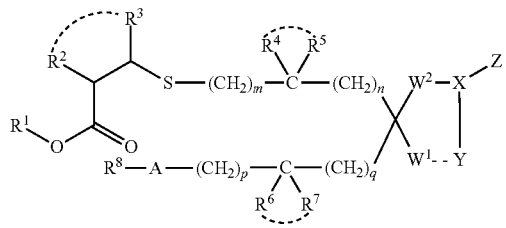

A lipid of Formula C can be prepared from an appropriate ketone of general structure 149 (Scheme 35), wherein A can be either O or S or a carbonyl (C═O), by converting the keto group into an ionizable head group of type 1-12. In turn, ketone 148 can be advantageously prepared from a thioac-etate of general formula 150. Methods for the synthesis of diverse thioacetates of general structure 150 wherein A is O or S or a carbonyl (C═O), have been thoroughly illustrated in the paragraphs above.

Scheme 35

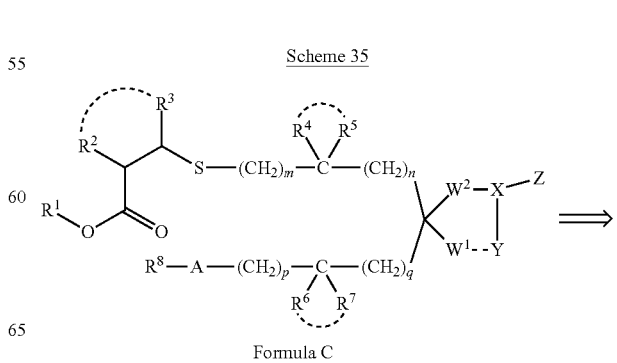

Formula C

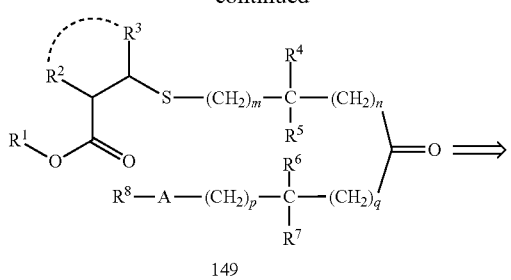

149

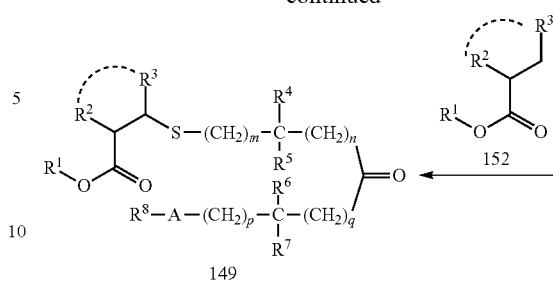

149

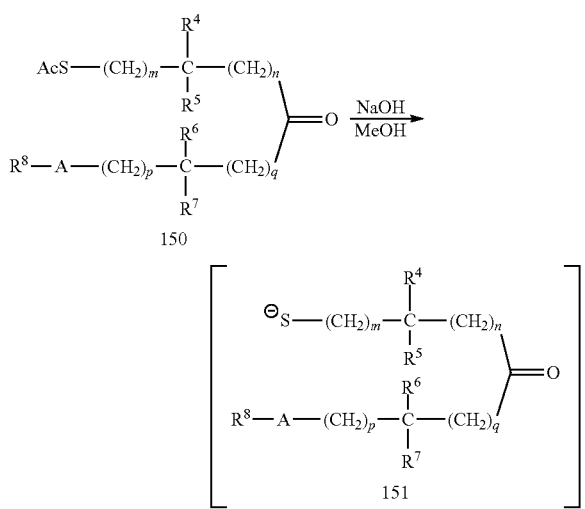

150

The conversion of a thioacetate of general formula 150 into a compound of general structure 149 can be achieved as outlined in Scheme 36. Treatment of 150 with, for example, methanolic $K_2CO_3$ in the presence of a conjugated ester of general formula 152 results in very fast release of the acetyl group. Ordinary ester groups possibly present in 150 and the ester group in 153 undergo transesterification to methyl ester at a negligible rate compared to the thioacetate ester. Accordingly, the foregoing treatment results in rapid liberation of a thiolate of general structure 151. The latter adds in a 1,4-mode to 152, resulting in formation of 149. Subsequently, the keto group in 149 can be transformed into an ionizable group of type 1-12 by the methods thoroughly illustrated in the paragraphs and schemes above, thus achieving the conversion of ketone 149 into an ionizable lipid of Formula C.

Formulation of the Above Lipids in a Delivery Vehicle

The lipids of the disclosure may be formulated in a variety of drug delivery vehicles (also referred to herein as a "delivery vehicle") known to those of ordinary skill in the art. An example of a delivery vehicle is a lipid nanoparticle, which includes liposomes, lipoplexes, polymer nanoparticles comprising lipids, polymer-based nanoparticles, emulsions, and micelles.

In one embodiment, a lipid having the structure of Formula A of the disclosure is formulated in a delivery vehicle by mixing it with additional lipids, including helper lipids, such as vesicle forming lipids and optionally an aggregation inhibiting lipid, such as a hydrophilic polymer-lipid conjugate (e.g., PEG-lipid).

As set forth previously, a helper lipid includes a sterol, a diacylglycerol, a ceramide or derivatives thereof.

Examples of sterols include cholesterol, or a cholesterol derivative, such as cholestanol, cholestanone, cholestenone, coprostanol, cholesteryl-2'-hydroxyethyl ether, cholesteryl-4'-hydroxybutyl ether, beta-sitosterol, fucosterol, and the like.

Examples of diacylglycerols include dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, a DSPC-cholesterol conjugate or mixtures thereof. These lipids may be synthesized or obtained from natural sources, such as from egg. The DSPC-cholesterol conjugate is a lipid in which one of the acyl chains is substituted with a cholesterol moiety link to the head group by a succinate linker.

A suitable ceramide derivative is egg sphingomyelin or dihydrosphingomyelin.

Delivery vehicles incorporating the lipids of the disclosure can be prepared using a wide variety of well described formulation methodologies known to those of skill in the art, including but not limited to extrusion, ethanol injection and in-line mixing. In one embodiment, the preparation method is an in-line mixing technique in which aqueous and organic solutions are mixed using a rapid-mixing device as described in Kulkarni et al., 2018, *ACS Nano*, 12:4787 and Kulkarni et al., 2017, *Nanoscale*, 36:133347, each of which is incorporated herein by reference in its entirety.

The delivery vehicle can also be a nanoparticle that is a lipoplex that comprises a lipid core stabilized by a surfactant. Vesicle-forming lipids may be utilized as stabilizers. The lipid nanoparticle in another embodiment is a polymer-lipid hybrid system that comprises a polymer nanoparticle core surrounded by stabilizing lipid. Nanoparticles comprising lipids of the disclosure may alternatively be prepared from polymers without lipids. Such nanoparticles may comprise a concentrated core of a therapeutic agent that is surrounded by a polymeric shell or may have a solid or a liquid dispersed throughout a polymer matrix.

Lipids described herein can also be incorporated into emulsions, which are drug delivery vehicles that contain oil droplets or an oil core. An emulsion can be lipid-stabilized. For example, an emulsion may comprise an oil filled core stabilized by an emulsifying component such as a monolayer or bilayer of lipids.

Lipids described herein may be incorporated into a micelle. Micelles are self-assembling particles composed of amphipathic lipids or polymeric components that are utilized for the delivery of agents present in the hydrophobic core.

Delivery of Nucleic Acid, Genetic Material, Proteins, Peptides or Other Charged Agents Lipids disclosed herein may facilitate the incorporation of a compound or molecule (referred to herein also as "cargo" or "cargo molecule") bearing a net negative or positive charge into the delivery vehicle and subsequent delivery to a target cell in vitro or in vivo.

In one embodiment, the cargo molecule is genetic material, such as a nucleic acid. The nucleic acid includes, without limitation, RNA, including small interfering RNA (siRNA), small nuclear RNA (snRNA), micro RNA (miRNA), messenger RNA (mRNA) or DNA such as vector DNA or linear DNA. The nucleic acid length can vary and can include nucleic acid of 5-50,000 nucleotides in length. The nucleic acid can be in any form, including single stranded DNA or RNA, double stranded DNA or RNA, or hybrids thereof. Single stranded nucleic acid includes antisense oligonucleotides.

In one embodiment, the cargo is an mRNA, which includes a polynucleotide that encodes at least one peptide, polypeptide or protein. The mRNA includes, but is not limited to, small activating RNA (saRNA) and trans-amplifying RNA (taRNA), as described in WO 2022/251953A1, which is incorporated herein by reference.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is a chemically synthesized molecule, the mRNA can comprise nucleoside analogs such as analogs having chemically modified bases or sugars, and/or backbone modifications. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNA of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to encapsulate mRNAs of a variety of lengths. In some embodiments, the present disclosure may be used to encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

In a further embodiment, the mRNA is circular. Advantageously, such mRNA lacks 5' and 3' ends and thus may be more stable in vivo due to its resistance to degradation by exonucleases. The circular mRNA may be prepared by any known method, including any one of the methods described in Deviatkin et al., 2023, "Cap-Independent Circular mRNA Translation Efficiency", *Vaccines*, 11(2), 238, which is incorporated herein by reference. Translation of the circular mRNA is carried out by a cap-independent initiation mechanism.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences may be incorporated into mRNA for in vitro studies or for in vivo studies in animal models to assess biodistribution.

In another embodiment, the cargo is an siRNA. An siRNA becomes incorporated into endogenous cellular machineries to result in mRNA breakdown, thereby preventing transcription. Since RNA is easily degraded, its incorporation into a delivery vehicle can reduce or prevent such degradation, thereby facilitating delivery to a target site.

The siRNA encompassed by embodiments of the disclosure may be used to specifically inhibit expression of a wide variety of target polynucleotides. The siRNA molecules targeting specific polynucleotides may be readily prepared according to procedures known in the art. An siRNA target site may be selected and corresponding siRNAs may be chemically synthesized, created by in vitro transcription, or expressed from a vector or PCR product. A wide variety of different siRNA molecules may be used to target a specific gene or transcript. The siRNA may be double-stranded RNA, or a hybrid molecule comprising both RNA and DNA, e.g., one RNA strand and one DNA strand. The siRNA may be of a variety of lengths, such as 15 to 30 nucleotides in length or 20 to 25 nucleotides in length. In certain embodiments, the siRNA is double-stranded and has 3' overhangs or 5' overhangs. In certain embodiments, the overhangs are UU or dTdT 3'. In particular embodiments, the siRNA comprises a stem loop structure.

In a further embodiment, the cargo molecule is a microRNA or small nuclear RNA. Micro RNAs (miRNAs) are short, noncoding RNA molecules that are transcribed from genomic DNA, but are not translated into protein. These RNA molecules are believed to play a role in regulation of gene expression by binding to regions of target mRNA. Binding of miRNA to target mRNA may down-regulate gene expression, such as by inducing translational repression, deadenylation or degradation of target mRNA. Small nuclear RNA (snRNA) are typically longer noncoding RNA molecules that are involved in gene splicing. The snRNA molecules may have therapeutic importance in diseases that are an outcome of splicing defects.

In another embodiment, the cargo is a DNA vector as described in co-owned and co-pending WO 2022/251959, which is incorporated herein by reference. The DNA vectors may be administered to a subject for the purpose of repairing, enhancing or blocking or reducing the expression of a cellular protein or peptide. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will preferably have some or all of the nucleotide linkages substituted with stable, non-phosphodiester linkages, including, for example, phosphorothioate, phosphorodithioate, phophoroselenate, or O-alkyl phosphotriester linkages.

The DNA vectors may include nucleic acids in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, *Faseb J.* 16(11):1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

In another embodiment, the DNA vector is a nanoplasmid or a minicircle.

Gene editing systems can also be incorporated into delivery vehicles comprising the charged lipid. This includes a Cas9-CRISPR, TALEN and zinc finger nuclease gene editing system. In the case of Cas9-CRISPR, a guide RNA (gRNA), together with a plasmid or mRNA encoding the Cas9 protein may be incorporated into a delivery vehicle comprising the lipids described herein. Optionally, a ribonucleoprotein complex may be incorporated into a delivery vehicle comprising the lipid described herein. Likewise, the disclosure includes embodiments in which genetic material encoding DNA binding and cleavage domains of a zinc finger nuclease or TALEN system are incorporated into a delivery vehicle together with the lipids of the disclosure.

While a variety of nucleic acid cargo molecules are described above, it will be understood that the above examples are non-limiting and the disclosure is not to be considered limiting with respect to the particular cargo molecule encapsulated in the delivery vehicle.

For example, the lipids described herein may also facilitate the incorporation of proteins and peptides into a delivery vehicle, which includes ribonucleoproteins. This includes both linear and non-linear peptides, proteins or ribonucleoproteins.

While pharmaceutical compositions are described above, the lipids described herein can be a component of any nutritional, cosmetic, cleaning or foodstuff product.

Pharmaceutical Formulations

The ionizable lipids of the disclosure may be present in a salt form. The salt is typically a pharmaceutically acceptable salt. Salts derived from inorganic bases include aluminum, ammonium, calcium, copper, ferric, ferrous, lithium, magnesium, manganic salts, manganous, potassium, sodium, and zinc. In one embodiment, the base is selected from ammonium, calcium, magnesium, potassium and sodium. Salts derived from pharmaceutically acceptable organic non-toxic bases include salts of primary, secondary and tertiary amines, substituted amines including naturally occurring substituted amines, cyclic amines and the like.

In some embodiments, the delivery vehicle comprising the cargo molecule is part of a pharmaceutical composition and is administered to treat and/or prevent a disease condition. The treatment may provide a prophylactic (preventive), ameliorative or a therapeutic benefit. The pharmaceutical composition will be administered at any suitable dosage.

In one embodiment, the pharmaceutical compositions is administered parentally, i.e., intra-arterially, intravenously, subcutaneously or intramuscularly. In yet a further embodiment, the pharmaceutical compositions are for intra-tumoral or in-utero administration. In another embodiment, the pharmaceutical compositions are administered intranasally, intravitreally, subretinally, intrathecally or via other local routes.

The pharmaceutical composition comprises pharmaceutically acceptable salts and/or excipients.

The compositions described herein may be administered to an individual, including a patient. The term patient as used herein is meant to be non-limiting and includes a human or a non-human subject and in which the treatment is prophylactic, diagnostic or therapeutic treatments.

The following examples are given for the purpose of illustration only and not by way of limitation on the scope of the invention.

EXAMPLES

Materials

The lipid 1,2-distearoyl-sn-glycero-3-phosphorylcholine (DSPC) and 1,2-dimyristoyl-rac-glycero-3-methoxypolyethylene glycol-2000 (PEG-DMG) were purchased from Avanti Polar Lipids (Alabaster, AL). Cholesterol and 10× Phosphate Buffered Saline (pH 7.4) were purchased from Sigma Aldrich (St Louis, MO). The ionizable amino-lipid was synthesized as previously described in WO 2022/246555, which is incorporated herein by reference.

An mRNA encoding firefly luciferase purchased from APExBIO Technology LLC (Houston, TX) was used to analyse luciferase activity.

Methods

Preparation of Lipid Nanoparticles (LNP) Containing mRNA

Lipids 1 and 5 to 35 described herein, DSPC, cholesterol, and PEG-DMG, were dissolved in ethanol at the appropriate ratios to a final concentration of 10 mM total lipid. Nucleic acid (siRNA or mRNA) was dissolved in an appropriate buffer such as 25 mM sodium acetate pH 4 or sodium citrate pH 4 to a concentration necessary to achieve the appropriate amine-to-phosphate ratios. The aqueous and organic solutions were mixed using a rapid-mixing device as described in Kulkarni et al., 2018, *ACS Nano*, 12:4787 and Kulkarni et al., 2017, *Nanoscale*, 36:133347 (each incorporated herein by reference) at a flow rate ratio of 3:1 (v/v; respectively) and a total flow rate of 20 mL/min. The resultant mixture was dialyzed directly against 1000-fold volume of PBS pH 7.4. All formulations were concentrated using an Amicon™ centrifugal filter unit and analysed using the methods described below.

Analysis of LNP

Particle size analysis of LNPs in PBS was carried out using backscatter measurements of dynamic light scattering with a Malvern Zetasizer™ (Worcestershire, UK). The reported particle sizes correspond to the number-weighted average diameters (nm). Total lipid concentrations were determined by extrapolation from the cholesterol content, which was measured using the Cholesterol E-Total Cholesterol Assay (Wako Diagnostics, Richmond, VA) as per the manufacturer's recommendations. Encapsulation efficiency of the formulations was determined using the Quant-iT RiboGreen™ Assay kit (Invitrogen, Waltham, MA). Briefly, the total siRNA or mRNA content in solution was measured by lysing lipid nanoparticles in a solution of TE containing 2% Triton Tx-100, and free DNA vector in solution (external to LNP) was measured based on the RiboGreen™ fluorescence in a TE solution without Triton. Total siRNA or mRNA content in the formulation was determined using a modified Bligh-Dyer extraction procedure. Briefly, LNP formulations containing siRNA or mRNA were dissolved in a mixture of chloroform, methanol, and PBS that results in a single phase and the absorbance at 260 nm measured using a spectrophotometer.

In Vivo Analysis in CD-1 Mice

LNP-mRNA encoding firefly luciferase were injected intravenously (tail-vein) into 6-8 week old CD-1 mice. Four hours following injection, the animals were euthanized and the liver and spleen and isolated. Tissue was homogenized in Glo Lysis buffer and a luciferase assay performed using the Steady Glo Luciferase assay kit (as per manufacturers recommendations).

Organic Synthesis of Lipids 5-35

Unless otherwise specified, all reagents and solvents were commercial products and were used without further purification, except THF (freshly distilled from Na/benzophenone under Ar), $CH_2Cl_2$ (freshly distilled from $CaH_2$ under Ar). "Dry methanol" was freshly distilled from magnesium turnings. All reactions were performed under an argon atmosphere. Reaction mixture from aqueous workups were dried by passing over a plug of anhydrous $Na_2SO_4$ held in a filter tube and concentrated under reduced pressure on a rotary evaporator. Thin-layer chromatography was performed on silica gel plates coated with silica gel (Merck 60 F254 plates) and column chromatography was performed on 230-400 mesh silica gel. Visualization of the developed chromatogram was performed by staining with $I_2$ or potassium permanganate solution. $^1H$ and $^{13}C$ nuclear magnetic resonance (NMR) spectra were recorded at room temperature in $CDCl_3$ solutions. $^1H$ NMR spectra were referenced to residual $CHCl_3$ (7.26 ppm) and $^{13}C$ NMR spectra were referenced to the central line of the $CDCl_3$ triplet (77.00 ppm). Chemical shifts are reported in parts per million (ppm) on the δ scale. Multiplicities are reported as "s"

(singlet), "d" (doublet), "t" (triplet), "q" (quartet), "m" (multiplet), and further qualified as "app" (apparent) and "br" (broad). Low- and high-resolution mass spectra (m/z) were obtained in the electrospray (ESI) and field desorption/field ionisation (FD/FI) mode.

The synthesis of lipids 5-15 from caprolactone was carried out as set forth below. As discussed, the synthesis of said lipids involves subjecting certain esters or lactones to Claisen condensation under Mukaiyama conditions. This technology is as set forth in co-owned and co-pending WO 2023/147657 (incorporated herein by reference). The products of such Claisen reactions are subsequently converted into the final products as outlined in the Schemes above and as described below.

Example 1: Methods for Chemically Synthesizing Ionizable Lipids (A) Preparation of Building Blocks (i) 3-(6-hydroxyhexanoyl)oxepan-2-one (61)

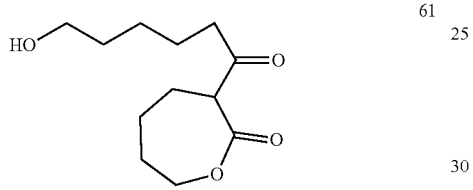

61

Titanium tetrachloride TiCl$_4$ (1.25 mL, 11.39 mmol, 1.3 equiv) was added by syringe pump over 30 minutes to a cold (−78° C.), well-stirred solution of caprolactone (0.97 mL, 8.77 mmol, 1.0 equiv.) and triethylamine (1.8 mL, 13.14 mmol, 1.5 equiv.) in dichloromethane (20 mL), under argon. The resulting mixture was warmed up to room temperature and stirring was continued for 2 h, followed by quenching with water (25 mL) at 0° C. The organic layer was removed and the aqueous layer was further extracted with dichloromethane (5×25 mL). The combined organic layers were washed with brine (sat. solution), dried (Na$_2$SO$_4$), filtered, and concentrated in vacuo. The residue was purified by flash column chromatography on silica gel by eluting with dichloromethane:acetone (9:1) to afford 61 (922 mg, 4.03 mmol, 92%) as a colorless oil. $^1$H NMR (300 MHz, CDCl$_3$) δ 4.39-4.13 (2H, m), 3.67-3.55 (3H, m), 2.61 (1H, dt, J 17.4, 7.4), 2.44 (1H, dt, J 17.4, 7.2), 2.17-1.85 (3H, m), 1.85-1.65 (2H, m), 1.65-1.46 (6H, m, 3×CH$_2$), 1.36 (2H, m). $^{13}$C NMR (75 MHz, CDCl$_3$) δ 205.0, 173.4, 69.7, 62.8, 56.4, 41.6, 32.6, 28.9, 27.4, 25.3, 25.1, 23.4.

(ii) 6-oxo-6-(2-oxooxepan-3-yl)hexyl 4-methylbenzenesulfonate (62)

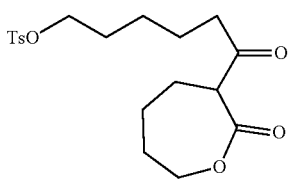

62

To a solution of 3-(6-hydroxyhexanoyl)oxepan-2-one, (1.0 gm, 4.38 mmol, 1.0 equiv), pyridine (0.46 mL, 5.69 mmol, 1.3 equiv) and N,N-dimethyl aminopyridine (tip of a spatulaful) in dichloromethane (10 mL) at room temperature was added p-toluenesulfonyl chloride (1.25 g, 6.57 mmol, 1.5 equiv). The resulting mixture was stirred at room temperature for 5 hrs then quenched with water (25 mL). The organic layer was removed, and the aqueous layer was further extracted with dichloromethane (3×25 mL). The combined organic layers were washed with brine (sat. solution), dried (Na$_2$SO$_4$), filtered, and concentrated in vacuo to afford 62 (1.40 g, 3.67 mmol, 84%) as a colorless oil. $^1$H NMR (300 MHz, CDCl$_3$) δ 7.75 (2H, d, J=8.3), 7.32 (2H, d, J=8.1), 4.33 (1H, dd, J=12.5, 4.1), 4.20 (1H, dd, J=12.5, 10), 3.98 (2H, t, J=6.4), 3.60 (1H, dd, J=11, 2), 2.57 (1H, dd, J=17.4, 7.3), 2.42 (3H, s), 2.36 (1H, dd, J 17.3, 7.4), 2.13-1.91 (2H, m), 1.80-1.15 (10H, m), 1.36-1.23 (2H, m). $^{13}$C NMR (75 MHz, CDCl$_3$) δ 204.4, 173.2, 144.8, 133.1, 129.9, 127.9, 70.4, 69.5, 56.1, 41.2, 28.7, 28.6, 27.3, 24.9, 24.8, 22.8, 21.6.

(iii) S-(6-oxo-6-(2-oxooxepan-3-yl)hexyl) ethanethioate (63)

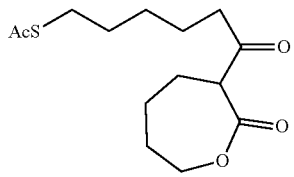

63

To a solution of 6-oxo-6-(2-oxooxepan-3-yl)hexyl 4-methylbenzenesulfonate (crude, 1.40 g, nominally 3.67 mmol) and TEA (1.3 mL, 964 mg, 9.5 mmol, 2.6 equiv) in DMF (10.0 mL) was added thioacetic acid (668 uL, 722 mg, 9.5 mmol, 2.6 equiv). The mixture was stirred at 60° C. for 16 hours, diluted with water (50.0 mL) and extracted with hexanes (3×40.0 mL). The combined extracts were washed (brine), dried (Na$_2$SO$_4$) and concentrated to yield 63 (745 mg, 71% over 2 steps). $^1$H NMR (400 MHz, CDCl$_3$) δ 4.33 (dd, J 12.5, 4.1, 1H), 4.20 (dd, J 12.5, 10, 1H), 3.60 (dd, J 11, 2, 1H), 2.84 (t, J=7.3 Hz, 2H), 2.56 (dd, J 17.4, 7.3, 1H), 2.42 (s, 3H), 2.36 (1H, dd, J 17.3, 7.4, CH$_2$CO), 2.31 (s, 3H), 2.13-1.91 (2H, m, CH$_2$), 1.80-1.151 (10H, m, 4×CH$_2$), 1.36-1.23 (2H, m, CH$_2$).

(iv) 1-hydroxy-11-((2-hydroxyoctyl)thio)undecan-6-one (64)

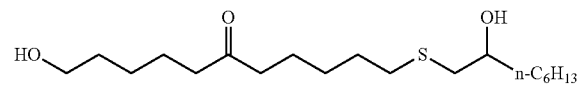

64

A solution of S-(6-oxo-6-(2-oxooxepan-3-yl)hexyl) ethanethioate (23, 760 mg, 2.65 mmol), 2-hexyloxirane (0.486 mL, 3.18 mmol) and NaOH (318 mg, 7.95 mmol) in EtOH (8.00 mL) was stirred at reflux for 4 hours under nitrogen, then it was cooled to rt, diluted with water (15.0 mL), acidified to pH 2 with conc. HCl and extracted with DCM (3×20.0 mL). The combined organics were dried (Na$_2$SO$_4$) and concentrated. The residue was purified by silica chromatography (0-75% EtOAc in hexanes) to yield 64 (829 mg, 90%). $^1$H NMR (400 MHz, CDCl$_3$) δ 3.62 (m, 2H), 3.58 (m, 1H), 2.71 (m, 1H), 2.47-2.32 (m, 7H), 1.68-1.18 (m, 22H), 0.87 (t, J=7.2 Hz, 3H).

(v) 11-((2-Hydroxyoctyl)thio)-6-oxoundecyl cyclo-pentadecanecarboxylate (65)

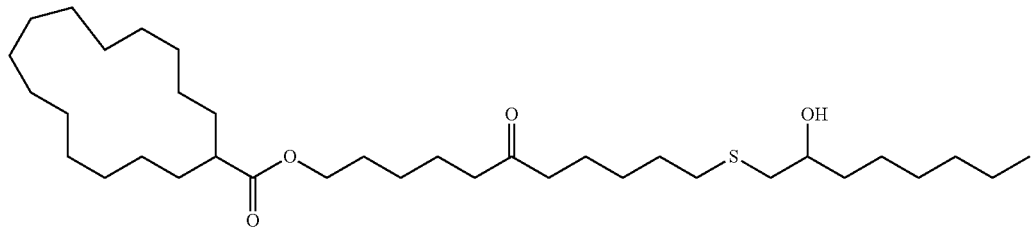

To a reaction vial containing starting cyclopentadecane carboxylic acid (520 mg, 2.04 mmol), under inert atmosphere was added $CH_2Cl_2$ (3 mL), EDCI-HCl (361 mg, 1.88 mmol), and DMAP (192 mg, 1.57 mmol). Then alcohol 64 (500 mg, 1.57 mmol) was added to the mixture. The mixture was stirred for 18 h then washed with NaOH (0.1 M, 10 mL). The aq. phase was back-extracted with $CH_2Cl_2$ (2×10 mL), collected, dried over $Na_2SO_4$, filtered, and evaporated to yield a crude product. The product 0.55 g, 60% was purified by column chromatography (20% EtOAc/Hexanes). $^1$H NMR (400 MHz, $CDCl_3$) δ 4.04 (td, J=6.63, 1.77 Hz, 2H), 3.69-3.52 (m, 1H), 2.72 (dt, J=13.59, 2.77 Hz, 1H), 2.59-2.48 (m, 3H), 2.44-2.31 (m, 6H), 1.76-1.17 (m, 50H), 0.85 (q, J=9.69 Hz, 3H). LRMS m/z 605 [M+Na]$^+$.

(vi) 11-((2-((3-Cyclohexylpropanoyl)oxy)octyl)thio)-6-oxoundecyl cyclopentadecane-carboxylate (54)

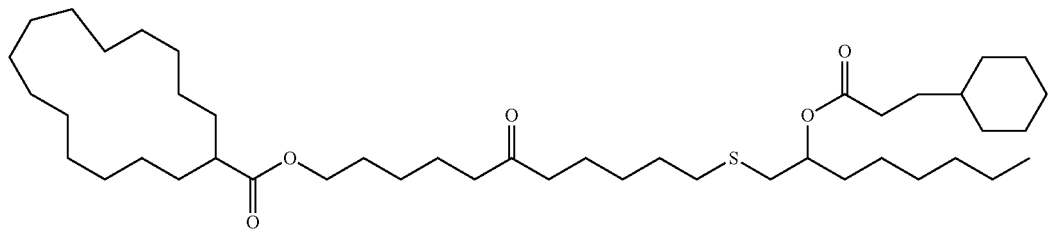

To a reaction vial containing 3-cyclohexylpropanoic acid (386 mg, 2.47 mmol), under inert atmosphere was added DCM (3 mL), EDCI-HCl (592 mg, 3.1 mmol), and DMAP (377 mg, 3.1 mmol). Then alcohol 65 (1.2 g, 2.06 mmol) was added to the mixture. The mixture was stirred for 18 h then washed with NaHCO$_3$ (sat, 2×10 mL). The aq. phase was back-extracted with DCM (2×10 mL), collected, dried over Na$_2$SO$_4$, filtered, and evaporated. The residue was purified by silica chromatography (10% EtOAc/Hex) to yield desired product (1.0 g, 67%) as a colorless liquid. $^1$H NMR (400 MHz, CDCl$_3$) δ 5.02-4.82 (m, 1H), 4.04 (t, J=6.61 Hz, 2H), 2.68-2.57 (m, 2H), 2.52 (m, 2H), 2.43-2.35 (m, 5H), 2.35-2.25 (m, 2H), 1.75-1.46 (m, 21H), 1.44-1.01 (m, 40H), 0.92-0.79 (m, 5H). LRMS m/z 743 [M+Na]$^+$.

(vii) 11-((2-hydroxyoctyl)thio)-6-oxoundecyl 2-hexyldecanoate (66)

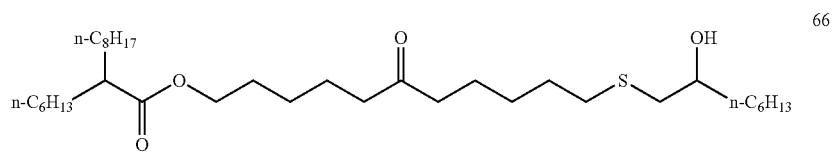

To a solution of 64 (500 mg, 1.45 mmol), EDCI-HCl (307 mg, 1.60 mmol) and DMAP (195 mg, 1.60 mmol) in DCM (6.00 mL) was added 2-hexyldecanoic acid (372 mg, 1.45 mmol) at room temperature under an atmosphere of nitrogen. The reaction was stirred for 18 hours at room temperature, concentrated, then the residue was purified by silica chromatography (0-35% EtOAc in hexanes) to yield 66 (692 mg, 82%). $^1$H NMR (400 MHz, CDCl$_3$) δ 4.06 (t, J=6.6 Hz, 2H), 3.68-3.57 (m, 1H), 2.73 (dd, J=13.6, 3.3 Hz, 1H), 2.52 (t, J=7.3 Hz, 2H), 2.47-2.36 (m, 5H), 2.35-2.24 (m, 1H), 1.73-1.18 (m, 46H), 0.94-0.82 (m, 9H).

(viii) 11-((2-(Octanoyloxy)octyl)thio)-6-oxoundecyl 2-hexyldecanoate (55)

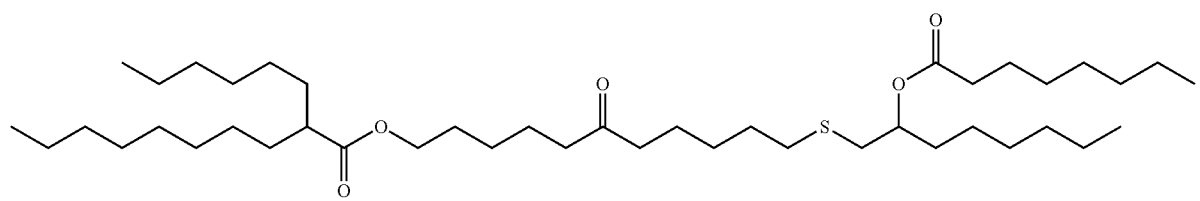

Prepared from 66 and octanoic acid according to the procedure of part (vii) above. $^1$H NMR (400 MHz, CDCl$_3$) δ 5.02-4.89 (m, 1H), 4.06 (t, J=6.6 Hz, 2H), 2.65-2.61 (m, 2H), 2.53 (td, J=7.3, 2.1 Hz, 2H), 2.39 (td, J=7.4, 2.2 Hz, 4H), 2.34-2.26 (m, 3H), 1.71-1.13 (m, 55H), 0.94-0.80 (br t, 12H).

(ix) 11-((2-((6-Methylheptanoyl)oxy)octyl)thio)-6-oxoundecyl 2-hexyldecanoate (56)

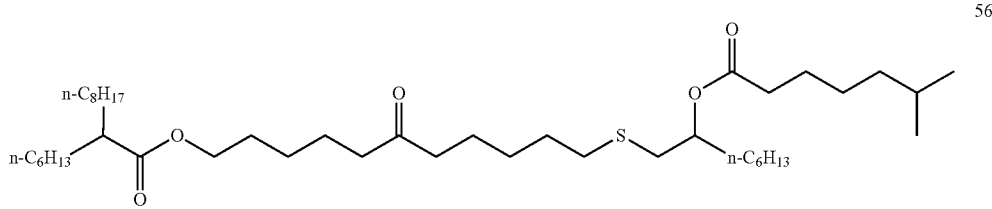

Prepared from 66 and 6-methylheptanoic acid according to the procedure of part (vii) above. $^1$H NMR (400 MHz, CDCl$_3$) δ 5.02-4.89 (m, 1H), 4.06 (t, J=6.6 Hz, 2H), 2.65-2.61 (m, 2H), 2.53 (td, J=7.3, 2.1 Hz, 2H), 2.39 (td, J=7.4, 2.2 Hz, 4H), 2.34-2.26 (m, 3H), 1.71-1.13 (m, 53H), 0.94-0.80 (m, 15H).

(x) 11-((2-((3-cyclohexylpropanoyl)oxy)octyl)thio)-6-oxoundecyl 2-hexyldecanoate (57)

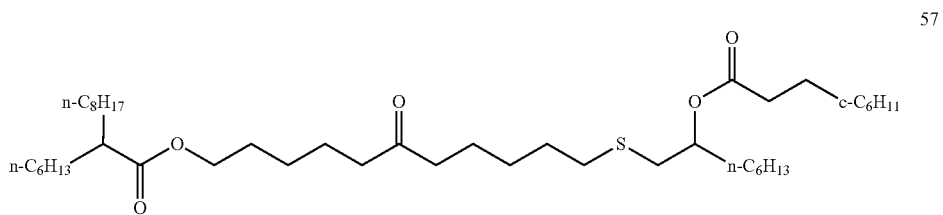

Prepared from 66 and cyclohexylpropanoic acid according to the procedure of part (vii) above. $^1$H NMR (400 MHz, CDCl$_3$) δ 5.00-4.84 (m, 1H), 4.05 (t, J=6.6 Hz, 2H), 2.68-2.57 (m, 1H), 2.57-2.48 (m, 2H), 2.39 (td, J=7.4, 2.1 Hz, 4H), 2.34-2.25 (m, 4H), 1.78-1.05 (m, 57H), 0.95-0.81 (m, 11H).

(xi) 1-((11-((2-Hexyldecanoyl)oxy)-6-oxoundecyl)thio)octan-2-yl cycloheptane-carboxylate (58)

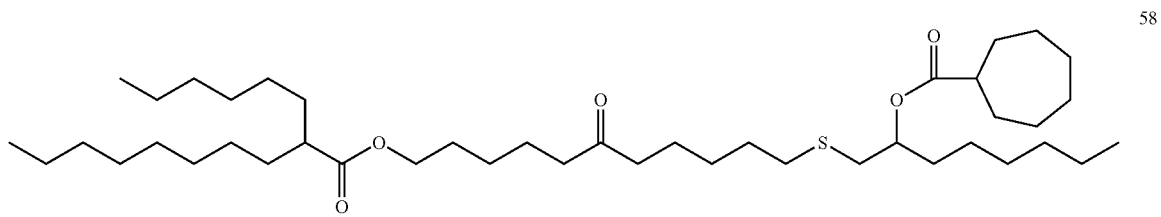 [SMILES: CCCCCCCCC(CCCCCC)C(=O)OCCCCCC(=O)CCCCCSCC(CCCCCC)OC(=O)C1CCCCCC1]

Prepared from 66 and cycloheptane carboxylic acid according to the procedure of part (vii) above. $^1$H NMR (400 MHz, CDCl$_3$) δ 4.93 (m, 1H), 4.06 (t, J=6.6 Hz, 2H), 2.70-2.59 (m, 2H), 2.58-2.53 (m, 4H), 2.52-2.44 (m, 1H), 2.41 (br t, 2H), 2.35-2.24 (m, 1H), 2.01-1.90 (m, 2H), 1.80-1.23 (m, 56H), 0.94-0.82 (m, 9H).

(xii) 11-((2-(2-Cycloheptylacetoxy)octyl)thio)-6-oxoundecyl 2-hexyldecanoate (59)

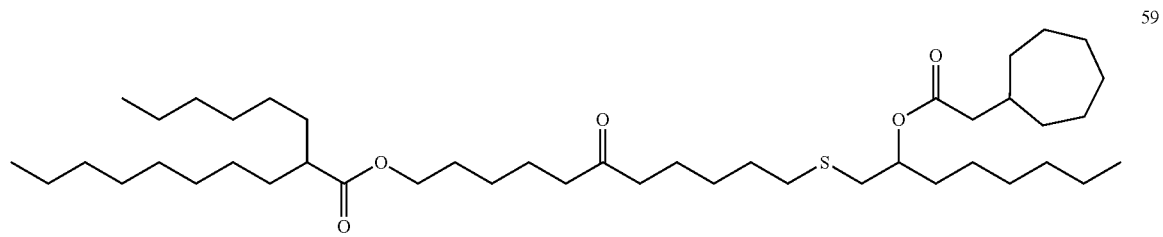 [SMILES: CCCCCCCCC(CCCCCC)C(=O)OCCCCCC(=O)CCCCCSCC(CCCCCC)OC(=O)CC1CCCCCC1]

Prepared from 66 and 2-cycloheptylacetic acid according to the procedure of part (vii) above. $^1$H NMR (400 MHz, CDCl$_3$) δ 5.01-4.90 (m, 1H), 4.06 (t, J=6.6 Hz, 2H), 2.70-2.60 (m, 2H), 2.59-2.50 (m, 4H), 2.49-2.40 (m, 1H), 2.36-2.26 (m, 1H), 2.22 (d, J=7.3 Hz, 2H), 2.06-1.95 (m, 1H), 1.78-1.15 (m, 59H), 0.91-0.84 (br t, 9H).

(xiii) 5-Pentyloxepan-2-one (71)

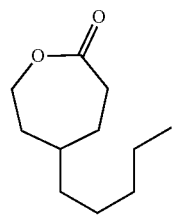

To a solution of meta-chloroperoxybenzoic acid (16.24 gm, 94.08 mmol, 2 equiv.) in CH$_2$Cl$_2$ (30 mL) at 0° C. was added 4-pentylcyclohexanone (7.9, 47.04 mmol, 1.0 equiv.). After stirring for 5 days at 40° C., the reaction mixture was filtered, washed with saturated aq. Na$_2$S$_2$O$_3$, saturated aq. NaHCO$_3$ and water, dried over Na$_2$SO$_4$ and concentrated in vacuo to afford 71 (8.6 g, ~quantitative) as a colorless oil that was used for the next step without further purification. $^1$H NMR (400 MHz, CDCl$_3$) 4.34-4.29 (m, 1H), 4.21-4.15 (m, 1H), 3.70-3.65 (m, 1H), 2.73-2.57 (m, 2H), 2.02-1.90 (m, 2H), 1.63-1.29 (s, 8H), 0.92-0.88 (t, 3H, J=6.82 Hz).

(xiv) 3-(4-(2-Hydroxyethyl)nonanoyl)-5-pentyloxepan-2-one (72)

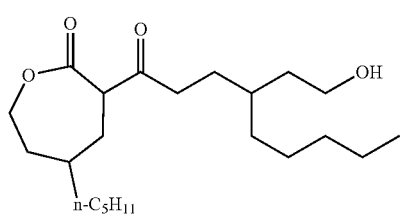

Prepared from 71 according to the procedure of part (i) above. $^1$H NMR (400 MHz, CDCl$_3$) δ 7.81-7.79 (d, 2H, J=6.96 Hz), 7.38-7.36 (d, 2H, J=6.96 Hz), 4.41-4.25 (m, 2H), 4.10-4.01 (m, 2H), 3.69-3.66 (m, 1H), 2.65-2.57 (m, 1H), 2.49-2.35 (m, 4H), 2.20-2.16 (m, 1H), 2.02-1.99 (m, 1H), 1.61-1.14 (s, 24H), 0.91-0.84 (m, 6H).

(xv) 3-(3-Oxo-3-(2-oxo-5-pentyloxepan-3-yl)propyl) octyl 4-methylbenzenesulfonate (73)

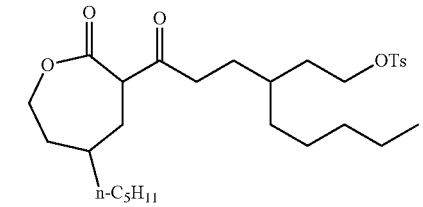

Prepared from 72 according to the procedure of part (ii) above. $^1$H NMR (400 MHz, CDCl$_3$) δ 7.81-7.79 (d, 2H, J=6.96 Hz), 7.38-7.36 (d, 2H, J=6.96 Hz), 4.41-4.25 (m, 2H), 4.10-4.01 (m, 2H), 3.69-3.66 (m, 1H), 2.65-2.57 (m, 1H), 2.49-2.35 (m, 4H), 2.20-2.16 (m, 1H), 2.02-1.99 (m, 1H), 1.61-1.14 (s, 24H), 0.91-0.84 (m, 6H).

(xvi) S-(3-(3-Oxo-3-(2-oxo-5-pentyloxepan-3-yl)propyl)octyl) ethanethioate (74)

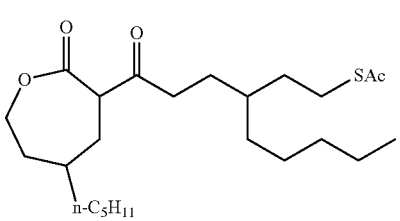

Prepared from 73 according to the procedure of part (iii) above. ¹H NMR (400 MHz, CDCl₃) δ 4.40-4.23 (m, 2H), 3.69-3.66 (m, 1H), 2.84 (br, J=7.3 Hz, 2H), 2.65-2.57 (m, 1H), 2.49-2.35 (m, 4H), 2.31 (s, 3H), 2.20-2.16 (m, 1H), 2.02-1.99 (m, 1H), 1.61-1.14 (s, 24H), 0.91-0.84 (m, 6H).

(xvii) 6-(2-Hydroxyethyl)-12-(2-((2-hydroxyhexyl)thio)ethyl)heptadecan-9-one (75)

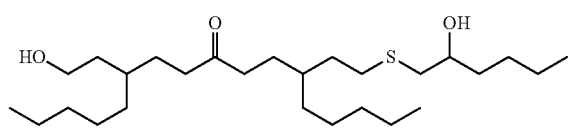

Prepared from 74 and 1-hexene oxide according to the procedure of part (iv) above. ¹H NMR (400 MHz, CDCl₃) δ 3.76-3.66 (m, 3H), 2.56-2.52 (m, 2H), 2.49-2.39 (m, 4H), 2.99 (brs, 2H), 1.67-1.27 (s, 34H), 0.95-0.88 (m, 9H).

(xviii) 6-(2-(((1R,2R)-2-Hydroxycyclohexyl)thio)ethyl)-12-(2-hydroxyethyl)hepta-decan-9-one (76)

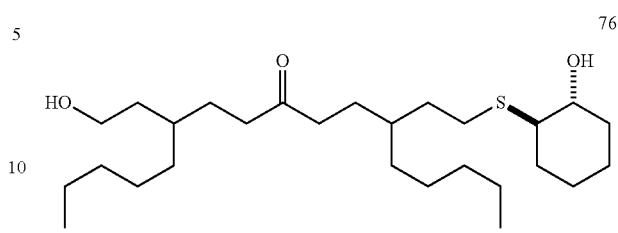

Prepared from 74 and cyclohexene oxide according to the procedure of part (iv) above. ¹H NMR (400 MHz, CDCl₃) δ 3.76-3.65 (m, 2H), 3.35-3.29 (m, 1H), 2.61-2.53 (m, 2H), 2.47-2.34 (m, 4H), 2.19-2.08 (m, 3H), 1.79-1.73 (m, 3H), 1.67-1.43 (s, 11H), 1.32-1.27 (m, 20H), 0.92-0.88 (m, 6H).

(xix) 1-((9-(2-(Octanoyloxy)ethyl)-6-oxo-3-pentyltetradecyl)thio)hexan-2-yl octanoate (67)

A solution of 75 (1.03 g, 2.24 mmol), octanoic acid (806 mg, 5.60 mmol), EDCI-HCl (1.12 g, 5.83 mmol) and DMAP (712 mg, 5.83 mmol) in CH₂Cl₂ (20.0 mL) was stirred at room temperature under nitrogen for 18 hours then concentrated. The residue was purified by silica chromatography (0-10% EtOAc in Hexanes) to yield 67 (1.4 g, 1.95 mmol 87%). ¹H NMR (400 MHz, CDCl₃) δ 5.03-4.94 (m, 1H), 4.12-4.08 (t, 2H, J=7.01 Hz),

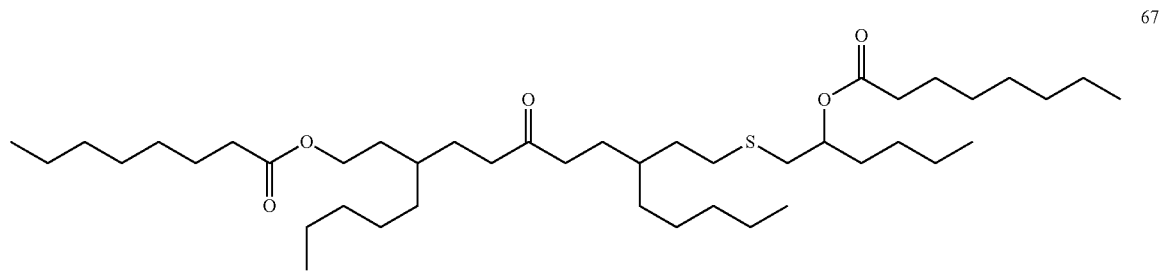 [SMILES: CCCCCCCC(=O)OCCC(CCCCC)CCC(=O)CCC(CCCCC)CCSCC(CCCC)OC(=O)CCCCCCC]

2.67-2.65 (m, 2H), 2.57-2.51 (m, 2H), 2.43-2.39 (m, 4H), 2.34-2.28 (m, 4H), 1.68-1.27 (m, 55H), 0.93-0.88 (m, 12H).

(xx) 1-((9-(2-((3-Cyclohexylpropanoyl)oxy)ethyl)-6-oxo-3-pentyltetradecyl)thio)-hexan-2-yl 3-cyclohexylpropanoate (68)

Prepared from 76 and 3-

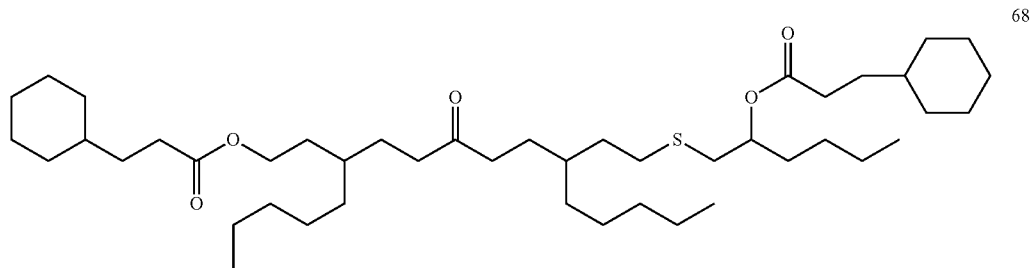 [SMILES: CCCCCC(CCOC(=O)CCC1CCCCC1)CCC(=O)CCC(CCCCC)CCSCC(CCCC)OC(=O)CCC1CCCCC1]

cyclohexylpropanoic acid according to the procedure of part (xix) above. $^1$H NMR (400 MHz, CDCl$_3$) δ 4.99-4.93 (m, 1H), 4.10-4.08 (t, 2H, J=7.06 Hz), 2.67-2.65 (m, 2H), 2.56-2.53 (m, 2H), 2.43-2.39 (m, 4H), 2.35-2.29 (m, 4H), 1.73-1.09 (m, 55H), 0.92-0.88 (m, 12H).

(xxi) 9-(2-(((1R*,2R*)-2-(Octanoyloxy)cyclohexyl)thio)ethyl)-6-oxo-3-pentyltetradecyl octanoate (69)

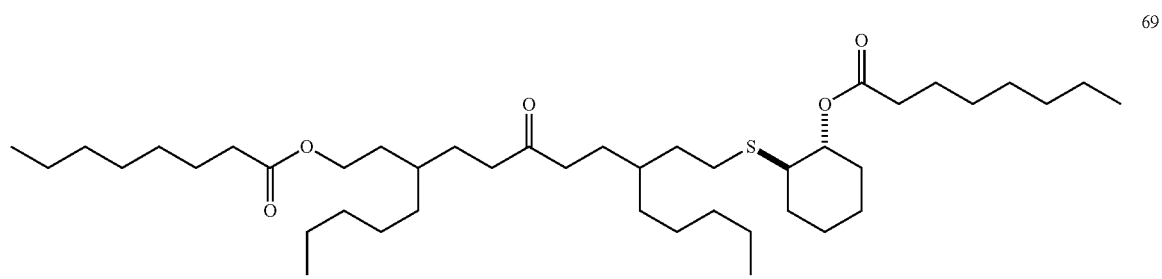

Prepared from 76 and octanoic acid according to the procedure of part (xix) above. $^1$H NMR (400 MHz, CDCl$_3$) δ 4.80-4.74 (m, 1H), 4.12-4.08 (t, 2H, J=7.06 Hz), 2.70-2.55 (m, 3H), 2.43-2.29 (m, 8H), 2.11-2.03 (m, 2H), 1.71-1.27 (m, 50H), 0.92-0.88 (m, 12H).

(xxii) 9-(2-(((1R*,2R*)-2-((3-Cyclohexylpropanoyl)oxy)cyclohexyl)thio)ethyl)-6-oxo-3-pentyltetradecyl 3-cyclohexylpropanoate (70).)

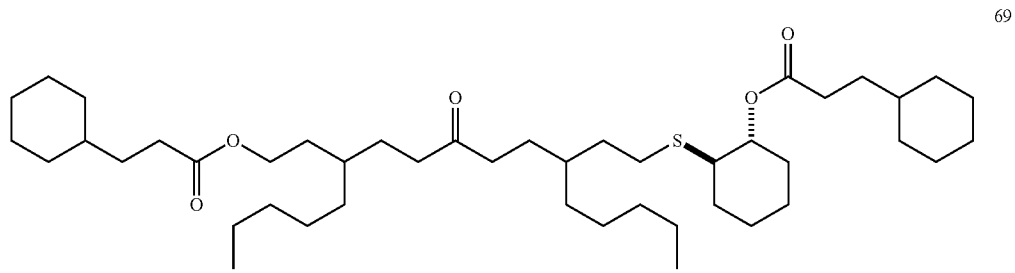

Prepared from 76 and 3-cyclohexylpropanoic acid according to the procedure of part (xix) above. $^1$H NMR (400 MHz, CDCl$_3$) δ 4.79-4.73 (m, 1H), 4.11-4.08 (m, 2H), 2.70-2.55 (m, 3H), 2.43-2.29 (m, 7H), 2.11-2.03 (m, 2H), 1.73-1.13 (m, 56H), 0.95-0.87 (m, 9H).

(xxiii) Methyl 6-(acetylthio)hexanoate (89)

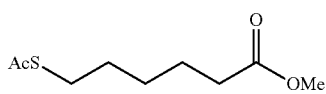

To an RBF under inert atmosphere was added DMF (225 mL) and ethyl 6-bromohexanoate (50.0 g, 40 mL, 224 mmol). The solution was degassed by sparging with N$_2$ for 10 min, then triethylamine (34.0 g, 44 mL, 336 mmol) and thioacetic acid (20.0 g, 19 mL, 336 mmol) were added in order at ambient temperature (initial exothermic reaction (~50° C.) was observed when thioacetic acid was added). The mixture was stirred 1.5 h at 60° C., then diluted with water (250 mL) and extracted with hexanes (250 mL). The aqueous phase was back-extracted with hexanes (2×150 mL). The combined organic phases were washed with water (300 mL), dried (Na$_2$SO$_4$), decolorized with carbon, filtered and evaporated to yield crude 89 (51.5 g, 236 mmol, >95% yield), which was carried forward without purification. $^1$H NMR (400 MHz, CDCl$_3$) δ=4.11 (q, J=7.2 Hz, 2H), 2.85 (t, J=7.3 Hz, 2H), 2.31 (s, 3H), 2.28 (t, J=7.5 Hz, 2H), 1.67-1.53 (m, 4H), 1.43-1.33 (m, 2H), 1.24 (t, J=7.2 Hz, 3H). $^{13}$C NMR (101 MHz, CDCl$_3$) δ=195.8, 173.5, 60.2, 34.1, 30.6, 29.1, 28.8, 28.2, 24.4, 14.2.

(xxiv) Methyl 6-((2-hydroxyhexyl)thio)hexanoate (90)

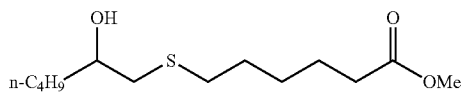

To an RBF containing NaOMe (11.7 g, 217 mmol) and sealed under inert atmosphere was added methanol (110 mL). The solution was degassed with N$_2$ (20 min needle sparge) then crude thioester 89 (25.5 g, 118 mmol) was added via syringe. The mixture was stirred for 20 min at RT, then neat 1-hexene oxide (11 g, 110 mmol) was added under cooling with a water bath (epoxide addition was exothermic). The reaction was stirred for 15 min, then quenched with sat. NH$_4$Cl (200 mL) and extracted with hexanes (300 mL). The layers were separated and the organic phase was collected. The aqueous phase was back-extracted with hexanes (2×100 mL). The combined organic phases were dried (Na$_2$SO$_4$), filtered and evaporated to yield the crude 90 (27 g, 103 mmol, 87%) as a yellow oil. This product was advanced to the next step without purification. $^1$H NMR (400 MHz, CDCl$_3$) δ=3.67 (s, 3H), 3.66-3.59 (m, J=3.5, 8.7 Hz, 1H), 2.73 (dd, J=3.3, 13.6 Hz, 1H), 2.60 (br. s., 1H), 2.53 (t, J=7.3 Hz, 2H), 2.43 (dd, J=9.0, 13.6 Hz, 1H), 2.32 (t, J=7.4 Hz, 2H), 1.69-1.56 (m, 4H), 1.54-1.24 (m, 8H), 0.88 (t, J=6.5 Hz, 3H).

(xxv) methyl 6-((2-hydroxyoctyl)thio)hexanoate (91)

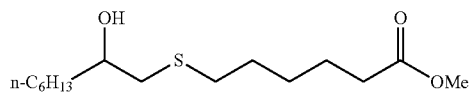

To an RBF containing NaOMe (23.5 g, 435 mmol) and sealed under inert atmosphere was added methanol (220 mL). The solution was degassed with N$_2$ (20 min needle sparge) then crude thioester 89 (51.5 g, 236 mmol) was added via syringe. The mixture was stirred for 20 min at RT, then neat 1-octene oxide (28 g, 33 mL, 218 mmol) was added under cooling with a water bath (epoxide addition was exothermic). The reaction was stirred for 15 min, then quenched with sat. NH$_4$Cl (200 mL) and extracted with hexanes (300 mL). The layers were separated and the organic phase was collected. The aqueous phase was back-extracted with hexanes (2×200 mL). The combined organic phases were dried (Na$_2$SO$_4$), filtered and evaporated to yield the crude 91 (55.5 g, 191 mmol, 81%) as a yellow oil. This product was advanced to the next step without purification. $^1$H NMR (400 MHz, CDCl$_3$) δ=3.67 (s, 3H), 3.66-3.59 (m, J=3.5, 8.7 Hz, 1H), 2.73 (dd, J=3.3, 13.6 Hz, 1H), 2.60 (br. s., 1H), 2.53 (t, J=7.3 Hz, 2H), 2.43 (dd, J=9.0, 13.6 Hz, 1H), 2.32 (t, J=7.4 Hz, 2H), 1.69-1.56 (m, 4H), 1.54-1.24 (m, 12H), 0.88 (t, J=6.5 Hz, 3H). $^{13}$C NMR (101 MHz, CDCl$_3$) δ=174.0, 69.1, 51.5, 40.2, 36.2, 33.8, 31.9, 31.7, 29.3, 29.3, 28.2, 25.7, 24.4, 22.5, 14.0.

(xxvi) Methyl 6-((2-((tert-butyldimethylsilyl)oxy)hexyl)thio)hexanoate (92)

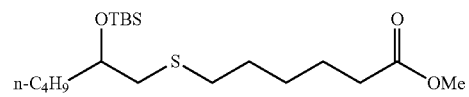

A solution of 90 (5 g, 19 mmol), TBS-C$_1$ (3.3 g, 22.8 mmol, 1.2 equiv), and imidazole (1.9 g, 28.5 mmol, 1.5 equiv) in CH$_2$Cl$_2$ (15 mL) was stirred at room temperature under nitrogen for 18 hours, whereupon TLC and NMR showed that the reaction was complete. The mixture was diluted with NH$_4$Cl (15 mL) and the CH$_2$Cl$_2$ phase was separated and retained. The aqueous phase was extracted with CH$_2$Cl$_2$ (2×10 mL). The combined organic phases were dried (Na$_2$SO$_4$), and concentrated to yield crude 92 (6.9 g, 18.3 mmol, >95% yield). This product was advanced to the next step without purification. $^1$H NMR (400 MHz, CDCl$_3$) δ 3.75 (s, 1H), 3.67 (s, 3H), 2.58-2.50 (m, 4H), 2.32 (t, J=7.5 Hz, 2H), 1.69-1.55 (m, 6H), 1.50-1.23 (m, 10H), 0.93-0.85 (m, 8H), 0.09-0.05 (m, 6H).

(xxvii) Methyl 6-((2-((tert-butyldimethylsilyl)oxy)octyl)thio)hexanoate (93)

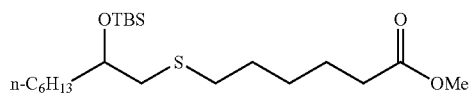

A solution of 91 (51.6 g, 178 mmol), TBS-Cl (31.2 g, 213 mmol, 1.2 equiv), and imidazole (18.1 g, 267 mmol, 1.5 equiv) in CH$_2$Cl$_2$ (180 mL) was stirred at room temperature under nitrogen for 18 hours, whereupon TLC and NMR showed that the reaction was complete. The mixture was diluted with NH$_4$Cl (150 mL) and the CH$_2$Cl$_2$ phase was separated and retained. The aqueous phase was extracted with CH$_2$Cl$_2$ (2×100 mL). The combined organic phases were dried (Na$_2$SO$_4$), and concentrated to yield crude 93 (71.9 g, 177 mmol, >95% yield). This product was advanced to the next step without purification. $^1$H NMR (400 MHz, CDCl$_3$) d=3.75 (s, 1H), 3.67 (s, 3H), 2.58-2.50 (m, 4H), 2.32 (t, J=7.5 Hz, 2H), 1.69-1.55 (m, 6H), 1.50-1.23 (m, 10H), 0.93-0.85 (m, 12H), 0.09-0.05 (m, 6H).

(xxviii) 1,11-bis((2-Hydroxyoctyl)thio)undecan-6-one (97)

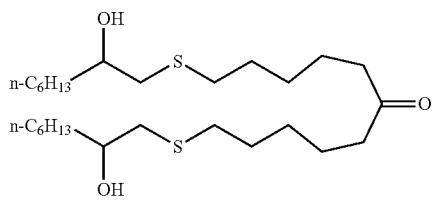

A 9.1 M solution of TiCl$_4$ (50.6 g, 267 mmol) in toluene (29 mL) was added over 90 minutes (syringe pump) to a cold (−20° C.), well-stirred solution of crude 93 (72 g, 178 mmol) and Bu$_3$N (59 g, 76 mL, 320 mmol) in toluene (285 mL), under a nitrogen atmosphere. Upon completion of the 90-minute addition, TLC and NMR indicated completion. The mixture was removed from the cooling bath then first diluted with hexanes (150 mL), followed by quenching by slow addition of water (150 mL) under rapid stirring (clumping of Ti salts will occur with inadequate stirring). The layers were separated and the organic phase was collected. The aqueous phase was extracted with hexanes (2×150 mL). The combined extracts were washed with brine (1×100 mL), dried (Na$_2$SO$_4$), filtered, and concentrated to yield crude 94 as a mixture of keto and enol tautomers. A solution of this crude material (ca. 70 g) in 1,4-dioxane (130 mL) maintained under inert atmosphere was treated at room temperature with 7.5 N NaOH (80 mL, 600 mmol). The mixture was stirred for 18 hours at room temperature, then it was acidified to pH 5 with aq. HCl and heated at 65° C. for 1.5 h, whereupon decarboxylation of the intermediate beta-ketoacid occurred. The layers were separated and the organic phase was collected. The aqueous phase was extracted with hexanes (2×150 mL). The combined extracts were washed with brine (1×100 mL), dried (Na$_2$SO$_4$), filtered, and evaporated to yield a mixture of 97 and silylated derivatives thereof. Complete desilylation was achieved by redissolving this mixture in DCM (92 mL) and treating the solution with HF pyridine (18.1 g, 16.5 mL, 183 mmol) at 0° C. The mixture was stirred at 0° C. for 20 min, then it was quenched with sat. NaHCO$_3$ and extracted with DCM (50 mL). The organic phase was collected. The aqueous phase was extracted with DCM (2×50 mL). The combined organic phases were washed with water (1×100 mL), 1N HCl (1×100 mL), dried (Na$_2$SO$_4$), filtered, and evaporated to yield the crude solid diol. The crude solid was suspended in hot hexanes (100 mL), then EtOAc was slowly added while swirling under heating by heat gun to give a clear amber solution (final amount of EtOAc added was 50 mL). The solution was cooled with an ice bath to precipitate the diol, which was filtered off and collected to yield 97 of a beige solid (25.4 g, 52 mmol, 57% yield). $^1$H NMR (400 MHz, CDCl$_3$) δ 3.67-3.59 (m, 2H), 2.73 (dd, J=3.3, 13.6 Hz, 2H), 2.57 (br. s., 2H), 2.53 (t, J=7.4 Hz, 4H), 2.47-2.37 (m, 6H), 1.66-1.22 (m, 32H), 0.89 (t, J=6.7 Hz, 6H).

(xxix) 1,11-bis((2-Hydroxyhexyl)thio)undecan-6-one (96)

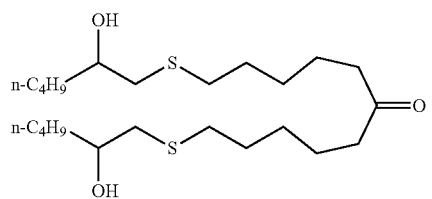

Prepared from 92 by procedure xxviii above. $^1$H NMR (400 MHz, CDCl$_3$) δ 3.67-3.59 (m, 2H), 2.73 (dd, J=3.3, 13.6 Hz, 2H), 2.57 (br. s., 2H), 2.53 (t, J=7.4 Hz, 4H), 2.47-2.37 (m, 6H), 1.66-1.22 (m, 24H), 0.89 (t, J=6.7 Hz, 6H).

(xxx) 1,11-dihydroxyundecan-6-one (100)

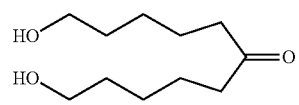

Titanium tetrachloride TiCl$_4$ (28.8 mL, 262.8 mmol, 1.3 equiv) was added dropwise over 30 minutes (syringe pump) to a cold (−78° C.), well-stirred solution of caprolactone (19.4 mL, 175.2 mmol, 1.0 equiv.) and triethylamine (44 mL, 315.4 mmol, 1.5 equiv.) in dichloromethane (100 mL), under argon. The resulting mixture was allowed to warm up to room temperature and stirring was continued for 5 h. The solution was cooled to 0° C. and water (100 mL) was cautiously added. The organic layer was removed, the aqueous layer was further extracted with dichloromethane:methanol (95:5) (5×100 mL). The combined organic layers were evaporated in vacuo. The residue was diluted with 1 M HCl (50 mL) and heated at 60° C. for 5 h, then extracted with dichloromethane:methanol (95:5) (5×100 mL). The combined organic layers were washed with brine, dried (Na$_2$SO$_4$), filtered, and concentrated in vacuo. The solid residue was purified by crystallization from ethyl ether:n-hexane (2:1) to afford 100 (16.1 g, 79.6 mmol, 91%) as an off white solid, m.p. 57° C. (lit. m.p. 58.5° C.). $^1$H NMR (400 MHz, CDCl$_3$) δ 3.63 (t, J=6.5 Hz, 4H), 2.41 (t, J=7.4 Hz, 4H), 1.63-1.52 (m, 8H), 1.38-1.30 (m, 4H). $^{13}$C NMR (100 MHz, CDCl$_3$) δ 211.7, 62.5, 42.6, 32.3, 25.3, 23.4.

(xxxi) 6-oxoundecane-1,11-diyl dimethanesulfonate (101)

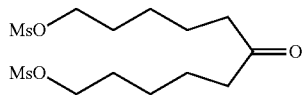

MsCl (2.10 mL, 27.2 mmol) was added to a solution of 100 (2.50 g, 12.4 mmol) and TEA (4.31 mL, 30.9 mmol) in DCM (30.0 mL) at 0° C. under nitrogen. The reaction was warmed to room temperature and stirred for 2 hours, diluted with water and extracted with DCM (3×20.0 mL). The combined extracts were dried (Na$_2$SO$_4$) and concentrated to yield 101 (4.5 g, crude), which was used in the next step without further purification. 1H NMR (400 MHz, CDCl$_3$) δ 4.21 (t, J=6.4 Hz, 4H), 3.00 (s, 6H), 2.41 (t, J=7.2 Hz, 4H), 1.81-1.68 (m, 4H), 1.66-1.54 (m, 4H), 1.46-1.34 (m, 4H).

(xxxii) S,S'-(6-oxoundecane-1,11-diyl) diethanethioate (102)

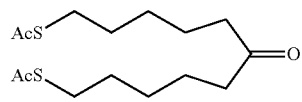

To a solution of 101 (4.5 g, crude) and TEA (2.30 mL, 32.6 mmol) in DMF (20.0 mL) was added thioacetic acid (2.30 mL, 32.6 mmol). The mixture was stirred at 60 degrees for 16 hours, diluted with water (50.0 mL) and extracted with hexanes (3×40.0 mL). The combined extracts were washed (brine), dried (Na$_2$SO$_4$) and concentrated to yield 102 (2.46 g, 62% over 2 steps). $^1$H NMR (400 MHz, CDCl$_3$) δ 2.84 (t, J=7.3 Hz, 4H), 2.38 (t, J=7.4 Hz, 4H), 2.31 (s, 6H), 1.56 (m, 8H), 1.39-1.27 (m, 4H).

(xxxiii) 1,11-bis((2-hydroxyoctyl)thio)undecan-6-one (97) from 102

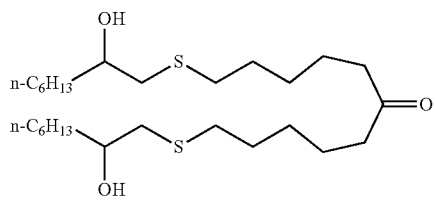

To a solution of 102 (2.46 g, 7.71 mmol), 2-hexyloxirane (2.94 mL, 19.3 mmol) in EtOH (20.0 mL) was added NaOH (1.23 g, 30.8 mmol) at rt under nitrogen. The reaction was stirred at reflux for 4 hours, cooled to rt, diluted with water (40.0 mL) and extracted with DCM (3×40.0 mL). The combined organics were dried (Na$_2$SO$_4$) and concentrated. The residue was purified by silica chromatography (0-50% EtOAc in Hexanes) to yield 97 (3.42 g, 90%). $^1$H NMR (400 MHz, CDCl3) δ 3.65-3.54 (m, 2H), 2.71 (dd, J=13.6, 3.3 Hz, 2H), 2.51 (t, J=7.3 Hz, 4H), 2.47-2.32 (m, 6H), 1.70-1.18 (m, 32H), 0.92-0.82 (m, 6H).

(xxxiv) ((6-Oxoundecane-1,11-diyl)bis(sulfanediyl))bis(octane-1,2-diyl) dinonanoate (78)

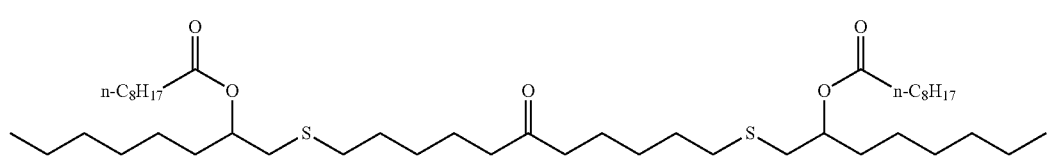

A solution of 97 (1.10 g, 2.24 mmol), nonanoic acid (887 mg, 5.60 mmol), EDCI-HCl (1.12 g, 5.83 mmol) and DMAP (712 mg, 5.83 mmol) in DCM (20.0 mL) was stirred at rt under nitrogen for 18 hours then concentrated. The residue was purified by silica chromatography (0-10% EtOAc in Hexanes) to yield 78 (1.56 g, 90%). $^1$H NMR (400 MHz, CDCl$_3$) δ 5.00-4.89 (m, 2H), 2.68-2.57 (m, 4H), 2.57-2.48 (m, 4H), 2.39 (t, J=7.4 Hz, 4H), 2.30 (t, J=7.5 Hz, 4H), 1.58 (m, 16H), 1.46-1.17 (m, 40H), 0.95-0.80 (m, 12H).

(xxxv) ((6-Oxoundecane-1,11-diyl)bis(sulfanediyl)) bis(hexane-1,2-diyl) bis(3-cyclohexyl-propanoate) (79)

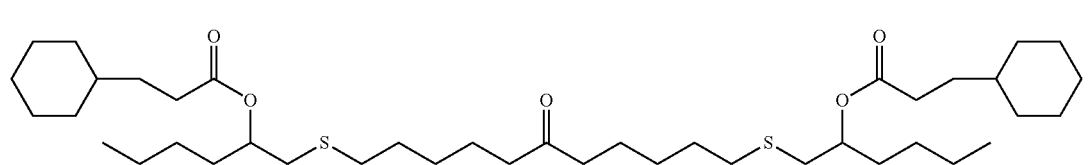

Prepared from 96 and 3-cyclohexylpropanoic acid by procedure (xxxiv) above. $^1$H NMR (400 MHz, CDCl$_3$) δ 5.16-4.78 (m, 2H), 2.68-2.58 (m, 4H), 2.57-2.48 (m, 4H), 2.39 (t, J=7.4 Hz, 4H), 2.31 (t, J=7.2 Hz, 4H), 1.78-1.05 (m, 46H), 0.97-0.78 (m, 10H).

(xxxvi) ((6-Oxoundecane-1,11-diyl)bis(sulfanediyl)) bis(octane-1,2-diyl) dioctanoate (77)

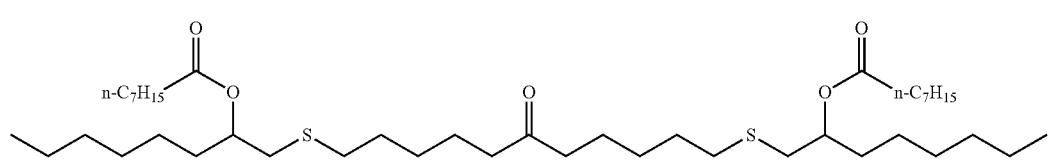

Prepared from 97 and octanoic acid by procedure (xxxiv) above. $^1$H NMR (400 MHz, CDCl$_3$) δ 4.98-4.89 (m, 2H), 2.68-2.58 (m, 4H), 2.56-2.49 (m, 4H), 2.39 (t, J=7.4 Hz, 4H), 2.30 (t, J=7.5 Hz, 4H), 1.76-1.02 (m, 52H), 0.87 (t, J=6.5 Hz, 12H).

(xxxvii) ((6-oxoundecane-1,11-diyl)bis(sulfanediyl)) bis(octane-1,2-diyl) bis(3-cyclo-hexylpropanoate) (80)

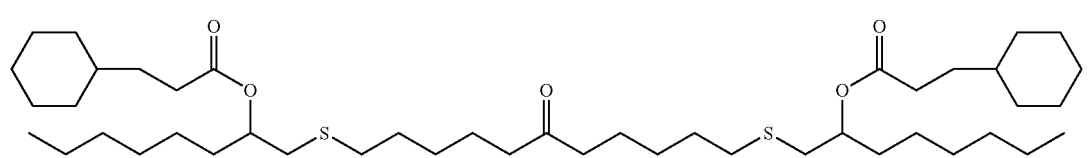

Prepared from 97 and 3-cyclohexylpropanoic acid by the procedure of part (xxxvi) above. ¹H NMR (400 MHz, CDCl₃) δ 5.16-4.78 (m, 2H), 2.68-2.58 (m, 4H), 2.57-2.48 (m, 4H), 2.39 (t, J=7.4 Hz, 4H), 2.31 (t, J=7.2 Hz, 4H), 1.78-1.05 (m, 54H), 0.97-0.78 (m, 10H).

(xxxviii) 1-((11-((2-Hydroxyoctyl)thio)-6-oxoundecyl)thio)octan-2-yl heptanoate (120)

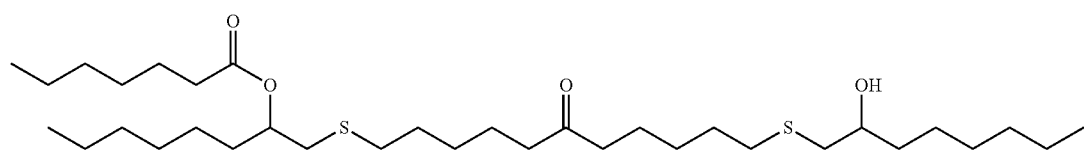

A solution of 97 (1.10 g, 2.24 mmol), heptanoic acid (290 mg, 2.2 mmol), EDCI-HCl (500 g, 2.9 mmol) and DMAP (350 mg, 2.9 mmol) in CH₂Cl₂ (10.0 mL) was stirred at rt under nitrogen for 18 hours then concentrated. The residue was purified by silica chromatography (0-20% EtOAc in Hexanes) to yield 120 (810 mg, 60%). ¹H NMR (400 MHz, CDCl₃) δ 4.98-4.89 (m, 1H), 3.65-3.54 (m, 1H), 2.72 (m, 2H), 2.68-2.58 (m, 2H), 2.56-2.49 (m, 4H), 2.39 (t, J=7.4 Hz, 4H), 2.30 (t, J=7.5 Hz, 2H), 1.76-1.02 (m, 40H), 0.87 (br t, 9H).

(xxxix) 1-((11-((2-((3-cyclohexylpropanoyl)oxy)octyl)thio)-6-oxoundecyl)thio)octan-2-yl heptanoate (81)

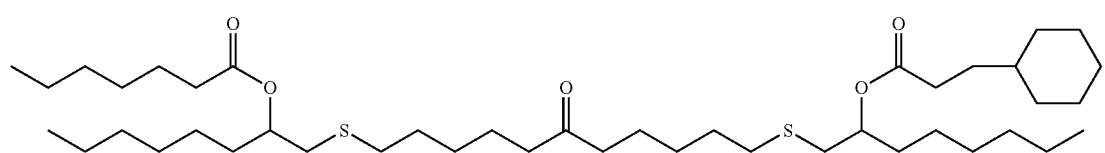

Prepared from 120 and 3-cyclohexylpropanoic acid according to procedure (xxxviii) above. ¹H NMR (400 MHz, CDCl₃) δ 5.16-4.78 (m, 1H), 4.98-4.89 (m, 1H), 2.68-2.58 (m, 4H), 2.57-2.48 (m, 4H), 2.39 (t, J=7.4 Hz, 4H), 2.31 (t, J=7.2 Hz, 2H), 2.30 (t, J=7.5 Hz, 2H), 1.78-1.05 (m, 48H), 0.97-0.78 (m, 13H).

(x) ((6-oxoundecane-1,11-diyl)bis(sulfanediyl))bis(octane-1,2-diyl) dicycloheptane-carboxylate (82)

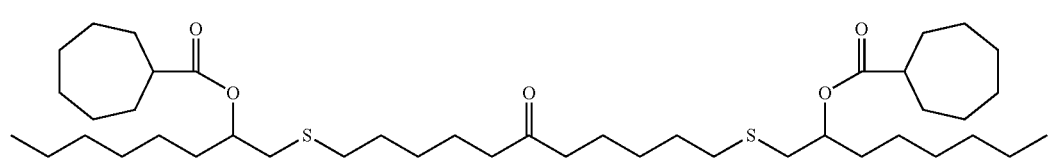

Prepared from 97 and cycloheptanecarboxylic acid by procedure (xxxiv) above. $^1$H NMR (400 MHz, CDCl$_3$) δ=4.93 (dtd, J=8.2, 6.1, 4.4 Hz, 2H), 2.70-2.59 (m, 4H), 2.58-2.53 (m, 4H), 2.52-2.44 (m, 2H), 2.41 (t, J=7.4 Hz, 4H), 2.01-1.90 (m, 4H), 1.80-1.23 (m, 52H), 0.89 (td, J=6.4, 3.0 Hz, 6H). $^{13}$C NMR (101 MHz, CDCl$_3$) δ=210.9, 176.7, 72.5, 45.3, 42.6, 36.0, 33.2, 32.5, 31.7, 31.0, 30.9, 29.4, 29.1, 28.4, 28.3, 28.3, 26.4, 25.3, 23.4, 22.6, 14.1.

(xli) ((6-Oxoundecane-1,11-diyl)bis(sulfanediyl))bis(octane-1,2-diyl)-bis(adamantane-1-carboxylate) (83)

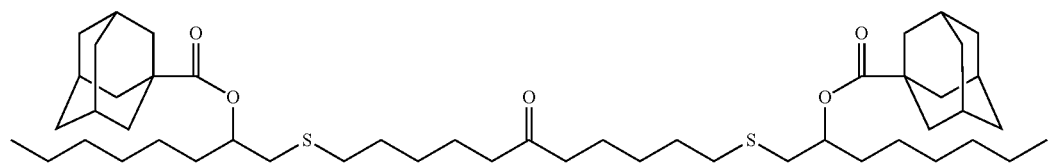

83

Prepared from 97 and adamantanecarboxylic acid by procedure (xxxiv) above. $^1$H NMR (400 MHz, CDCl$_3$) δ=4.95-4.85 (m, 2H), 2.67-2.56 (m, 4H), 2.53 (t, J=7.1 Hz, 4H), 2.39 (t, J=7.4 Hz, 4H), 2.01 (s, 6H), 1.89 (d, J=2.9 Hz, 12H), 1.77-1.65 (m, 14H), 1.63-1.52 (m, 10H), 1.41-1.20 (m, 20H), 0.91-0.85 (m, 6H). $^{13}$C NMR (101 MHz, CDCl$_3$) δ=211.1, 177.4, 72.4, 42.8, 40.9, 39.0, 36.7, 36.2, 33.2, 32.6, 31.8, 29.5, 29.2, 28.5, 28.1, 25.4, 23.5, 14.2.

(xlii) 4-((tert-Butyldiphenylsilyl)oxy)butan-1-amine (122)

122

A solution of tert-butyl(chloro)-diphenylsilane (TBDP-SCl; 6.8 g, 24.7 mmol, 1.1 equiv) in CH$_2$Cl$_2$ (4 mL) was added dropwise during 15 min to a well-stirred solution of 4-amino-1-butanol (2.0 g, 22.4 mmol, 1.0 equiv) and imidazole (3.4 g, 49.3 mmol, 2.2 equiv) in CH$_2$Cl$_2$ (5 mL). The mixture was stirred overnight at room temperature. The reaction mixture was sequentially washed with sat. aq. NaHCO$_3$ solution (2×5 mL), water (2×5 mL), and sat. aq. NaCl chloride solution (2×5 mL), then dried over anhydrous Na$_2$SO$_4$, filtered, and concentrated under reduced pressure to furnish 122 (6.72 g, 92%) as a yellow oil. $^1$H NMR (300 MHz, CDCl$_3$) δ 7.71-7.68 (m, 4H), 7.40-7.36 (m, 6H), 3.70 (t, J=6.0 Hz, 2H), 2.67 (t, J=6.6 Hz, 2H), 1.86 (s, 2H), 1.65-1.48 (m, 4H), 1.09 (s, 9H); $^{13}$C NMR (75 MHz, CDCl$_3$) δ 135.4, 133.8, 129.4, 127.5, 63.6, 41.8, 29.9, 29.8, 26.7, 19.0.

(xliii) 2-(2-((tert-Butyldiphenylsilyl)oxy)ethoxy)ethan-1-amine (131)

131

Prepared from 2-(2-aminoethoxy)ethan-1-ol by procedure (xlii) above. $^1$H NMR (400 MHz, CDCl$_3$) δ 7.75-7.64 (m, 4H), 7.45-7.34 (m, 6H), 3.81 (t, J=5.2 Hz, 2H), 3.57 (m, 2H), 3.48 (t, J=5.2 Hz, 2H), 2.82 (t, J=5.2 Hz, 2H), 1.05 (s, 9H). $^{13}$C NMR (101 MHz, CDCl$_3$) δ 135.7, 133.9, 129.8, 127.8, 73.6, 72.4, 63.6, 42.1, 26.9, 19.3.

(xliv) 2-((2-((tert-Butyldiphenylsilyl)oxy)ethyl)thio)ethan-1-amine (132)

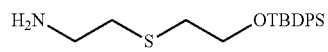

132

Prepared from 2-((2-aminoethyl)thio)ethan-1-ol by procedure (xlii) above. $^1$H NMR (400 MHz, CDCl$_3$) δ 7.74-7.63 (m, 4H), 7.46-7.33 (m, 6H), 3.79 (t, J=7.1 Hz, 2H), 2.74 (t, J=6.3 Hz, 2H), 2.63 (t, J=7.1 Hz, 2H), 2.50 (t, J=6.3 Hz, 2H), 1.06 (s, 9H). $^{13}$C NMR (101 MHz, CDCl$_3$) δ 135.7, 135.0, 129.9, 127.8, 64.0, 41.3, 36.7, 33.8, 26.9, 26.8, 19.3.

(xlv) cis-3-((tert-Butyldiphenylsilyl)oxy)cyclobutan-1-amine (133)

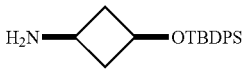

133

Prepared from cis-3-aminocyclobutan-1-ol by procedure (xlii) above. $^1$H NMR (400 MHz, CDCl$_3$) δ 7.68-7.61 (m, 4H), 7.45-7.34 (m, 6H), 3.86 (tt, J=7.7, 6.6 Hz, 1H), 2.77 (tt, J=8.7, 6.8 Hz, 1H), 2.57-2.47 (m, 2H), 1.80-1.70 (m, 2H), 1.03 (s, 9H). $^{13}$C NMR (101 MHz, CDCl$_3$) δ 135.6, 134.3, 129.7, 127.7, 61.2, 45.2, 39.7, 26.9, 19.1.

(B) Preparation of Lipids 5-35.
(a) General Procedure for the Reduction of a Ketone to an Alcohol (i) 11-((2-((3-cyclohexylpropanoyl)oxy)octyl)thio)-6-hydroxyundecyl cyclopenta-decanecarboxylate (121)

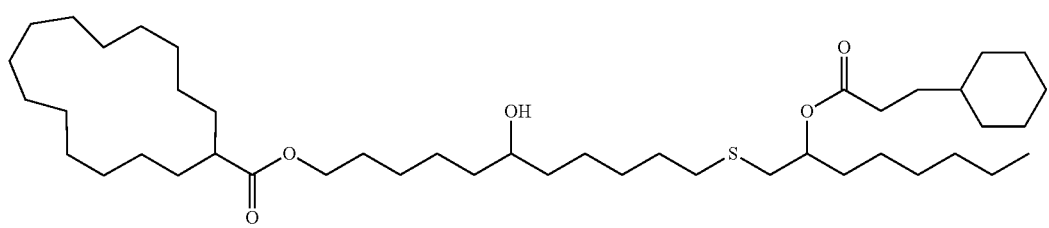

121

Solid NaBH$_4$ (13.7 mg, 3.63 mmol) was added to a solution of 54 (200 mg, 0.277 mmol) in EtOH (2 mL) at rt under nitrogen. The mixture was stirred for 30 minutes, whereupon TLC showed complete conversion. The reaction was quenched with sat. aq. NH$_4$Cl (2 mL), diluted with water (5 mL) and extracted with CH$_2$Cl$_2$ (3×5 mL). The combined extracts were dried (Na$_2$SO$_4$) and concentrated to yield 121 (198 mg, quantitative) which was used in the next step without purification. $^1$H NMR (400 MHz, CDCl$_3$) δ 4.99-4.87 (m, 1H), 4.06 (t, J=6.64 Hz, 2H), 3.69-3.47 (m, 1H), 2.71-2.47 (m, 4H), 2.39 (t, J=6.68 Hz, 1H), 2.34-2.26 (m, 2H), 1.78-1.09 (m, 66H), 0.98-0.75 (m, 5H). LRMS m/z 745 [M+Na]$^+$.

The following compounds were prepared by the same method:

(ii) ((6-Hydroxyundecane-1,11-diyl)bis(sulfanediyl)) bis(octane-1,2-diyl) dioctanoate

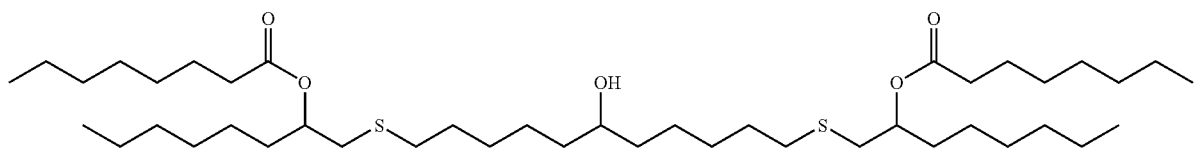 [SMILES: CCCCCCCC(=O)OC(CCCCCC)CSCCCCCC(O)CCCCCSCC(CCCCCC)OC(=O)CCCCCCC]

From ketone 77. $^1$H NMR (400 MHz, CDCl$_3$) δ 4.99-4.90 (m, 2H), 3.63-3.54 (m, 1H), 2.74-2.47 (m, 8H), 2.30 (t, J=7.5 Hz, 4H), 1.76-1.17 (m, 56H), 0.94-0.80 (m, 12H).

(iii) ((6-Hydroxyundecane-1,11-diyl)bis(sulfanediyl))bis(octane-1,2-diyl) dinonanoate

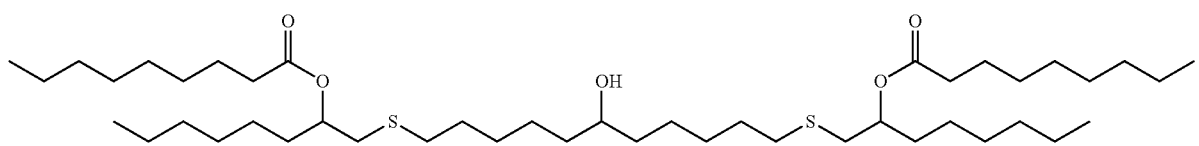 [SMILES: CCCCCCCCC(=O)OC(CCCCCC)CSCCCCCC(O)CCCCCSCC(CCCCCC)OC(=O)CCCCCCCC]

From ketone 78. ¹H NMR (400 MHz, CDCl₃) δ 5.02-4.87 (m, 2H), 3.64-3.53 (m, 1H), 2.74-2.45 (m, 8H), 2.30 (t, J=7.5 Hz, 4H), 1.80-1.17 (m, 60H), 0.92-0.81 (m, 12H).

(iv) ((6-Hydroxyundecane-1,11-diyl)bis(sulfanediyl))bis(hexane-1,2-diyl) bis(3-cyclohexylpropanoate)

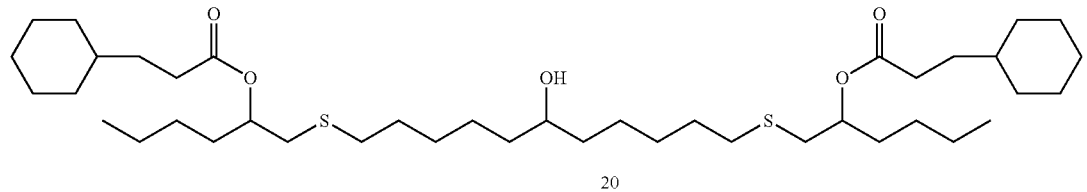

From ketone 79. H NMR (400 MHz, CDCl₃) δ 5.02-4.89 (m, 2H), 3.62-3.49 (m, 1H), 2.68-2.57 (m, 4H), 2.57-2.48 (m, 4H), 2.35-2.29 (m, 2H), 1.76-1.04 (m, 52H), 0.95-0.82 (m, 10H).

(v) ((6-Hydroxyundecane-1,11-diyl)bis(sulfanediyl)) bis(octane-1,2-diyl) bis(3-cyclo-hexylpropanoate)

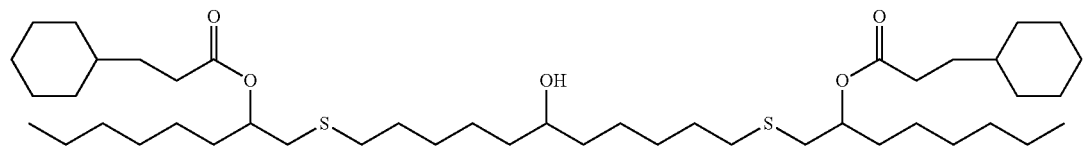 [SMILES: CCCCCCC(CSCCCCCC(O)CCCCCSCC(CCCCCC)OC(=O)CCC1CCCCC1)OC(=O)CCC1CCCCC1]

From ketone 80. ¹H NMR (400 MHz, CDCl₃) δ 5.02-4.89 (m, 2H), 3.62-3.49 (m, 1H), 2.68-2.57 (m, 4H), 2.57-2.48 (m, 4H), 2.35-2.29 (m, 2H), 1.76-1.04 (m, 60H), 0.95-0.82 (m, 10H).

(b) General Procedure for the Conversion of an Alcohol to a Type 1 Ionizable Head Group.

(i) 11-((2-((3-Cyclohexylpropanoyl)oxy)octyl)thio)-6-((4-(dimethylamino)butanoyl)-oxy)-undecyl cyclopentadecanecarboxylate (5)

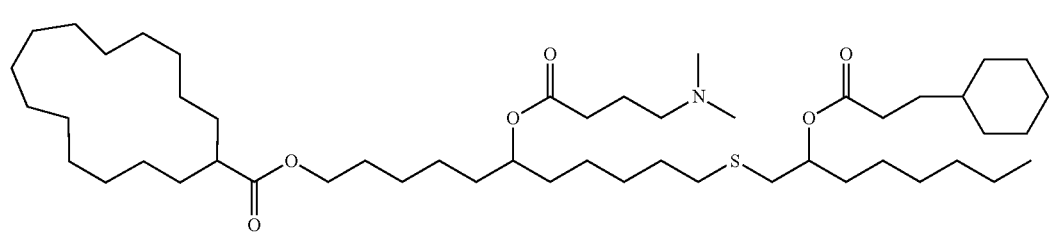

A solution of 121 (198 mg, 0.274 mmol), 4-(dimethylamino)butanoic acid hydrochloride (65.0 mg, 0.388 mmol), EDCI-HCl (99.2 mg, 0.517 mmol) and DMAP (63.2 mg, 0.517 mmol) in CH$_2$Cl$_2$ (2.00 mL) was stirred at room temperature under nitrogen for 18 hours. The mixture was concentrated and the residue purified by silica chromatography (0-5% MeOH in CH$_2$Cl$_2$) to yield 5 (130 mg, 57%). $^1$H NMR (400 MHz, CDCl$_3$) δ 4.98-4.89 (m, 1H), 4.89-4.79 (m, 1H), 4.03 (t, J=6.63 Hz, 2H), 2.69-2.54 (m, 2H), 2.54-2.45 (m, 2H), 2.43-2.23 (m, 7H), 2.21 (s, 6H), 1.81-1.44 (m, 16H), 1.44-1.03 (m, 51H), 0.96-0.80 (m, 5H). LRMS m/z 836 [M+H]+.

The following compounds were prepared by the same method:

(ii) ((6-((4-(Dimethylamino)butanoyl)oxy)undecane-1,11-diyl)bis(sulfanediyl))bis-(octane-1,2-diyl) dioctanoate (16)

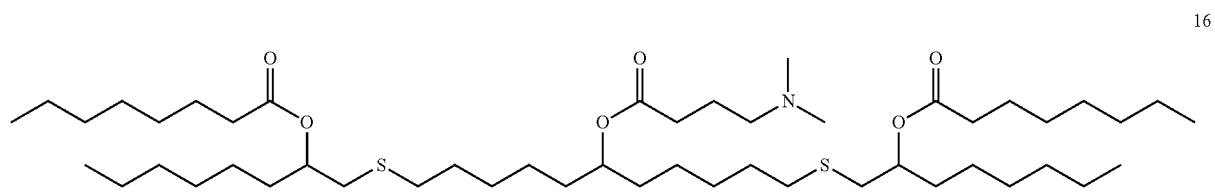 [SMILES: CCCCCCCC(=O)OC(CCCCCC)CSCCCCCC(CCCCCSCC(CCCCCC)OC(=O)CCCCCCC)OC(=O)CCCN(C)C]

From ((6-hydroxyundecane-1,11-diyl)bis(sulfanediyl))bis(octane-1,2-diyl) dioctanoate. $^1$H NMR (400 MHz, C$_6$D$_6$) δ 5.28-5.19 (m, 2H), 5.12-5.03 (m, 1H), 2.76-2.43 (m, 8H), 2.36 (t, J=7.3 Hz, 2H), 2.31-2.21 (m, 4H), 2.16 (t, J=6.9 Hz, 2H), 2.05 (s, 6H), 1.80 (p, J=7.1 Hz, 2H), 1.74-1.11 (m, 56H), 0.97-0.84 (m, 12H).

(iii) ((6-((4-(Dimethylamino)butanoyl)oxy)undecane-1,11-diyl)bis(sulfanediyl))bis-(octane-1,2-diyl) dinonanoate (17)

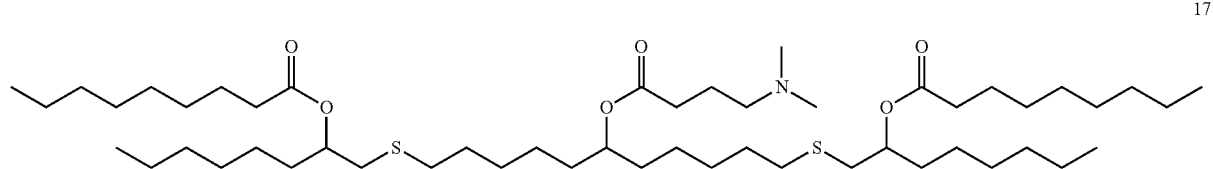 [SMILES: CCCCCCCCC(=O)OC(CCCCCC)CSCCCCCC(CCCCCSCC(CCCCCC)OC(=O)CCCCCCCC)OC(=O)CCCN(C)C]

From ((6-hydroxyundecane-1,11-diyl)bis(sulfanediyl))bis(octane-1,2-diyl) dinonanoate. $^1$H NMR (400 MHz, C$_6$D$_6$) δ 5.41-5.29 (m, 2H), 5.23-5.13 (m, 1H), 2.88-2.54 (m, 8H), 2.46 (t, J=7.3 Hz, 2H), 2.43-2.30 (m, 4H), 2.26 (t, J=6.9 Hz, 2H), 2.15 (s, 6H), 1.90 (p, J=7.1 Hz, 2H), 1.85-1.25 (m, 60H), 1.08-0.92 (m, 12H).

(iv) ((6-((4-(Dimethylamino)butanoyl)oxy)undecane-1,11-diyl)bis(sulfanediyl))bis(hexane-1,2-diyl) bis(3-cyclohexylpropanoate) (18)

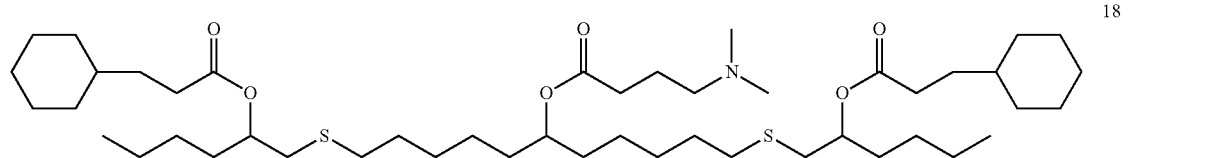 [SMILES: CCCCC(CSCCCCCC(CCCCCSCC(CCCC)OC(=O)CCC1CCCCC1)OC(=O)CCCN(C)C)OC(=O)CCC1CCCCC1]

From (((6-hydroxyundecane-1,11-diyl)bis-(sulfanediyl)) bis(hexane-1,2-diyl) bis(3-cyclohexyl-propanoate). ¹H NMR (400 MHz, C$_6$D$_6$) δ 5.29-5.18 (m, 2H), 5.12-5.03 (m, 1H), 2.74-2.44 (m, 8H), 2.37 (t, J=7.3 Hz, 2H), 2.33-2.26 (m, 4H), 2.16 (t, J=6.9 Hz, 2H), 2.05 (s, 6H), 1.80 (p, J=7.1 Hz, 3H), 1.76-1.00 (m, 49H), 0.89 (t, J=6.8 Hz, 6H), 0.84-0.72 (m, 4H).

(v) ((6-((4-(Dimethylamino)butanoyl)oxy)undecane-1,11-diyl)bis(sulfanediyl))bis-(octane-1,2-diyl) bis(3-cyclohexylpropanoate) (19)

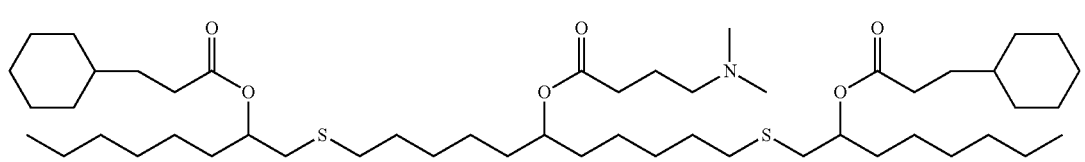

19

From (((6-hydroxyundecane-1,11-diyl)bis-(sulfanediyl)) bis(octane-1,2-diyl) bis(3-cyclohexyl-propanoate). ¹H NMR (400 MHz, C$_6$D$_6$) δ 5.29-5.18 (m, 2H), 5.12-5.03 (m, 1H), 2.74-2.44 (m, 8H), 2.37 (t, J=7.3 Hz, 2H), 2.33-2.26 (m, 4H), 2.16 (t, J=6.9 Hz, 2H), 2.05 (s, 6H), 1.80 (p, J=7.1 Hz, 3H), 1.76-1.00 (m, 57H), 0.89 (t, J=6.8 Hz, 6H), 0.84-0.72 (m, 4H).

(vi) ((6-((1-Methylazetidine-3-carbonyl)oxy)undecane-1,11-diyl)bis(sulfanediyl))bis-(octane-1,2-diyl) bis(3-cyclohexylpropanoate) (20)

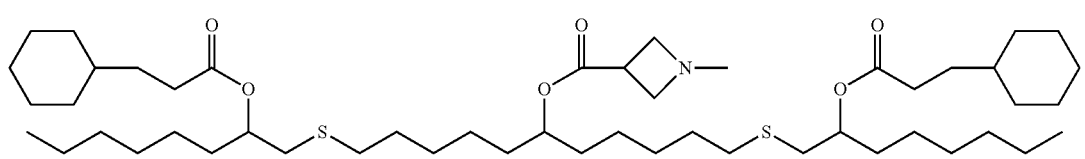

20

From (((6-hydroxyundecane-1,11-diyl)bis-(sulfanediyl)) bis(octane-1,2-diyl) bis(3-cyclohexyl-propanoate) and 1-methylazetidine-3-carboxylic acid. ¹H NMR (400 MHz, CDCl$_3$) δ 4.97-4.90 (m, 2H), 4.87 (p, J=6.4 Hz, 1H), 3.59-3.48 (m, 2H), 3.30-3.20 (m, 3H), 2.68-2.57 (m, 4H), 2.57-2.46 (m, 4H), 2.31 (t, J=7.6 Hz, 4H), 2.30 (s, 3H), 1.76-1.46 (m, 25H), 1.42-1.06 (m, 32H), 0.94-0.82 (m, 10H). ¹³C NMR (101 MHz, CDCl$_3$) δ 173.8, 172.9, 74.5, 72.8, 58.8, 45.9, 37.2, 36.0, 34.0, 33.2, 33.0, 32.6, 32.4, 32.2, 31.7, 29.5, 29.1, 28.7, 26.6, 26.3, 25.3, 25.0, 22.6, 14.1.

(b) General Procedure for the Reductive Amination of a Ketone with a Primary Amine.

(i) 6-((4-((tert-Butyldiphenylsilyl)oxy)butyl)amino)-11-((2-(octanoyloxy)octyl)thio)-undecyl 2-hexyldecanoate (123)

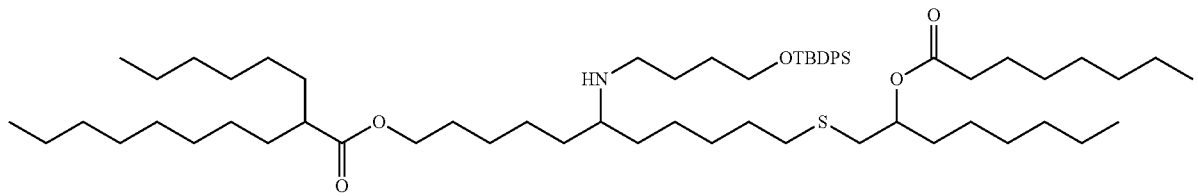

123

A solution of 55 (460 mg, 0.648 mmol), amine 122 (318 mg, 0.972 mmol), sodium triacetoxyborohydride (247 mg, 1.17 mmol) and HOAc (1 drop) in 1,2-dichloroethane (4 mL) was stirred at room temperature under nitrogen for 18 hours. The reaction was quenched with sat. aq. NaHCO$_3$ (2.00 mL), diluted with water (4.00 mL) and extracted with CH$_2$Cl$_2$ (3×5 mL). The combined extracts were dried (Na$_2$SO$_4$) and concentrated. The residue was purified by silica chromatography (0-5% MeOH in CH$_2$Cl$_2$) to yield 123 (536 mg, 81%). $^1$H NMR (400 MHz, CDCl$_3$) δ 7.69-7.62 (m, 4H), 7.46-7.33 (m, 6H), 5.03-4.88 (m, 1H), 4.06 (t, J=6.6 Hz, 2H), 3.66 (t, J=5.9 Hz, 2H), 2.73-2.49 (m, 6H), 2.49-2.41 (m, 1H), 2.35-2.24 (m, 3H), 1.71-1.16 (m, 64H), 1.04 (s, 9H), 0.95-0.77 (m, 12H).

The following compounds were prepared by the same method:

(ii) 6-((4-((tert-Butyldiphenylsilyl)oxy)butyl)amino)-11-((2-((6-methylheptanoyl)oxy)-octyl)thio)undecyl 2-hexyldecanoate From 56 and 122. $^1$H NMR (400 MHz, CDCl$_3$) δ 7.71-7.63 (m, 4H), 7.49-7.33 (m, 6H), 4.99-4.91 (m, 1H), 4.06 (t, J=6.6 Hz, 2H), 3.66 (t, J=6.0 Hz, 2H), 2.68-2.60 (m, 2H), 2.58-2.49 (m, 4H), 2.47-2.39 (m, 1H), 2.37-2.27 (m, 3H), 1.80-1.13 (m, 61H), 1.04 (s, 9H), 0.92-0.84 (m, 15H).

(iii) 6-((4-((tert-Butyldiphenylsilyl)oxy)butyl)amino)-11-((2-((3-cyclohexylpropanoyl)oxy)-octyl)thio)undecyl 2-hexyldecanoate

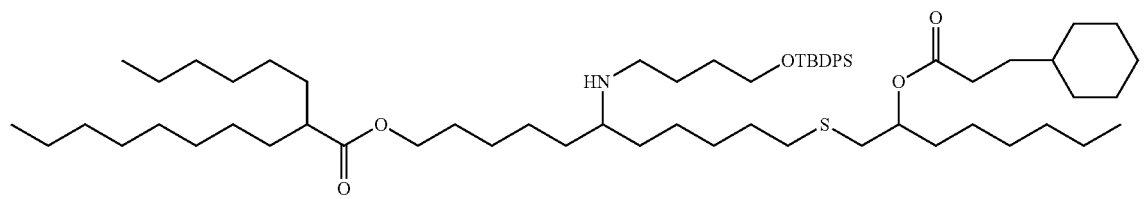

From 57 and 122. ¹H NMR (400 MHz, CDCl₃) δ 7.72-7.63 (m, 4H), 7.47-7.33 (m, 6H), 4.99-4.89 (m, 1H), 4.05 (t, J=6.7 Hz, 2H), 3.74-3.61 (m, 2H), 2.74-2.40 (m, 7H), 2.40-2.23 (m, 3H), 1.75-1.09 (m, 65H), 1.04 (s, 9H), 0.94-0.82 (m, 11H).

(iv) 10-(5-((2-Hexyldecanoyl)oxy)pentyl)-2,2-dimethyl-3,3-diphenyl-4-oxa-16-thia-9-aza-3-silatetracosan-18-yl cycloheptanecarboxylate

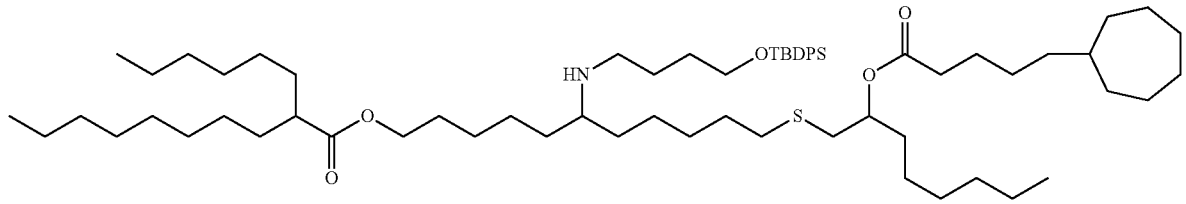

From 58 and 122. ¹H NMR (400 MHz, CDCl₃) δ 7.80-7.61 (m, 4H), 7.49-7.34 (m, 6H), 4.99-4.87 (m, 1H), 4.05 (t, J=6.7 Hz, 2H), 3.66 (t, J=5.9 Hz, 2H), 2.69-2.40 (m, 8H), 2.37-2.26 (m, 1H), 1.99-1.18 (m, 66H), 1.04 (s, 9H), 0.91-0.84 (m, 9H).

(v) 6-((4-((tert-Butyldiphenylsilyl)oxy)butyl)amino)-11-((2-(2-cycloheptylacetoxy)-octyl)thio)undecyl 2-hexyldecanoate

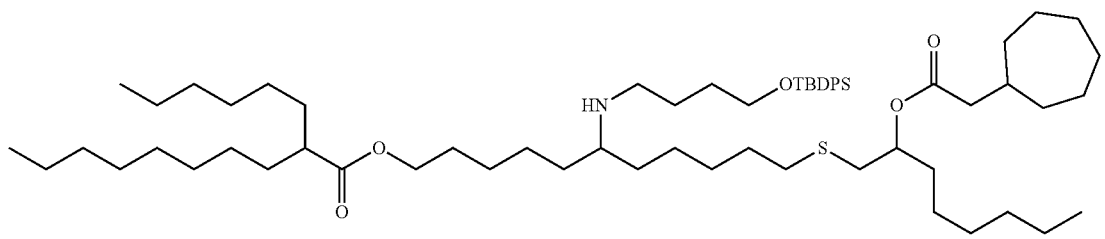

From 59 and 122. ¹H NMR (400 MHz, CDCl₃) δ 7.70-7.64 (m, 4H), 7.44-7.32 (m, 6H), 5.02-4.90 (m, 1H), 4.06 (t, J=6.7 Hz, 2H), 3.66 (t, J=5.9 Hz, 2H), 2.70-2.60 (m, 2H), 2.59-2.50 (m, 4H), 2.49-2.40 (m, 1H), 2.36-2.26 (m, 1H), 2.22 (d, J=7.3 Hz, 2H), 2.06-1.95 (m, 1H), 1.78-1.15 (m, 66H), 1.04 (s, 9H), 0.91-0.84 (m, 9H).

(vi) 6-((4-((tert-Butyldiphenylsilyl)oxy)butyl)amino)-11-((2-((3-cyclohexylpropanoyl)-oxy)octyl)thio)undecyl cyclopentadecanecarboxylate

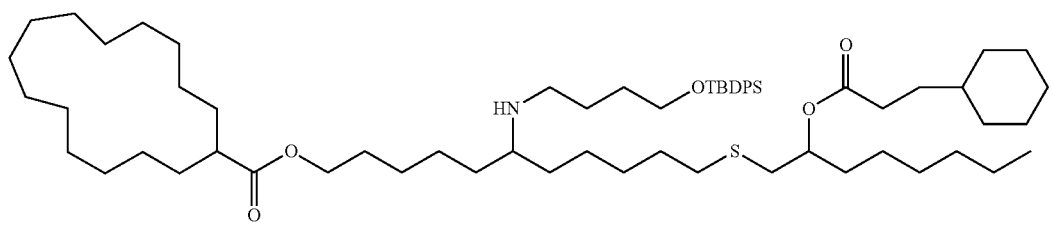

From 54 and 122. $^1$H NMR (400 MHz, CDCl$_3$) δ 7.80-7.58 (m, 4H), 7.55-7.31 (m, 6H), 5.13-4.79 (m, 1H), 4.05 (t, J=6.64 Hz, 2H), 3.83-3.48 (m, 2H), 2.63 (dd, J=6.12, 2.16 Hz, 2H), 2.60-2.35 (m, 5H), 2.31 (dd, J=8.41, 7.19 Hz, 2H), 1.76-1.48 (m, 21H), 1.45-1.16 (m, 50H), 1.04 (s, 9H), 0.94-0.79 (m, 5H). LRMS m/z 1032 [M+H]+.

(vii) 6-((4-((tert-Butyldiphenylsilyl)oxy)butyl)amino)-9-(2-((2-(octanoyloxy)hexyl)-thio)ethyl)-3-pentyltetradecyl octanoate

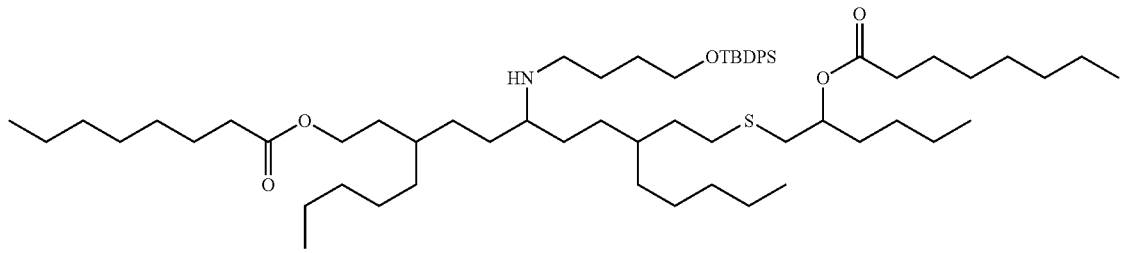

From 67 and 122. $^1$H NMR (400 MHz, CDCl$_3$) δ 7.68-7.66 (m, 4H), 7.44-7.38 (m, 6H), 4.97 (brs, 1H), 4.11-4.07 (m, 2H), 3.69-3.68 (m, 2H), 2.66-2.54 (m, 5H), 2.34-2.27 (m, 4H), 1.64-1.26 (m, 62H), 1.06 (m, 9H), 0.91-0.88 (m, 15H).

(viii) 6-((4-((tert-Butyldiphenylsilyl)oxy)butyl)amino)-9-(2-((2-((3-cyclohexylpropan-oyl)oxy)hexyl)thio)ethyl)-3-pentyltetradecyl 3-cyclohexyl propanoate

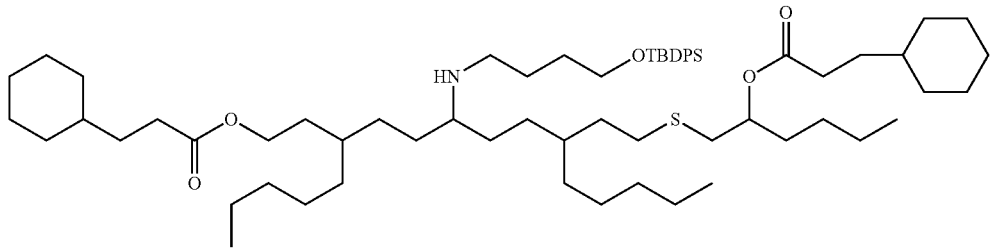

From 68 and 122. $^1$H NMR (400 MHz, CDCl$_3$) δ 7.68-7.66 (m, 4H), 7.44-7.37 (m, 6H), 5.00 (m, 1H), 4.11-4.07 (m, 2H), 3.69-3.68 (m, 2H), 2.66-2.54 (m, 6H), 2.35-2.29 (m, 4H), 1.72-1.13 (m, 64H), 1.06 (m, 9H), 0.91-0.88 (m, 12H).

(ix) 6-((4-((tert-Butyldiphenylsilyl)oxy)butyl)amino)-9-(2-(((1R*,2R*)-2-(octanoyl-oxy)cyclohexyl)thio)ethyl)-3-pentyltetradecyl octanoate

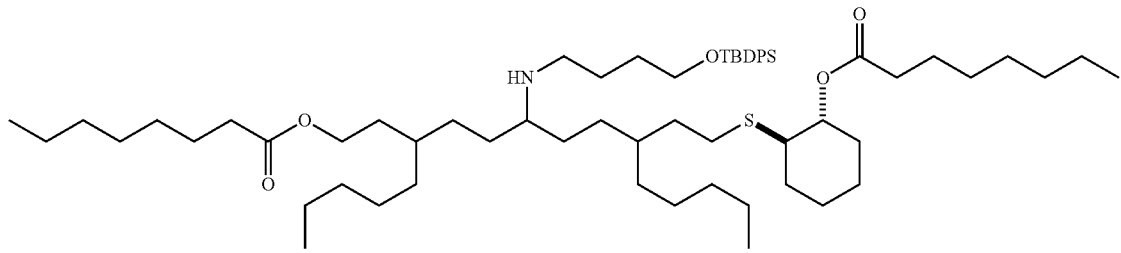

From 69 and 122. $^1$H NMR (400 MHz, CDCl$_3$) δ 7.68-7.66 (m, 4H), 7.44-7.37 (m, 6H), 4.85-4.77 (m, 1H), 4.11-4.07 (m, 2H), 3.69 (br t, 2H), 2.68-2.52 (m, 5H), 2.35-2.29 (m, 4H), 1.72-1.13 (m, 63H), 1.06 (br s, 9H), 0.91-0.88 (m, 12H).

(x) 6-((4-((tert-Butyldiphenylsilyl)oxy)butyl)amino)-9-(2-(((1R*,2R*)-2-((3-cyclohexyl-propanoyl)oxy)cyclohexyl)thio)ethyl)-3-pentyltetradecyl 3-cyclohexylpropanoate

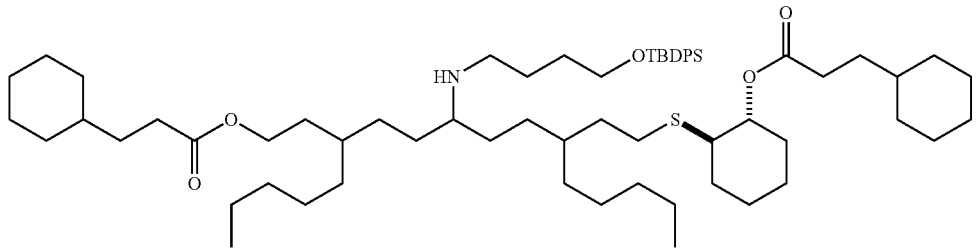

From 70 and 122. $^1$H NMR (400 MHz, CDCl$_3$) δ 7.68-7.66 (m, 4H), 7.44-7.37 (m, 6H), 4.85-4.77 (m, 1H), 4.11-4.07 (m, 2H), 3.69-3.68 (m, 2H), 2.68-2.52 (m, 5H), 2.35-2.29 (m, 4H), 1.72-1.13 (m, 65H), 1.06 (br s, 9H), 0.91-0.88 (m, 10H).

(xi) ((6-((4-(tert-Butydiphenylsilyloxy)butyl)amino)undecane-1,11-diyl)bis(sulfane-diyl))bis(octane-1,2-diyl) dinonanoate

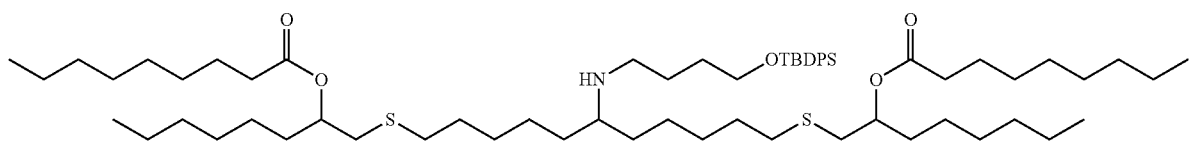

From 78 and 122. $^1$H NMR (400 MHz, CDCl$_3$) δ 7.71-7.64 (m, 4H), 7.48-7.32 (m, 6H), 4.96 (q, J=6.5 Hz, 2H), 3.76-3.55 (m, 2H), 2.69-2.41 (m, 11H), 2.30 (t, J=7.5 Hz, 4H), 1.42 (d, J=115.3 Hz, 64H), 1.04 (s, 9H), 0.91-0.84 (m, 12H).

(xii) ((6-((4-(tert-Butydiphenylsilyloxy)butyl)amino)undecane-1,11-diyl)bis(sulfane-diyl))bis(octane-1,2-diyl) dioctanoate

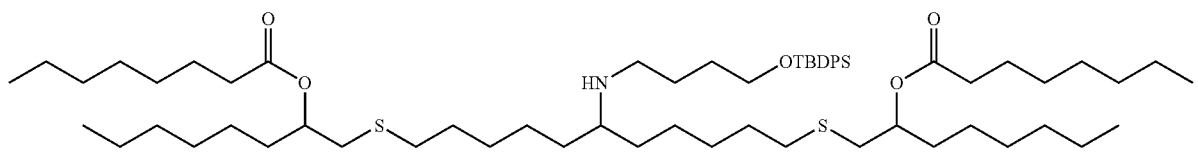

From 77 and 122. $^1$H NMR (400 MHz, CDCl$_3$) δ 7.69-7.63 (m, 4H), 7.46-7.33 (m, 6H), 5.03-4.87 (m, 2H), 3.77-3.61 (m, 2H), 2.72-2.42 (m, 11H), 2.30 (t, J=7.5 Hz, 4H), 1.84-1.14 (m, 60H), 1.04 (s, 9H), 0.92-0.81 (m, 12H).

(xiii) ((6-((4-(tert-Butydiphenylsilyloxy)butyl)amino)undecane-1,11-diyl)bis(sulfane-diyl))bis(octane-1,2-diyl) bis(3-cyclohexylpropanoate)

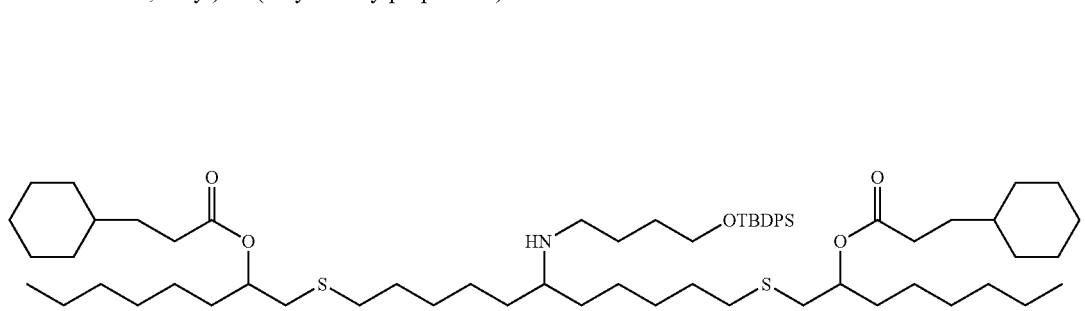

From 80 and 122. H NMR (400 MHz, C$_6$D$_6$) δ 7.88-7.79 (m, 4H), 7.33-7.24 (m, 6H), 5.30-5.19 (m, 2H), 3.73 (t, J=6.3 Hz, 2H), 2.76-2.48 (m, 10H), 2.46-2.39 (m, 1H), 2.35-2.22 (m, 4H), 1.80-1.01 (m, 71H), 0.94-0.85 (m, 6H), 0.84-0.70 (m, 4H).

(xiv) ((6-((2-(2-tert-Butydiphenylsilyloxy)ethyl)amino)undecane-1,11-diyl)bis(sulfane-diyl))bis(octane-1,2-diyl) bis(3-cyclohexylpropanoate)

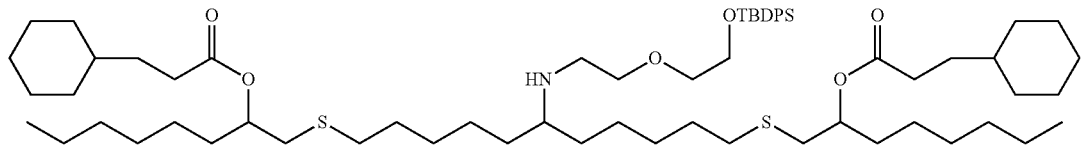

From 80 and 131. $^1$H NMR (400 MHz, CDCl$_3$) δ 7.71-7.64 (m, 4H), 7.45-7.33 (m, 6H), 4.98-4.89 (m, 2H), 3.81-3.77 (m, 2H), 3.59-3.55 (m, 4H), 2.76 (t, J=5.2 Hz, 2H), 2.67-2.57 (m, 4H), 2.56-2.48 (m, 5H), 2.34-2.27 (m, 4H), 1.75-1.09 (m, 58H), 1.04 (s, 9H), 0.93-0.82 (m, 10H).

(xv) ((6-((2-((2-tert-Butydiphenylsilyloxy)thio)ethyl)amino)undecane-1,11-diyl)bis-(sulfanediyl))bis(octane-1,2-diyl) bis(3-cyclohexylpropanoate)

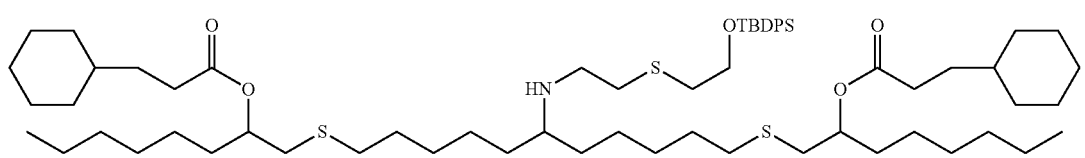

From 80 and 132. $^1$H NMR (400 MHz, CDCl$_3$) δ 7.71-7.64 (m, 4H), 7.45-7.33 (m, 6H), 4.98-4.89 (m, 2H), 3.81-3.77 (m, 2H), 2.76 (br t, J=5.2, 2H), 2.67-2.57 (m, 8H), 2.56-2.48 (m, 5H), 2.34-2.27 (m, 4H), 1.75-1.09 (m, 58H), 1.04 (s, 9H), 0.93-0.82 (m, 10H).

(xvi) 10-(5-((2-((3-Cyclohexylpropanoyl)oxy)octyl)thio)pentyl)-2,2-dimethyl-3,3-diphenyl-4-oxa-16-thia-9-aza-3-silatetracosan-18-yl heptanoate

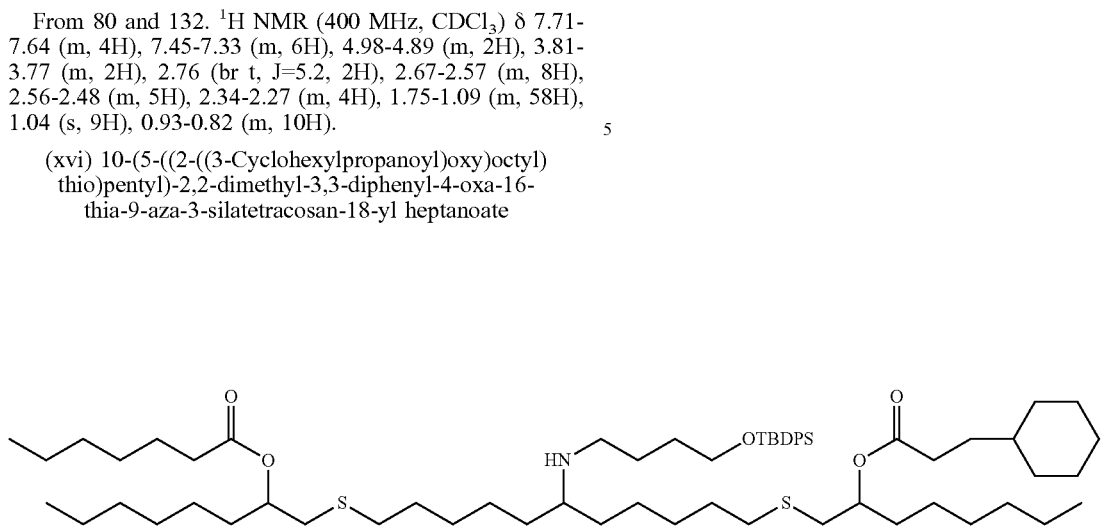

From 81 and 122. $^1$H NMR (400 MHz, CDCl$_3$) δ 7.69-7.64 (m, 4H), 7.45-7.34 (m, 4H), 5.02-4.87 (m, 2H), 3.73-3.63 (m, 2H), 2.74-2.44 (m, 11H), 2.37-2.25 (m, 4H), 1.85-1.10 (m, 61H), 1.04 (s, 9H), 0.93-0.83 (m, 11H).

(xvii) ((6-((4-tert-Butydiphenylsilyloxybutyl)amino)undecane-1,11-diyl)bis(sulfane-diyl))bis(octane-1,2-diyl) dicycloheptanecarboxylate

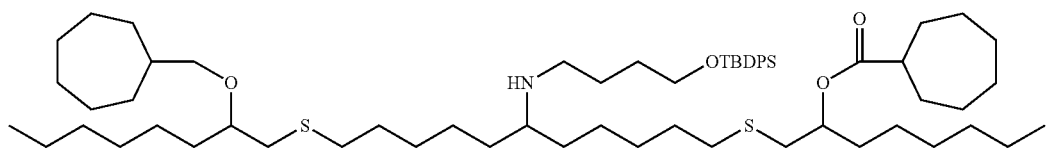

From 82 and 122. $^1$H NMR (400 MHz, CDCl$_3$) δ 7.85-7.77 (m, 4H), 7.30-7.23 (m, 6H), 5.27-5.17 (m, 2H), 3.73 (t, J=6.2 Hz, 2H), 2.75-2.46 (m, 12H), 2.43 (s, 1H), 2.09-1.94 (m, 4H), 1.91-1.16 (m, 69H), 0.89 (t, J=6.8 Hz, 6H).

(xviii) ((6-((4-tert-Butydiphenylsilyloxybutyl)amino)undecane-1,11-diyl)bis(sulfane-diyl))bis(octane-1,2-diyl)-bis(adamantane-1-carboxylate)

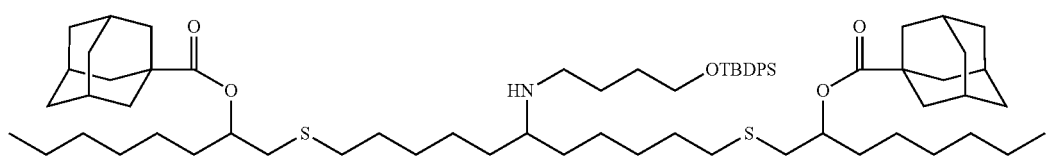

From 83 and 122. $^1$H NMR (400 MHz, CDCl$_3$) δ 7.84-7.79 (m, 4H), 7.30-7.24 (m, 6H), 5.22 (dt, J=10.6, 5.4 Hz, 2H), 3.73 (t, J=6.2 Hz, 2H), 2.74-2.49 (m, 10H), 2.46-2.38 (m, 1H), 2.10-2.06 (m, 12H), 1.91-1.86 (m, 6H), 1.77-1.18 (m, 52H), 1.21 (s, 9H), 0.92-0.86 (m, 6H).

(xix) ((6-cis-((3-((tert-Butyldiphenylsilyl)oxy)cyclobutyl)amino)undecane-1,11-diyl)-bis(sulfanediyl))bis(octane-1,2-diyl) bis(3-cyclohexylpropanoate)

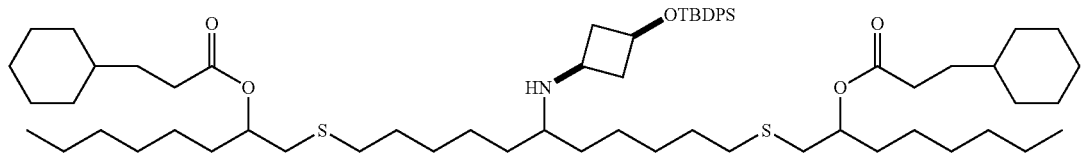

From 89 and 133. $^1$H NMR (400 MHz, CDCl$_3$) δ 7.67-7.62 (m, 4H), 7.44-7.33 (m, 6H), 5.00-4.89 (m, 2H), 3.96-3.88 (m, 1H), 2.72-2.57 (m, 4H), 2.57-2.41 (m, 6H), 2.35-2.27 (m, 4H), 1.87-1.06 (m, 62H), 1.02 (s, 9H), 0.93-0.80 (m, 10H).

(c) General Procedure for the Reductive Methylation of a Secondary Amine.

(i) 6-((4-((tert-Butyldiphenylsilyl)oxy)butyl)(methyl)amino)-11-((2-(octanoyloxy)-octyl)thio)undecyl 2-hexyldecanoate (124)

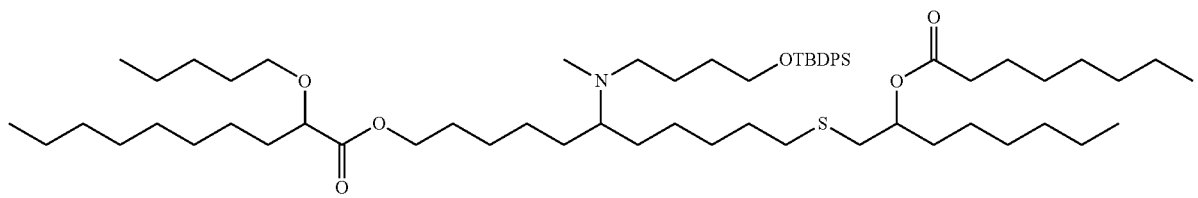

A solution of 123 (274 mg, 0.268 mmol), sodium triacetoxyborohydride (284 mg, 1.34 mmol) and aq. formaldehyde (37%, 0.75 mL) was stirred in THF (2 mL) under nitrogen for 2 days. The reaction was quenched with sat. aq. NaHCO$_3$ (2.00 mL), diluted with water (5 mL) and extracted with CH$_2$Cl$_2$ (3×5.00 mL). The combined organics were dried (Na$_2$SO$_4$) and concentrated. The residue was purified by silica chromatography (0-5% MeOH in CH$_2$Cl$_2$) to yield 124 (217 mg, 78%). $^1$H NMR (400 MHz, CDCl$_3$) δ 7.69-7.62 (m, 4H), 7.46-7.33 (m, 6H), 5.03-4.88 (m, 1H), 4.06 (t, J=6.6 Hz, 2H), 3.66 (t, J=5.9 Hz, 2H), 2.73-2.49 (m, 6H), 2.49-2.41 (m, 1H), 2.35-2.24 (m, 3H), 2.12 (s, 3H). 1.71-1.16 (m, 64H), 1.04 (s, 9H), 0.95-0.77 (m, 12H).

The following compounds were prepared by the same method:

(ii) 6-((4-((tert-Butyldiphenylsilyl)oxy)butyl)(methyl)amino)-11-((2-((6-methylheptan-oyl)oxy)octyl)thio)undecyl 2-hexyldecanoate

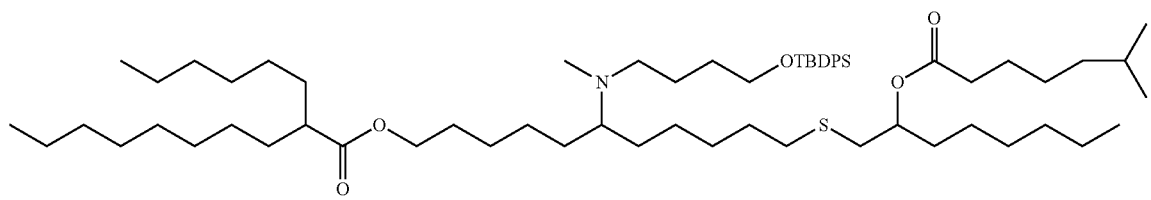

From 6-((4-((tert-butyldiphenylsilyl)oxy)-butyl)-amino)-11-((2-((6-methylheptanoyl)oxy)octyl)-thio)undecyl 2-hexyldecanoate. $^1$H NMR (400 MHz, CDCl$_3$) δ 7.71-7.60 (m, 4H), 7.46-7.32 (m, 6H), 5.00-4.91 (m, 1H), 4.05 (t, J=6.7 Hz, 2H), 3.66 (t, J=6.1 Hz, 2H), 2.69-2.58 (m, 2H), 2.53 (td, J=7.2, 1.3 Hz, 2H), 2.38-2.26 (m, 6H), 2.12 (s, 3H), 1.74-1.11 (m, 61H), 1.04 (s, 9H), 0.92-0.83 (m, 15H).

(iii) 6-((4-((tert-Butyldiphenylsilyl)oxy)butyl)(methyl)amino)-11-((2-((3-cyclohexyl-propanoyl)oxy)octyl)thio)undecyl 2-hexyldecanoate

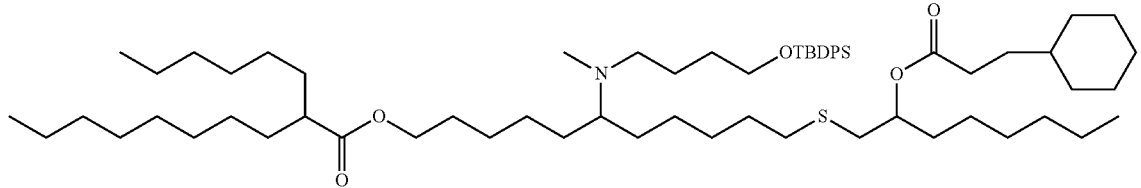

From 6-((4-((tert-butyldiphenylsilyl)-oxy)butyl)amino)-11-((2-((3-cyclohexylpropanoyl)oxy)-octyl)thio)-undecyl 2-hexyldecanoate. $^1$H NMR (400 MHz, CDCl$_3$) δ 7.73-7.62 (m, 4H), 7.43-7.32 (m, 6H), 5.01-4.90 (m, 1H), 4.05 (t, J=6.7 Hz, 2H), 3.66 (t, J=6.1 Hz, 2H), 2.68-2.59 (m, 2H), 2.59-2.49 (m, 2H), 2.38-2.23 (m, 6H), 2.13 (s, 3H), 1.84-1.11 (m, 65H), 1.04 (s, 9H), 0.92-0.78 (m, 12H).

(iii) 10-(5-((2-Hexyldecanoyl)oxy)pentyl)-2,2,9-trimethyl-3,3-diphenyl-4-oxa-16-thia-9-aza-3-silatetracosan-18-yl cycloheptanecarboxylate

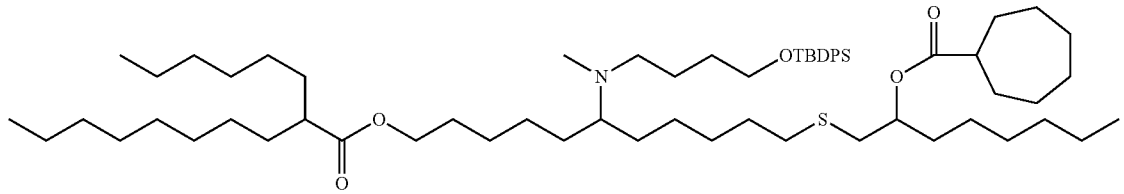

From 10-(5-((2-hexyldecanoyl)-oxy)-pentyl)-2,2-dimethyl-3,3-diphenyl-4-oxa-16-thia-9-aza-3-silatetra-cosan-18-yl cycloheptanecarboxylate. $^1$H NMR (400 MHz, CDCl$_3$) δ 7.80-7.61 (m, 4H), 7.49-7.34 (m, 6H), 4.99-4.87 (m, 1H), 4.05 (t, J=6.7 Hz, 2H), 3.66 (t, J=5.9 Hz, 2H), 2.69-2.40 (m, 8H), 2.37-2.26 (m, 1H), 2.13 (s, 3H), 1.99-1.18 (m, 66H), 1.04 (s, 9H), 0.91-0.84 (m, 9H).

(iv) 6-((4-((tert-Butyldiphenylsilyl)oxy)butyl)(methyl)amino)-11-((2-(2-cycloheptyl-acetoxy)octyl)thio)undecyl 2-hexyldecanoate

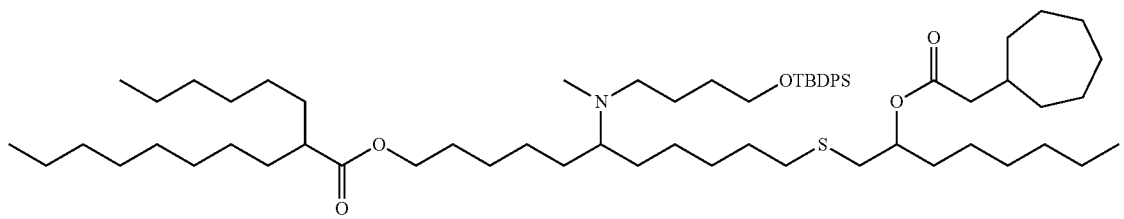

From 6-((4-((tert-butyldiphenylsilyl)oxy)-butyl)amino)-11-((2-(2-cycloheptylacetoxy)octyl)-thio)undecyl 2-hexyl-decanoate. ¹H NMR (400 MHz, CDCl₃) δ 7.73-7.61 (m, 4H), 7.46-7.34 (m, 6H), 5.00-4.91 (m, 1H), 4.05 (t, J=6.7 Hz, 2H), 3.66 (t, J=6.1 Hz, 2H), 2.72-2.59 (m, 2H), 2.57-2.48 (m, 2H), 2.40-2.26 (m, 4H), 2.22 (d, J=7.3 Hz, 2H), 2.12 (s, 3H), 2.06-1.95 (m, 1H), 1.78-1.12 (m, 66H), 1.04 (s, 9H), 0.93-0.83 (m, 9H).

(v) 6-((4-((tert-Butyldiphenylsilyl)oxy)butyl)(methyl)amino)-11-((2-((3-cyclohexyl-propanoyl)oxy)octyl)thio)undecyl cyclopentadecanecarboxylate

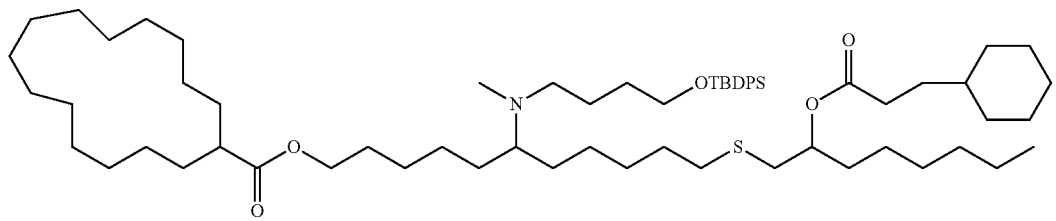

From 6-((4-((tert-butyldiphenyl-silyl)oxy)butyl)amino)-11-((2-((3-cyclohexylpropanoyl)oxy)octyl)thio)-undecyl cyclopenta-decanecarboxylate. ¹H NMR (400 MHz, CDCl₃) δ 7.78-7.54 (m, 4H), 7.48-7.28 (m, 6H), 5.03-4.81 (m, 1H), 4.04 (t, J=6.66 Hz, 2H), 3.81-3.45 (m, 2H), 2.63 (dd, J=6.14, 2.09 Hz, 2H), 2.53 (t, J=7.19 Hz, 2H), 2.44-2.27 (m, 5H), 2.12 (s, 3H), 1.76-1.44 (m, 20H), 1.44-1.09 (m, 50H), 1.04 (s, 9H), 0.95-0.80 (m, 5H). LRMS m/z 1048 [M+H]⁺.

(vi) 6-((4-((tert-butyldiphenylsilyl)oxy)butyl)(methyl)amino)-9-(2-((2-(octanoyloxy)-hexyl)thio)ethyl)-3-pentyltetradecyl octanoate

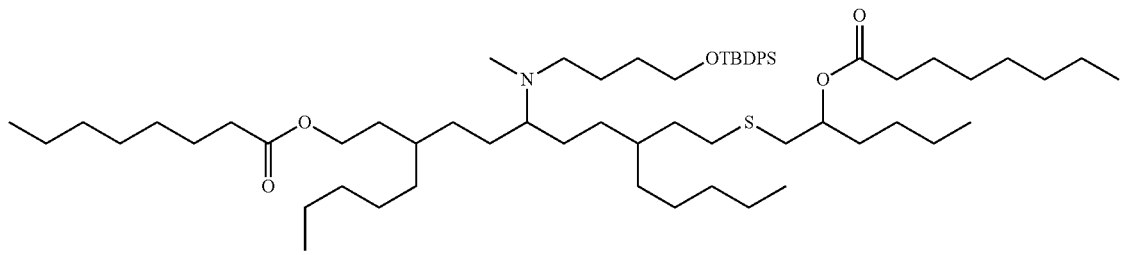

From 6-((4-((tert-butyldiphenylsilyl)oxy)butyl)-amino)-9-(2-((2-(octanoyloxy)hexyl)thio)-ethyl)-3-pentyltetradecyl octanoate. ¹H NMR (400 MHz, CDCl₃) δ 7.80-7.60 (m, 4H), 7.47-7.34 (m, 6H), 5.25-5.24 (m, 1H), 4.30-4.17 (m, 2H), 3.80-3.45 (m, 2H), 2.91 (brs, 1H), 2.80-2.59 (m, 6H), 2.42 (br s, 3H), 2.34-2.23 (m, 4H), 1.77-1.21 (m, 60H), 1.04 (br s, 9H), 0.99-0.95 (br t, 6H), 0.90-0.86 (br t, 9H).

(vii) 6-((4-((tert-Butyldiphenylsilyl)oxy)butyl)(methyl)amino)-9-(2-((2-((3-cyclohexyl-propanoyl)oxy)hexyl)thio)ethyl)-3-pentyltetradecyl 3-cyclohexylpropanoate

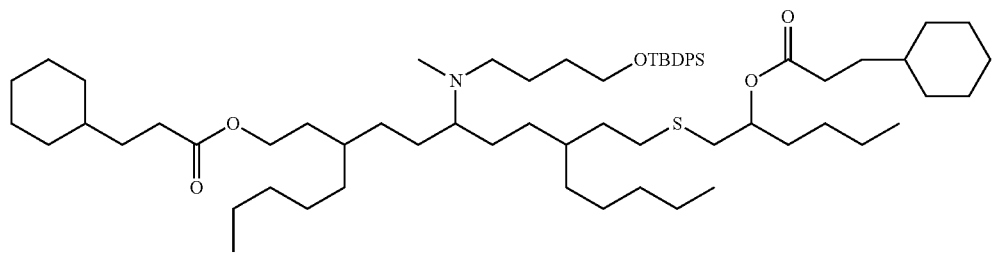

From 6-((4-((tert-Butyldiphenylsilyl)oxy)butyl)amino)-9-(2-((2-((3-cyclohexylpropanoyl)oxy)-hexyl)thio)ethyl)-3-pentyltetradecyl 3-cyclohexylpropanoate. ¹H NMR (400 MHz, CDCl₃) δ 7.80-7.60 (m, 4H), 7.47-7.34 (m, 6H), 5.28-5.22 (m, 1H), 4.30-4.20 (m, 2H), 3.80-3.45 (m, 2H), 2.93 (brs, 1H), 2.78-2.64 (m, 5H), 2.46 (brs, 3H), 2.34-2.27 (m, 3H), 1.78-0.75 (m, 77H); 1.04 (br s, 9H)

(viii) 1-((9-(2-(((3-Cyclohexylpropanoyl)oxy)ethyl)-6-((4-hydroxybutyl)(methyl)-amino)-3-pentyltetradecyl)thio)hexan-2-yl 3-cyclohexylpropanoate (13)

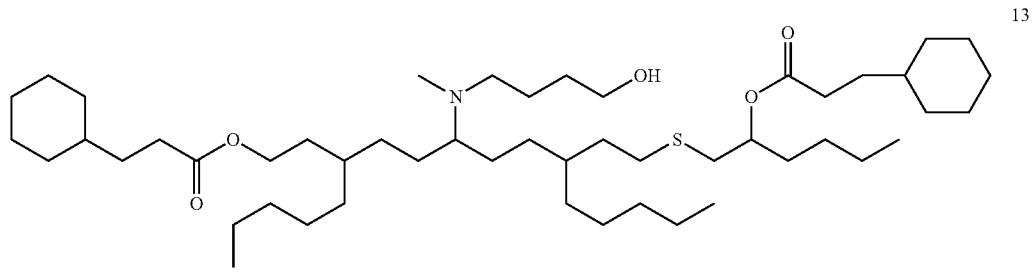 [SMILES: CCCCCC(CCOC(=O)CCC1CCCCC1)CCC(CCC(CCCCC)CCSCC(CCCC)OC(=O)CCC1CCCCC1)N(C)CCCCO]

From 6-((4-((tert-butyldiphenylsilyl)oxy)butyl)(methyl)amino)-9-(2-((2-((3-cyclohexyl-propanoyl)-oxy)hexyl)thio)ethyl)-3-pentyltetradecyl 3-cyclohexylpropanoate. $^1$H NMR (400 MHz, C$_6$D$_6$) δ 5.28-5.22 (m, 1H), 4.30-4.20 (m, 2H), 3.66-3.63 (m, 2H), 2.93 (brs, 1H), 2.78-2.64 (m, 5H), 2.46 (brs, 3H), 2.34-2.27 (m, 3H), 1.78-0.75 (m, 77H).

(viii) 6-((4-((tert-Butyldiphenylsilyl)oxy)butyl)(methyl)amino)-9-(2-(((1R*,2R*)-2-(octanoyl-oxy)cyclohexyl)thio)ethyl)-3-pentyltetradecyl octanoate

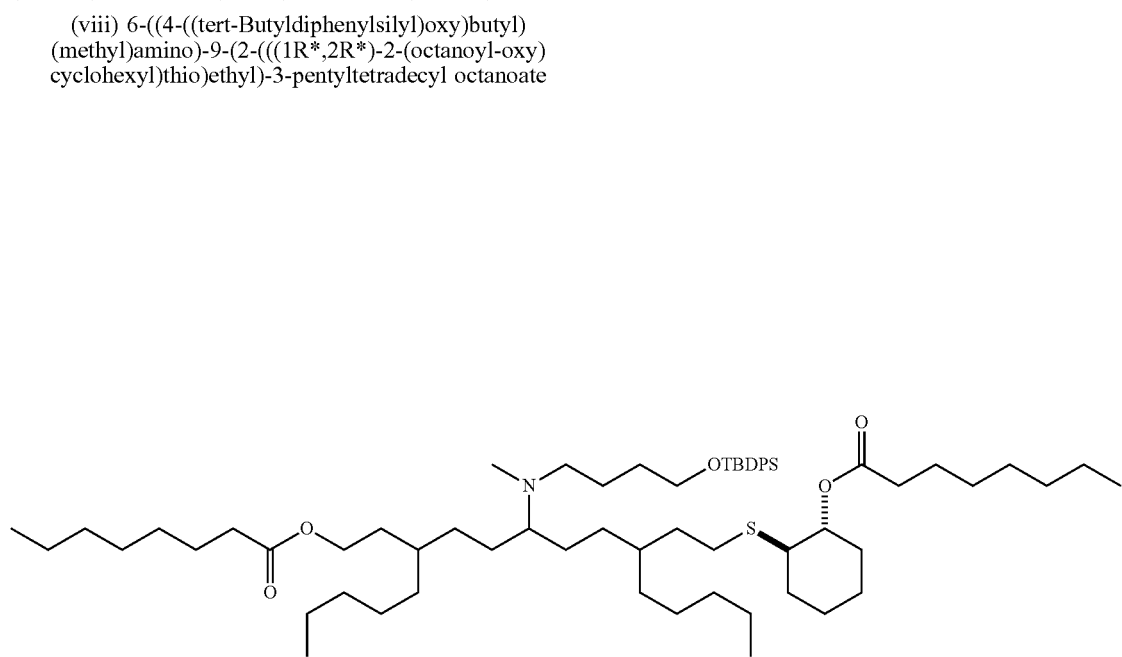

From 6-((4-((tert-butyldiphenylsilyl)-oxy)butyl)amino)-9-(2-(((1R*,2R*)-2-(octanoyloxy)cyclohexyl)thio)-ethyl)-3-pentyltetradecyl octanoate. $^1$H NMR (400 MHz, CDCl$_3$) δ 7.80-7.60 (m, 4H), 7.47-7.34 (m, 6H), 5.13-5.09 (m, 1H), 4.30-4.14 (m, 2H), 3.78-3.44 (m, 2H), 2.90 (brs, 1H), 2.77-2.58 (m, 4H), 2.41-2.23 (m, 6H), 2.13-2.09 (m, 2H), 1.70-1.21 (m, 62H), 1.04 (br s, 9H), 0.98-0.95 (m, 6H), 0.91-0.86 (m, 6H).

(ix) 6-((4-Hydroxybutyl)(methyl)amino)-9-(2-(((1R*,2R*)-2-(octanoyloxy)cyclohexyl)-thio)ethyl)-3-pentyltetradecyl octanoate (14)

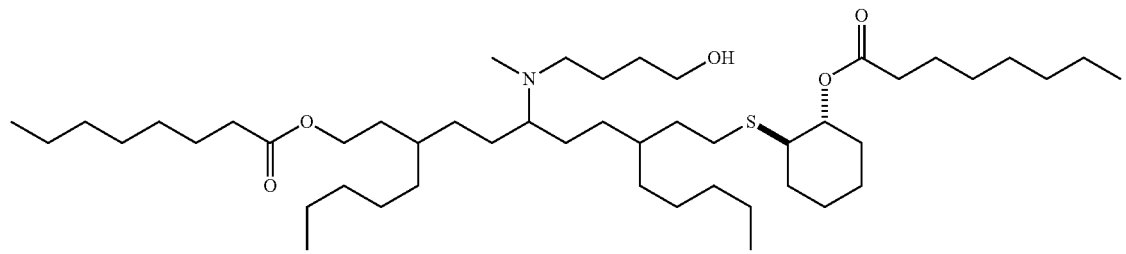

14

From 6-((4-((tert-butyldiphenylsilyl)oxy)butyl)-(methyl) amino)-9-(2-(((1R*,2R*)-2-(octanoyloxy)cyclo-hexyl)thio) ethyl)-3-pentyltetradecyl octanoate. $^1$H NMR (400 MHz, C$_6$D$_6$) δ 5.13-5.09 (m, 1H), 4.30-4.14 (m, 2H), 3.63-3.60 (m, 2H), 2.90 (brs, 1H), 2.77-2.58 (m, 4H), 2.41-2.23 (m, 6H), 2.13-2.09 (m, 2H), 1.70-1.21 (m, 62H), 0.98-0.95 (m, 6H), 0.91-0.86 (m, 6H).

(ix) 6-((4-((tert-Butyldiphenylsilyl)oxy)butyl) (methyl)amino)-9-(2-(((1R*,2R*)-2-((3-cyclo-hexyl-propanoyl)oxy)cyclohexyl)thio)ethyl)-3-pentyltetra-decyl 3-cyclohexylpropanoate

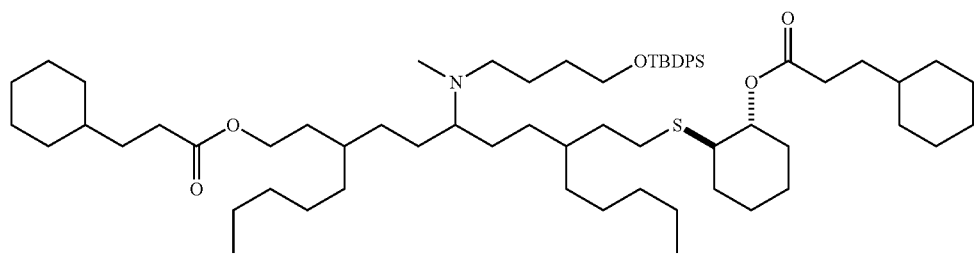

From 6-((4-((tert-butyldiphenylsilyl)oxy)butyl)amino)-9-(2-(((1R*,2R*)-2-((3-cyclohexyl-propanoyl)oxy)-cyclo-hexyl)thio)ethyl)-3-pentyltetradecyl 3-cyclohexylpropano-ate. $^1$H NMR (400 MHz, CDCl$_3$) δ 7.80-7.60 (m, 4H), 7.47-7.34 (m, 6H), 5.12-5.05 (m, 1H), 4.29-4.17 (m, 2H), 3.79-3.45 (m, 2H), 2.89-2.24 (m, 11H), 2.14-2.08 (m, 2H), 1.67-1.05 (m, 64H), 1.04 (br s, 9H), 0.98-0.95 (m, 6H), 0.91-0.76 (m, 4H).

(x) 9-(2-(((1R*,2R*)-2-((3-cyclohexylpropanoyl) oxy)cyclohexyl)thio)ethyl)-6-((4-hydroxy-butyl) (methyl)amino)-3-pentyltetradecyl 3-cyclohexylpro-panoate (15)

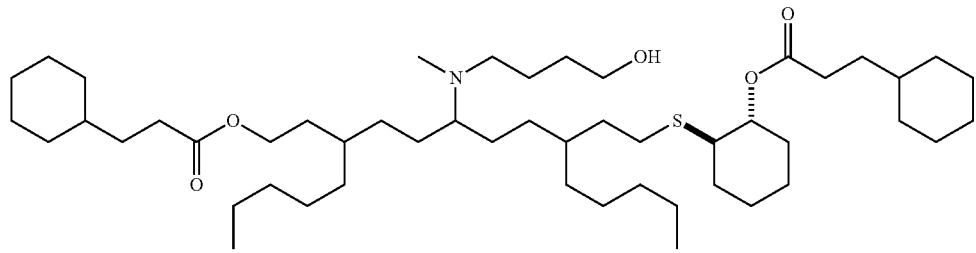

15

From 6-((4-(((tert-butyldiphenylsilyl)oxy)butyl)(methyl)amino)-9-(2-(((1R*,2R*)-2-((3-cyclohexylpropanoyl)oxy)-cyclohexyl)thio)ethyl)-3-pentyltetradecyl 3-cyclohexylpropan-oate. $^1$H NMR (400 MHz, C$_6$D$_6$) δ 5.12-5.05 (m, 1H), 4.29-4.17 (m, 2H), 3.64-3.60 (m, 2H), 2.89-2.24 (m, 11H), 2.14-2.08 (m, 2H), 1.67-1.05 (m, 62H), 0.98-0.95 (m, 6H), 0.91-0.76 (m, 4H).

(x) ((6-((4-(tert-Butydiphenylsilyloxybutyl)(methyl)amino)undecane-1,11-diyl)bis-(sulfanediyl))bis(octane-1,2-diyl) dinonanoate

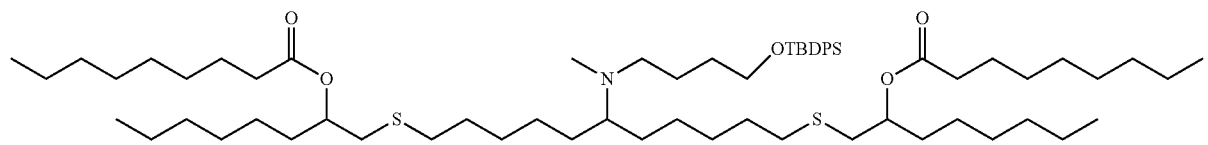

From ((6-((4-(tert-butydiphenylsilyloxy)butyl)-amino)undecane-1,11-diyl)bis(sulfanediyl))bis-(octane-1,2-diyl) dinonanoate. $^1$H NMR (400 MHz, CDCl$_3$) δ 7.80-7.60 (m, 4H), 7.47-7.34 (m, 6H), 5.00-4.91 (m, 2H), 3.66 (t, J=6.1 Hz, 2H), 2.72-2.57 (m, 4H), 2.57-2.48 (m, 4H), 2.39-2.26 (m, 7H), 2.12 (s, 3H), 1.84-1.11 (m, 64H), 1.04 (s, 9H), 0.97-0.83 (m, 12H).

(xi) ((6-((4-(tert-Butydiphenylsilyloxybutyl)(methyl)amino)undecane-1,11-diyl)bis-(sulfanediyl))bis(octane-1,2-diyl) dioctanoate

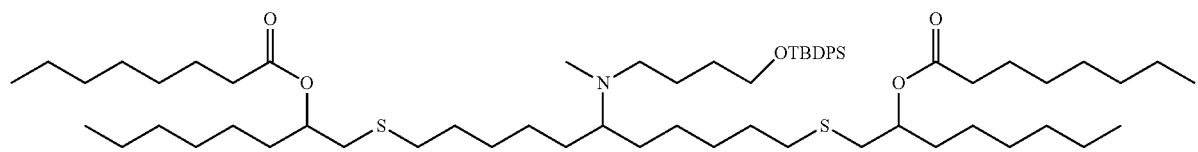

From ((6-((4-(tert-butydiphenylsilyloxy)butyl)-amino)undecane-1,11-diyl)bis(sulfanediyl))bis-(octane-1,2-diyl) dioctanoate. $^1$H NMR (400 MHz, CDCl$_3$) δ 7.73-7.59 (m, 4H), 7.47-7.32 (m, 6H), 5.06-4.88 (m, 2H), 3.66 (t, J=6.2 Hz, 2H), 2.72-2.57 (m, 4H), 2.53 (dd, J=7.9, 6.3 Hz, 4H), 2.38-2.25 (m, 7H), 2.12 (s, 3H), 1.76-1.10 (m, 60H), 1.04 (s, 9H), 0.94-0.83 (m, 12H).

(xii) ((6-((4-(tert-Butyldiphenylsilyloxybutyl)(methyl)amino)undecane-1,11-diyl)bis-(sulfanediyl))bis(octane-1,2-diyl) bis(3-cyclohexylpropanoate)

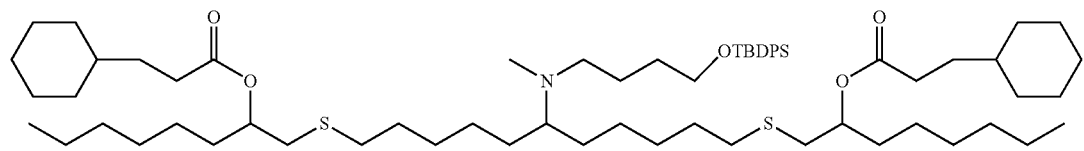

From ((6-((4-(tert-butydiphenylsilyl-oxy)butyl)amino)undecane-1,11-diyl)bis(sulfanediyl))bis-(octane-1,2-diyl) bis(3-cyclohexyl-propanoate). $^1$H NMR (400 MHz, C$_6$D$_6$) δ 7.90-7.75 (m, 4H), 7.31-7.25 (m, 6H), 5.32-5.19 (m, 2H), 3.74 (t, J=6.2 Hz, 2H), 2.76-2.48 (m, 8H), 2.43-2.34 (m, 3H), 2.33-2.24 (m, 4H), 2.13 (s, 3H), 1.82-0.98 (m, 71H), 0.96-0.86 (m, 6H), 0.83-0.71 (m, 4H).

(xiii) ((6-((2-(2-tert-Butyldipheylsilyloxy)ethoxy)ethyl)(methyl)amino)undecane-1,11-diyl)-bis(sulfanediyl))bis(octane-1,2-diyl) bis(3-cyclohexylpropanoate)

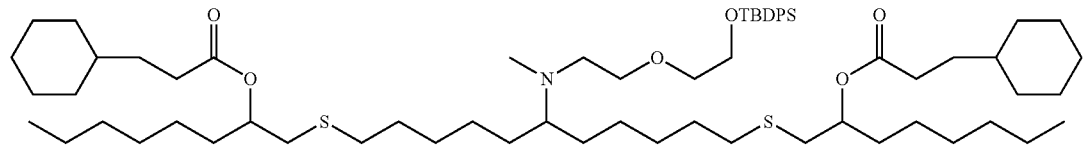

From ((6-((2-(2-tert-butydiphenylsilyloxy)ethyl)amino)undecane-1,11-diyl)bis(sulfanediyl))-bis(octane-1,2-diyl) bis(3-cyclohexylpropanoate). $^1$H NMR (400 MHz, CDCl$_3$) δ 7.70-7.62 (m, 4H), 7.46-7.32 (m, 6H), 4.95 (dtd, J=8.1, 6.1, 4.4 Hz, 2H), 3.83-3.76 (m, 2H), 3.60-3.54 (m, 2H), 3.50 (t, J=6.6 Hz, 2H), 2.69-2.58 (m, 4H), 2.58-2.46 (m, 7H), 2.31 (dd, J=8.4, 7.1 Hz, 4H), 2.21 (s, 3H), 1.74-1.09 (m, 58H), 1.05 (s, 9H), 0.94-0.82 (m, 10H).

(xiv) ((6-((2-((2-tert-Butydiphenylsilyloxy)thio)ethyl)(methyl)amino)undecane-1,11-diyl)bis(sulfane-diyl))bis(octane-1,2-diyl) bis(3-cyclohexylpropanoate)

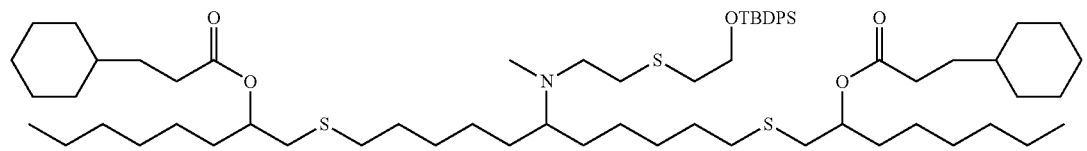

From ((6-((2-((2-tert-Butydiphenylsilyloxy)thio)ethyl)amino)undecane-1,11-diyl)bis(sulfanediyl))bis-(octane-1,2-diyl) bis(3-cyclohexylpropanoate). $^1$H NMR (400 MHz, CDCl$_3$) δ 7.70-7.65 (m, 4H), 7.44-7.34 (m, 6H), 4.99-4.90 (m, 2H), 3.79 (t, J=7.1 Hz, 2H), 2.70-2.60 (m, 6H), 2.54 (dd, J=7.3, 1.6 Hz, 4H), 2.51 (s, 3H), 2.34-2.27 (m, 4H), 1.77-1.08 (m, 63H), 1.05 (s, 9H), 0.93-0.82 (m, 10H).

(xv) ((6-((4-tert-Butydiphenylsilyloxybutyl)(methyl)amino)undecane-1,11-diyl)bis-(sulfanediyl))bis(octane-1,2-diyl) dicycloheptanecarboxylate

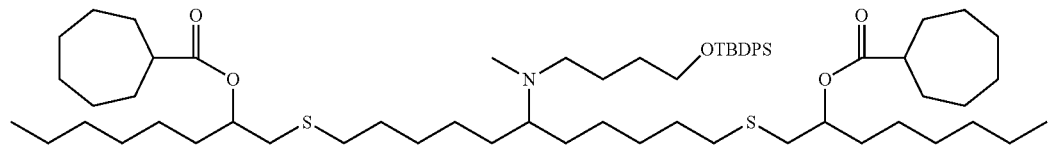

From ((6-((4-tert-butydiphenyl-silyloxybutyl)amino)undecane-1,11-diyl)bis(sulfanediyl))bis-(octane-1,2-diyl) dicycloheptane-carboxylate. $^1$H NMR (400 MHz, CDCl$_3$) δ 7.85-7.79 (m, 4H), 7.30-7.24 (m, 6H), 5.27-5.18 (m, 2H), 3.75 (t, J=6.2 Hz, 2H), 2.74-2.48 (m, 10H), 2.42-2.33 (m, 3H), 2.13 (s, 3H), 2.07-1.95 (m, 4H), 1.90-1.52 (m, 20H), 1.46-1.12 (m, 50H), 0.89 (t, J=6.8 Hz, 6H).

(xvi) ((6-((4-tert-Butydiphenylsilyloxybutyl)(methyl)amino)undecane-1,11-diyl)bis-(sulfanediyl))bis(octane-1,2-diyl)-bis(adamantane-1-carboxylate)

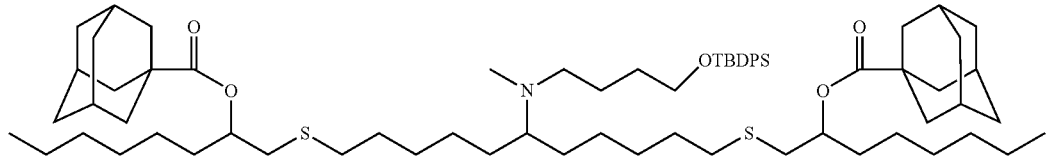

From ((6-((4-tert-butyl-diphenylsilyloxybutyl)amino)undecane-1,11-diyl)bis(sulfane-diyl))bis(octane-1,2-diyl)-bis(adamantane-1-carboxylate). $^1$H NMR (400 MHz, CDCl$_3$) δ 7.84-7.79 (m, 4H), 7.30-7.24 (m, 6H), 5.26-5.18 (m, 2H), 3.75 (t, J=6.2 Hz, 2H), 2.74-2.49 (m, 8H), 2.37 (q, J=6.5 Hz, 3H), 2.13 (s, 3H), 2.10-2.06 (m, 12H), 1.89 (s, 6H), 1.82-0.99 (m, 52H), 1.22 (s, 9H), 0.89 (t, J=6.9 Hz, 6H).

(xvii) ((6-cis-((3-((tert-Butyldiphenylsilyl)oxy)cyclobutyl)(methyl)amino)undecane-1,11-diyl)bis-(sulfanediyl))bis(octane-1,2-diyl) bis(3-cyclohexylpropanoate)

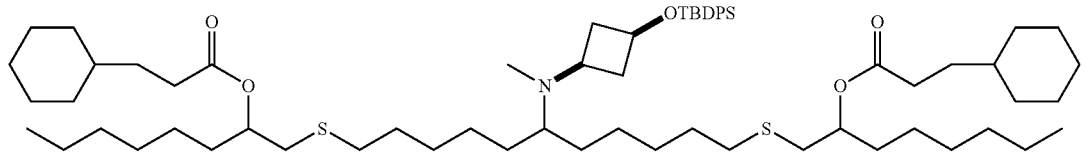

From ((6-cis-((3-((tert-butyldiphenylsilyl)oxy)cyclobutyl)amino)undecane-1,11-diyl)bis(sulfane-diyl))bis(octane-1,2-diyl) bis(3-cyclohexylpropanoate). $^1$H NMR (400 MHz, CDCl$_3$) δ 7.68-7.63 (m, 4H), 7.45-7.34 (m, 6H), 4.99-4.90 (m, 2H), 3.96-3.85 (m, 1H), 3.78-3.71 (m, 1H), 2.69-2.58 (m, 4H), 2.57-2.49 (m, 4H), 2.48-2.40 (m, 1H), 2.37-2.21 (m, 6H), 1.96 (s, 3H), 2.01-1.05 (m, 60H), 1.02 (s, 9H), 0.93-0.82 (m, 10H).

(d) General Procedure for the Reductive Alkylation of a Secondary Amine.

Same as procedure (i) in part (c), except that a homologue of formaldehyde was used. The following compounds were thus prepared:

(i) ((6-(ethyl(4-tert-Butyldiphenylsilyoxybutyl)amino)undecane-1,11-diyl)bis(sulfane-diyl))bis(octane-1,2-diyl) dinonanoate

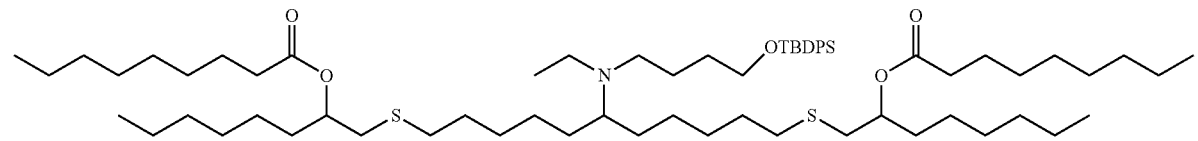

From ((6-(4-tert-butyldiphenylsilyoxybutyl)amino)undecane-1,11-diyl)bis(sulfanediyl))bis(octane-1,2-diyl) dinonanoate and acetaldehyde. ¹H NMR (400 MHz, CDCl₃) δ 7.80-7.60 (m, 4H), 7.47-7.34 (m, 6H), 5.00-4.91 (m, 2H), 3.66 (t, J=6.1 Hz, 2H), 2.72-2.57 (m, 4H), 2.57-2.48 (m, 4H), 2.39-2.26 (m, 7H), 2.12 (s, 3H), 1.84-1.11 (m, 64H), 1.04 (s, 9H), 0.97-0.83 (m, 12H).

(ii) 10-(5-((2-((3-Cyclohexylpropanoyl)oxy)octyl)thio)pentyl)-9-ethyl-2,2-dimethyl-3,3-diphenyl-4-oxa-16-thia-9-aza-3-silatetracosan-18-yl heptanoate

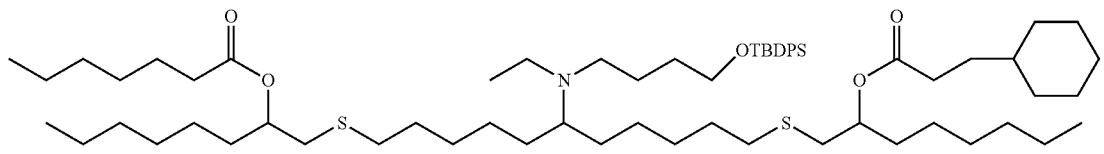

From 10-(5-((2-((3-cyclohexylpropanoyl)oxy)octyl)thio)pentyl)-2,2-dimethyl-3,3-diphenyl-4-oxa-16-thia-9-aza-3-silatetracosan-18-yl heptanoate and acetaldehyde. ¹H NMR (400 MHz, CDCl₃) δ 7.70-7.61 (m, 4H), 7.45-7.34 (m, 6H), 5.01-4.89 (m, 2H), 3.65 (t, J=6.3 Hz, 2H), 2.68-2.59 (m, 4H), 2.58-2.48 (m, 4H), 2.41-2.24 (m, 9H), 1.79-1.08 (m, 59H), 1.04 (s, 9H), 0.94 (t, J=7.0 Hz, 3H), 0.91-0.85 (m, 11H).

(iii) ((6-(Ethyl(4-tert-Butyldiphenylsilyoxybutyl)amino)undecane-1,11-diyl)bis-(sulfanediyl))bis(octane-1,2-diyl) bis(3-cyclohexylpropanoate)

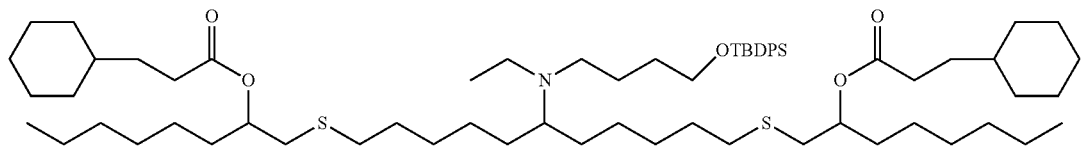

From ((6-((4-(tert-butydiphenylsilyloxy)-butyl)amino)undecane-1,11-diyl)bis(sulfanediyl))bis-(octane-1,2-diyl) bis(3-cyclohexylpropan-oate) and acetaldehyde. ¹H NMR (400 MHz, CDCl₃) δ 7.70-7.61 (m, 4H), 7.48-7.33 (m, 6H), 5.01-4.89 (m, 2H), 3.65 (t, J=6.3 Hz, 2H), 2.69-2.58 (m, 4H), 2.52 (t, J=7.0 Hz, 4H), 2.43-2.27 (m, 9H), 1.80-1.08 (m, 62H), 1.04 (s, 9H), 0.94 (t, J=7.0 Hz, 3H), 0.92-0.84 (m, 10H).

(e) General Procedures for the Perdeuteroalkylation of a Secondary Amine.

(i) ((6-((4-tert-Butyldiphenylsilyloxybutyl)(methyl-d₃)amino)undecane-1,11-diyl)bis-(sulfanediyl))bis(octane-1,2-diyl) bis(3-cyclohexylpropanoate)

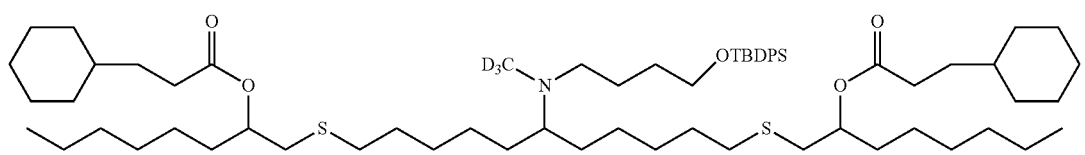

To a reaction vial under inert atmosphere was added ((6-((4-(tert-butydiphenylsilyloxy)butyl)amino)undecane-1,11-diyl)bis(sulfanediyl))bis-(octane-1,2-diyl) bis(3-cyclohexylpropanoate) (1.0 mmol, 1.07 g), DMF (1.0 mL), and iodomethane-d$_3$ (1.5 mmol, 0.09 mL). The vial was covered in Al foil and was stirred at RT for 18 h, then the solution was diluted with water (2 ml) and hexanes (2 ml). The layers were separated and the organic phase was collected. The aq. phase was back-extracted with hexanes (2×2 mL). The combined organics were washed with 0.1M NaOH (1×5 mL), dried (Na$_2$SO$_4$), filtered, and evaporated to yield a crude mixture of starting material, desired tertiary amine, and quaternary ammonium product. The crude mixture was diluted with CH$_2$Cl$_2$ (1.0 mL) under inert atmosphere, then triethylamine (1.5 mmol, 0.2 mL) and Boc anhydride (1.0 mmol, 0.216 g) were added. The mixture was stirred for 18 h then diluted with water (2 ml) and hexanes (2 ml). The layers were separated and the organic phase was collected. The aq. phase was back extracted with hexanes (2×2 mL). The combined organics were washed with 0.1M NaOH (1×5 mL), dried (Na$_2$SO$_4$), filtered, and evaporated to yield a mixture of Boc protected starting material and crude product. This was purified by automated chromatography [0-7% (9:1 MeOH:NH$_4$OH) in DCM over 12 CV] to yield the desired tertiary amine (0.214 mmol, 0.234 g, 22% yield). $^1$H NMR (400 MHz, CDCl$_3$) δ 7.69-7.63 (m, 4H), 7.45-7.33 (m, 6H), 4.99-4.90 (m, 2H), 3.66 (t, J=6.1 Hz, 2H), 2.68-2.58 (m, 4H), 2.55-2.49 (m, 4H), 2.36-2.27 (m, 7H), 1.77-1.09 (m, 62H), 1.04 (s, 9H), 0.94-0.81 (m, 10H). $^{13}$C NMR (101 MHz, CDCl$_3$) δ 173.8, 135.6, 134.1, 129.5, 127.6, 72.8, 63.9, 62.8, 53.2, 37.2, 36.0, 33.2, 33.0, 32.8, 32.4, 32.2, 31.7, 30.5, 29.8, 29.7, 29.3, 29.1, 27.1, 26.9, 26.6, 26.3, 25.3, 24.7, 22.6, 19.2, 14.1.

(ii) ((6-((4-tert-Butyldiphenylsilyloxybutyl)(ethyl-d$_5$)amino)undecane-1,11-diyl)bis-(sulfanediyl))bis(octane-1,2-diyl) bis(3-cyclohexylpropanoate)

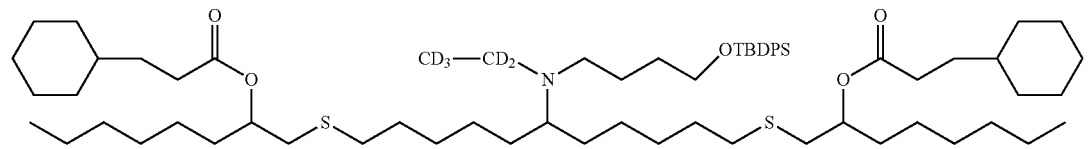

To a reaction vial under inert atmosphere was added ((6-((4-(tert-butydiphenylsilyloxy)butyl)amino)undecane-1,11-diyl)bis(sulfanediyl))bis-(octane-1,2-diyl) bis(3-cyclohexylpropanoate) (0.37 mmol, 0.403 g), DMF (0.37 mL), and iodoethane-d$_5$ (0.45 mmol, 0.04 mL). The vial was covered in Al foil and was stirred at RT for 18 h then diluted with water (2 ml) and hexanes (2 ml). The layers were separated and the organic phase was collected. The aq. phase was back-extracted with hexanes (2×2 mL). The combined organics were washed with 0.1M NaOH (1×5 mL), dried (Na$_2$SO$_4$), filtered, and evaporated to yield a crude mixture of starting material, desired tertiary amine, and quaternary ammonium product. The crude mixture was diluted with CH$_2$Cl$_2$ (0.37 mL) under inert atmosphere, then triethylamine (0.56 mmol, 0.08 mL) and Boc anhydride (0.37 mmol, 0.082 g) were added. The mixture was stirred for 18 h then diluted with water (2 ml) and hexanes (2 ml). The layers were separated and the organic phase was collected. The aq. phase was back extracted with hexanes (2×2 mL). The combined organics were washed with 0.1M NaOH (1×5 mL), dried (Na$_2$SO$_4$), filtered, and evaporated to yield a mixture of Boc protected starting material and crude product. This was purified by automated chromatography [0-7% (9:1 MeOH:NH$_4$OH) in DCM over 12 CV] to yield the desired tertiary amine (0.127 mmol, 0.142 g, 34% yield). $^1$H NMR (400 MHz, C$_6$D$_6$) δ 7.85-7.79 (m, 4H), 7.30-7.24 (m, 6H), 5.28-5.20 (m, 2H), 3.75 (t, J=6.2 Hz, 2H), 2.70 (dd, J=13.6, 6.3 Hz, 2H), 2.66-2.50 (m, 6H), 2.48-2.41 (m, 1H), 2.38 (t, J=7.0 Hz, 2H), 2.33-2.26 (m, 4H), 1.76-1.03 (m, 71H), 0.89 (t, J=6.9 Hz, 6H), 0.84-0.71 (m, 4H). $^{13}$C NMR (101 MHz, C$_6$D$_6$) δ=173.2, 136.1, 134.6, 130.0, 128.1, 72.8, 64.4, 60.1, 49.9, 37.4, 36.5, 33.7, 33.2, 33.1, 32.9, 32.3, 32.1, 31.0, 30.8, 30.2, 29.6, 29.5, 27.6, 27.2, 26.9, 26.6, 26.3, 25.8, 23.0, 14.3.

(e) General Procedures for Silyl Group Release.

(i) 6-((4-Hydroxybutyl)(methyl)amino)-11-((2-(octanoyloxy)octyl)thio)undecyl 2-hexyl-decanoate (6)

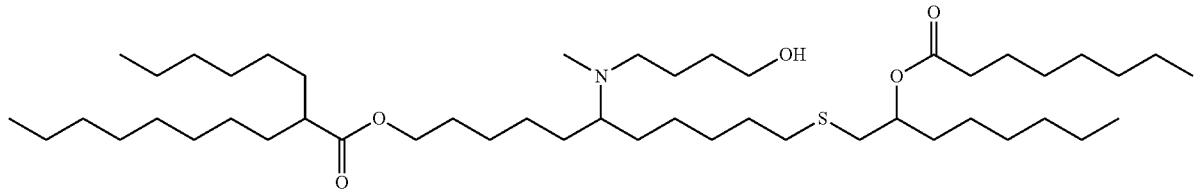

6

To a solution of 124 (188 mg, 0.182 mmol) in THF (2 mL) was added HF-pyridine (0.2 mL) at 0° C. under inert atmosphere. The reaction was warmed to room temperature and stirred for 18 hours. Water (5 mL) was added, and the mixture was extracted with $CH_2Cl_2$ (3×5 mL). The combined extracts were dried ($Na_2SO_4$) and concentrated. The residue was purified by silica chromatography (0-5% MeOH in $CH_2Cl_2$) to yield 6 (103 mg, 71%). $^1$H NMR (400 MHz, $C_6D_6$) δ 5.33-5.20 (m, 1H), 4.19 (t, J=6.7 Hz, 2H), 3.73-3.58 (m, 2H), 2.89-2.46 (m, 8H), 2.37 (s, 3H), 2.33-2.24 (m, 2H), 1.97-0.99 (m, 64H), 0.98-0.86 (m, 12H).

The following compounds were prepared by the same method:

(ii) 6-((4-Hydroxybutyl)(methyl)amino)-11-((2-((6-methylheptanoyl)oxy)octyl)thio)-undecyl 2-hexyldecanoate (7)

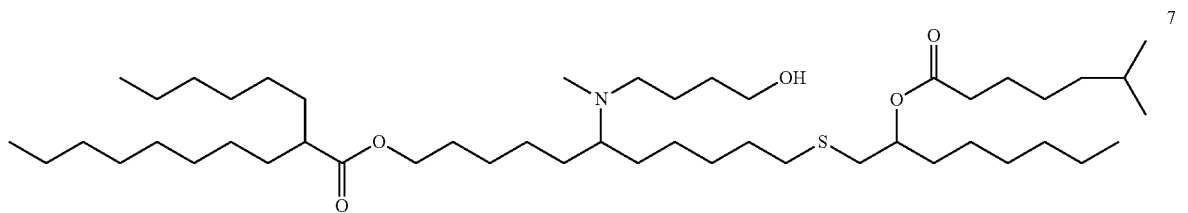 [SMILES: CCCCCCCCC(CCCCCC)C(=O)OCCCCCC(CCCCCSCC(CCCCCC)OC(=O)CCCCC(C)C)N(C)CCCCO]

7

From 6-((4-((tert-butyldiphenylsilyl)oxy)-butyl)(methyl) amino)-11-((2-((6-methylheptanoyl)-oxy)octyl)thio)undecyl 2-hexyldecan-oate. $^1$H NMR (400 MHz, $C_6D_6$) δ 5.36-5.20 (m, 1H), 4.19 (t, J=6.7 Hz, 2H), 3.74-3.54 (m, 2H), 2.86-2.46 (m, 8H), 2.42-2.36 (m, 3H), 2.29 (td, J=7.4, 3.0 Hz, 2H), 1.91-1.01 (m, 61H), 0.99-0.89 (m, 9H), 0.87 (d, J=6.6 Hz, 6H).

(iii) 11-((2-((3-Cyclohexylpropanoyl)oxy)octyl)thio)-6-((4-hydroxybutyl)(methyl)-amino)undecyl 2-hexyldecanoate (8)

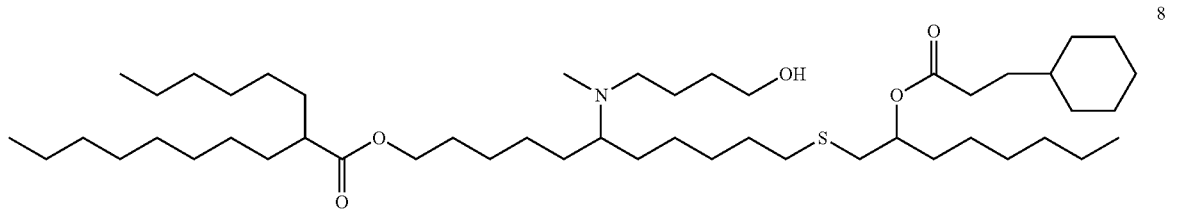 [SMILES: CCCCCCCCC(CCCCCC)C(=O)OCCCCCC(CCCCCSCC(CCCCCC)OC(=O)CCC1CCCCC1)N(C)CCCCO]

8

From 6-((4-((tert-butyldiphenylsilyl)oxy)-butyl)(methyl) amino)-11-((2-((3-cyclohexyl-propanoyl)oxy)octyl)thio)undecyl 2-hexyl-decanoate. $^1$H NMR (400 MHz, C$_6$D$_6$) δ 5.34-5.19 (m, 1H), 4.19 (t, J=6.7 Hz, 2H), 3.75-3.58 (m, 2H), 2.89-2.44 (m, 8H), 2.43-2.27 (m, 5H), 1.97-1.01 (m, 65H), 1.00-0.85 (m, 9H), 0.87-0.73 (m, 2H).

(iv) 1-((11-((2-Hexyldecanoyl)oxy)-6-((4-hydroxy-butyl)(methyl)amino)undecyl)thio)-octan-2-yl cyclo-heptanecarboxylate (9)

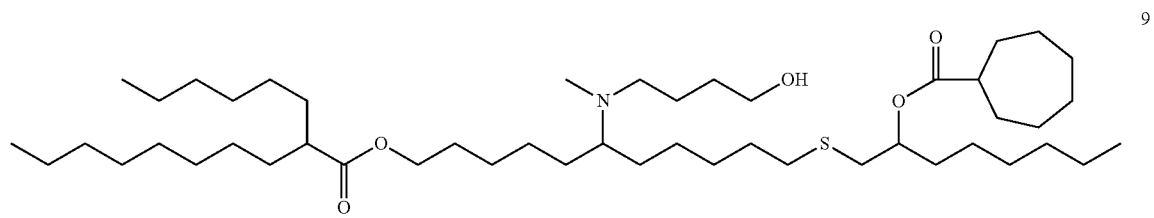 [SMILES: CCCCCCCCC(CCCCCC)C(=O)OCCCCCC(CCCCCSCC(CCCCCC)OC(=O)C1CCCCCC1)N(C)CCCCO]

From 10-(5-((2-hexyldecanoyl)oxy)pentyl)-2,2,9-trimethyl-3,3-diphenyl-4-oxa-16-thia-9-aza-3-silatetracosan-18-yl cycloheptane-carboxylate. $^1$H NMR (400 MHz, C$_6$D$_6$) δ 5.30-5.20 (m, 1H), 4.19 (t, J=6.7 Hz, 2H), 3.62 (t, J=5.2 Hz, 2H), 2.92-2.45 (m, 9H), 2.35 (s, 3H), 2.13-1.96 (m, 2H), 1.90-1.08 (m, 64H), 0.97-0.85 (m, 9H).

(v) 11-((2-(2-Cycloheptylacetoxy)octyl)thio)-6-((4-hydroxybutyl)(methyl)amino)-undecyl 2-hexyldecanoate (10)

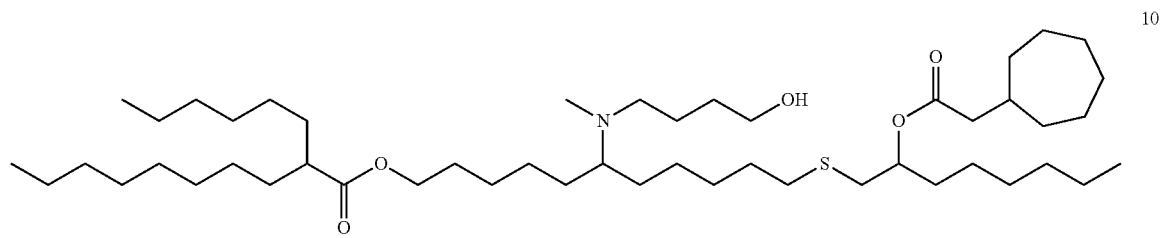 [SMILES: CCCCCCCCC(CCCCCC)C(=O)OCCCCCC(CCCCCSCC(CCCCCC)OC(=O)CC1CCCCCC1)N(C)CCCCO]

From 6-((4-((tert-butyldiphenylsilyl)oxy)butyl)(methyl) amino)-11-((2-(2-cycloheptylacetoxy)octyl)thio)-undecyl 2-hexyldecanoate. $^1$H NMR (400 MHz, C$_6$D$_6$) δ 5.30-5.23 (m, 1H), 4.19 (t, J=6.7 Hz, 2H), 3.70-3.60 (m, 2H), 2.85-2.47 (m, 8H), 2.34 (s, 3H), 2.25 (d, J=6.5 Hz, 2H), 2.13 (s, 1H), 1.91-1.06 (m, 66H), 0.97-0.87 (m, 9H).

(vi) 11-((2-((3-Cyclohexylpropanoyl)oxy)octyl) thio)-6-((4-hydroxybutyl)(methyl)-amino)undecyl cyclopentadecanecarboxylate (11)

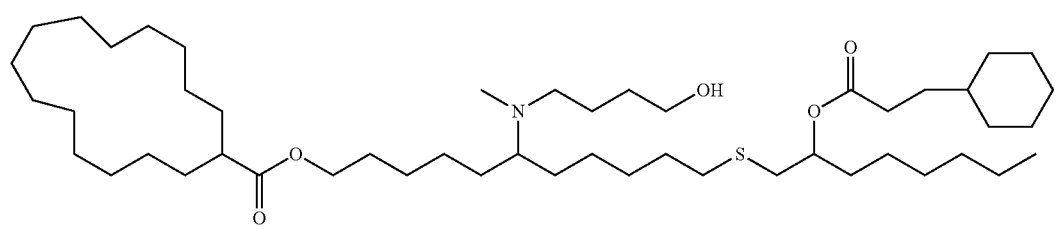

From 6-((4-((tert-butyldiphenylsilyl)oxy)butyl)-(methyl)amino)-11-((2-((3-cyclohexylpropanoyl)oxy)octyl)-thio)undecyl cyclopentadecane-carboxylate. $^1$H NMR (400 MHz, CDCl$_3$) δ 4.98-4.84 (m, 1H), 4.06 (t, J=6.65 Hz, 2H), 3.73 (t, J=5.30 Hz, 2H), 3.32-3.00 (m, 3H), 2.78 (s, 3H), 2.71-2.45 (m, 4H), 2.39 (p, J=6.68 Hz, 1H), 2.34-2.24 (m, 2H), 2.02-1.85 (m, 2H), 1.82-1.47 (m, 16H), 1.47-0.98 (m, 51H), 0.94-0.75 (m, 5H). LRMS m/z 808 [M+H]$^+$.

(vii) 6-((4-Hydroxybutyl)(methyl)amino)-9-(2-((2-(octanoyloxy)hexyl)thio)ethyl)-3-pentyltetradecyl octanoate (12)

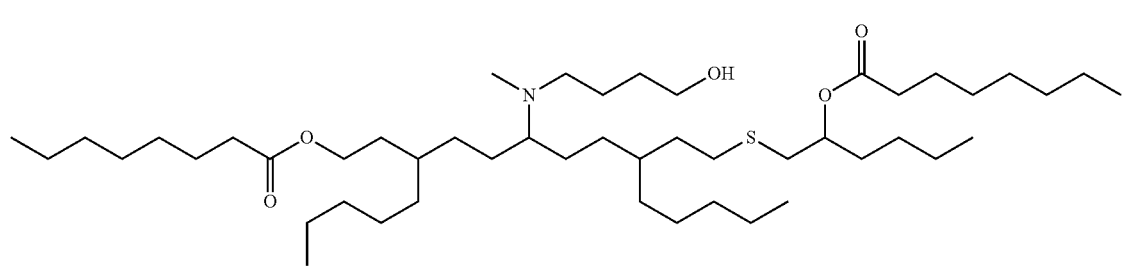

From 6-((4-((tert-butyldiphenylsilyl)oxy)butyl)(methyl)-amino)-9-(2-((2-(octanoyloxy)hexyl)-thio)ethyl)-3-pentyltetradecyl octanoate. $^1$H NMR (400 MHz, C$_6$D$_6$) δ 5.25-5.24 (m, 1H), 4.30-4.17 (m, 2H), 3.64-3.61 (m, 2H), 2.91 (brs, 1H), 2.80-2.59 (m, 6H), 2.42 (brs, 3H), 2.42 (brs, 3H), 2.34-2.23 (m, 4H), 1.77-1.21 (m, 60H), 0.99-0.95 (m, 6H), 0.90-0.86 (m, 9H).

(viii) 1-((9-(2-((3-Cyclohexylpropanoyl)oxy)ethyl)-6-((4-hydroxybutyl)(methyl)-amino)-3-pentyltetradecyl)thio)hexan-2-yl 3-cyclohexylpropanoate (13)

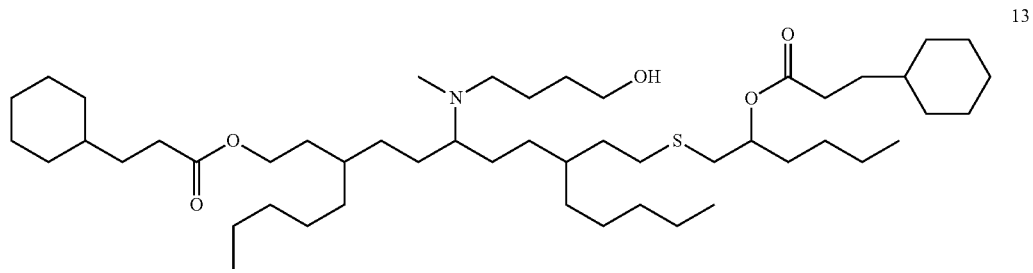 [SMILES: CCCCCC(CCOC(=O)CCC1CCCCC1)CCC(CCC(CCCCC)CCSCC(CCCC)OC(=O)CCC1CCCCC1)N(C)CCCCO]

From 6-((4-((tert-butyldiphenylsilyl)oxy)butyl)(methyl)amino)-9-(2-((2-((3-cyclohexylpropanoyl)-oxy)hexyl)-thio)ethyl)-3-pentyltetradecyl 3-cyclohexylpropanoate. $^1$H NMR (400 MHz, C$_6$D$_6$) δ 5.28-5.22 (m, 1H), 4.30-4.20 (m, 2H), 3.66-3.63 (m, 2H), 2.93 (brs, 1H), 2.78-2.64 (m, 5H), 2.46 (brs, 3H), 2.34-2.27 (m, 3H), 1.78-0.75 (m, 77H).

(ix) 6-((4-Hydroxybutyl)(methyl)amino)-9-(2-(((1R*,2R*)-2-(octanoyloxy)cyclohexyl)-thio)ethyl)-3-pentyltetradecyl octanoate (14)

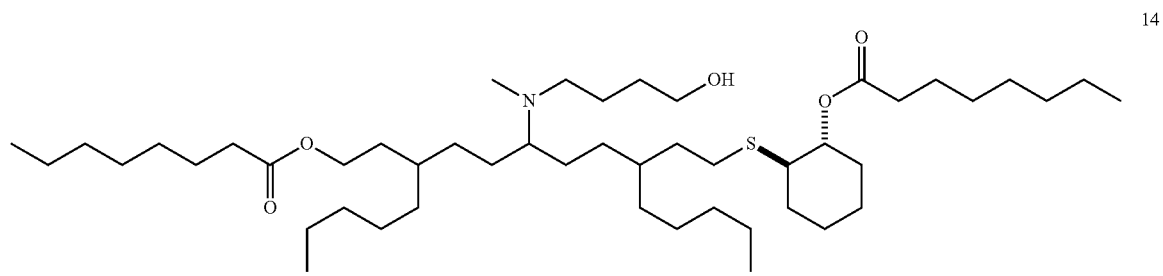

From 6-((4-((tert-butyldiphenylsilyl)-oxy)butyl)(methyl)amino)-9-(2-(((1R*,2R*)-2-(octanoyl-oxy)cyclohexyl)thio)ethyl)-3-pentyltetradecyl octanoate. $^1$H NMR (400 MHz, C$_6$D$_6$) δ 5.13-5.09 (m, 1H), 4.30-4.14 (m, 2H), 3.63-3.60 (m, 2H), 2.90 (brs, 1H), 2.77-2.58 (m, 4H), 2.41-2.23 (m, 6H), 2.13-2.09 (m, 2H), 1.70-1.21 (m, 62H), 0.98-0.95 (m, 6H), 0.91-0.86 (m, 6H).

(x) 9-(2-(((1R*,2R*)-2-((3-cyclohexylpropanoyl)oxy)cyclohexyl)thio)ethyl)-6-((4-hydroxy-butyl)(methyl)amino)-3-pentyltetradecyl 3-cyclohexylpropanoate (15)

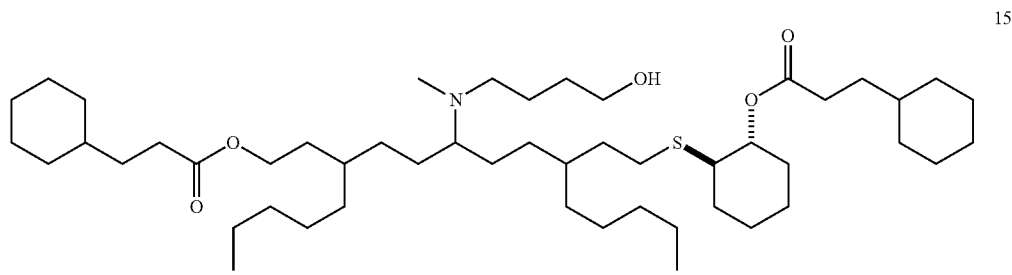

From 6-((4-((tert-butyldiphenylsilyl)oxy)butyl)(methyl) amino)-9-(2-(((1R*,2R*)-2-((3-cyclo-hexylpropanoyl)oxy) cyclohexyl)thio)ethyl)-3-pentyltetradecyl 3-cyclohexylpropanoate. $^1$H NMR (400 MHz, C$_6$D$_6$) δ 5.12-5.05 (m, 1H), 4.29-4.17 (m, 2H), 3.64-3.60 (m, 2H), 2.89-2.24 (m, 11H), 2.14-2.08 (m, 2H), 1.67-1.05 (m, 62H), 0.98-0.95 (m, 6H), 0.91-0.76 (m, 4H).

(xi) ((6-((4-Hydroxybutyl)(methyl)amino)undecane-1,11-diyl)bis(sulfanediyl))bis-(octane-1,2-diyl) dinonanoate (23)

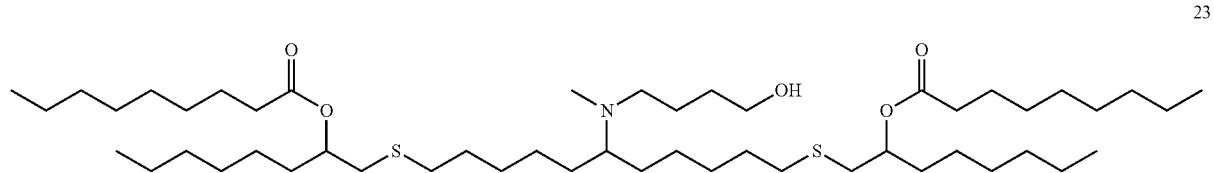 [SMILES: CCCCCCCCC(=O)OC(CCCCCC)CSCCCCCC(CCCCCSCC(CCCCCC)OC(=O)CCCCCCCC)N(C)CCCCO]

23

From ((6-((4-(tert-butydiphenylsilyloxy-butyl)(methyl) amino)-undecane-1,11-diyl)bis(sulfane-diyl))bis(octane-1,2-diyl) dinonan-oate. $^1$H NMR (400 MHz, C$_6$D$_6$) δ 5.32-5.23 (m, 2H), 3.68-3.61 (m, 2H), 2.88-2.80 (m, 1H), 2.80-2.47 (m, 10H), 2.37 (s, 3H), 2.35-2.24 (m, 4H), 1.88-1.02 (m, 64H), 1.00-0.86 (m, 12H).

(xii) ((6-((H-hydroxybutyl)(methyl)amino)undecane-1,11-diyl)bis(sulfanediyl))bis-(octane-1,2-diyl) dioctanoate (24)

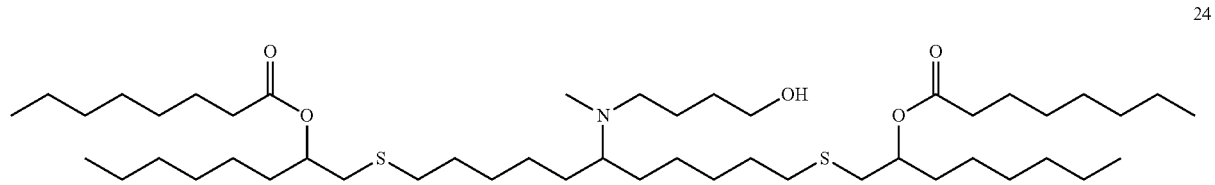 [SMILES: CCCCCCCC(=O)OC(CCCCCC)CSCCCCCC(CCCCCSCC(CCCCCC)OC(=O)CCCCCCC)N(C)CCCCO]

24

From ((6-((4-(tert-butydiphenylsilyloxy)(methyl)-amino) undecane-1,11-diyl)bis(sulfane-diyl))bis(octane-1,2-diyl) dioctanoate. $^1$H NMR (400 MHz, C$_6$D$_6$) δ 5.37-5.16 (m, 2H), 3.67 (t, J=5.4 Hz, 2H), 2.91-2.83 (m, 1H), 2.81-2.49 (m, 10H), 2.42 (s, 3H), 2.37-2.18 (m, 4H), 1.89-0.99 (m, 60H), 0.99-0.83 (m, 12H).

(xiii) ((6-(Ethyl(4-hydroxybutyl)amino)undecane-1,11-diyl)bis(sulfanediyl))bis-(octane-1,2-diyl) dinonanoate (25)

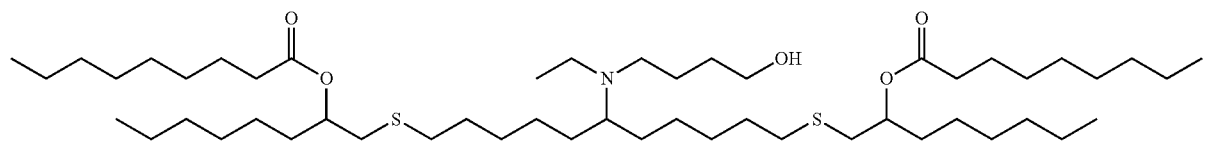

25

From ((6-(ethyl(4-tert-butyldiphenylsilyoxybutyl)-amino)undecane-1,11-diyl)bis(sulfanediyl))-bis(octane-1,2-diyl) dinonanoate. ¹H NMR (400 MHz, C$_6$D$_6$) δ 5.31-5.19 (m, 2H), 3.66 (t, J=5.5 Hz, 2H), 2.95-2.85 (m, 1H), 2.81-2.53 (m, 12H), 2.36-2.27 (m, 4H), 1.94-1.02 (m, 67H), 0.98-0.86 (m, 12H).

(xiv) 1-((11-((2-((3-Cyclohexylpropanoyl)oxy)octyl)thio)-6-(ethyl(4-hydroxybutyl)-amino)undecyl)thio)octan-2-yl heptanoate (26)

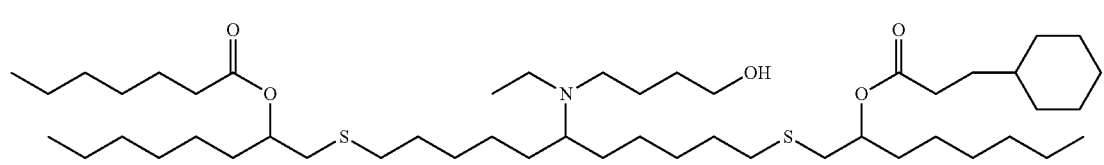

26

From 10-(5-((2-((3-cyclohexyl-propanoyl)oxy)-octyl)thio)pentyl)-9-ethyl-2,2-dimethyl-3,3-diphenyl-4-oxa-16-thia-9-aza-3-silatetracosan-18-yl heptanoate. ¹H NMR (400 MHz, C$_6$D$_6$) δ 5.33-5.20 (m, 2H), 3.73-3.63 (m, 2H), 2.96-2.86 (m, 1H), 2.83-2.51 (m, 12H), 2.38-2.24 (m, 4H), 1.87-1.03 (m, 59H), 0.97-0.74 (m, 14H).

(xv) ((6-((4-Hydroxybutyl)(methyl)amino)undecane-1,11-diyl)bis(sulfanediyl))bis-(octane-1,2-diyl) bis(3-cyclohexylpropanoate) (27)

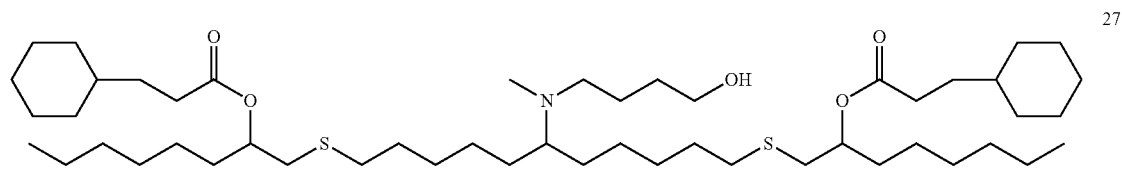 [SMILES: CCCCCCC(CSCCCCCC(CCCCCSCC(CCCCCC)OC(=O)CCC1CCCCC1)N(C)CCCCO)OC(=O)CCC1CCCCC1]

27

From ((6-((4-(tert-butyldiphenylsilyloxybutyl)-(methyl)amino)undecane-1,11-diyl)bis(sulfanediyl))bis-(octane-1,2-diyl) bis(3-cyclohexyl-propanoate). ¹H NMR (400 MHz, C$_6$D$_6$) δ 5.38-5.20 (m, 2H), 3.75-3.58 (m, 2H), 2.87-2.79 (m, 1H), 2.80-2.45 (m, 10H), 2.41-2.26 (m, 7H), 1.93-0.98 (m, 62H), 0.94-0.88 (m, 6H), 0.88-0.73 (m, 4H).

(xvi) ((6-((4-Hydroxybutyl)(methyl-d3)amino)undecane-1,11-diyl)bis(sulfanediyl))bis-(octane-1,2-diyl) bis(3-cyclohexylpropanoate) (28)

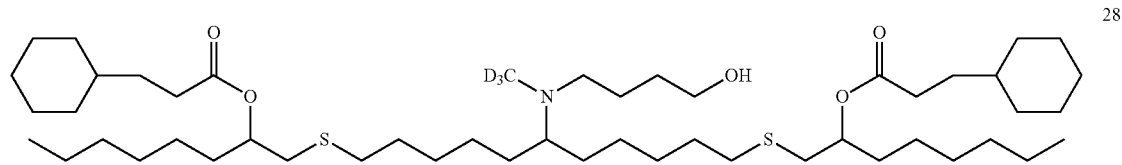 [SMILES: [2H]C([2H])([2H])N(CCCCO)C(CCCCCSCC(CCCCCC)OC(=O)CCC1CCCCC1)CCCCCSCC(CCCCCC)OC(=O)CCC1CCCCC1]

28

From ((6-((4-tert-butyldiphenylsilyloxy-butyl)(methyl-d₃)amino)undecane-1,11-diyl)bis(sulfanediyl))bis-(octane-1,2-diyl) bis(3-cyclo-hexylpropanoate). ¹H NMR (400 MHz, CDCl₃) δ 5.00-4.89 (m, 2H), 3.55 (t, J=4.9 Hz, 2H), 2.68-2.58 (m, 4H), 2.57-2.50 (m, 4H), 2.48-2.35 (m, 3H), 2.35-2.28 (m, 4H), 1.77-1.43 (m, 32H), 1.42-0.99 (m, 50H), 0.94-0.82 (m, 22H). ¹³C NMR (101 MHz, CDCl₃) δ 174.0, 73.0, 63.6, 62.9, 54.5, 37.3, 36.1, 34.8, 33.3, 33.1, 32.9, 32.6, 32.4, 32.3, 31.9, 31.7, 30.1, 29.7, 29.4, 29.2, 29.2, 27.4, 26.7, 26.4, 26.3, 25.4, 22.8, 22.7, 14.3, 14.2, 11.6.

(xvii) ((6-(Ethyl(4-hydroxybutyl)amino)undecane-1,11-diyl)bis(sulfanediyl))bis-(octane-1,2-diyl) bis(3-cyclohexylpropanoate) (29)

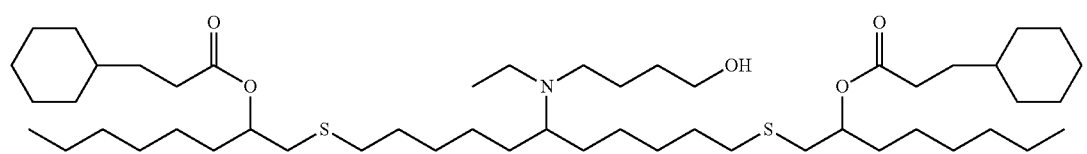

From ((6-(ethyl(4-tert-butyldiphenylsilyoxybutyl)-amino)undecane-1,11-diyl)bis(sulfanediyl))-bis(octane-1,2-diyl) bis(3-cyclohexylpropanoate). ¹H NMR (400 MHz, C₆D₆) δ 5.34-5.21 (m, 2H), 3.70 (t, J=5.5 Hz, 2H), 2.98-2.88 (m, 1H), 2.82-2.51 (m, 12H), 2.33 (td, J=7.5, 2.0 Hz, 4H), 1.90-1.05 (m, 64H), 0.95-0.74 (m, 13H).

(xviii) ((6-((Ethyl-d5)(4-hydroxybutyl)amino)undecane-1,11-diyl)bis(sulfanediyl))bis-(octane-1,2-diyl) bis(3-cyclohexylpropanoate) (30)

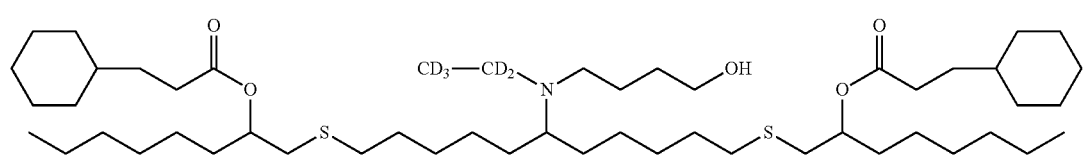

From ((6-((4-tert-butyldiphenylsilyloxy-butyl)(ethyl-d$_5$)amino)undecane-1,11-diyl)bis(sulfanediyl))bis-(octane-1,2-diyl) bis(3-cyclo-hexylpropanoate). $^1$H NMR (400 MHz, C$_6$D$_6$) δ 5.31-5.19 (m, 2H), 3.57 (t, J=5.9 Hz, 2H), 2.70 (dd, J=13.7, 6.3 Hz, 2H), 2.66-2.52 (m, 6H), 2.50-2.44 (m, 1H), 2.37-2.24 (m, 6H), 1.80-1.02 (m, 62H), 0.89 (t, J=6.5 Hz, 6H), 0.84-0.70 (m, 4H). $^{13}$C NMR (101 MHz, C$_6$D$_6$) δ 173.3, 72.8, 62.9, 59.7, 50.0, 37.4, 36.5, 33.7, 33.2, 33.0, 32.9, 32.9, 32.4, 32.1, 32.0, 30.6, 30.1, 29.6, 29.5, 27.6, 26.9, 26.6, 25.8, 23.0, 14.3.

(xix) ((6-((2-(2-Hydroxyethoxy)ethyl)(methyl)amino)undecane-1,11-diyl)bis(sulfane-diyl))bis(octane-1,2-diyl) bis(3-cyclohexylpropanoate) (31)

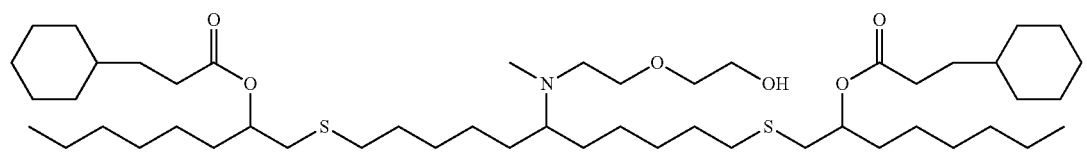

31

From ((6-((2-(2-tert-butyldipheylsilyloxy)ethoxy)ethyl)(methyl)amino)undecane-1,11-diyl)bis(sulfanediyl))-bis(octane-1,2-diyl) bis(3-cyclohexylpropanoate). $^1$H NMR (400 MHz, CDCl$_3$) δ 4.99-4.90 (m, 2H), 3.72-3.66 (m, 2H), 3.62-3.55 (m, 4H), 2.68-2.60 (m, 4H), 2.62-2.49 (m, 6H), 2.43-2.36 (m, 1H), 2.36-2.29 (m, 4H), 2.22 (s, 3H), 1.77-1.12 (m, 58H), 0.95-0.80 (m, 10H).

(xx) ((6-((2-((2-Hydroxyethyl)thio)ethyl)(methyl)amino)undecane-1,11-diyl)bis-(sulfanediyl))bis(octane-1,2-diyl) bis(3-cyclohexylpropanoate) (32)

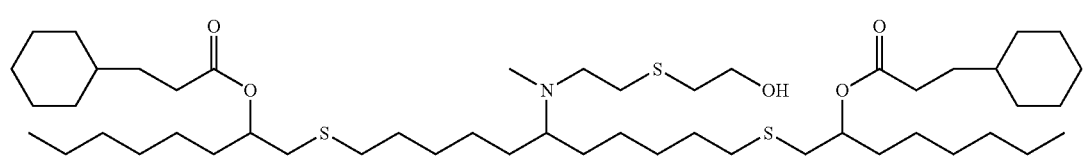

32

From ((6-((2-((2-tert-butydiphenylsilyloxy)thio)ethyl)(methyl)amino)undecane-1,11-diyl)bis(sulfane-diyl))bis(octane-1,2-diyl) bis(3-cyclohexylpropanoate). $^1$H NMR (400 MHz, CDCl$_3$) δ=4.99-4.90 (m, 2H), 3.73 (t, J=5.7 Hz, 2H), 2.74 (t, J=5.7 Hz, 2H), 2.65-2.59 (m, 8H), 2.57-2.51 (m, 4H), 2.40-2.28 (m, 5H), 2.19 (s, 3H), 1.76-1.08 (m, 58H), 0.94-0.82 (m, 10H). $^{13}$C NMR (101 MHz, CDCl$_3$) δ=174.0, 73.0, 63.5, 61.4, 54.0, 37.3, 37.1, 36.3, 36.2, 33.3, 33.1, 32.9, 32.6, 32.3, 31.9, 31.2, 30.2, 29.8, 29.3, 29.2, 27.2, 26.7, 26.4, 25.4, 22.7, 14.2.

(xxi) ((6-((4-Hydroxybutyl)(methyl)amino)undecane-1,11-diyl)bis(sulfanediyl))bis-(octane-1,2-diyl) dicycloheptanecarboxylate (33)

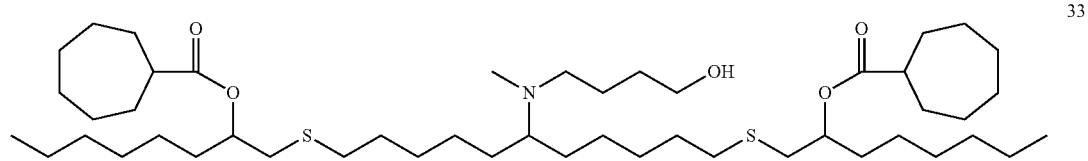 [SMILES: CCCCCCC(CSCCCCCC(CCCCCSCC(CCCCCC)OC(=O)C1CCCCCC1)N(C)CCCCO)OC(=O)C1CCCCCC1]

From ((6-((4-tert-butydiphenylsilyloxy-butyl)(methyl)amino)undecane-1,11-diyl)bis(sulfanediyl))bis-(octane-1,2-diyl) dicycloheptane-carboxylate. $^1$H NMR (400 MHz, C$_6$D$_6$) δ 5.26-5.18 (m, 2H), 3.61 (t, J=5.6 Hz, 2H), 2.70 (dd, J=13.6, 6.3 Hz, 2H), 2.66-2.49 (m, 8H), 2.40-2.32 (m, 1H), 2.29 (t, J=6.1 Hz, 2H), 2.02 (s, 3H), 2.07-1.95 (m, 4H), 1.90-1.53 (m, 18H), 1.52-1.05 (m, 43H), 0.89 (t, J=6.8 Hz, 6H). $^{13}$C NMR (101 MHz, C$_6$D$_6$) δ 176.2, 72.5, 63.6, 62.8, 54.3, 45.6, 36.6, 35.4, 33.7, 32.9, 32.2, 32.1, 31.4, 31.3, 30.1, 30.0, 29.5, 29.5, 28.7, 28.6, 27.4, 26.6, 26.6, 25.8, 23.0, 14.3.

(xxii) ((6-((4-Hydroxybutyl)(methyl)amino)undecane-1,11-diyl)bis(sulfanediyl))bis-(octane-1,2-diyl)-bis(adamantane-1-carboxylate) (34)

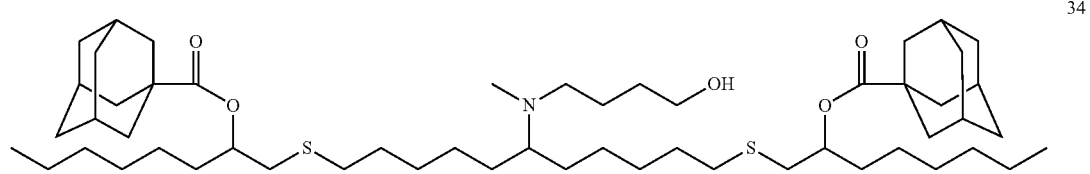 [SMILES: CCCCCCC(CSCCCCCC(CCCCCSCC(CCCCCC)OC(=O)C12CC3CC(CC(C3)C1)C2)N(C)CCCCO)OC(=O)C12CC3CC(CC(C3)C1)C2]

From (((6-((4-tert-butydiphenylsilyloxy-butyl)(methyl) amino)undecane-1,11-diyl)bis(sulfanediyl))bis-(octane-1,2-diyl)-bis(adamantane-1-carboxylate). $^1$H NMR (400 MHz, C$_6$D$_6$) δ 5.23 (dtd, J=8.4, 6.1, 4.2 Hz, 2H), 3.61 (t, J=5.6 Hz, 2H), 2.75-2.50 (m, 8H), 2.42-2.33 (m, 1H), 2.30 (t, J=6.1 Hz, 2H), 2.10-2.05 (m, 11H), 2.02 (s, 3H), 1.92-1.86 (m, 6H), 1.79-1.52 (m, 21H), 1.51-1.07 (m, 32H), 0.89 (t, J=6.8 Hz, 6H). $^{13}$C NMR (101 MHz, C$_6$D$_6$) δ 176.7, 72.3, 63.6, 62.8, 54.3, 41.2, 39.5, 36.8, 36.6, 35.6, 33.7, 32.9, 32.1, 30.1, 30.0, 29.5, 29.5, 28.5, 27.4, 25.8, 23.0, 14.3.

(xxiii) ((6-((cis-3-Hydroxycyclobutyl)(methyl) amino)undecane-1,11-diyl)bis(sulfane-diyl))bis(octane-1,2-diyl) bis(3-cyclohexylpropanoate) (35)

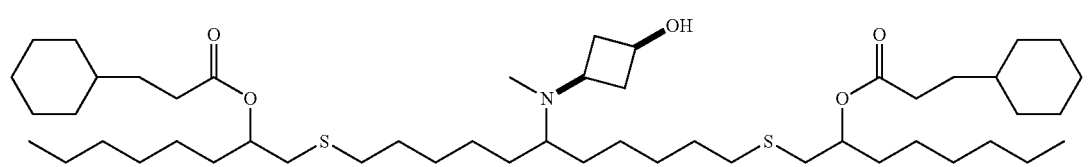

From ((6-cis-((3-((tert-butyldiphenylsilyl)oxy)cyclobutyl)(methyl)amino)undecane-1,11-diyl)bis(sulfanediyl))-bis-(octane-1,2-diyl) bis(3-cyclohexylpropanoate). $^1$H NMR (400 MHz, CDCl$_3$) δ (400 MHz, CDCl$_3$) δ 5.01-4.89 (m, 2H), 3.94 (p, J=7.4 Hz, 1H), 2.69-2.58 (m, 5H), 2.57-2.42 (m, 6H), 2.38-2.29 (m, 5H), 1.98 (s, 3H), 1.77-1.48 (m, 23H), 1.42-1.06 (m, 37H), 0.94-0.81 (m, 10H). $^{13}$C NMR (101 MHz, CDCl$_3$) δ 174.1, 72.9, 61.4, 47.8, 39.8, 37.3, 36.1, 36.1, 33.3, 33.1, 32.8, 32.8, 32.6, 32.3, 31.9, 31.0, 29.8, 29.7, 29.3, 29.2, 27.1, 26.7, 26.4, 25.4, 22.7, 14.2.

(f) General Procedure for the Conversion of a Ketone to a Type 2 Ionizable Head Group.

(i) (((4-(2-Hydroxyethyl)-1,3-dioxolane-2,2-diyl)bis(pentane-5,1-diyl))bis(sulfane-diyl))bis(octane-1,2-diyl) bis(3-cyclohexylpropanoate) (127)

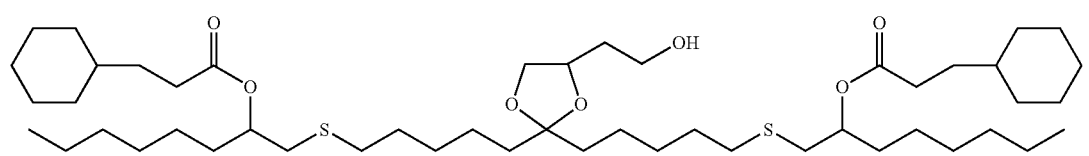

A solution of 80 (655 mg, 0.868 mmol), 1,2,4-butanetriol (184 mg, 1.74 mmol) and pyridinium p-toluene-sulfonate (44 mg, 0.174 mmol) in toluene (15 mL) was refluxed under nitrogen overnight with continuous removal of water (Dean-Stark trap). The mixture was cooled to room temperature, washed with water (2×10.0 mL), brine (10.0 mL) then dried ($Na_2SO_4$) and concentrated. The residue was purified by silica gel column chromatography (0-3% MeOH in DCM) to yield ketal 127 (474 mg, 64%) as an oil. $^1$H NMR (400 MHz, $CDCl_3$) δ 5.01-4.89 (m, 2H), 4.32-4.17 (m, 1H), 4.08 (dd, J=7.9, 6.0 Hz, 1H), 3.80 (td, J=5.9, 2.8 Hz, 2H), 3.52 (t, J=8.0 Hz, 1H), 2.71-2.58 (m, 4H), 2.58-2.48 (m, 4H), 2.35-2.28 (m, 4H), 2.01=1.03 (m, 60H), 0.96-0.79 (m, 10H).

(ii) (((4-(2-(Tosyloxy)ethyl)-1,3-dioxolane-2,2-diyl) bis(pentane-5,1-diyl))bis(sulfane-diyl))bis(octane-1, 2-diyl) bis(3-cyclohexylpropanoate) (128)

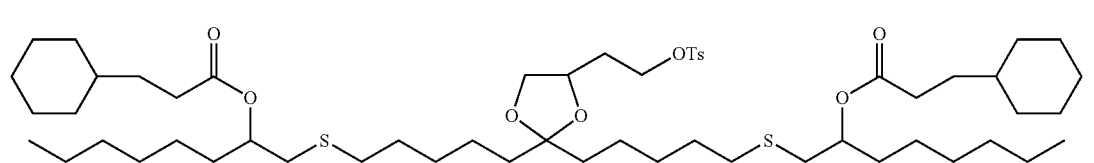

To a solution of 127 (189 mg, 0.221 mmol), TEA (0.0462 mL, 0.332 mmol) and DMAP (2.70 mg, 0.0221 mmol) in $CH_2Cl_2$ (2.00 mL) was added TsCl (50.6 mg, 0.265 mmol) at 0° C. under inert atmosphere. The reaction was warmed to room temperature and stirred for 18 hours. The reaction was quenched with water (3.00 mL) and extracted with $CH_2Cl_2$ (3×4.00 mL). The combined organics were dried ($Na_2SO_4$) and concentrated to yield 128 (221 mg, crude, quantitative) which was used in the next step without purification. $^1$H NMR (400 MHz, $CDCl_3$) δ 7.79 (d, J=8.4 Hz, 2H), 7.35 (d, J=8.0 Hz, 2H), 5.01-4.86 (m, 2H), 4.20-4.04 (m, 3H), 4.03-3.97 (m, 1H), 3.48-3.41 (m, 1H), 2.66-2.60 (m, 4H), 2.56-2.49 (m, 4H), 2.45 (s, 3H), 2.34-2.28 (m, 4H), 1.89 (q, J=6.2 Hz, 2H), 1.78-1.04 (m, 58H), 0.95-0.81 (m, 10H).

(iii) (((4-(2-(Dimethylamino)ethyl)-1,3-dioxolane-2, 2-diyl)bis(pentane-5,1-diyl))bis-(sulfanediyl))bis (octane-1,2-diyl) bis(3-cyclohexylpropanoate) (22)

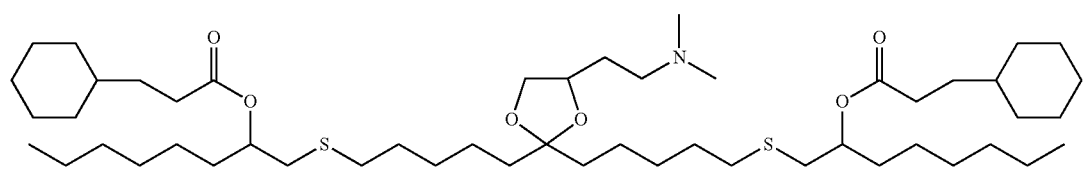

A solution of 128 (221 mg, crude), dimethyl amine (3.00 mL, 2 M in THF) and MeOH (3.00 mL) was heated in a microwave reactor (110° C., normal absorbance) for 15 minutes. The mixture was then concentrated, and the residue purified by silica chromatography (0-5% MeOH in DCM) to yield lipid 22 (165 mg, 85% over 2 steps) as an oil. $^1$H NMR (400 MHz, C$_6$D$_6$) δ 5.29-5.17 (m, 2H), 4.14-4.00 (m, 1H), 3.97-3.87 (m, 1H), 3.40 (t, J=7.6 Hz, 1H), 2.75-2.44 (m, 8H), 2.37-2.19 (m, 6H), 2.03 (s, 6H), 1.86-0.95 (m, 60H), 0.94-0.86 (m, 6H), 0.84-0.71 (m, 4H).

(g) General Procedure for the Conversion of an Alcohol to a Type 12 Ionizable Head Group.

(i) ((6-(2-Bromo-1-ethoxyethoxy)undecane-1,11-diyl)bis(sulfanediyl))bis(octane-1,2-diyl) bis(3-cyclohexylpropanoate) (126)

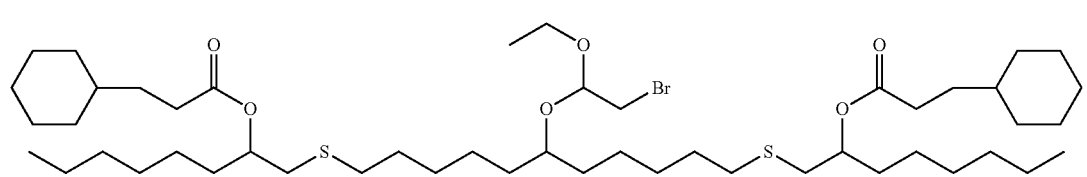

126

To a sealed reaction vial under inert atmosphere was added ((6-hydroxyundecane-1,11-diyl)bis(sulfanediyl))bis(octane-1,2-diyl) bis(3-cyclohexyl-propanoate) (0.15 mmol, 116 mg), DCM (0.3 mL), (Z)-1-bromo-2-ethoxyethylene (0.75 mmol, 0.08 mL), and PPTS (0.015 mmol, 4 mg). The mixture was stirred at RT for 18 h, then diluted with hexanes (3 mL) and sat. NH$_4$Cl (3 ml). The layers were separated and the organic phase was collected. The aq. phase was back-extracted with hexanes (2×2 mL). The combined organics were dried (Na$_2$SO$_4$), filtered, and evaporated to yield crude product. This was purified by silica chromatography (0-10% EtOAc in hexanes over 12 CV), yielding 126 (0.13 mmol, 122 mg, 88% yield). $^1$H NMR (400 MHz, CDCl$_3$) δ 4.92 (dtd, J=8.3, 6.2, 4.4 Hz, 2H), 4.69-4.61 (m, 1H), 3.74-3.44 (m, 3H), 3.38-3.26 (m, 2H), 2.67-2.57 (m, 4H), 2.56-2.45 (m, 4H), 2.33-2.27 (m, 4H), 1.76-1.00 (m, 61H), 0.93-0.79 (m, 10H). $^{13}$C NMR (101 MHz, CDCl$_3$) δ 173.9, 100.8, 77.7, 72.9, 61.7, 37.3, 36.1, 34.5, 33.8, 33.2, 33.1, 32.7, 32.7, 32.5, 32.5, 32.2, 31.8, 29.7, 29.6, 29.2, 29.1, 26.6, 26.3, 25.4, 25.1, 24.6, 22.7, 15.4, 14.2.

(ii) ((6-(2-(Dimethylamino)-1-ethoxyethoxy)unde-cane-1,11-diyl)bis(sulfanediyl))bis-(octane-1,2-diyl) bis(3-cyclohexylpropanoate) (21)

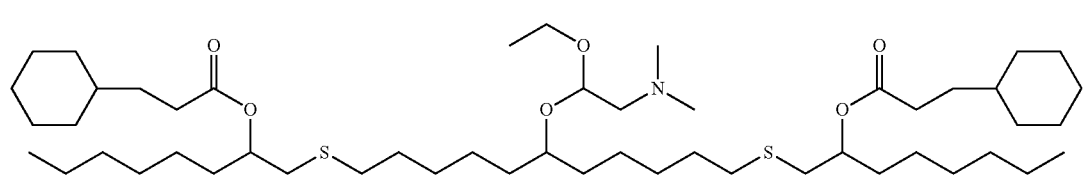

21

To a solution of 126 (0.13 mmol, 122 mg) in a microwave vial under inert atmosphere was added 2 M dimethyl amine in THF (2.7 mmol, 1.3 mL). The mixture was heated by microwave irradiation at 110° C. for 45 minutes. The mixture was then concentrated, diluted with hexanes (5 mL) and washed with 0.1M NaOH (5 mL). The collected organic phase was dried ($Na_2SO_4$), filtered, and evaporated. The residue purified by silica chromatography (0-7% MeOH in $CH_2Cl_2$) to yield 21 (0.07 mmol, 62 mg, 53% yield). $^1H$ NMR (400 MHz, $CDCl_3$) δ 4.96 (dtd, J=8.0, 6.1, 4.4 Hz, 2H), 4.64 (dd, J=6.3, 4.3 Hz, 1H), 3.73-3.63 (m, 1H), 3.61-3.50 (m, 2H), 2.71-2.59 (m, 4H), 2.60-2.50 (m, 5H), 2.40-2.26 (m, 4H), 2.30 (s, 6H), 1.82-1.08 (m, 61H), 0.97-0.83 (m, 10H). $^{13}C$ NMR (101 MHz, $CDCl_3$) δ 173.9, 100.3, 72.9, 62.6, 60.9, 46.5, 37.3, 36.1, 34.6, 33.9, 33.3, 33.1, 32.9, 32.8, 32.6, 32.3, 31.8, 29.8, 29.8, 29.3, 29.3, 29.2, 26.7, 26.4, 25.4, 25.2, 24.9, 22.7, 15.5, 14.2.

Example 2: mRNA-Containing LNPs Comprising the Ionizable, Cationic, Amino Lipids of the Disclosure Exhibit In Vivo Delivery of mRNA to the Liver and Spleen that is Superior to the Nor-MC3 Benchmark Lipid nanoparticle (LNP) formulations containing 50/10/38.5/1.5 mol % of ionizable lipids 1, 5-13 and 16-35/DSPC/chol/PEG-DMG with a nitrogen-to-phosphorous ratio (N/P) of 6 and mRNA encoding luciferase were prepared as described in the Materials and Methods. The ionizable lipids 5-13 and 16-35 are set forth in Example 1 and Table 1. The nor-MC3 benchmark lipid 1 is disclosed in co-owned and co-pending WO 2022/246571, which is incorporated herein by reference in its entirety. The polydispersity index (PDI), encapsulation efficiency and size of the LNP formulations are shown in FIG. 1.

The LNP formulations were subsequently tested for in vivo transfection efficiency in the liver and spleen after injection to CD-1 mice. The mRNA dose was 1 mg/kg. Luminescence intensity in the liver and spleen was measured at 4 hours post-injection.

Figure 2A:
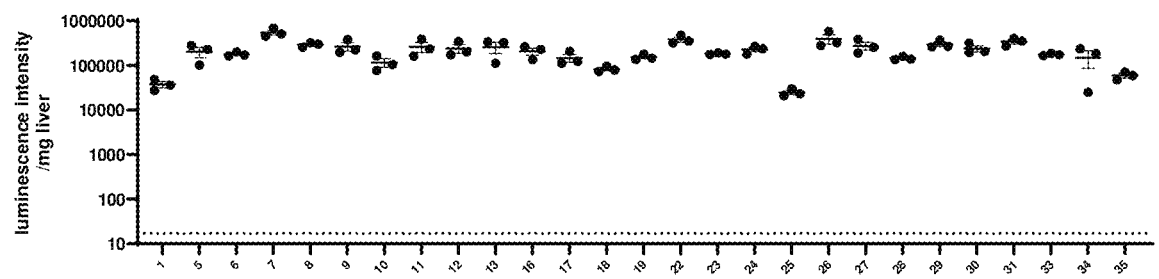
FIG. 2A shows luminescence intensity/mg in the liver for the mRNA-containing LNPs comprising the ionizable lipids 1, 5-13, 16-19, 22-31, 33, 34 and 35 after 4 hours post-intravenous administration to CD-1 mice. The LNPs contain 50/10/38.5/1.5 mol % of ionizable lipid/DSPC/chol/PEG$_{2000}$-DMG (N/P=6).
Figure 2B:
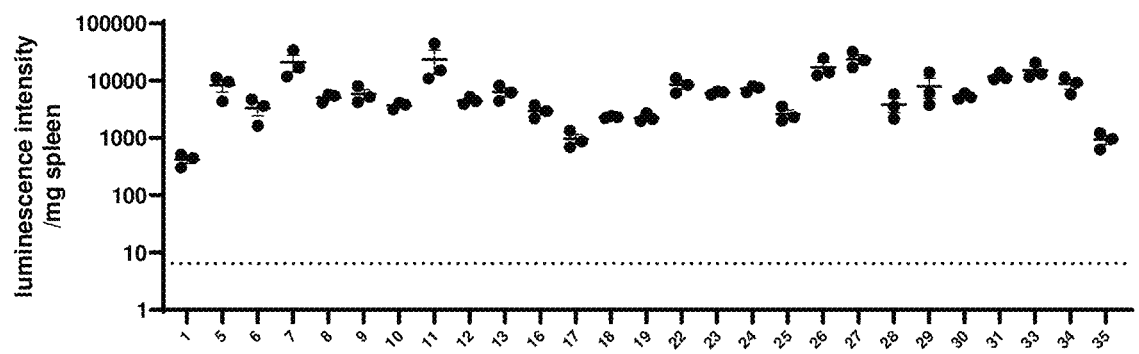
FIG. 2B shows luminescence intensity/mg in the spleen for the mRNA-containing LNPs comprising the ionizable lipids 1, 5-13, 16-19, 22-31, 33, 34 and 35 after 4 hours post-intravenous administration to CD-1 mice. The LNPs contain 50/10/38.5/1.5 mol % of ionizable lipid/DSPC/chol/PEG$_{2000}$-DMG (N/P=6).

Surprising increases in luminescence intensity per mg liver and spleen were observed for the sulfur-containing, ionizable, cationic, amino lipids of the disclosure formulated in lipid nanoparticles. The results in FIG. 2A show luminescence intensity per mg liver for the ionizable lipids of the disclosure vs the norMC3 benchmark. Results for luminescence intensity per mg spleen relative to the norMC3 benchmark are shown in FIG. 2B.

The examples are intended to illustrate the preparation of specific ionizable, cationic amino lipids and lipid nanoparticle nucleic acid preparations and properties thereof but are in no way intended to limit the scope of the invention.

The article "a" or "an" as used herein is meant to include both singular and plural, unless otherwise indicated.

We claim:

1. An ionizable, cationic amino lipid or a pharmaceutically acceptable salt thereof comprising:
   a protonatable amino head group;
   two lipophilic chains, wherein the protonatable amino head group has a central carbon atom to which each of the two lipophilic chains are directly bonded;
   at least one of the two lipophilic chains has a structure of Formula A.1:

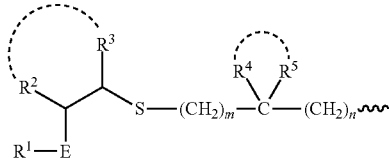

Formula A.1 wherein the wavy line represents a bond to the central carbon atom;
wherein m and n are independently 2 to 8;
E is an ester group that is (C=O)O or O(C=O);
$R^1$ is a linear, branched, monocyclic or polycyclic, optionally substituted, $C_3$ to $C_{20}$ alkyl group, comprising 0-2 carbon-carbon double bonds;
$R^2$ is a linear or branched, optionally substituted, $C_4$ to $C_{10}$ alkyl group, comprising 0-2 carbon-carbon double bonds, or $R^2$ is bound to $R^3$ to form a ring structure as indicated by the dashed curved line;
$R^3$ is H, or a linear or branched, optionally substituted, $C_4$ to $C_{10}$ alkyl group, comprising 0-2 carbon-carbon double bonds, or $R^3$ is bound to $R^2$ to form a ring structure as indicated by the dashed curved line;
$R^4$ and $R^5$ are, independently, H, or a linear or branched, optionally substituted, $C_1$ to $C_{10}$ alkyl group, comprising 0-2 carbon-carbon double bonds, or $R^4$ and $R^5$ are bound to each other to form a ring structure;
each lipophilic chain has between 15 and 40 carbon atoms in total; and
wherein (i) a nitrogen atom of the protonatable amino head group of the lipid is positively charged below its $pK_a$; and (ii) the lipid has a Clog P of at least 11.

2. The ionizable, cationic amino lipid or pharmaceutically acceptable salt of claim 1, wherein a second one of the two lipophilic chains bonded to the central carbon atom of the head group has a structure as defined by Formula D:

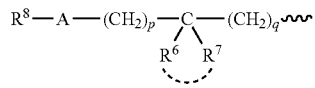

Formula D wherein the wavy line represents a bond to the central carbon atom of the head group;
$R^6$ and $R^7$ are, independently, H, or a linear or branched, optionally substituted, $C_1$ to $C_{10}$ alkyl group, comprising 0-2 carbon-carbon double bonds, or $R^6$ and $R^7$ are bonded to each other to form a ring structure,
A is O, S or a carbonyl (C=O), and
if A is O, then $R^8$ is an acyl group

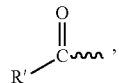

wherein the wavy line represents the bond to the A, and wherein the R' is as defined above for $R^1$;
if A is the carbonyl (C=O), then $R^8$ is an

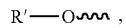

wherein the wavy line represents the bond to the A, and wherein the R' is as defined above for R¹;

if A is S, then R⁸ is a group of Formula E:

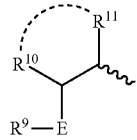

Formula E wherein the E is the ester group that is (C=O)O or O(C=O); and wherein the wavy line represents the bond to A, and wherein $R^9$ is as defined above for $R^1$, $R^{10}$ is as defined above for $R^2$, and $R^{11}$ is as defined above for $R^3$.

3. The ionizable, cationic amino lipid or pharmaceutically acceptable salt of claim 1, wherein the lipid, when formulated in a lipid nanoparticle comprising an mRNA, results in an increase in biodistribution of the lipid nanoparticle of at least about 10-fold in the spleen relative to an otherwise identical lipid nanoparticle containing norDLin-MC3-DMA (nor-MC3) as measured by luminescence of the mRNA in vivo in the spleen, wherein nor-MC3 has the following structure:

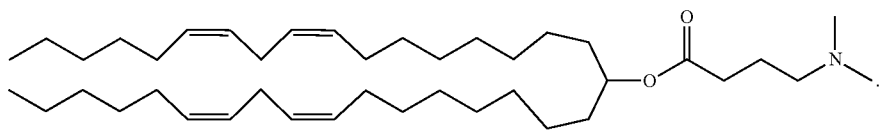 [SMILES: CCCCC/C=C\C/C=C\CCCCCCCC(CCCCCCC/C=C\C/C=C\CCCCC)OC(=O)CCCN(C)C]

4. The ionizable, cationic amino lipid or pharmaceutically acceptable salt of claim 2, wherein the lipid, when formulated in a lipid nanoparticle comprising an mRNA, results in an increase in biodistribution of the lipid nanoparticle of at least about 10-fold in the spleen relative to an otherwise identical lipid nanoparticle containing nor-DLin-MC3-DMA (nor-MC3) as measured by luminescence of the mRNA in vivo in the spleen, wherein nor-MC3 has the following structure:

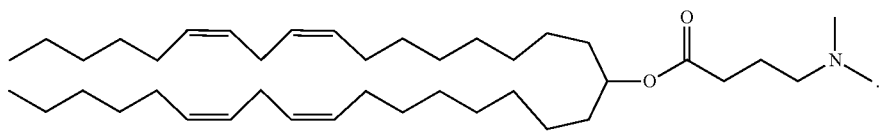 [SMILES: CCCCC/C=C\C/C=C\CCCCCCCC(CCCCCCC/C=C\C/C=C\CCCCC)OC(=O)CCCN(C)C]

5. The ionizable, cationic amino lipid or pharmaceutically acceptable salt of claim 1, wherein the lipid, when formulated in a lipid nanoparticle comprising an mRNA, results in an increase in biodistribution of the lipid nanoparticle of at least about 2-fold in the liver relative to a lipid nanoparticle containing norDLin-MC3-DMA (nor-MC3) as measured by luminescence of the mRNA in vivo in the liver, wherein nor-MC3 has the following structure:

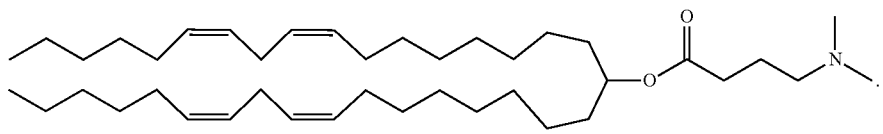 [SMILES: CCCCC/C=C\C/C=C\CCCCCCCC(CCCCCCC/C=C\C/C=C\CCCCC)OC(=O)CCCN(C)C]

6. The ionizable, cationic amino lipid or pharmaceutically acceptable salt of claim 2, wherein the lipid, when formulated in a lipid nanoparticle comprising an mRNA, results in an increase in biodistribution of the lipid nanoparticle of at least about 2-fold in the liver relative to a lipid nanoparticle containing norDLin-MC3-DMA (nor-MC3) as measured by luminescence of the mRNA in vivo in the liver, wherein nor-MC3 has the following structure:

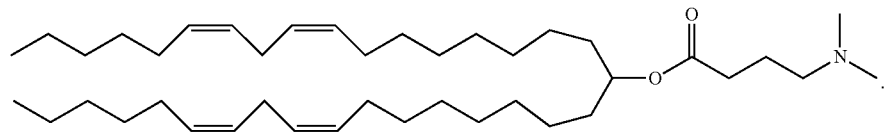 [SMILES: CCCCC/C=C\C/C=C\CCCCCCCC(CCCCCCC/C=C\C/C=C\CCCCC)OC(=O)CCCN(C)C]

7. The ionizable, cationic amino lipid of claim 1, having a structure of any one of compounds 5-35 as defined below or a pharmaceutically acceptable salt thereof:

5

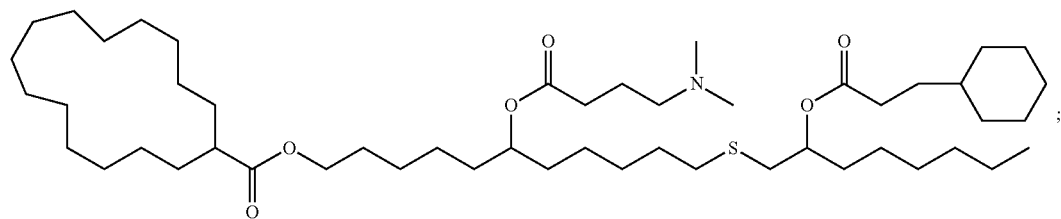

6

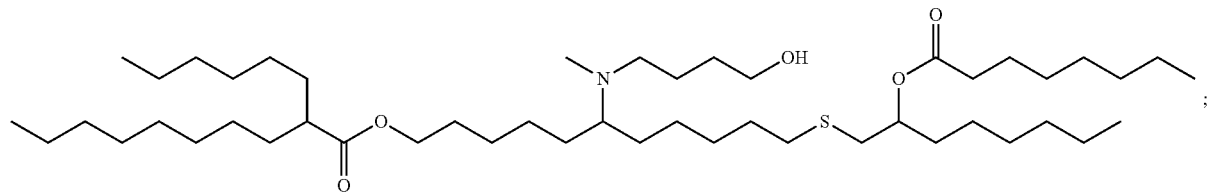

7

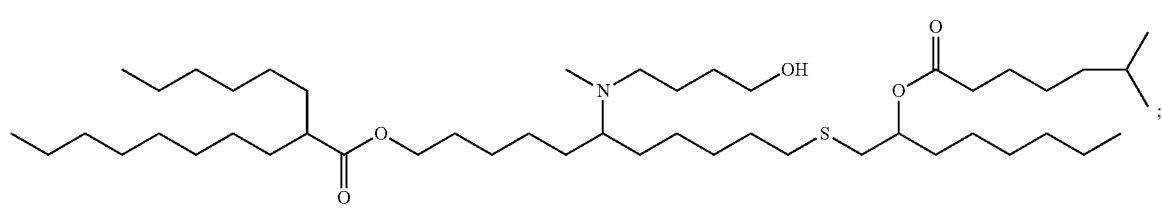

8

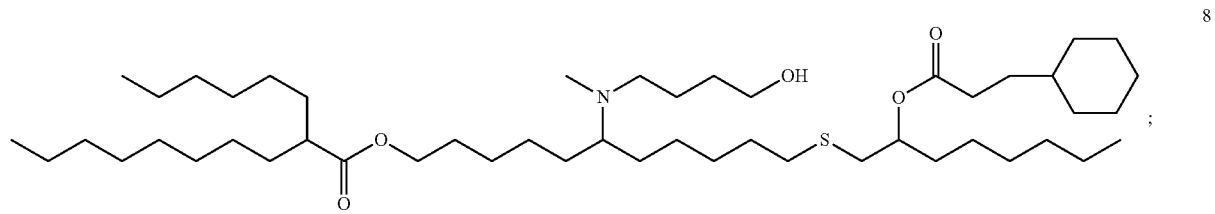

9

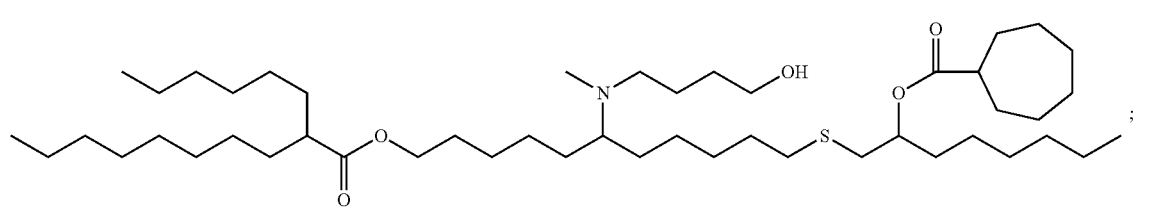

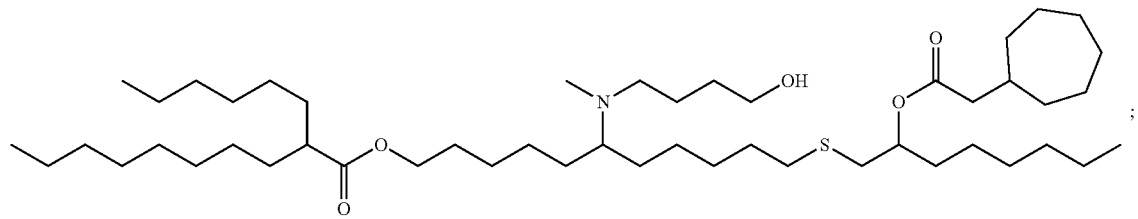
10
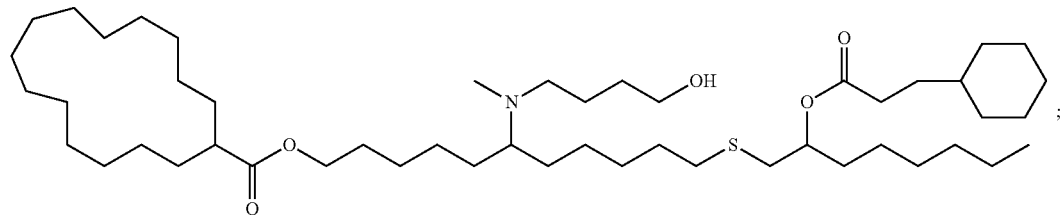
11
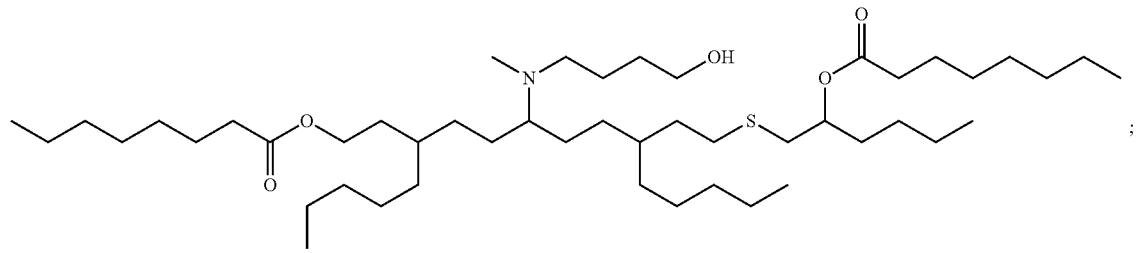
12
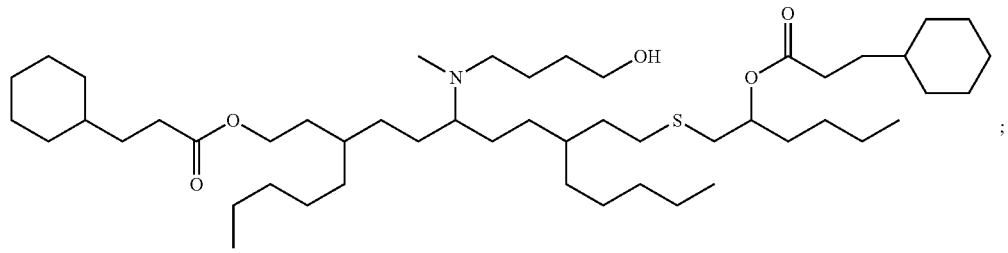
13
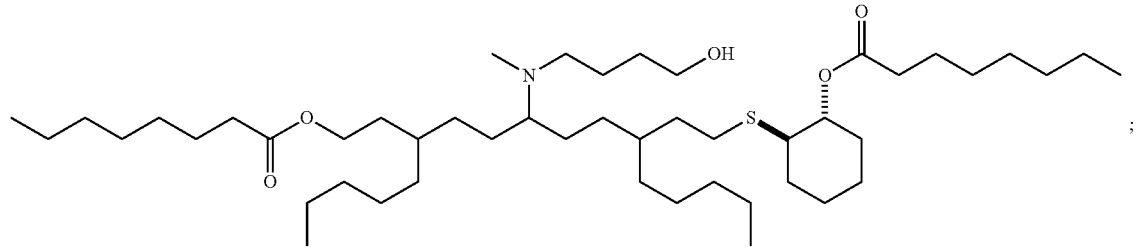
14
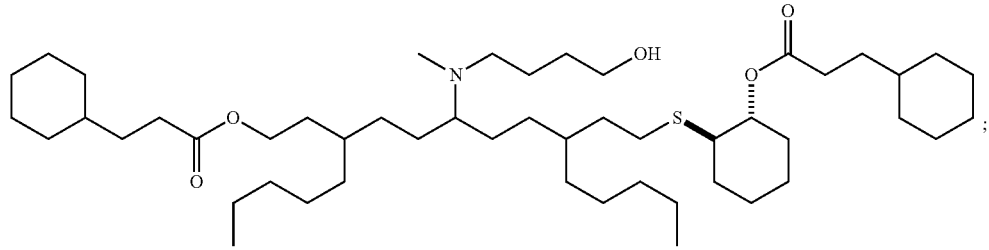
15

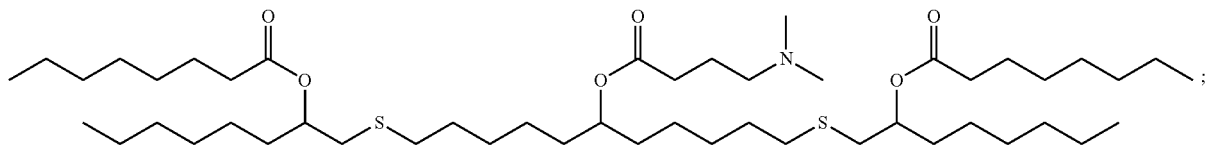
16
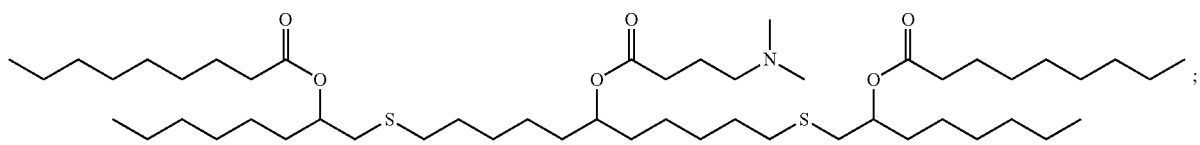
17
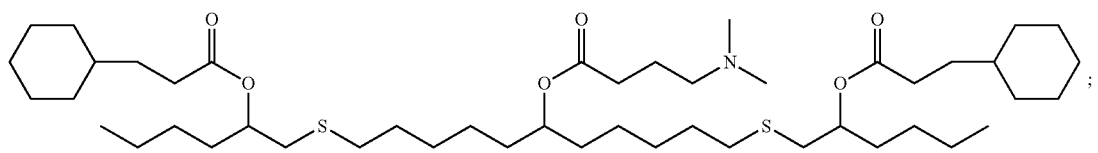
18
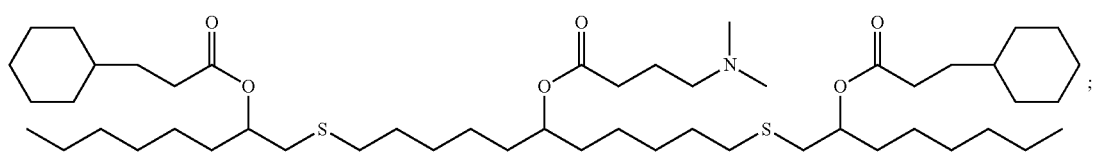
19
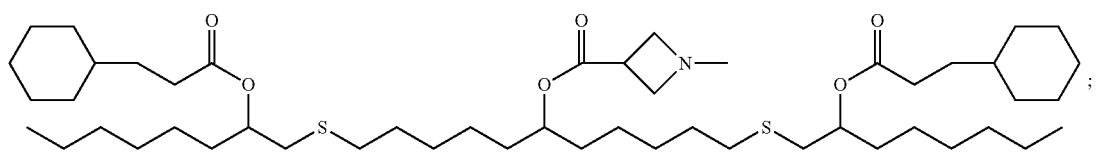
20
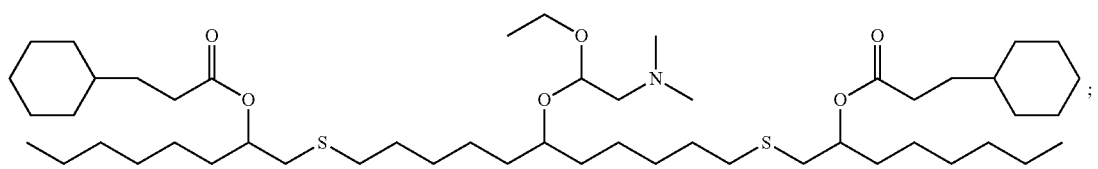
21
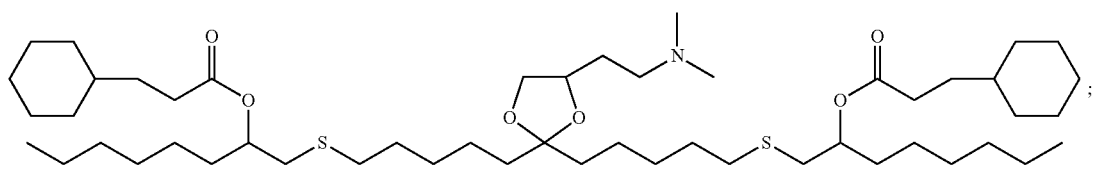
22
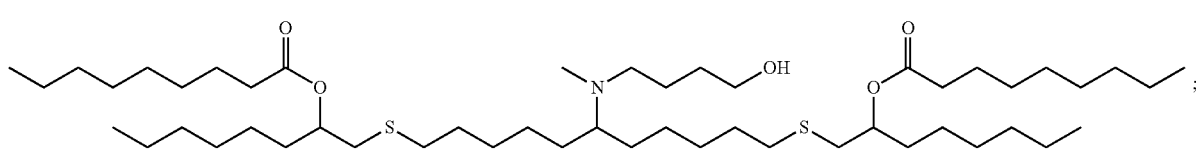
23
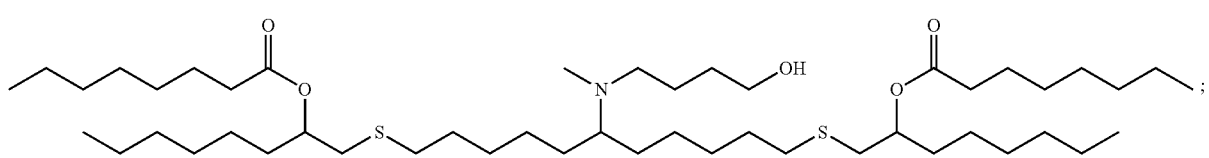
24

-continued
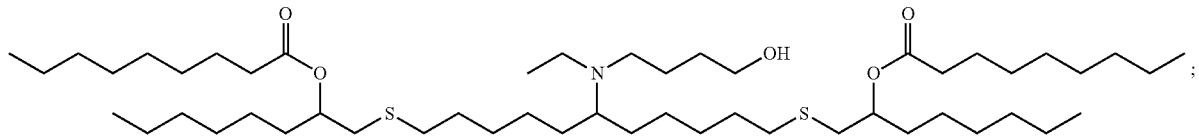
25
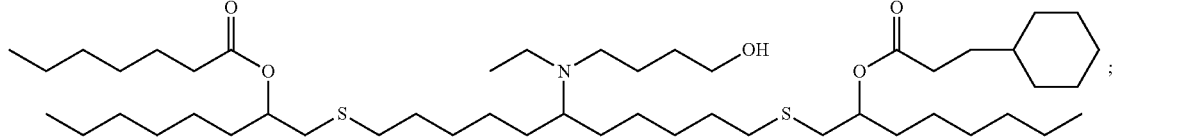
26
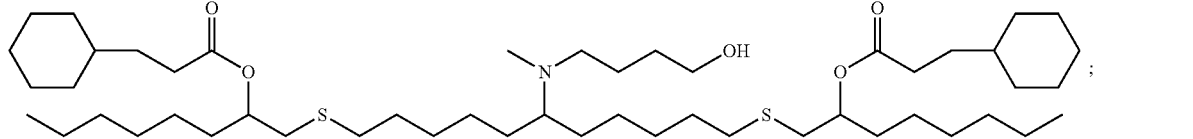
27
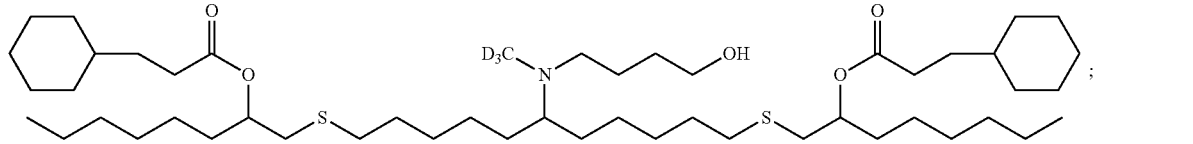
28
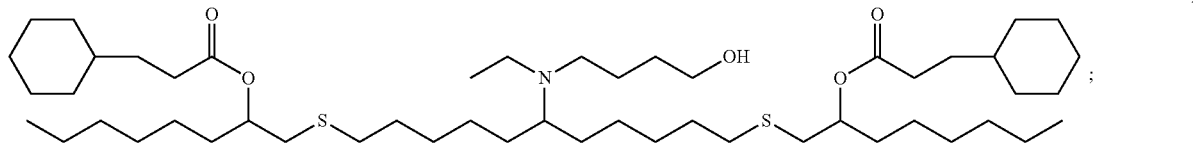
29
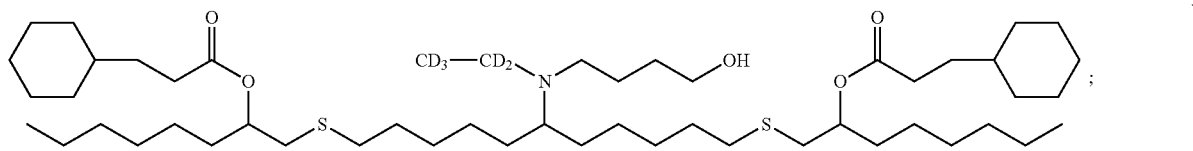
30
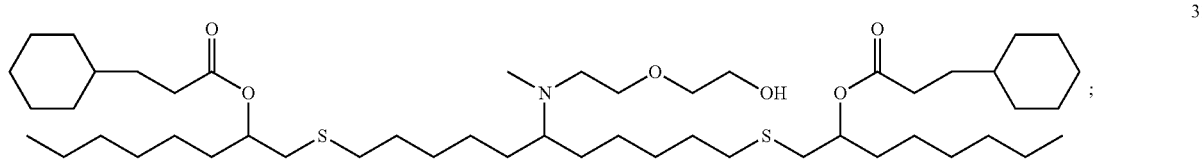
31
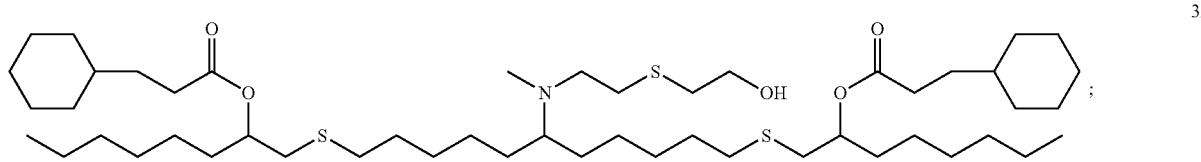
32
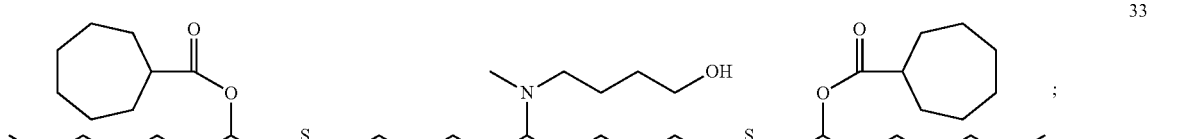
33
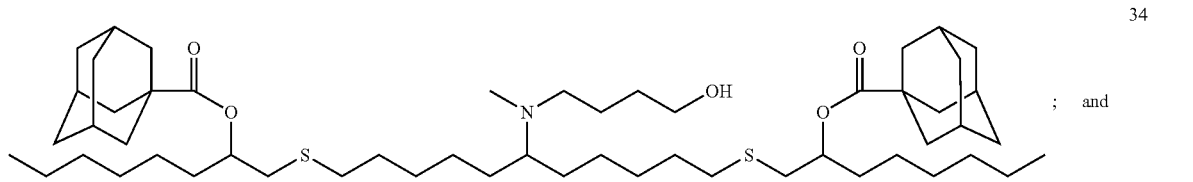
34
; and

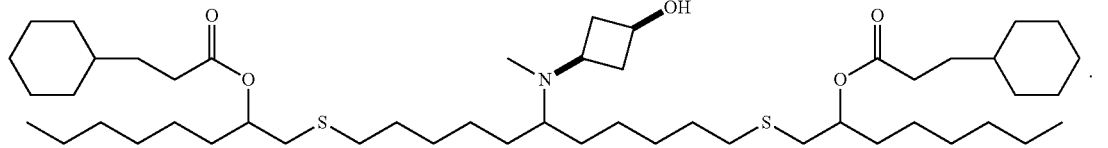

8. The ionizable, cationic amino lipid or the pharmaceutically acceptable salt of claim 7, having the structure of any one of compounds 5-13, 16-19, 22-31 or 33-35.

9. The ionizable, cationic amino lipid or pharmaceutically acceptable salt of claim 1, wherein $R^2$ is a linear or branched, optionally substituted, $C_4$ to $C_{10}$ alkyl group, comprising 0-2 carbon-carbon double bonds.

10. The ionizable, cationic amino lipid of claim 1 having the structure of Formula A:

Formula A

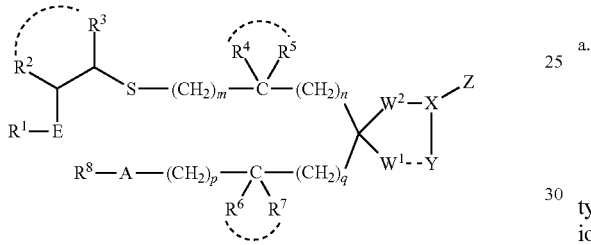

or pharmaceutically acceptable salt thereof;
wherein:
m, n, p, and q of Formula A are, independently 2 to 8;
A is O, S or a carbonyl (C=O), and
   if A is O, then $R^8$ is an acyl group

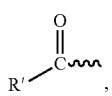

wherein the wavy line represents the bond to the A, and wherein the R' is as defined above for $R^1$;
   if A is the carbonyl (C=O), then $R^8$ is an

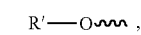

wherein the wavy line represents the bond to the A, and wherein the R' is as defined above for $R^1$;
   if A is S, then $R^8$ is a group of structure:

Formula B

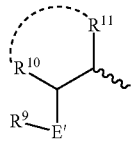

wherein E is an ester group that is (C=O)O or O(C=O), wherein the wavy line represents the bond to A, and wherein $R^9$ is as defined for $R^1$, $R^{10}$ is as defined for $R^2$, and $R^{11}$ is as defined for $R^3$;
$W^1$ and Y are either bonded to each other or not bonded to each other, and
   if $W^1$ and Y are bonded to each other, then
     $W^1$ is O or S;
     $W^2$ is O or S;
     X is CH;
     Y is $(CH_2)_t$, wherein t is 1 or 2;
     Z is selected from one of structures a-c below, wherein the wavy line represents the bond to X:

a.

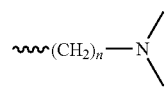

type 2 ionizable head group, wherein n of the type 2 ionizable head group is 1 to 5;

b.

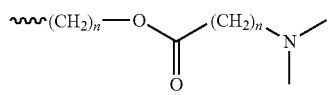

type 3 ionizable head group, wherein m and n of the type 3 ionizable head group are independently 1 to 5; and c.

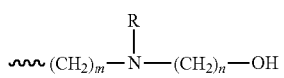

type 4 ionizable head group, wherein m and n of the type 4 ionizable head group are independently 2 to 5;
   if $W^1$ and Y are not bonded to each other, then
     $W^1$ is H;
     $W^2$ is O, S, NH or $NR^{12}$, wherein $R^{12}$ is a $C_1$ to $C_4$ alkyl optionally substituted with an OH group; and
     the moiety

of Formula A is a group selected from any one of structures d to l below, wherein the wavy line represents the bond to $W^2$ d.

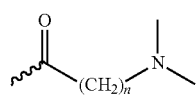

type 1 ionizable head group, wherein n of the type 1 ionizable head group is 1 to 5;

e.

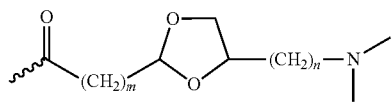

type 5 ionizable head group, wherein m and n of the type 5 ionizable head group are independently 1 to 5;

f.

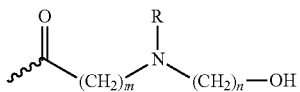

type 6 ionizable head group, wherein m of the type 6 ionizable head group is 1 to 5 and n of the type 6 ionizable head group is independently 2 to 5 and wherein R is $C_1$-$C_6$ alkyl, cycloalkyl, deuterated alkyl or deuterated cycloalkyl;

g.

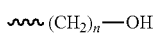

type 7 ionizable head group, wherein $W^2$ is NH or $NR^{12}$, wherein n of the type 7 ionizable head group is 1 to 5, and wherein a methylene ($CH_2$) of the $(CH_2)_n$ of the type 7 ionizable head group is optionally substituted with a sulfur or an oxygen atom;

h.

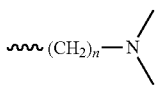

type 8 ionizable head group, wherein n of the type 8 ionizable head group is 1 to 5;

i.

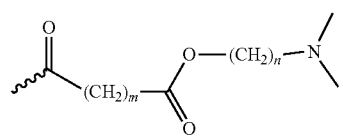

type 9 ionizable head group, wherein m and n of the type 9 ionizable head group are independently 1 to 5;

j.

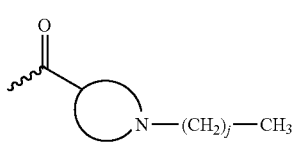

type 10 ionizable head group, wherein the curved lines represent atoms of a ring structure comprising the N atom, wherein the ring structure has 2 to 8 carbon atoms and wherein j of the type 10 ionizable head group is 0 to 5;

k.

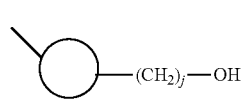

type 11 ionizable head group, wherein $W^2$ is NH or $NR^{12}$, wherein the circle represents a homocyclic or heterocyclic ring comprising from 3 to 8 atoms, and wherein j of the type 11 ionizable head group is 0 to 5; and l.

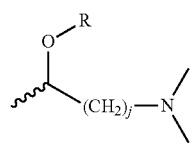

type 12 ionizable head group, wherein R=$C_1$-$C_6$ alkyl, cycloalkyl, deuterated alkyl or deuterated cycloalkyl, and wherein j of the type 12 ionizable head group ranges from 1 to 5.

* * * * *